United States Patent
Asada et al.

(10) Patent No.: US 9,905,767 B2
(45) Date of Patent: Feb. 27, 2018

(54) HIGH-MOLECULAR COMPOUND AND LIGHT-EMITTING ELEMENT USING SAME

(71) Applicant: Sumitomo Chemical Company, Limited, Tokyo (JP)

(72) Inventors: Kohei Asada, Tsukuba (JP); Kazuei Ohuchi, Tsukuba (JP); Osamu Goto, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 475 days.

(21) Appl. No.: 14/408,430

(22) PCT Filed: Jun. 7, 2013

(86) PCT No.: PCT/JP2013/066413
§ 371 (c)(1),
(2) Date: Dec. 16, 2014

(87) PCT Pub. No.: WO2013/191088
PCT Pub. Date: Dec. 27, 2013

(65) Prior Publication Data
US 2015/0207077 A1 Jul. 23, 2015

(30) Foreign Application Priority Data
Jun. 19, 2012 (JP) ................................ 2012-137537

(51) Int. Cl.
*H01L 51/00* (2006.01)
*C09K 11/06* (2006.01)
(Continued)

(52) U.S. Cl.
CPC ........ *H01L 51/0039* (2013.01); *C07D 251/24* (2013.01); *C08G 61/02* (2013.01); *C08G 61/12* (2013.01); *C08G 61/122* (2013.01); *C08G 73/026* (2013.01); *C08G 73/0644* (2013.01); *C08J 5/18* (2013.01); *C09K 11/06* (2013.01); *H01L 51/0003* (2013.01); *H01L 51/0035* (2013.01); *H01L 51/0043* (2013.01); *H01L 51/5056* (2013.01); *C08G 2261/12* (2013.01); *C08G 2261/135* (2013.01); *C08G 2261/148* (2013.01); *C08G 2261/1412* (2013.01); *C08G 2261/1414* (2013.01); *C08G 2261/312* (2013.01); *C08G 2261/3142* (2013.01); *C08G 2261/3162* (2013.01); *C08G 2261/3221* (2013.01); *C08G 2261/342* (2013.01); *C08G 2261/411* (2013.01); *C08G 2261/95* (2013.01); *C08J 2365/00* (2013.01);
(Continued)

(58) Field of Classification Search
CPC ...... C07D 251/24; C08G 61/02; C08G 61/12; C08G 61/122; C08G 73/026; C08G 73/0644; C08G 2261/12; C08G 2261/135; C08G 2261/1412; C08G 2261/1414; C08G 2261/148; C08G 2261/312; C08G 2261/3142; C08J 5/18; C09K 11/06; H01L 51/0085; H01L 51/5012; H01L 51/5016; H01L 51/0003; H01L 51/0035; H01L 51/0043; H01L 51/5056
See application file for complete search history.

(56) References Cited

U.S. PATENT DOCUMENTS

2008/0254320 A1 10/2008 Akino et al.
2010/0013377 A1 1/2010 Male et al.
(Continued)

FOREIGN PATENT DOCUMENTS

CN 102070771 A 5/2011
JP H11-140168 A 5/1999
(Continued)

OTHER PUBLICATIONS

CAS Abstract 2014/0151660 (2014).*
(Continued)

*Primary Examiner* — Alexander R Pagano
(74) *Attorney, Agent, or Firm* — Panitch Schwarze Belisario & Nadel LLP

(57) ABSTRACT

A high-molecular compound including a group indicated by general formula (11) as a repeating unit.

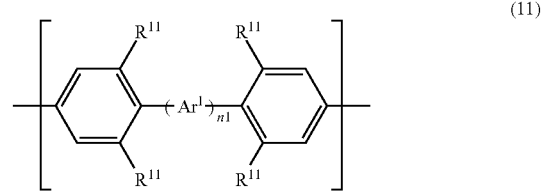

In formula (11) n1 indicates an integer of 1-3. $Ar^1$ indicates an arylene group, a divalent aromatic heterocyclic group, or a divalent aromatic amine residue, and these groups may have a substituent group. If there is a plurality of $Ar^1$, the $Ar^1$ can be the same or can be different. $R^{11}$ indicates a hydrogen atom, an alkyl group, an aryl group, a monovalent aromatic heterocyclic group, or an aralkyl group, and said groups may have a substituent group. The plurality of $R^{11}$ can be the same or can be different. However, at least three of the $R^{11}$ are an alkyl group, an aryl group, a monovalent aromatic heterocyclic group, or an aralkyl group.

15 Claims, No Drawings

(51) Int. Cl.
*C08G 61/12* (2006.01)
*H01L 51/50* (2006.01)
*C08G 61/02* (2006.01)
*C07D 251/24* (2006.01)
*C08G 73/02* (2006.01)
*C08G 73/06* (2006.01)
*C08J 5/18* (2006.01)

(52) U.S. Cl.
CPC ........ *C08J 2379/02* (2013.01); *C08J 2379/04* (2013.01); *C09K 2211/1416* (2013.01); *C09K 2211/1425* (2013.01); *C09K 2211/1466* (2013.01); *H01L 51/0085* (2013.01); *H01L 51/5012* (2013.01); *H01L 51/5016* (2013.01)

(56) References Cited

U.S. PATENT DOCUMENTS

| | | |
|---|---|---|
| 2011/0272686 A1 | 11/2011 | Ohuchi et al. |
| 2014/0151660 A1* | 6/2014 | Kamtekar ............... C07F 5/025 257/40 |

FOREIGN PATENT DOCUMENTS

| | | |
|---|---|---|
| JP | 2006302636 A | 11/2006 |
| JP | 2010-503193 A | 1/2010 |
| WO | 2008/025997 A1 | 3/2008 |
| WO | 2011068638 A1 | 6/2011 |

OTHER PUBLICATIONS

Office Action dated Sep. 30, 2016 in JP Application No. 2014-521416.

Written Opinion dated Sep. 17, 2013 in International Application No. PCT/JP2013/066413.

Rose et al, "N-Heterocyclic carbene containing element organic frameworks as heterogeneous organocatalysts," Chemical Communications, vol. 47, No. 16, pp. 4814-4816 (2011).

Kostas, et al, "Synthesis of a halo-methylphenylene periphery-functionalized triazine-based dendritic molecule with a 3,3'-dimethyl-biphenyl linker using tris(halo-methylphenylene)triazines as building blocks," Tetrahedron Letters, vol. 50, No. 16, pp. 1851-1854 (2009).

Liddell, et al, "Porphyrin-Based Hole Conducting Electropolymer," Chemistry of Materials, vol. 20, No. 1, pp. 135-142 (2008).

Int'l Search Report dated Sep. 17, 2013 in International Application No. PCT/JP2013/066413.

* cited by examiner

HIGH-MOLECULAR COMPOUND AND LIGHT-EMITTING ELEMENT USING SAME

CROSS-REFERENCE TO RELATED APPLICATION

This application is a Section 371 of International Application No. PCT/JP2013/066413, filed Jun. 7, 2013, which was published in the Japanese language on Dec. 27, 2013, under International Publication No. WO 2013/191088 A1, and the disclosure of which is incorporated herein by reference.

TECHNICAL FIELD

The present invention relates to a polymer compound and a raw material monomer of the polymer compound, and a composition, an organic film and a light emitting device containing the polymer compound.

BACKGROUND ART

As a light emitting material used in a light emitting layer of a light emitting device, a composition is known obtained by doping a host material with a phosphorescent compound showing light emission from the triplet excited state. Since light emission of the triplet excited state attains 4 times light emission efficiency in principle as compared with light emission from the singlet excited state, a light emitting device using a phosphorescent compound is paid to attention as a display device in display application and a planar light source in illumination application.

The above-described display device and planar light source are desired to realize high luminance at low current density (namely, realizing high current efficiency) and to realize low power consumption by reducing driving voltage (namely, realizing high light emission efficiency).

For realizing high current efficiency, it is important that the lowest triplet excited state (hereinafter, referred to as "$T_1$" in some cases) of a host material used in a composition with a phosphorescent compound is located at high energy level.

For realizing high light emission efficiency, it is important that a host material has a high conductive property.

As a host material for a phosphorescent compound, a polymer compound containing as a repeating unit a 1,4-phenylene group having specific substituents at 2-position and 5-position is known (Patent document 1). As another host material, a polymer compound containing as a repeating unit a fluorene-2,7-diyl group and a 1,4-phenylene group having specific substituents at 2-position and 5-position is known (Patent document 2).

PRIOR ART DOCUMENT

Patent Document

Patent document 1: WO 2011/068638
Patent document 2: WO 2007/032437

SUMMARY OF THE INVENTION

Problem to be Solved by the Invention

In a light emitting device produced by using the above-described polymer compound as a host material for a phosphorescent compound, the resultant current efficiency and light emission efficiency are not necessarily sufficient.

Thus, the present invention has an object of providing a polymer compound useful for producing a light emitting device excellent in current efficiency and light emission efficiency. Also, the present invention has an object of providing a composition, an organic film and a light emitting device containing the polymer compound. Further, the present invention has an object of providing a raw material monomer useful for production of the polymer compound.

Means for Solving the Problem

That is, the present invention provides a polymer compound described below and a raw material monomer of the polymer compound, and a composition, an organic film and a light emitting device containing the polymer compound.

[1] A polymer compound comprising as a repeating unit a group represented by the following general formula (11):

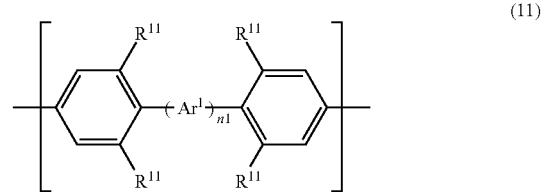

[in the formula (11),
n1 represents an integer of 1 to 3.
$Ar^1$ represents an arylene group, a divalent aromatic heterocyclic group or a divalent aromatic amine residue, and these groups may have a substituent. When there are a plurality of $Ar^1$, these may be mutually the same or different.
$R^{11}$ represents a hydrogen atom, an alkyl group, an aryl group, a monovalent aromatic heterocyclic group or an aralkyl group, and these groups may have a substituent. A plurality of $R^{11}$ may be mutually the same or different. Here, at least three groups $R^{11}$ are an alkyl group, an aryl group, a monovalent aromatic heterocyclic group or an aralkyl group.].

[2] The polymer compound according to [1], wherein the group represented by the above-described general formula (11) is a group represented by the following formula (1):

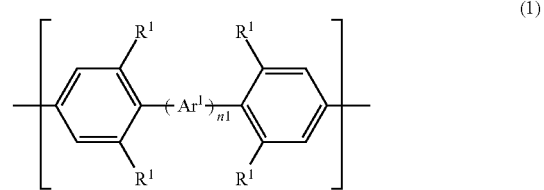

[in the formula (1),
n1 represents an integer of 1 to 3.
$Ar^1$ represents an arylene group, a divalent aromatic heterocyclic group or a divalent aromatic amine residue, and these groups may have a substituent. When there are a plurality of $Ar^1$, these may be mutually the same or different.
$R^1$ represents an alkyl group, an aryl group, a monovalent aromatic heterocyclic group or an aralkyl group, and these groups may have a substituent. A plurality of $R^1$ may be mutually the same or different.].

[3] The polymer compound according to [2], wherein the group represented by the above-described general formula (1) is a group represented by the following formula (1B):

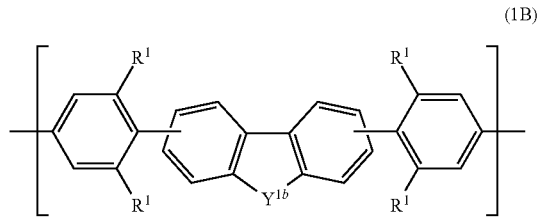

[in the formula (1B), $Y^{1b}$ represents —O—, —S—, —N(Ra)-, —C(Ra)$_2$- or —[C(Ra)$_2$]$_2$-. Ra represents an alkyl group, an aryl group, a monovalent aromatic heterocyclic group or an aralkyl group, and these groups may have a substituent. When there are a plurality of Ra, these may be mutually the same or different and may be mutually linked to form a ring structure together with a carbon atom to which they are linked.

$R^1$ represents the same meaning as described above.].

[4] The polymer compound according to any one of [1] to [3], further comprising as a repeating unit at least one group selected from the group consisting of a group represented by the following general formula (2) and a group represented by the following general formula (3):

 (2)

[in the formula (2), $Ar^2$ represents an arylene group, a divalent aromatic heterocyclic group, or a divalent group obtained by mutually linking 2 to 10 groups selected from the group consisting of an arylene group and a divalent aromatic heterocyclic group, and these groups may have a substituent.

Here, in the group represented by the formula (2), at least one of carbon atoms adjacent to a carbon atom forming a bond to the other repeating unit has an alkyl group, an aryl group, a monovalent aromatic heterocyclic group or an aralkyl group as a substituent.]

 (3)

[in the formula (3), $Ar^3$ represents an arylene group, a divalent aromatic heterocyclic group, a divalent aromatic amine residue, or a divalent group obtained by mutually linking 2 to 10 groups selected from the group consisting of an arylene group and a divalent aromatic heterocyclic group, and these groups may have a substituent.

Here, the group represented by the formula (3) is different from the group represented by the above-described formula (11) and the group represented by the above-described formula (2).].

[5] The polymer compound according to [4], wherein the group represented by the above-described general formula (2) is a group represented by the following general formula (2C):

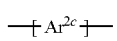 (2C)

[in the formula (2C), $Ar^{2c}$ represents an arylene group or a divalent aromatic heterocyclic group, and these groups may have a substituent.

Here, in the group represented by the formula (2C), at least one of carbon atoms adjacent to a carbon atom forming a bond to the other repeating unit has an alkyl group, an aryl group, a monovalent aromatic heterocyclic group or an aralkyl group as a substituent.].

[6] The polymer compound according to [5], wherein the group represented by the above-described general formula (2C) is a group represented by the following general formula (2D):

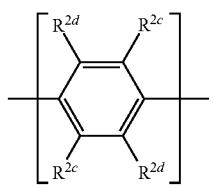 (2D)

[in the formula (2D), $R^{2c}$ represents an alkyl group, an aryl group, a monovalent aromatic heterocyclic group or an aralkyl group, and these groups may have a substituent. A plurality of $R^{2c}$ may be mutually the same or different.

$R^{2d}$ represents a hydrogen atom, an alkyl group, an aryl group, a monovalent aromatic heterocyclic group or an aralkyl group, and these groups may have a substituent. A plurality of $R^{2d}$ may be mutually the same or different.].

[7] The polymer compound according to [4], wherein the group represented by the above-described general formula (3) is a group represented by the following general formula (3B):

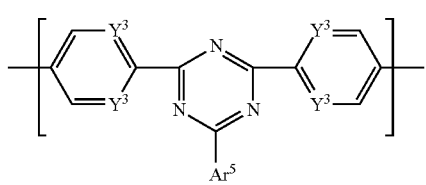 (3B)

[in the formula (3B), $Y^3$ represents a carbon atom or a nitrogen atom, and the carbon atom may have an alkyl group, an aryl group, a monovalent aromatic heterocyclic group or an aralkyl group as a substituent. A plurality of $Y^3$ may be mutually the same or different.

$Ar^5$ represents an aryl group or a monovalent aromatic heterocyclic group, and these groups may have a substituent.].

[8] The polymer compound according to [7], wherein the group represented by the above-described general formula (3B) is a group represented by the following general formula (3C):

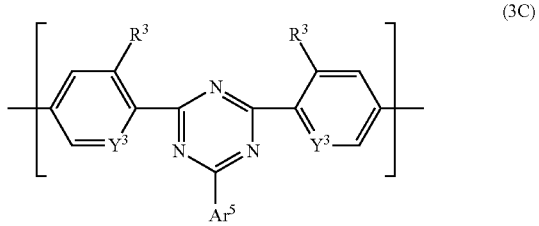

[in the formula (3C),

Y³ and Ar⁵ represent the same meaning as described above.

R³ represents an alkyl group, an aryl group, a monovalent aromatic heterocyclic group or an aralkyl group. A plurality of R³ may be mutually the same or different.].

[9] The polymer compound according to [4], wherein the group represented by the above-described general formula (2) is a group represented by the following general formula (2B):

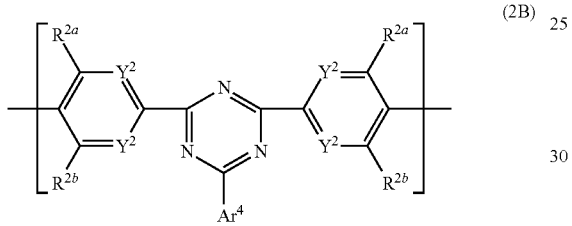

[in the formula (2B),

Y² represents a carbon atom or a nitrogen atom, and the carbon atom may have an alkyl group, an aryl group, a monovalent aromatic heterocyclic group or an aralkyl group as a substituent. A plurality of Y² may be mutually the same or different.

$R^{2a}$ represents an alkyl group, an aryl group, a monovalent aromatic heterocyclic group or an aralkyl group, and these groups may have a substituent. A plurality of $R^{2a}$ may be mutually the same or different.

$R^{2b}$ represents a hydrogen atom, an alkyl group, an aryl group, a monovalent aromatic heterocyclic group or an aralkyl group, and these groups may have a substituent. A plurality of $R^{2b}$ may be mutually the same or different.

Ar⁴ represents an aryl group or a monovalent aromatic heterocyclic group, and these groups may have a substituent.].

[10] The polymer compound according to any one of [4] to [9], wherein the content of the groups represented by the above-described formula (3) is 50 mol % or less with respect to the total content of repeating units contained in the polymer compound and the groups represented by the above-described formula (3) are not substantially adjacent.

[11] The polymer compound according to any one of [4] to [10], wherein the content of the group represented by the above-described formula (2) is 50 mol % or more with respect to the total content of repeating units contained in the polymer compound and the groups represented by the above-described formula (11), and the group represented by the above-described formula (11) and the group represented by the above-described formula (3) are not substantially adjacent.

[12] A composition comprising the polymer compound according to any one of [1] to [11] and at least one material selected from the group consisting of a hole transporting material, an electron transporting material and a light emitting material.

[13] The composition according to [12], wherein the above-described light emitting material is a phosphorescent compound.

[14] A liquid composition comprising the polymer compound according to any one of [1] to [11] and a solvent.

[15] An organic film comprising the polymer compound according to any one of [1] to [11].

[16] A light emitting device comprising an anode, a cathode and an organic layer disposed between the anode and the cathode, wherein the organic layer contains the polymer compound according to any one of [1] to [11].

[17] A compound represented by the following general formula (M11):

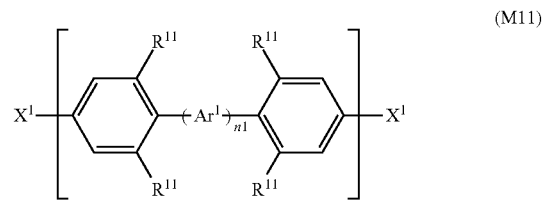

[in the formula (M11), n1 represents an integer of 1 to 3.

Ar¹ represents an arylene group, a divalent aromatic heterocyclic group or a divalent aromatic amine residue, and these groups may have a substituent. When there are a plurality of Ar¹, these may be mutually the same or different.

R¹¹ represents a hydrogen atom, an alkyl group, an aryl group, a monovalent aromatic heterocyclic group or an aralkyl group, and these groups may have a substituent. A plurality of R¹¹ may be mutually the same or different. Here, at least three groups R¹¹ are an alkyl group, an aryl group, a monovalent aromatic heterocyclic group or an aralkyl group.

X¹ represents a group selected from the following substituent group (a) or a group selected from the following substituent group (b). A plurality of X¹ may be mutually the same or different.

(Substituent Group (a))

a chlorine atom, a bromine atom, an iodine atom and a group represented by —O—S(=O)₂R²⁰ (R²⁰ represents an alkyl group, or an aryl group which may have an alkyl group, an alkoxy group, a nitro group, a fluorine atom or a cyano group as a substituent.).

(Substituent Group (b))

a group represented by —B(OR²¹)₂ (R² represents a hydrogen atom or an alkyl group. A plurality of R²¹ may be mutually the same or different and may be mutually linked to form a ring together with an oxygen atom to which they are linked.), a group represented by —BF₄Q¹ (Q¹ represents a monovalent cation of lithium, sodium, potassium, rubidium or cesium.), a group represented by —Sn(R²²)₃ (R²² represents a hydrogen atom or an alkyl group. A plurality of R²² may be mutually the same or different and may be mutually linked to form a ring together with a tin atom to which they are linked, a group represented by —MgY¹ (Y¹ represents a chlorine atom, a bromine atom or an iodine atom.) and a group represented by —ZnY$^2$ (Y$^2$ represents a chlorine atom, a bromine atom or an iodine atom.).].

[18] A compound represented by the following general formula (M2B):

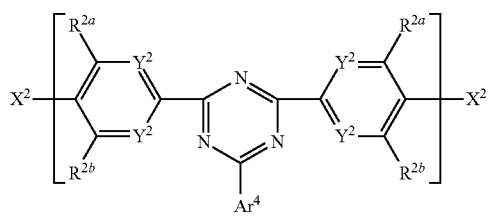

(M2B)

[in the formula (M2B),

Y$^2$ represents a carbon atom or a nitrogen atom, and the carbon atom may have an alkyl group, an aryl group, a monovalent aromatic heterocyclic group or an aralkyl group as a substituent. A plurality of Y$^2$ may be mutually the same or different.

R$^{2a}$ represents an alkyl group, an aryl group, a monovalent aromatic heterocyclic group or an aralkyl group, and these groups may have a substituent. A plurality of R$^{2a}$ may be mutually the same or different.

R$^{2b}$ represents a hydrogen atom, an alkyl group, an aryl group, a monovalent aromatic heterocyclic group or an aralkyl group, and these groups may have a substituent. A plurality of R$^{2b}$ may be mutually the same or different.

Ar$^4$ represents an aryl group or a monovalent aromatic heterocyclic group, and these groups may have a substituent.

X$^2$ represents a group selected from the following substituent group (a) or a group selected from the following substituent group (b). A plurality of X$^2$ may be mutually the same or different.

(Substituent Group (a))

a chlorine atom, a bromine atom, an iodine atom and a group represented by —O—S(=O)$_2$R$^{20}$ (R$^{20}$ represents an alkyl group, or an aryl group which may have an alkyl group, an alkoxy group, a nitro group, a fluorine atom or a cyano group as a substituent.).

(Substituent Group (b))

a group represented by —B(OR$^{21}$)$_2$ (R$^{21}$ represents a hydrogen atom or an alkyl group. A plurality of R$^{21}$ may be mutually the same or different and may be mutually linked to form a ring together with an oxygen atom to which they are linked.), a group represented by —BF$_4$Q$^1$ (Q$^1$ represents a monovalent cation of lithium, sodium, potassium, rubidium or cesium.), a group represented by —Sn(R$^{22}$)$_3$ (R$^{22}$ represents a hydrogen atom or an alkyl group. A plurality of R$^{22}$ may be mutually the same or different and may be mutually linked to form a ring together with a tin atom to which they are linked), a group represented by —MgY$^1$ (Y$^1$ represents a chlorine atom, a bromine atom or an iodine atom.) and a group represented by —ZnY$^2$ (Y$^2$ represents a chlorine atom, a bromine atom or an iodine atom.).].

[19] A compound represented by the following general formula (M3C):

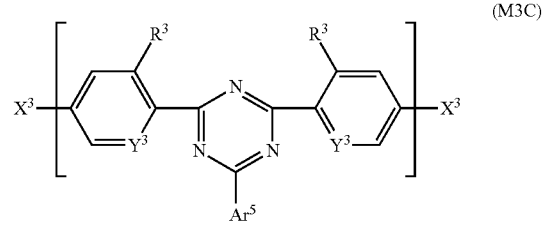

(M3C)

[in the formula (M3C),

Y$^3$ represents a carbon atom or a nitrogen atom, and the carbon atom may have an alkyl group, an aryl group, a monovalent aromatic heterocyclic group or an aralkyl group as a substituent. A plurality of Y$^3$ may be mutually the same or different.

Ar$^5$ represents an aryl group or a monovalent aromatic heterocyclic group, and these groups may have a substituent.

R$^3$ represents an alkyl group, an aryl group, a monovalent aromatic heterocyclic group or an aralkyl group. A plurality of R$^3$ may be mutually the same or different.

X$^3$ represents a group selected from the following substituent group (a) or a group selected from the following substituent group (b). A plurality of X$^3$ may be mutually the same or different.

(Substituent Group (a))

a chlorine atom, a bromine atom, an iodine atom and a group represented by —O—S(=O)$_2$R$^{20}$ (R$^{20}$ represents an alkyl group, or an aryl group which may have an alkyl group, an alkoxy group, a nitro group, a fluorine atom or a cyano group as a substituent.).

(Substituent Group (b))

a group represented by —B(OR$^{21}$)$_2$ (R$^{21}$ represents a hydrogen atom or an alkyl group. A plurality of R$^{21}$ may be mutually the same or different and may be mutually linked to form a ring together with an oxygen atom to which they are linked.), a group represented by —BF$_4$Q$^1$ (Q$^1$ represents a monovalent cation of lithium, sodium, potassium, rubidium or cesium.), a group represented by —Sn(R$^{22}$)$_3$ (R$^{22}$ represents a hydrogen atom or an alkyl group. A plurality of R$^{22}$ may be mutually the same or different and may be mutually linked to form a ring together with a tin atom to which they are linked), a group represented by —MgY$^1$ (Y$^1$ represents a chlorine atom, a bromine atom or an iodine atom.) and a group represented by —ZnY$^2$ (Y$^2$ represents a chlorine atom, a bromine atom or an iodine atom.).].

Effect of the Invention

According to the present invention, a polymer compound useful for producing a light emitting device excellent in current efficiency and light emission efficiency can be provided. Also, according to the present invention, a composition, an organic film and a light emitting device containing the polymer compound can be provided. Further, according to the present invention, a raw material monomer useful for producing the polymer compound can be provided.

The polymer compound of the present invention is particularly useful as a host material of a phosphorescent compound showing an emission color in the blue range.

MODES FOR CARRYING OUT THE INVENTION

Suitable embodiments of the present invention will be illustrated in detail below.

[Explanation of Term]

Terms in the present specification will be explained.

"Current efficiency" is a value obtained by dividing the luminance of a light emitting device by the input current per unit area, and [cd/A] is usually used as its unit.

"Light emission efficiency" is a value obtained by dividing the total luminous flux from the light-emitting face by the input current, and [lm/W] is usually used as its unit.

"Luminance life" is driving time until luminance reaches a certain rate with respect to the initial value, and usually denotes a value obtained when driving at the constant current density. "Luminance life" is one of indices of the stability of a light emitting device.

In structural formulae in the present specification, the bond represented by an arrow represents a coordinate bond and the bond represented by a broken line represents a covalent bond or a coordinate bond.

"Residue" denotes "a k-valent group represented by an atomic group remaining after removing k hydrogen atoms from a compound", and the number represented by k and the positions of the hydrogen atoms to be removed will be illustrated in more detail in the present specification if necessary.

"Polymer compound" is a polymer having molecular weight distribution obtained by a polymerization reaction using monomers, and particularly denotes one having a polystyrene-equivalent number-average molecular weight of $1 \times 10^3$ to $1 \times 10^8$. "Small molecule compound" is a compound which does not have molecular weight distribution as shown by a polymer compound, and denotes one having a molecular weight of usually 5000 or less.

"Constitutional unit" denote a unit appearing once or more in a polymer compound, and it is preferable that this constitutional unit is present as "repeating unit" (unit appearing twice or more in a polymer compound) in the polymer compound. That is, the repeating unit is a constitutional unit or constitutional sequence formed by partial structures excluding a leaving group (polymerization active group) capable of forming a linkage in a polymerization reaction in producing a polymer compound. "Constitutional sequence" denotes a structure formed by linking two or more constitutional units via a single bond in a polymer compound.

"n-valent aromatic heterocyclic group" (n represents an integer of 1 or more) denotes an atomic group remaining after removing n hydrogen atoms among hydrogen atoms linking directly to carbon atoms constituting a ring from a monocyclic or condensed-cyclic heterocyclic compound showing aromaticity. "Heterocyclic compound" denotes an organic compound having a cyclic structure in which atoms constituting the ring include not only a carbon atom but also a hetero atom such as an oxygen atom, a sulfur atom, a nitrogen atom, a phosphorus atom, a boron atom, a silicon atom or the like.

"Aromatic heterocyclic compound" is a heterocyclic compound having a hetero atom such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole, dibenzophosphole and the like, and denotes a compound in which the heterocyclic ring itself shows aromaticity and a compound in which the hetero atom-containing heterocyclic ring itself does not show aromaticity but an aromatic ring is condensed to the heterocyclic ring such as phenoxazine, phenothiazine, dibenzoborole, dibenzosilole, benzopyran and the like.

In the present specification, Me represents a methyl group, Et represents an ethyl group, i-Pr represents an isopropyl group, n-Bu represents a n-butyl group, and tBu, t-Bu and t-butyl group represent a tert-butyl group.

[Explanation of Substituent]

Various sorts of substituents shown in the present specification will be explained. In the present specification, each group is as described below unless otherwise stated. Further, in the present specification, a hydrogen atom of a compound, a constitutional unit and a repeating unit may be optionally substituted with a deuterium atom, and also other atoms may be substituted with various isotopes occurring naturally in a similar fashion.

(Alkyl Group)

The alkyl group may be any of linear, branched or cyclic, and a linear alkyl group is preferable. The number of carbon atoms of the alkyl group, not including the number of carbon atoms of a substituent described later, is preferably 1 to 20 (in the case of a branched alkyl group and a cyclic alkyl group, 3 to 20), more preferably 1 to 15 (in the case of a branched alkyl group and a cyclic alkyl group, 3 to 15), further preferably 1 to 12 (in the case of a branched alkyl group and a cyclic alkyl group, 3 to 12). The substituent which the alkyl group may have includes, for example, an aryl group, a monovalent aromatic heterocyclic group, an alkoxy group, an aryloxy group, an arylalkoxy group, a substituted amino group, a substituted carbonyl group, a substituted oxycarbonyl group, a fluorine atom and a cyano group.

Examples of the alkyl group include a methyl group, an ethyl group, a propyl group, an isopropyl group, a butyl group, a sec-butyl group, an isobutyl group, a tert-butyl group, a pentyl group, an isoamyl group, a hexyl group, a cyclohexyl group, a heptyl group, an octyl group, a 2-ethylhexyl group, a nonyl group, a decyl group, a 3,7-dimethyloctyl group, a dodecyl group, a trifluoromethyl group, a pentafluoroethyl group, a perfluorobutyl group, a perfluorohexyl group and a perfluorooctyl group.

(Aryl Group)

The aryl group is an atomic group remaining after removing from a monocyclic or condensed-cyclic aromatic hydrocarbon one hydrogen atom linking directly to a carbon atom constituting its ring. The number of carbon atoms of the aryl group, not including the number of carbon atoms of a substituent described later, is preferably 6 to 60, more preferably 6 to 48, further preferably 6 to 20, particularly preferably 6 to 14. The substituent which the aryl group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the aryl group include a phenyl group and a naphthyl group.

(Monovalent Aromatic Heterocyclic Group)

The number of carbon atoms of the monovalent aromatic heterocyclic group, not including the number of carbon atoms of a substituent described later, is preferably 2 to 60, more preferably 3 to 20. The substituent which the monovalent aromatic heterocyclic group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the monovalent aromatic heterocyclic group include a 2-oxadiazolyl group, a 2-thiadiazolyl group, a 2-thiazolyl group, a 2-oxazolyl group, a 2-thienyl group, a 2-pyrrolyl group, a 2-furyl group, a 2-pyridyl group, a 3-pyridyl group, a 4-pyridyl group, a 2-pyrazyl group, a 2-pyrimidyl group, a 2-triazyl group, a 3-pyridazyl group, a 3-carbazolyl group, a 2-phenoxazinyl group, a 3-phenoxazinyl group, a 2-phenothiazinyl group and a 3-phenothiazinyl group.

(Alkoxy Group)

The alkoxy group may be any of linear, branched or cyclic, and a linear alkoxy group is preferable. The number of carbon atoms of the alkoxy group, not including the number of carbon atoms of a substituent described later, is preferably 1 to 20 (in the case of a branched alkoxy group and a cyclic alkoxy group, 3 to 20). The substituent which the alkoxy group may have includes, for example, an aryl group, a monovalent aromatic heterocyclic group, an alkoxy group, an aryloxy group, an arylalkoxy group, a substituted amino group, a substituted carbonyl group, a substituted oxycarbonyl group, a fluorine atom and a cyano group.

Examples of the alkoxy group include a methoxy group, an ethoxy group, a propyloxy group, an isopropyloxy group, a butoxy group, a sec-butoxy group, an isobutoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a dodecyloxy group, a trifluoromethoxy group, a pentafluoroethoxy group, a perfluorobutoxy group, a perfluorohexyloxy group, a perfluorooctyloxy group, a methoxymethyloxy group, a 2-methoxyethyloxy group and a 2-ethoxyethyloxy group.

(Aryloxy Group)

The number of carbon atoms of the aryloxy group, not including the number of carbon atoms of a substituent described later, is preferably 6 to 60. The substituent which the aryloxy group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the aryloxy group include a phenoxy group, a $C_1$ to $C_{12}$ alkoxyphenoxy group ("$C_1$ to $C_{12}$ alkoxy" means that the number of carbon atoms of the alkoxy portion is 1 to 12. The same shall apply hereinafter.), a $C_1$ to $C_{12}$ alkylphenoxy group, a 1-naphthyloxy group, a 2-naphthyloxy group and a pentafluorophenyloxy group.

(Aralkyl Group)

The number of carbon atoms of the aralkyl group, not including the number of carbon atoms of a substituent described later, is preferably 7 to 60.

The substituent which the aralkyl group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the aralkyl group include a phenyl-$C_1$ to $C_{12}$ alkyl group, a $C_1$ to $C_{12}$ alkoxyphenyl-$C_1$ to $C_{12}$ alkyl group and a $C_1$ to $C_{12}$ alkylphenyl-$C_1$ to $C_{12}$ alkyl group.

(Arylalkoxy Group)

The number of carbon atoms of the arylalkoxy group, not including the number of carbon atoms of a substituent described later, is preferably 7 to 60. The substituent which the arylalkoxy group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the arylalkoxy group include a phenyl-$C_1$ to $C_{12}$ alkoxy group, a $C_1$ to $C_{12}$ alkoxyphenyl-$C_1$ to $C_{12}$ alkoxy group and a $C_1$ to $C_{12}$ alkylphenyl-$C_1$ to $C_{12}$ alkoxy group.

(Substituted Amino Group)

The number of carbon atoms of the substituted amino group, including the number of carbon atoms of a substituent, is preferably 2 to 60. The substituent which the substituted amino group has includes, for example, an alkyl group, an aryl group, an aralkyl group and a monovalent aromatic heterocyclic group. The substituted amino group may also be a group in which substituents which the amino group has are mutually linked directly to form a ring structure together with a nitrogen atom to which they are linked and a group in which substituents which the amino group has are mutually linked via a carbon atom, an oxygen atom, a sulfur atom or the like to form a ring structure together with a nitrogen atom to which they are linked. The substituted amino group is preferably a dialkyl substituted amino group or a diaryl substituted amino group.

Examples of the substituted amino group include a dimethylamino group, a diethylamino group, a diphenylamino group, a di-4-tolylamino group, a di-4-tert-butylphenylamino group, a bis(3,5-di-tert-butylphenyl)amino group, a N-carbazolyl group, a N-phenoxazinyl group, a N-acridinyl group and a N-phenothiazinyl group.

(Substituted Carbonyl Group)

The number of carbon atoms of the substituted carbonyl group, including the number of carbon atoms of a substituent, is preferably 2 to 60.

The substituted carbonyl group includes a group represented by —$COR^{23}$ ($R^{23}$ represents a prescribed substituent) in which $R^{23}$ is an alkyl group, an aryl group, an aralkyl group or a monovalent aromatic heterocyclic group.

Examples of the substituted carbonyl group include an acetyl group, a butylyl group and a benzoyl group.

(Substituted Oxycarbonyl Group)

The number of carbon atoms of the substituted oxycarbonyl group, including the number of carbon atoms of a substituent, is preferably 2 to 60.

The substituted oxycarbonyl group is preferably a group represented by —$COOR^{24}$ ($R^{24}$ represents a substituent) in which $R^{24}$ is an alkyl group, an aryl group, an aralkyl group or a monovalent aromatic heterocyclic group.

Examples of the substituted oxycarbonyl group include a methoxycarbonyl group, an ethoxycarbonyl group, a butoxycarbonyl group, a phenoxycarbonyl group and a benzyloxycarbonyl group.

(Arylene Group)

The arylene group denotes an atomic group remaining after removing from a monocyclic or condensed-cyclic aromatic hydrocarbon two hydrogen atoms bonding directly to a carbon atom constituting the ring. The number of carbon atoms of the arylene group, not including the number of carbon atoms of a substituent described later, is preferably 6 to 60, more preferably 6 to 48, further preferably 6 to 30, particularly preferably 6 to 18. The substituent which the arylene group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the arylene group include phenylene groups such as a 1,4-phenylene group (the following formula 001), a 1,3-phenylene group (the following formula 002), a 1,2-phenylene group (the following formula 003) and the like; naphthalenediyl groups such as a naphthalene-1,4-diyl group (the following formula 004), a naphthalene-1,5-diyl group (the following formula 005), a naphthalene-2,6-diyl group (the following formula 006) and the like; dihydrophenanthrenediyl groups such as a 9,10-dihydrophenanthrene-2,7-diyl group (the following formula 007) and the like; fluorenediyl groups such as a fluorene-3,6-diyl group (the following formula 008), a fluorene-2,7-diyl group (the following formula 009) and the like.

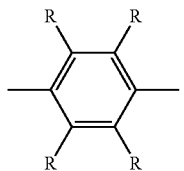

001

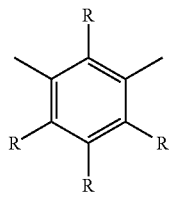

002

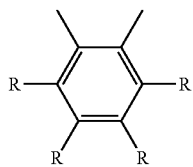

003

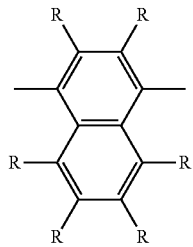

004

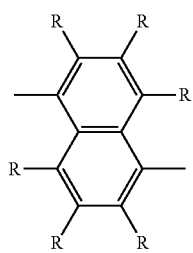

005

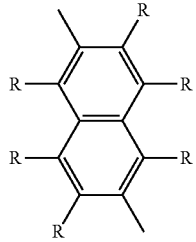

006

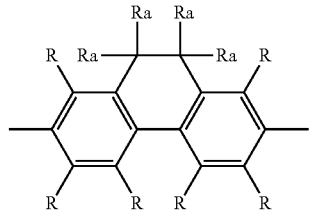

007

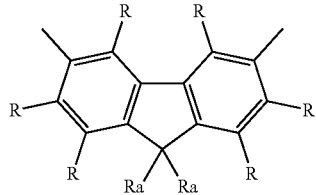

008

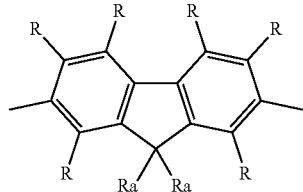

009

In the formulae 001 to 009, R represents a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom or a cyano group. Ra represents an alkyl group, an aryl group, a monovalent aromatic heterocyclic group or an aralkyl group. A plurality of R may be mutually the same or different and may be mutually linked to form a ring structure together with a carbon atom to which they are linked. A plurality of Ra may be mutually the same or different and may be mutually linked to form a ring structure together with a carbon atom to which they are linked.

In the formulae 001 to 009, R is preferably a hydrogen atom, an alkyl group, an aryl group, a monovalent aromatic heterocyclic group, an alkoxy group, an aryloxy group, an aralkyl group or a substituted amino group, more preferably a hydrogen atom, an alkyl group or an aryl group.

In the formulae 001 to 009, Ra is preferably an aryl group or an alkyl group, more preferably an aryl group which may be substituted with an alkyl group, an alkoxy group or an aryl group, or an alkyl group, and it is further preferable that at least one Ra is an aryl group which may have an alkyl group, an alkoxy group or an aryl group as a substituent.

In the formulae 001 to 009, the ring structure formed by R and Ra is preferably a cyclopentyl ring which may have an alkyl group as a substituent, a cyclohexyl ring which may have an alkyl group as a substituent or a cycloheptyl ring which may have an alkyl group as a substituent. The ring structure may also be a condensed ring structure obtained by further condensing a benzene ring and the like.

(Divalent Aromatic Heterocyclic Group)

The number of carbon atoms of the divalent aromatic heterocyclic group, not including the number of carbon atoms of a substituent described later, is preferably 2 to 60, more preferably 3 to 20. The substituent which the divalent aromatic heterocyclic group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the divalent aromatic heterocyclic group include pyridinediyl groups such as a pyridine-2,5-diyl group (the following formula 101), a pyridine-2,6-diyl group (the following formula 102) and the like; pyrimidinediyl groups such as a pyrimidine-4,6-diyl group (the following formula 103) and the like; triazinediyl groups such as a triazine-2,4-diyl group (the following formula 104) and the like; pyrazinediyl groups such as a pyrazine-2,5-diyl group (the following formula 105) and the like; pyridazinediyl groups such as a pyridazine-3,6-diyl group (the following formula 106) and the like; quinolinediyl groups such as a quinoline-2,6-diyl group (the following formula 107) and the like; isoquinolinediyl groups such as a isoquinoline-1,4-diyl group (the following formula 108) and the like; quinoxalinediyl groups such as a quinoxaline-5,8-diyl group (the following formula 109) and the like; carbazolediyl groups such as a carbazole-3,6-diyl group (the following formula 110), a carbazole-2,7-diyl group (the following formula III) and the like; dibenzofurandiyl groups such as a dibenzofuran-4,7-diyl group (the following formula 112), a dibenzofuran-3,8-diyl group (the following formula 113) and the like; dibenzothiophenediyl groups such as a dibenzothiophene-4,7-diyl group (the following formula 114), a dibenzothiophene-3,8-diyl group (the following formula 115) and the like; dibenzosilolediyl groups such as a dibenzosilole-4,7-diyl group (the following formula 116), a dibenzosilole-3,8-diyl group (the following formula 117) and the like; phenoxazinediyl groups such as a phenoxazine-3,7-diyl group (the following formula 118), a phenoxazine-2,8-diyl group (the following formula 119) and the like; phenothiazinediyl groups such as a phenothiazine-3,7-diyl group (the following formula 120), a phenothiazine-2,8-diyl group (the following formula 121) and the like; dihydroacridinediyl groups such as a dihydroacridine-2,7-diyl group (the following formula 122) and the like; a divalent group represented by the following formula 123; pyrrolediyl groups such as a pyrrole-2,5-diyl group (the following formula 124) and the like; furandiyl groups such as a furan-2,5-diyl group (the following formula 125) and the like; thiophenediyl groups such as a thiophene-2,5-diyl group (the following formula 126) and the like; diazolediyl groups such as a diazole-2,5-diyl group (the following formula 127) and the like; triazolediyl groups such as a triazole-2,5-diyl group (the following formula 128) and the like; oxazolediyl groups such as an oxazole-2,5-diyl group (the following formula 129) and the like; an oxadiazole-2,5-diyl group (the following formula 130); triazolediyl groups such as a triazole-2,5-diyl group (the following formulae 131) and the like; and a thiadiazole-2,5-diyl group (the following formula 132).

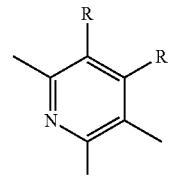

101

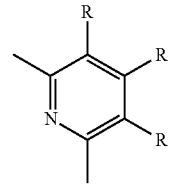

102

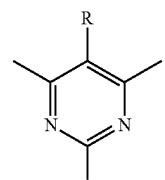

103

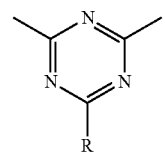

104

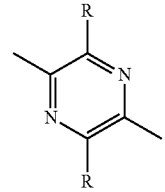

105

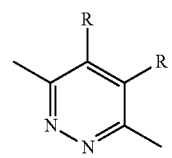

106

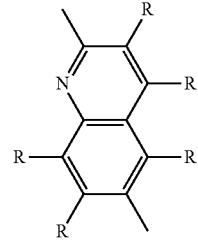

107

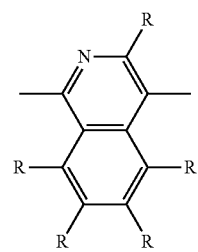

108

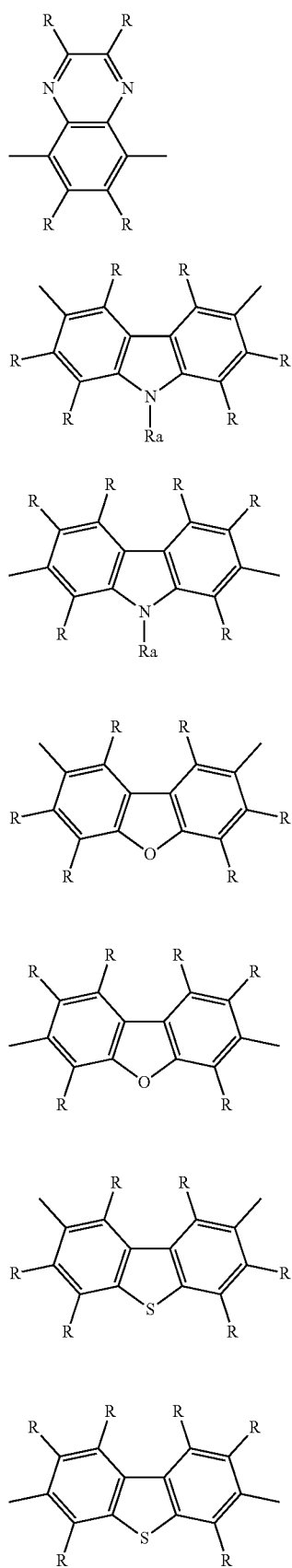
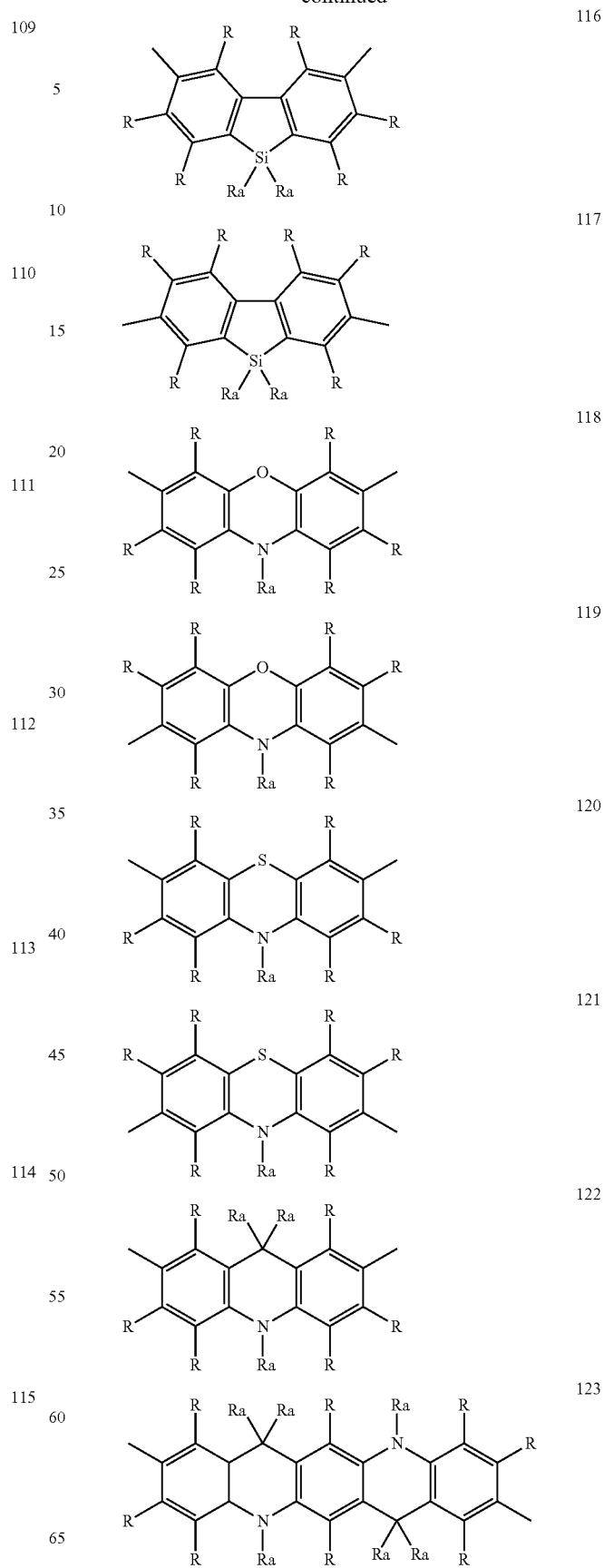

124 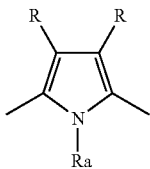

125 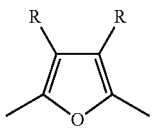

126 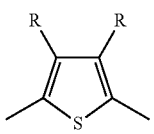

127 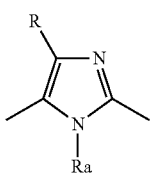

128 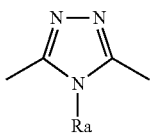

129 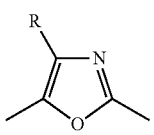

130 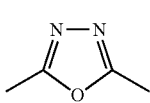

131 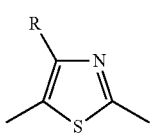

132 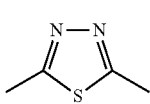

In the formulae 101 to 132, R and Ra represent the same meaning as described above.

(Divalent Aromatic Amine Residue)

The divalent aromatic amine residue is represented by, for example, the following general formula (5).

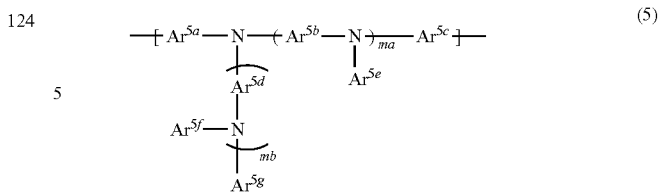 (5)

In the formula (5), $Ar^{5a}$, $Ar^{5b}$, $Ar^{5c}$ and $Ar^{5d}$ represent each independently an arylene group or a divalent aromatic heterocyclic group, and these groups may have a substituent.

$Ar^{5e}$, $Ar^{5f}$ and $Ar^{5g}$ represent each independently a hydrogen atom, an alkyl group, an aryl group or a monovalent aromatic heterocyclic group, and these groups may have a substituent.

The substituent which $Ar^{5a}$, $Ar^{5b}$, $Ar^{5c}$, $Ar^{5d}$, $Ar^{5e}$, $Ar^{5f}$ and $Ar^{5g}$ may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group, and an alkyl group, an aryl group and an aralkyl group are preferable.

The group represented by $Ar^{5d}$, $Ar^{5e}$, $Ar^{5f}$ and $Ar^{5g}$ may be bonded directly to or bonded via a group represented by —O—, —S—, —C(=O)—, —C(=O)—O—, —N($R^A$)—, —C(=O)—N($R^A$)— or C($R^A$)$_2$— to the other group than the group linked to a nitrogen atom to which the group is linked, and this ring structure is preferably a 5 to 7-membered ring. $R^A$ represents an alkyl group, an aryl group, a monovalent aromatic heterocyclic group or an aralkyl group, and these groups may have a substituent. When there are a plurality of $R^A$, these may be mutually the same or different and may be mutually linked to form a ring structure together with a carbon atom to which they are linked.

ma and mb represent each independently 0 or 1.

(Trivalent Aromatic Hydrocarbon Group)

Trivalent aromatic hydrocarbon group denotes an atomic group remaining after removing from a monocyclic or condensed-cyclic aromatic hydrocarbon three hydrogen atoms linking directly to carbon atoms constituting the ring. The number of carbon atoms of the trivalent aromatic hydrocarbon group, not including the number of carbon atoms of a substituent described later, is preferably 6 to 60, more preferably 6 to 48, further preferably 6 to 20, particularly preferably 6 to 14. The substituent which the trivalent aromatic hydrocarbon group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the trivalent aromatic hydrocarbon group include an atomic group remaining after removing from an aromatic hydrocarbon such as benzene, naphthalene, anthracene, phenanthrene, naphthacene, fluorene, pyrene, perylene and the like three hydrogen atoms linking directly to carbon atoms constituting the ring.

(Trivalent Aromatic Heterocyclic Group)

The trivalent aromatic heterocyclic group denotes an atomic group remaining after removing from a monocyclic or condensed-cyclic heterocyclic compound showing aromaticity three hydrogen atoms linking directly to carbon atoms or hetero atoms constituting the ring. The number of carbon atoms of the trivalent aromatic heterocyclic group, not including the number of carbon atoms of a substituent described later, is preferably 2 to 60, more preferably 3 to 20. The substituent which the trivalent aromatic heterocyclic group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the trivalent aromatic heterocyclic group include an atomic group remaining after removing from an aromatic heterocyclic compound such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole, dibenzophosphole, phenoxazine, phenothiazine, dibenzoborole, dibenzosilole, benzopyran and the like three hydrogen atoms linking directly to carbon atoms or hetero atoms constituting the ring.

[Polymer Compound]

Suitable embodiments of the polymer compound of the present invention will be explained.

The polymer compound of the present invention contains the group represented by the formula (11) described above as a repeating unit. In a more suitable embodiment, the polymer compound of the present invention contains at least one selected from the group consisting of the group represented by the formula (2) described above and the group represented by the formula (3) described above as a repeating unit, in addition to the group represented by the formula (11). The polymer compound of the present embodiment may contain as a repeating unit the other group than the group represented by the formula (11), the group represented by the formula (2) and the group represented by the formula (3). The groups represented by the formula (11), the groups represented by the formula (2) and the groups represented by the formula (3) may each be contained singly or may each be contained in combination. These groups will be explained below.

(Groups Represented by the Formulae (11) and (1))

The group represented by the formula (11) is preferably a group represented by the formula (1).

The group represented by the formula (11) (may be a group represented by the formula (1), the same shall apply in the following descriptions unless otherwise stated) is contained as a repeating unit in the polymer compound of the present invention, and when there are plural methods for recognizing the group represented by the formula (11) in a polymer chain, a group in which the value of n1 is lowest is recognized as the group represented by the formula (11).

$R^{11}$ in the formula (11) and $R^1$ in the formula (1) represent preferably an alkyl group, more preferably a methyl group, an ethyl group or a propyl group, further preferably a methyl group, since synthesis of raw material monomers of the polymer compound of the present embodiment is simpler.

$Ar^1$ in the formulae (11) and (1) is preferably an arylene group or a divalent aromatic heterocyclic group, more preferably a 1,4-phenylene group (the formula 001), a 9,10-dihydrophenanthrene-2,7-diyl group (the formula 007), a fluorene-3,6-diyl group (the formula 008), a fluorene-2,7-diyl group (the formula 009), a 1,3,5-triazine-2,4-diyl group (the formula 104), a carbazole-3,6-diyl group (the formula 110), a carbazole-2,7-diyl group (the formula III), a dibenzofuran-4,7-diyl group (the formula 112), a dibenzofuran-3,8-diyl group (the formula 113), a dibenzothiophene-4,7-diyl group (the formula 114) or a dibenzothiophene-3,8-diyl group (the formula 115).

When $Ar^1$ in the formulae (11) and (1) is a 1,4-phenylene group (the formula 001), it is preferable that n1 is 1 or 2, and the group represented by $Ar^1$ includes a group represented by the following formula 1-422.

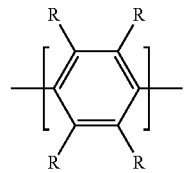

1-422

(wherein, R represents the same meaning as described above.)

When $Ar^1$ is a group selected from the group consisting of a 9,10-dihydrophenanthrene-2,7-diyl group (the formula 007), a fluorene-3,6-diyl group (the formula 008), a fluorene-2,7-diyl group (the formula 009), a carbazole-3,6-diyl group (the formula 110), a carbazole-2,7-diyl group (the formula III), a dibenzofuran-4,7-diyl group (the formula 112), a dibenzofuran-3,8-diyl group (the formula 113), a dibenzothiophene-4,7-diyl group (the formula 114) and a dibenzothiophene-3,8-diyl group (the formula 115), it is preferable that n1 is 1.

When $Ar^1$ in the formulae (11) and (1) includes a 1,3,5-triazine-2,4-diyl group (the formula 104), it is preferable that n1 is 3, and the divalent group obtained by directly linking three moieties $Ar^1$ includes, for example, groups represented by the following formulae 1-301 to 1-321, and groups represented by the formulae 1-301, 1-302, 1-303, 1-304, 1-305, 1-306, 1-307, 1-308 and 1-309 are preferable, groups represented by the formulae 1-301, 1-303, 1-304, 1-308 and 1-309 are more preferable since synthesis of raw material monomers of the polymer compound of the present embodiment is simpler.

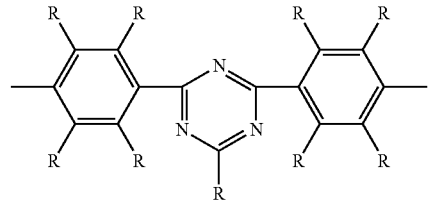

1-301

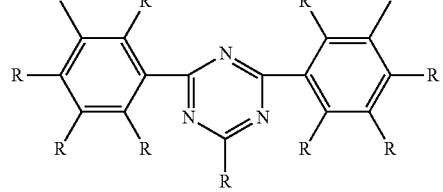

1-302

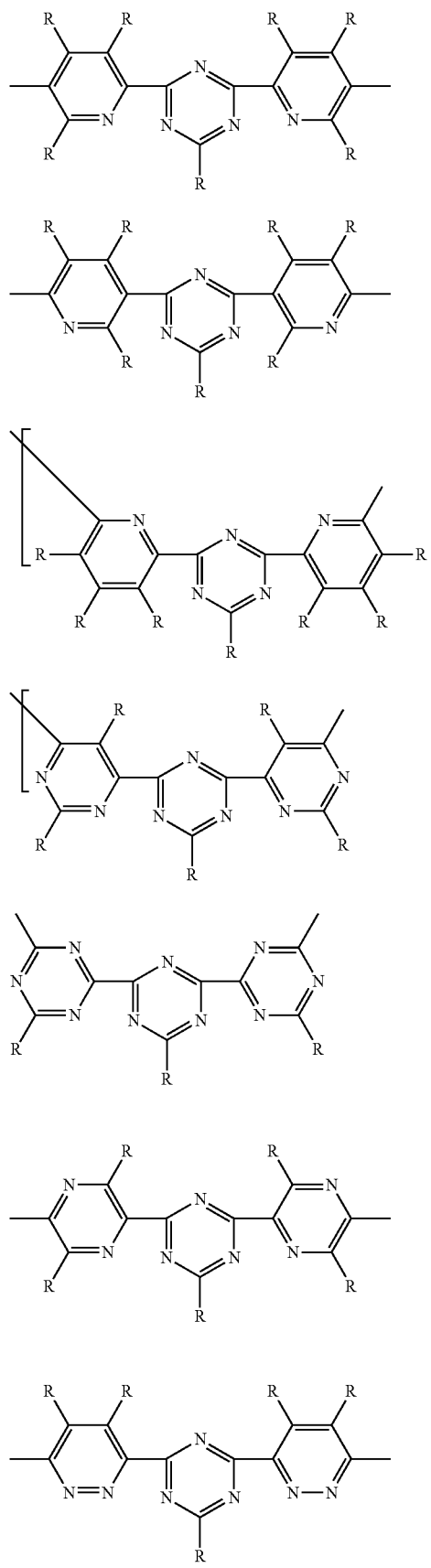
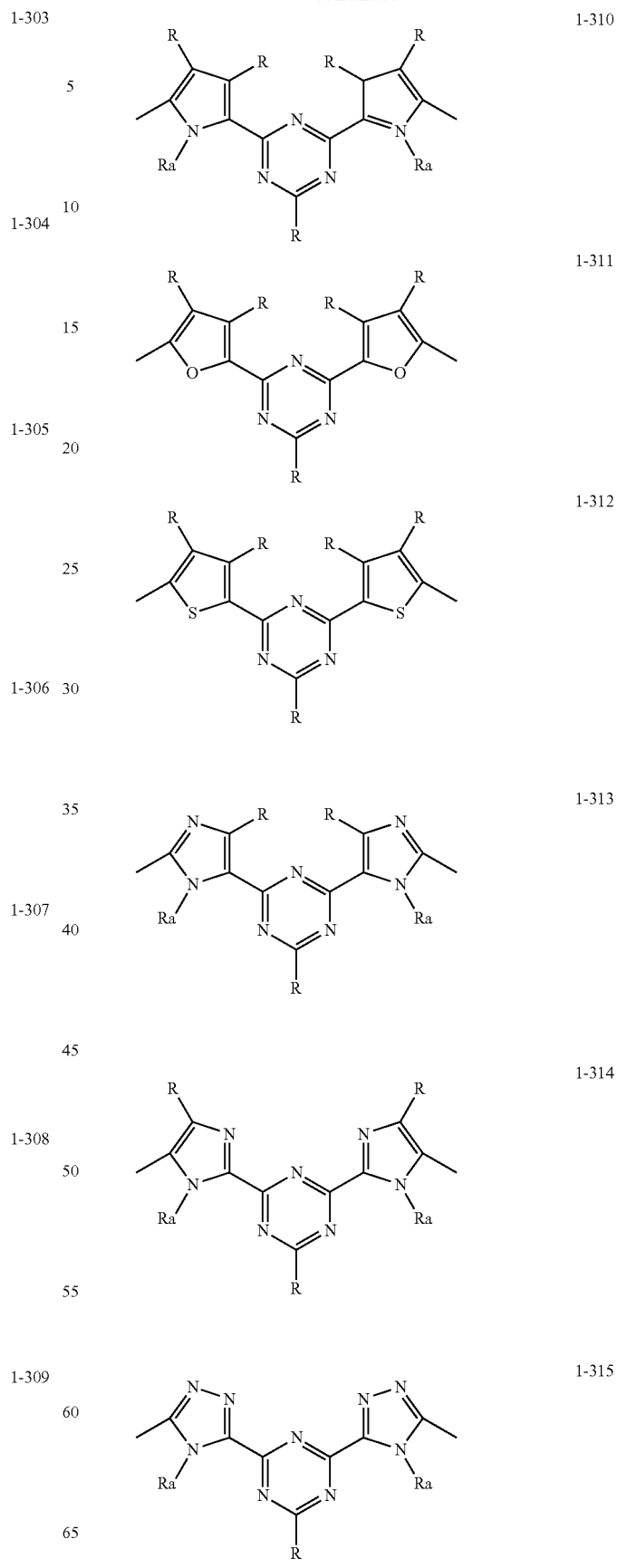

1-316 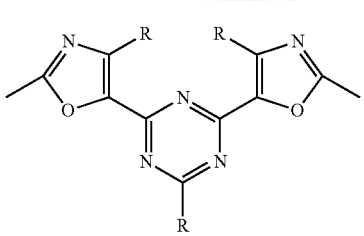

1-317 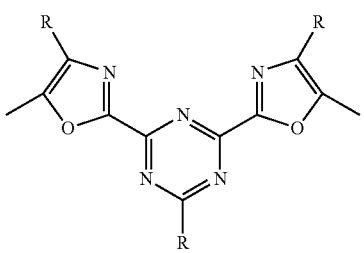

1-318 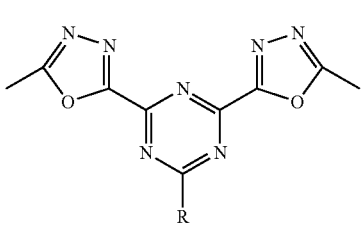

1-319 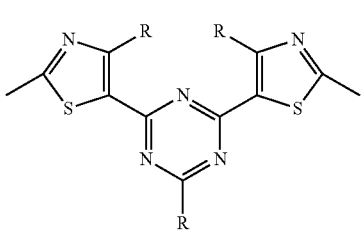

1-320 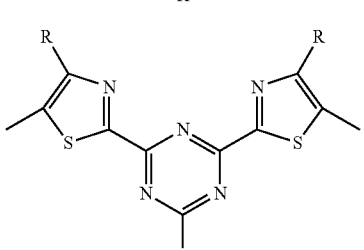

1-321 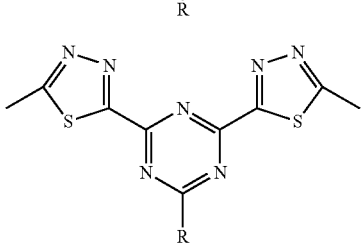

(wherein, R and Ra represent the same meaning as described above.)

The group represented by the formula (1) is more preferably a group represented by the formula (1B) described above.

$Y^{1b}$ in the formula (1B) is preferably —C(Ra)$_2$- or —[C(Ra)$_2$]$_2$- from the standpoint of solubility, and the group represented by the formula (IB) includes, for example, groups represented by the following formulae 1B-001 to 1B-022 and 1B-101 to 110, and groups represented by the formulae 1B-005 to 1B-018, 1B-022 and 1B-102 to 1B-110 are preferable, groups represented by the formulae 1B-005 to 1B-018 are more preferable since the luminance life of a light emitting device using the polymer compound of the present embodiment is more excellent.

1B-001
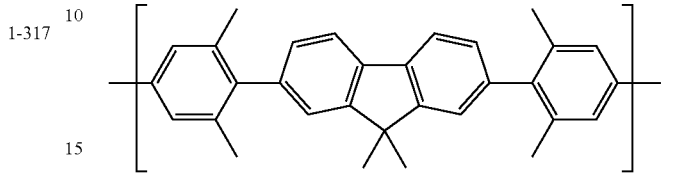

1B-002
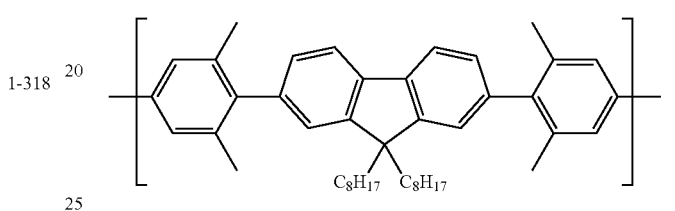

1B-003
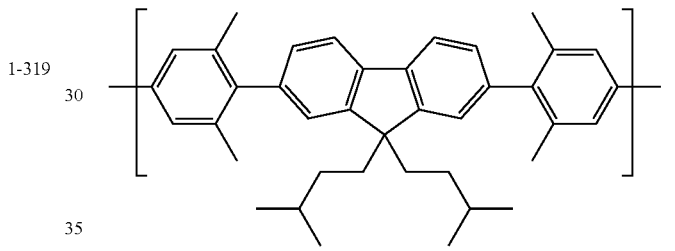

1B-004
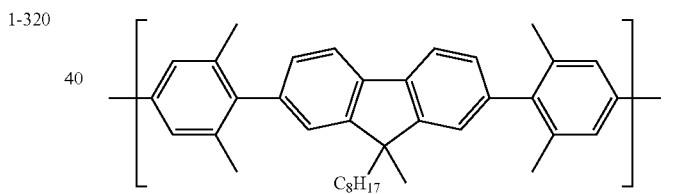

1B-005
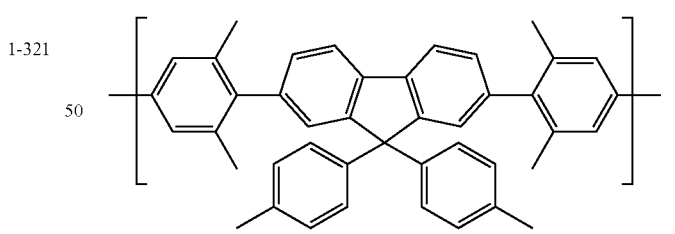

1B-006
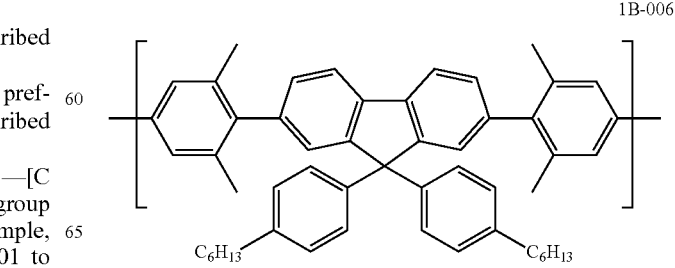

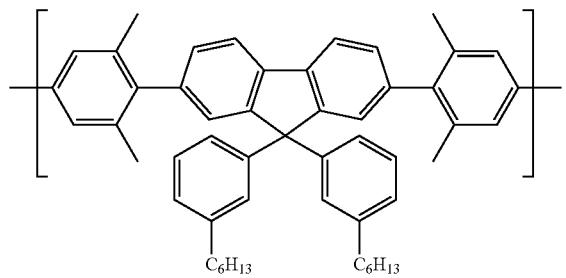
1B-007
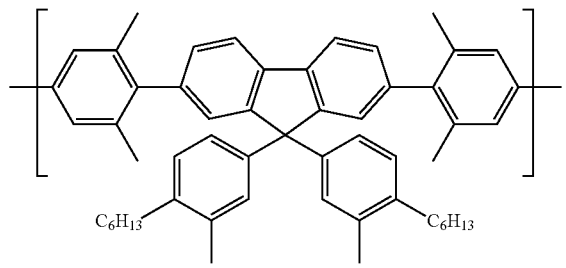
1B-008
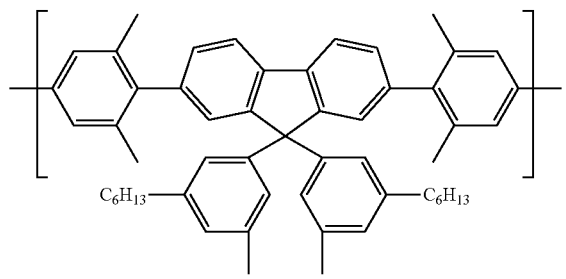
1B-009
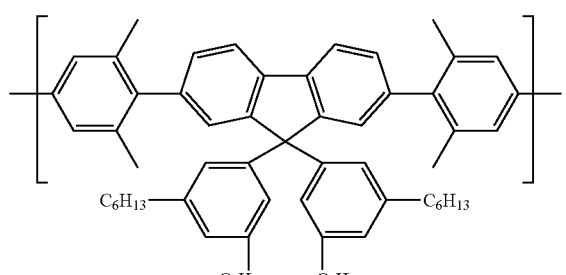
1B-010
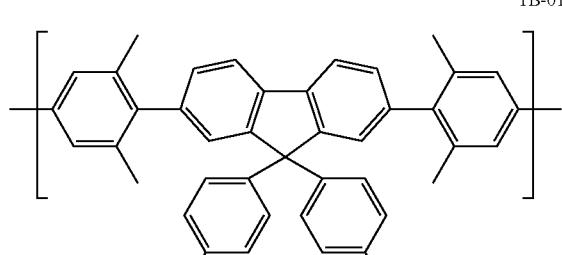
1B-011
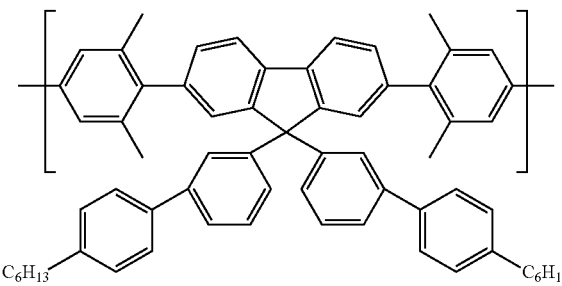
1B-012
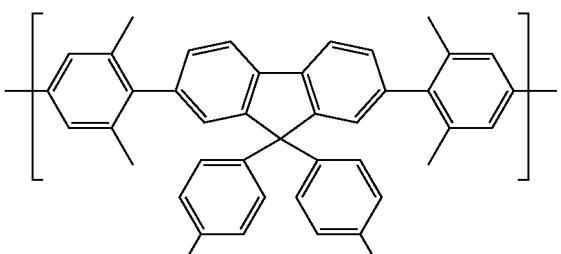
1B-013
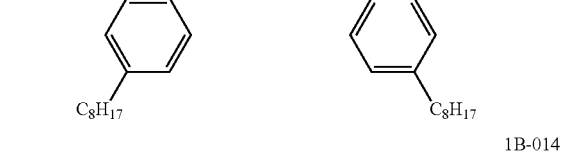
1B-014
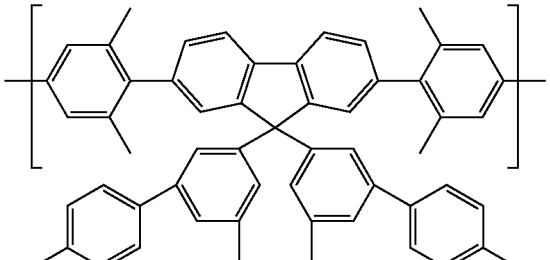
1B-015
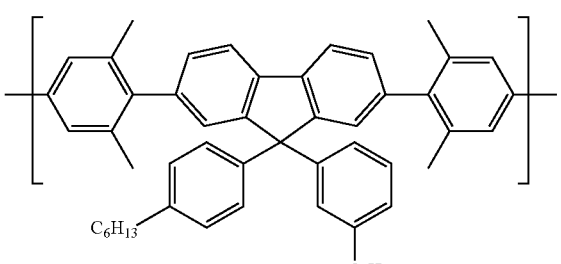
1B-016

-continued
1B-017
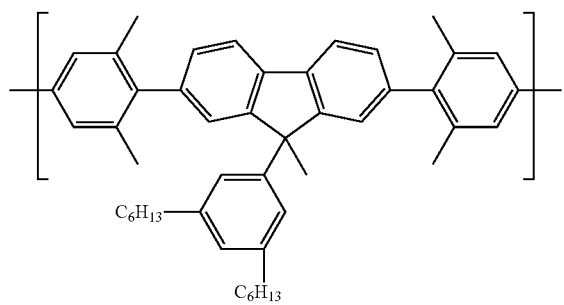
1B-018
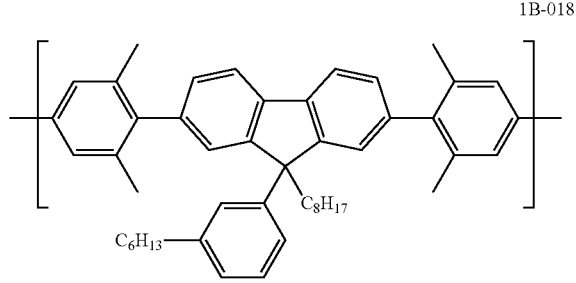
1B-019
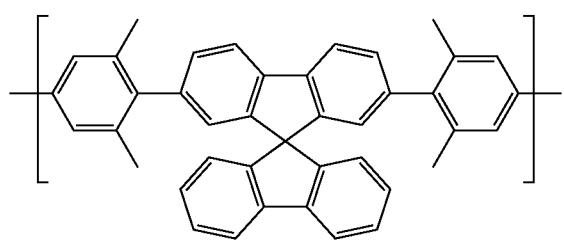
1B-020
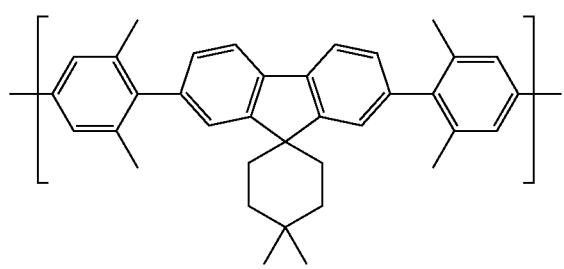
1B-021
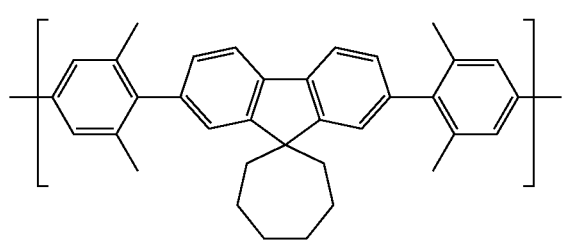
-continued
1B-022
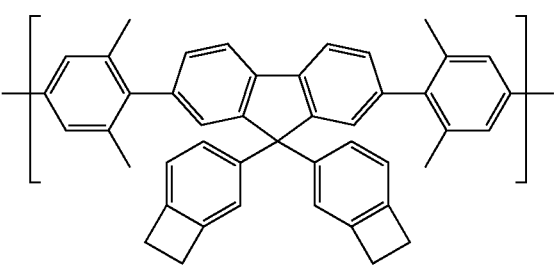
1B-101
1B-102
1B-103
1B-104
1B-105
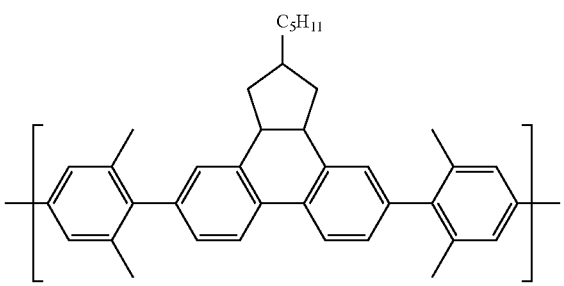

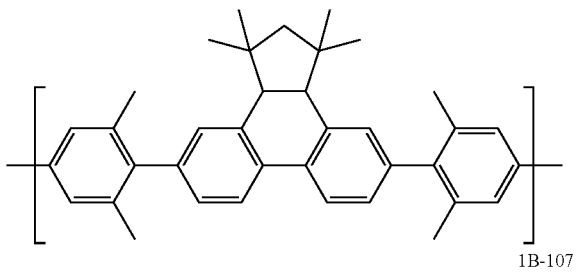

1B-106

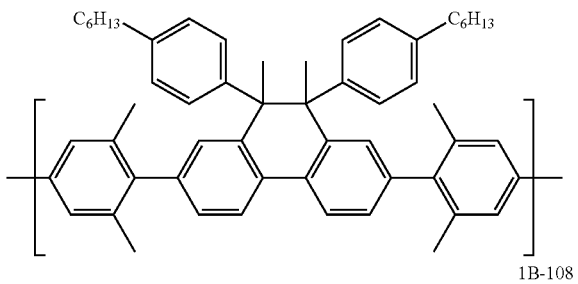

1B-107

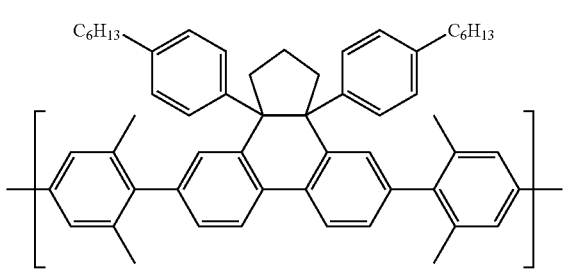

1B-108

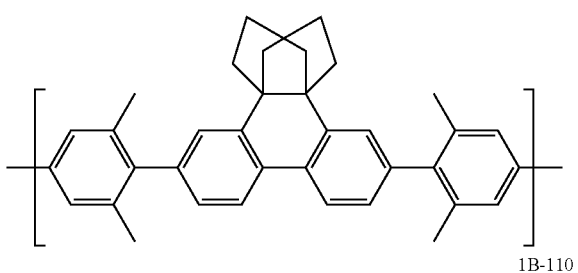

1B-109

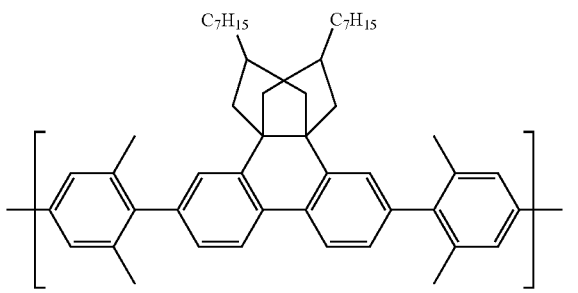

1B-110

(Group Represented by the Formula (2))

The group represented by the formula (2) can be contained as a repeating unit in the polymer compound of the present embodiment, and when there are plural methods for recognizing the group represented by the formula (2) in a polymer chain, a group in which the number of $Ar^2$ is least is recognized as the group represented by the formula (2).

In the group represented by the formula (2), at least one of carbon atoms adjacent to a carbon atom forming a bond to the other repeating unit has an alkyl group, an aryl group, a monovalent aromatic heterocyclic group or an aralkyl group as a substituent. By this, it becomes possible to enhance the $T_1$ energy level of the polymer compound of the present embodiment. Of these groups, an alkyl group is preferable since synthesis of raw material monomers of the polymer compound of the present embodiment is simpler.

The group represented by the formula (2) is preferably a group represented by the formula (2C) described above since the $T_1$ energy level of the polymer compound of the present embodiment is higher.

In the group represented by the formula (2C), at least one of carbon atoms adjacent to a carbon atom forming a bond to the other repeating unit is an arylene group having an alkyl group, an aryl group, a monovalent aromatic heterocyclic group or an aralkyl group as a substituent, or a divalent aromatic heterocyclic group.

By this, it becomes possible to further enhance the $T_1$ energy level of the polymer compound of the present embodiment. Of these substituents, an alkyl group or an aralkyl group is preferable since the heat resistance of the polymer compound of the present embodiment and the solubility thereof in an organic solvent are obtained with good balance. Further, an alkyl group is preferable since synthesis of raw material monomers of the polymer compound of the present embodiment is simpler.

The group represented by the formula (2C) is preferably a group represented by the formula (2D) described above since the $T_1$ energy level of the polymer compound of the present embodiment is still higher.

$R^{2c}$ in the formula (2D) represents preferably an alkyl group or an aralkyl group, more preferably an alkyl group, particularly preferably a methyl group, an ethyl group, a propyl group, an isopropyl group, a butyl group, a sec-butyl group, an isobutyl group, a pentyl group, an isoamyl group, a hexyl group, a cyclohexyl group, a heptyl group, a cyclohexylmethyl group, an octyl group, a 2-ethylhexyl group, a 2-cyclohexylethyl group, a nonyl group, a decyl group, a 3,7-dimethyloctyl group or a dodecyl group since the heat resistance of the polymer compound of the present embodiment and the solubility thereof in an organic solvent are obtained with good balance.

$R^{2d}$ in the formula (2D) represents preferably a hydrogen atom, an alkyl group or an aralkyl group, more preferably a hydrogen atom or an alkyl group, further preferably a hydrogen atom since the heat resistance of the polymer compound of the present embodiment and the solubility thereof in an organic solvent are obtained with good balance and reactivity in polymerizing raw material monomers of the polymer compound of the present embodiment is more excellent.

The group represented by the formula (2D) includes, for example, groups represented by the following formulae 2D-001 to 2D-019 and 2D-101 to 2D-105, and groups represented by the formulae 2D-003 to 2D-015 and 2D-018 to 2D-019 are preferable, groups represented by the formula 2D-005 to 2D-015 and 2D-019 are more preferable since the solubility of the polymer compound of the present embodiment in an organic solvent is more excellent.

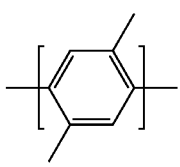

2D-001

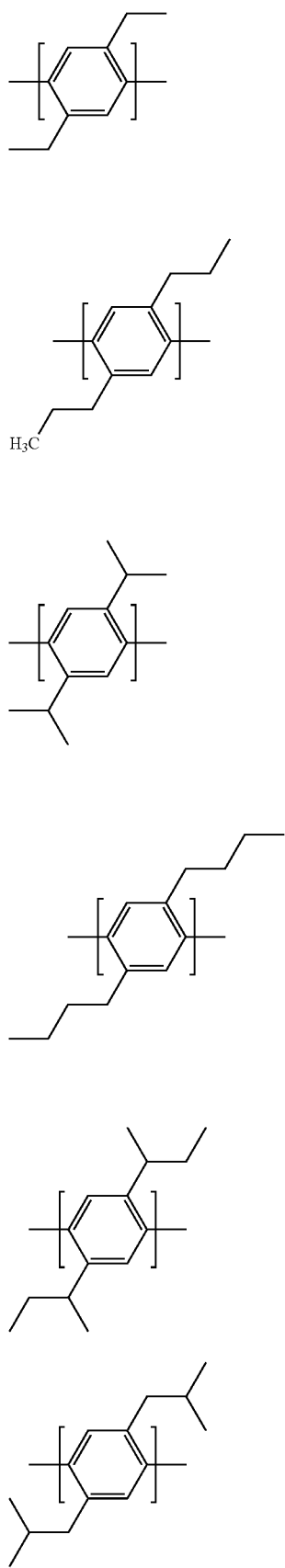

2D-013
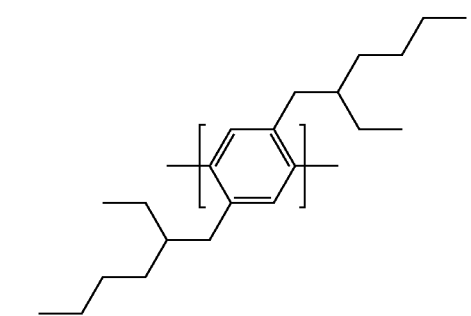
2D-014
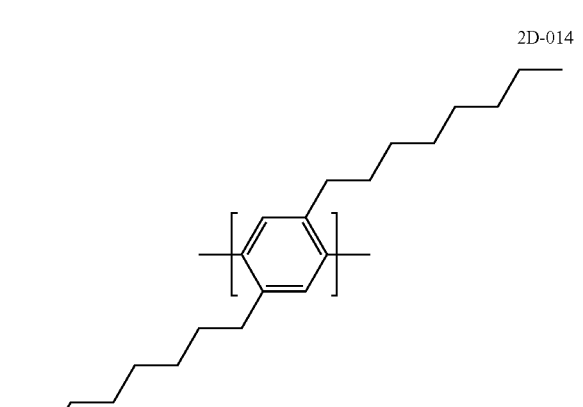
2D-015
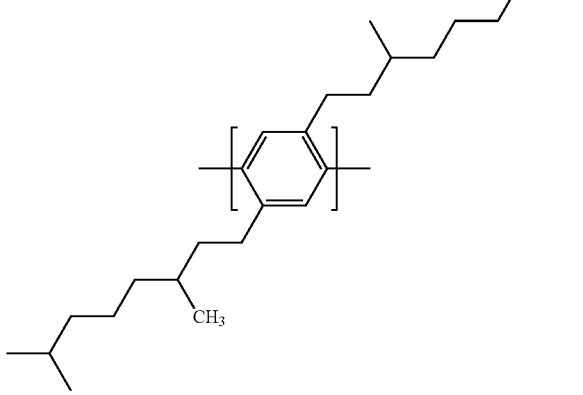
2D-016
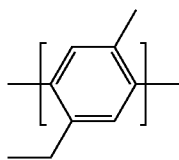
2D-017
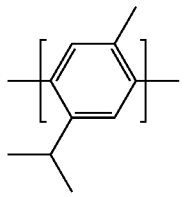
2D-018
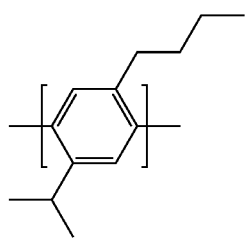
2D-019
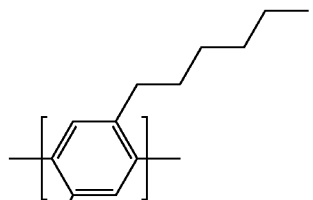
2D-101
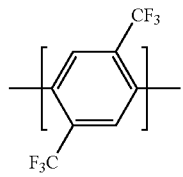
2D-102
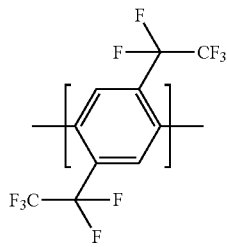
2D-103
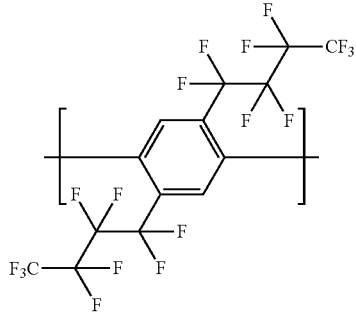

-continued

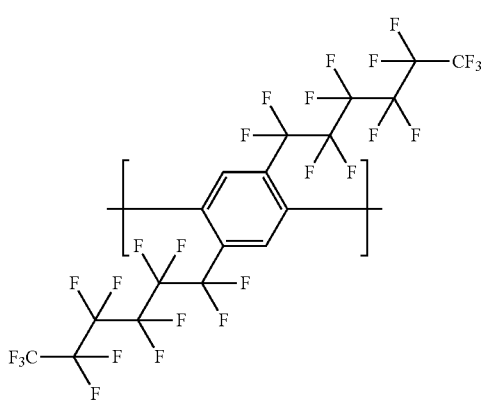

2D-104

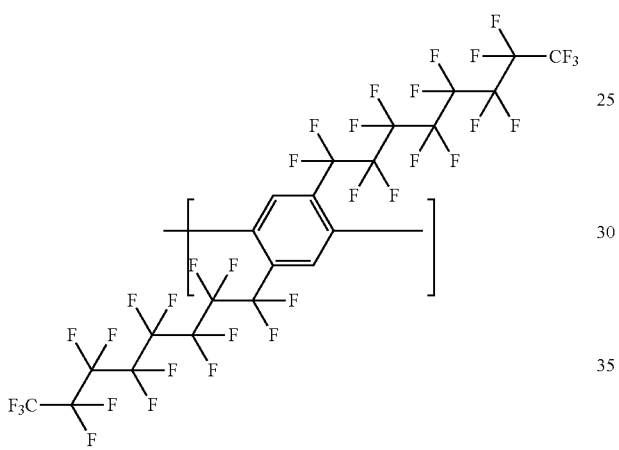

2D-105

The group represented by the formula (2) is preferably a group represented by the formula (2B) described above since the $T_1$ energy level of the polymer compound of the present embodiment rises and the light emission efficiency of a light emitting device using the polymer compound of the present embodiment is more excellent.

$Y^2$ in the formula (2B) is preferably a carbon atom or nitrogen atom which may be substituted with an alkyl group.

$Ar^2$ in the formula (2B) is preferably an aryl group or a monovalent aromatic heterocyclic group, more preferably an aryl group having an alkyl group as a substituent or a monovalent aromatic heterocyclic group having an alkyl group as a substituent, particularly preferably an aryl group having an alkyl group as a substituent since the light emission efficiency of a light emitting device using the polymer compound of the present embodiment is more excellent.

$R^{2a}$ in the formula (2B) is preferably an alkyl group or an aralkyl group, more preferably an alkyl group, further preferably a methyl group, an ethyl group, a propyl group, an isopropyl group, a butyl group, a sec-butyl group, an isobutyl group, a pentyl group, an isoamyl group, a hexyl group, a cyclohexyl group, a heptyl group, a cyclohexylmethyl group, an octyl group, a 2-ethylhexyl group, a 2-cyclohexylethyl group, a nonyl group, a decyl group, a 3,7-dimethyloctyl group or an dodecyl group since the heat resistance of the polymer compound of the present embodiment and the solubility thereof in an organic solvent are obtained with good balance.

$R^{2b}$ in the formula (2B) is preferably a hydrogen atom, an alkyl group or an aralkyl group, more preferably a hydrogen atom or an alkyl group, further preferably a hydrogen atom since the heat resistance of the polymer compound of the present embodiment and the solubility thereof in an organic solvent are obtained with good balance and reactivity in polymerizing raw material monomers of the polymer compound of the present embodiment is more excellent.

The group represented by the formula (2B) includes, for example, groups represented by the following formulae 2B-001 to 2B-012, 2B-101 to 2B-103, 2B-201 to 2B-203, 2B-301 to 2B-303 and 2B-401 to 2B-403, and groups represented by the formulae 2B-001 to 2B-012 are preferable since the driving voltage of a light emitting device using the polymer compound of the present embodiment decreases more.

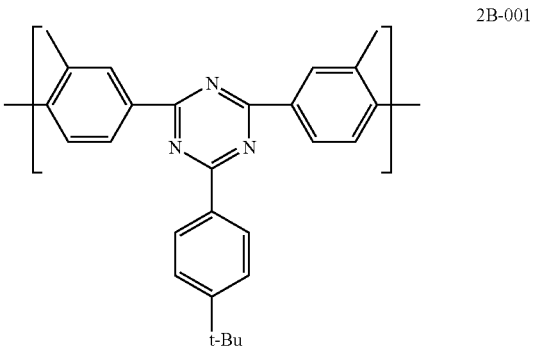

2B-001

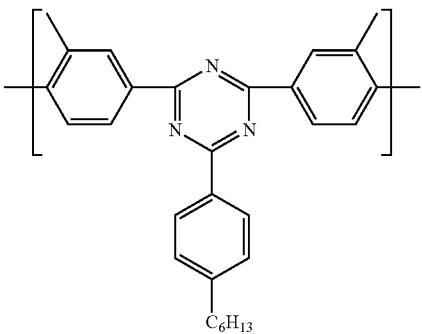

2B-002

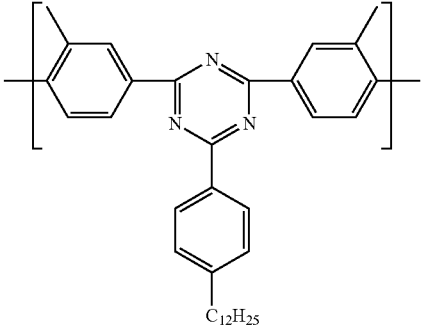

2B-003

2B-004
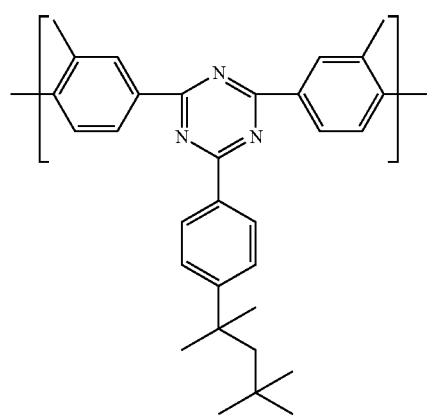
2B-005
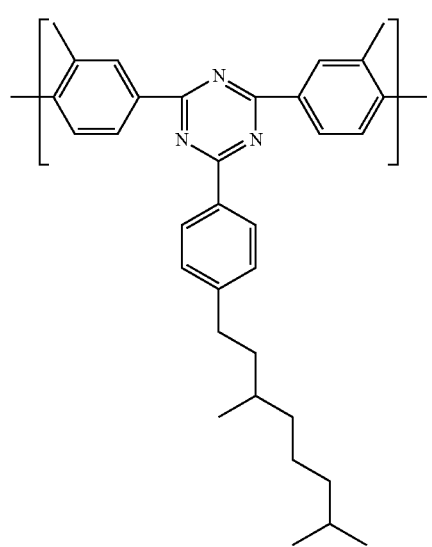
2B-006
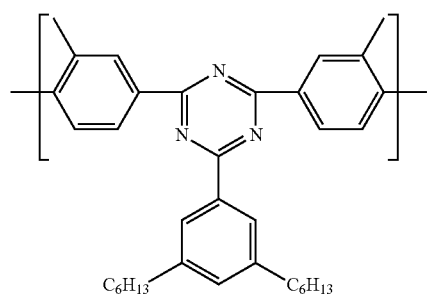
2B-007
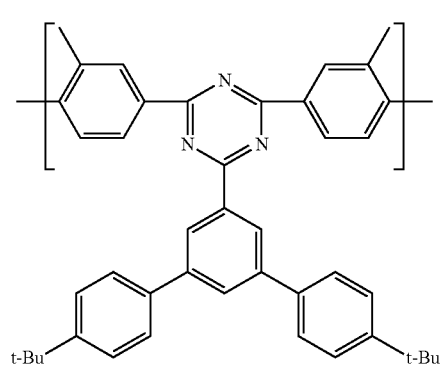
2B-008
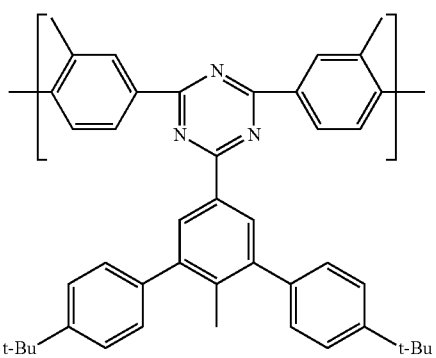
2B-009
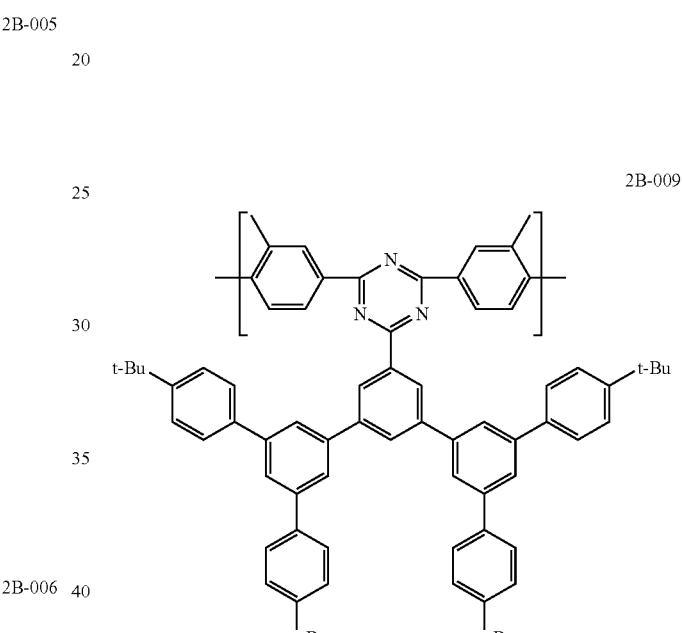
2B-010
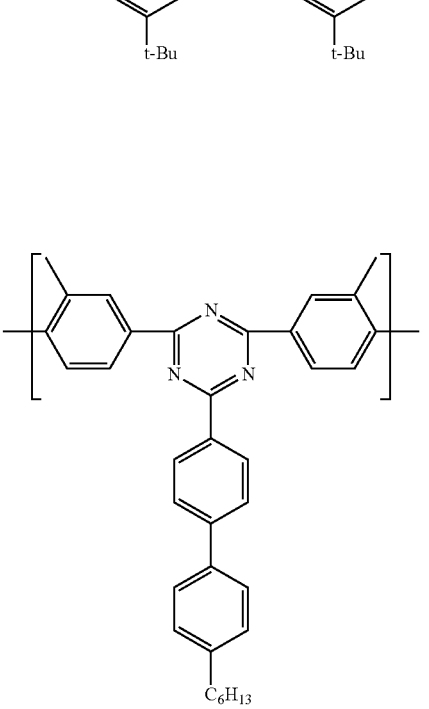

-continued
2B-011
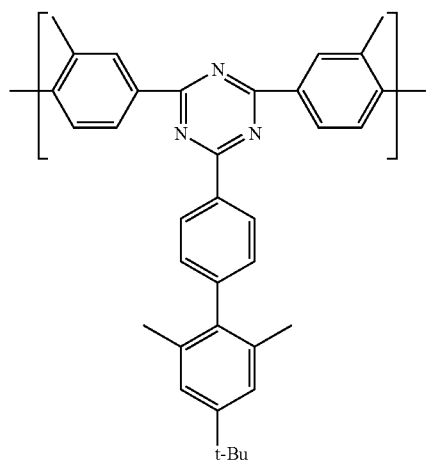
2B-012
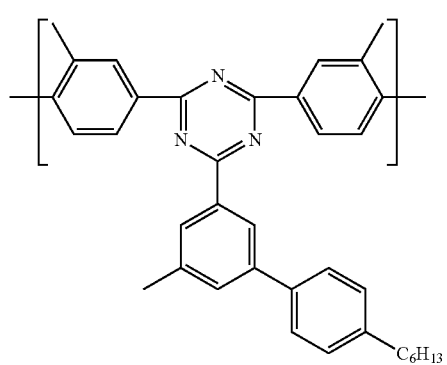
2B-101
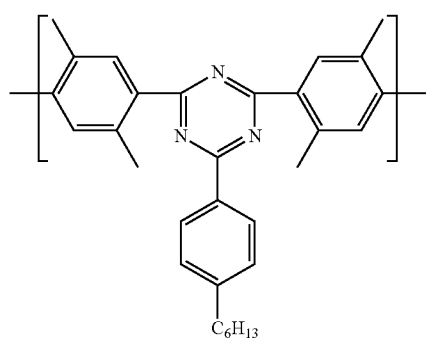
2B-102
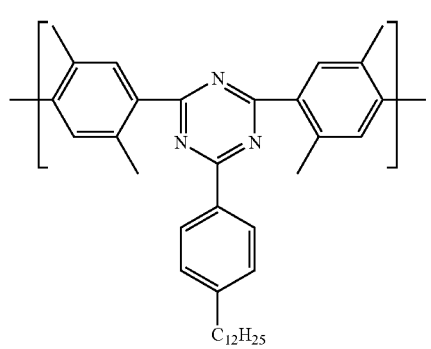
-continued
2B-103
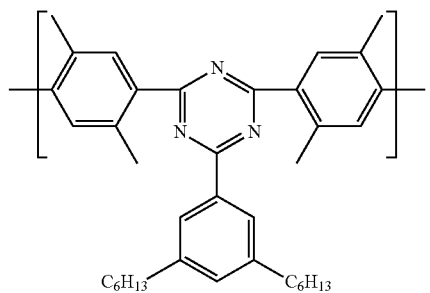
2B-201
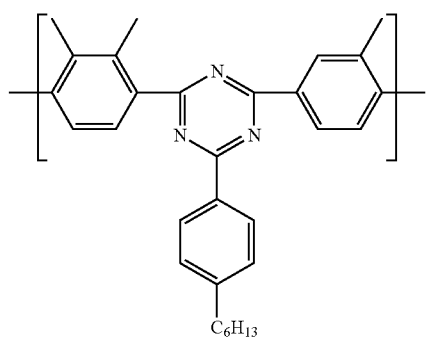
2B-202
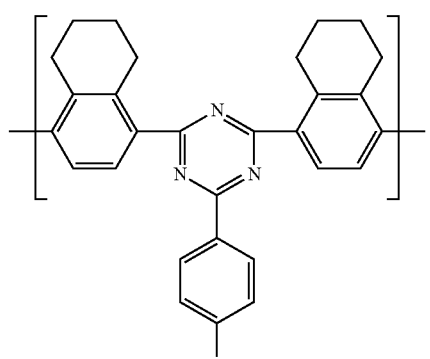
2B-203
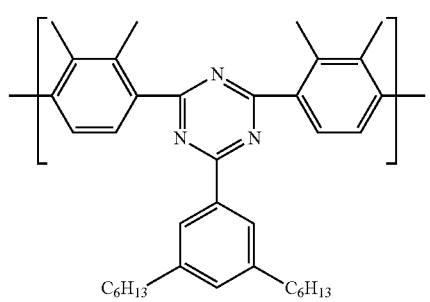
2B-301
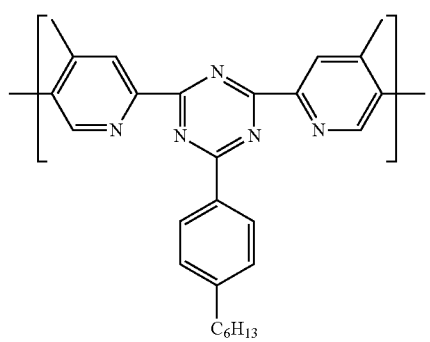

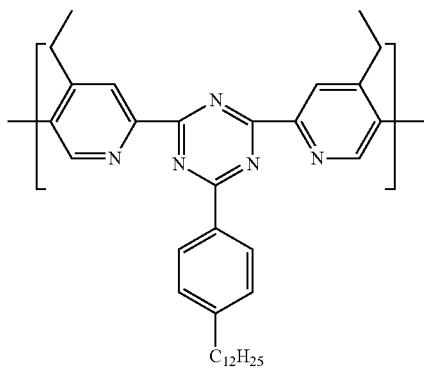

2B-302

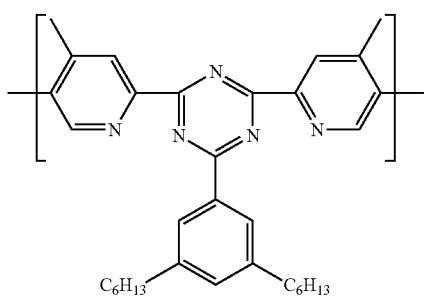

2B-303

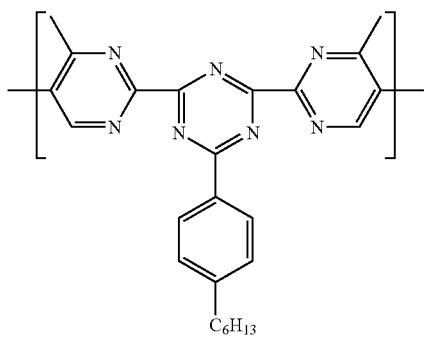

2B-401

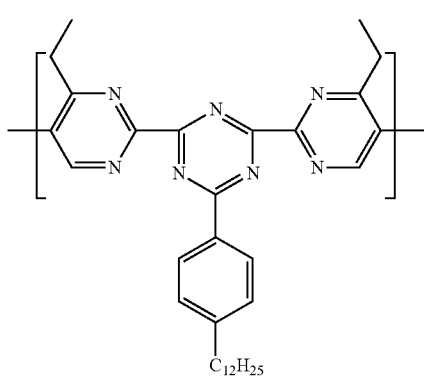

2B-402

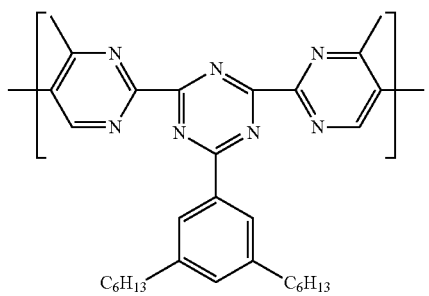

2B-403

(Group Represented by the Formula (3))

The group represented by the formula (3) can be contained in the polymer compound of the present embodiment as a repeating unit, and when there are plural methods for recognizing the group represented by the formula (3) in a polymer chain, a group in which the number of $Ar^3$ is least is recognized as the group represented by the formula (3).

The group represented by the formula (3) is a group different from the group represented by the formula (11) and the group represented by the formula (2). By this, synthesis of the polymer compound of the present embodiment becomes simpler and the driving voltage of a light emitting device using the polymer compound of the present embodiment decreases more.

The group represented by the formula (3) is preferably a group represented by the formula (3B) described above since the driving voltage of a light emitting device using the polymer compound of the present embodiment decreases more.

$Y^3$ in the formula (3B) is preferably a carbon atom or nitrogen atom which may be substituted with an alkyl group.

$Ar^3$ in the formula (3B) is preferably an aryl group or a monovalent aromatic heterocyclic group, more preferably an aryl group having an alkyl group as a substituent or a monovalent aromatic heterocyclic group having an alkyl group as a substituent, particularly preferably an aryl group having an alkyl group as a substituent since the light emission efficiency of a light emitting device using the polymer compound of the present embodiment is more excellent.

The constitutional unit represented by the formula (3B) includes, for example, groups represented by the following formulae 3B-001 to 3B-012, 3B-301 to 3B-303 and the formulae 3B-401 to 3B-403, and groups represented by the formulae 3B-001 to 3B-012 are preferable since the luminance life of a light emitting device using the polymer compound of the present embodiment is more excellent.

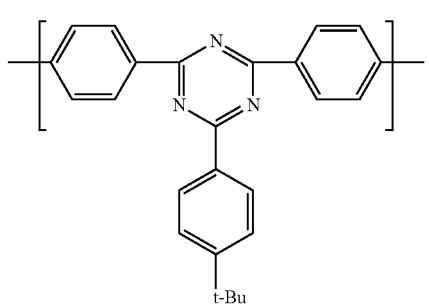

3B-001

-continued
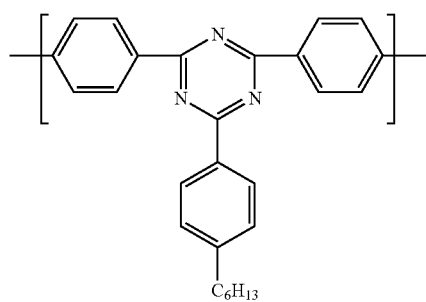
3B-002
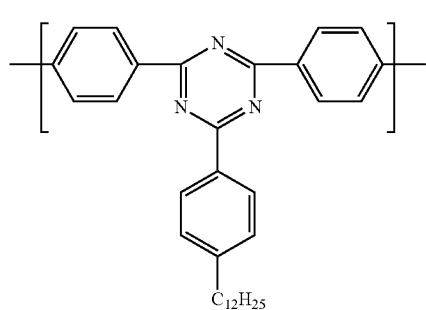
3B-003
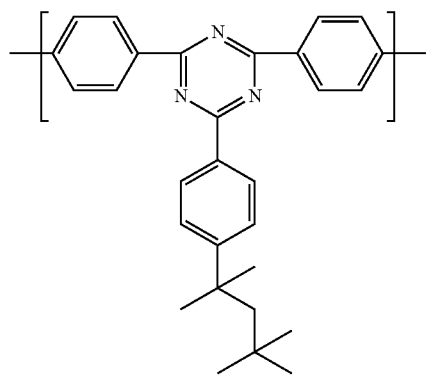
3B-004
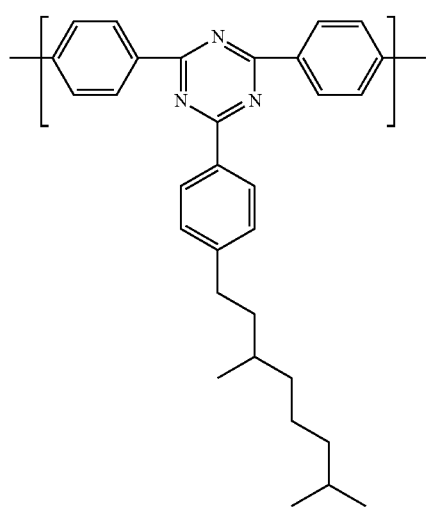
3B-005
-continued
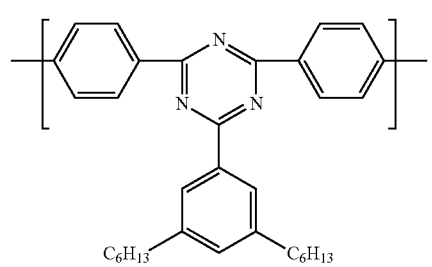
3B-006
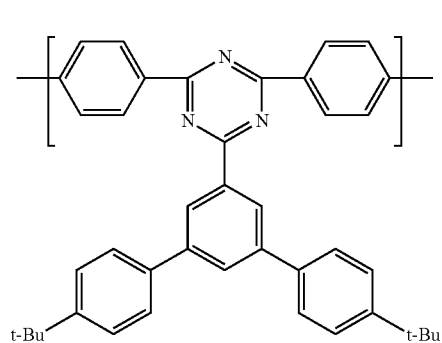
3B-007
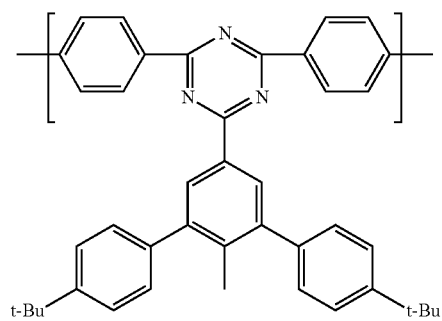
3B-008
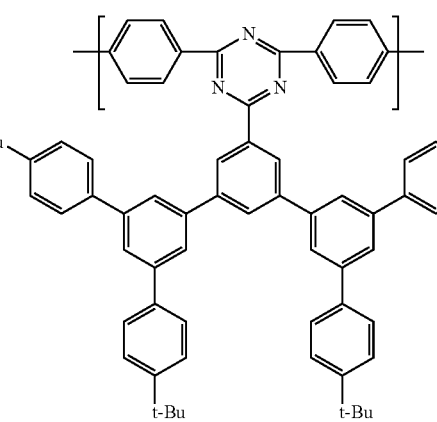
3B-009

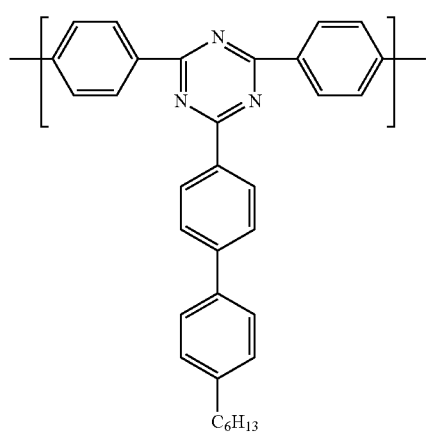
3B-010
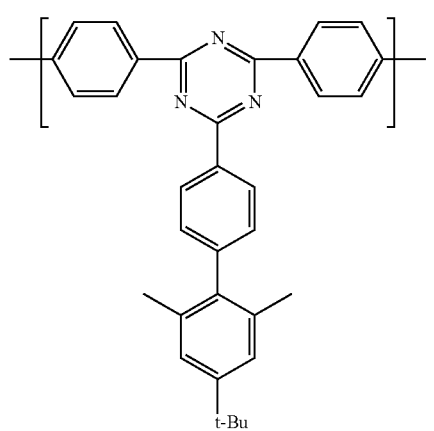
3B-011
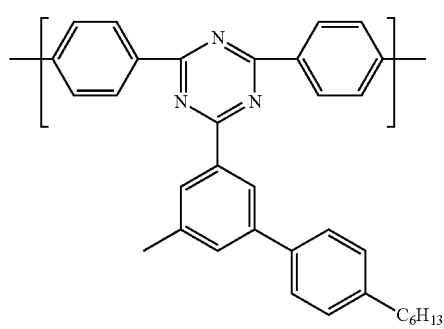
3B-012
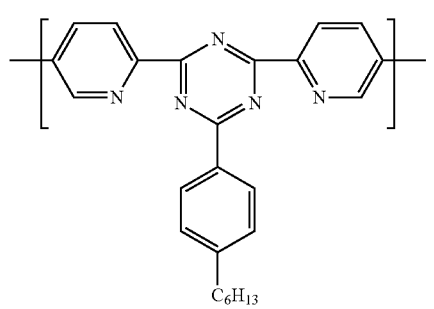
3B-301
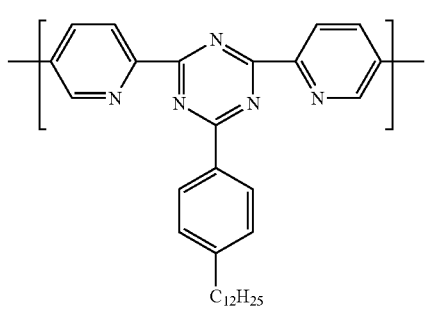
3B-302
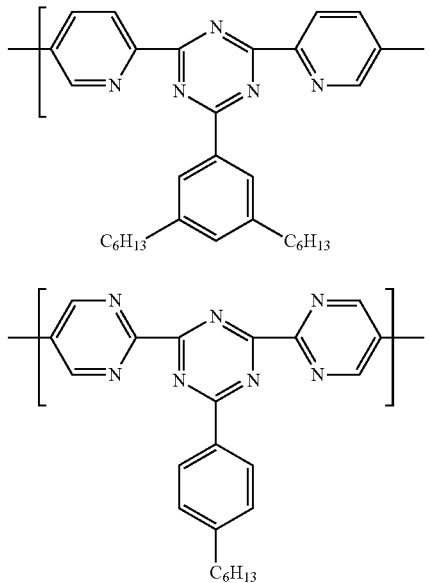
3B-303
3B-401
3B-402
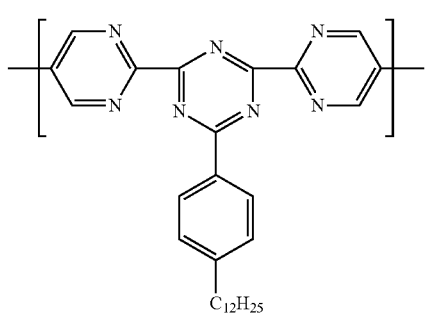
3B-403
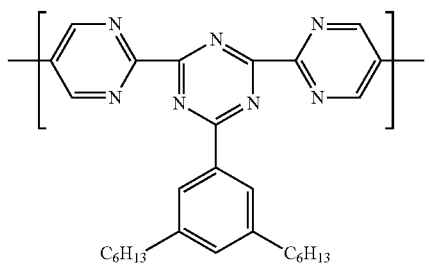
The group represented by the formula (3B) is preferably a group represented by the formula (3C) described above since the $T_1$ energy level of the polymer compound of the present embodiment rises more.

$R^3$ in the formula (3C) is preferably an alkyl group, more preferably a methyl group since synthesis of raw material monomers of the polymer compound of the present embodiment becomes simpler.

$Y^3$ in the formula (3C) is preferably a carbon atom or nitrogen atom which may be substituted with an alkyl group, more preferably a carbon atom or nitrogen atom.

The group represented by the formula (3C) includes, for example, groups represented by the following formulae 3C-001 to 3C-012 and the formulae 3C-301 to 3C-303, and groups represented by the formulae 3C-001 to 3C-012 are preferable since the luminance life of a light emitting device using the polymer compound of the present embodiment is more excellent.

3C-001

3C-002

3C-003

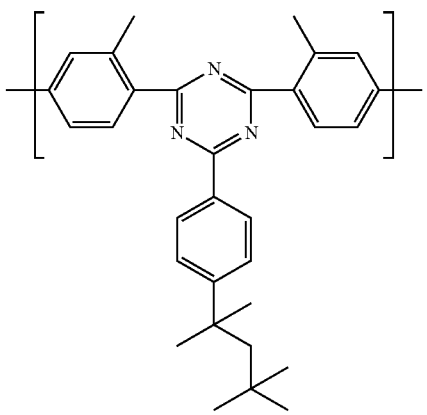

3C-004

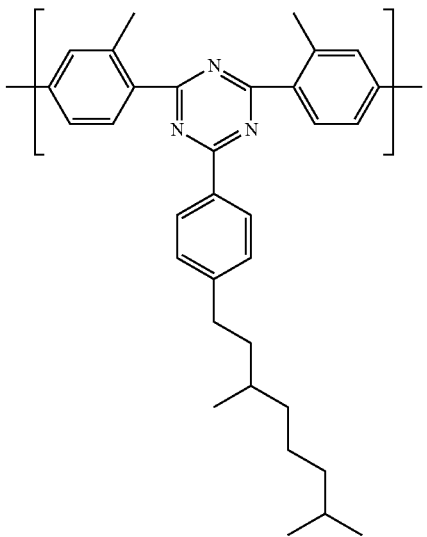

3C-005

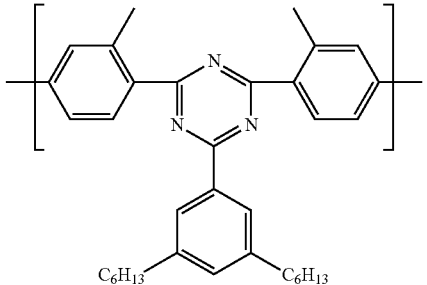

3C-006

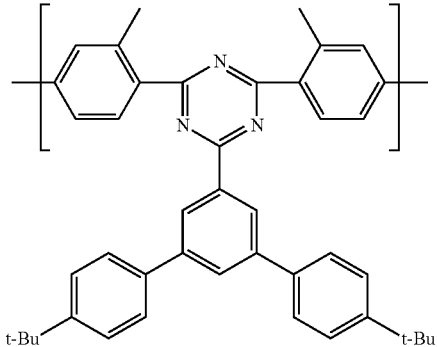

3C-007

3C-008
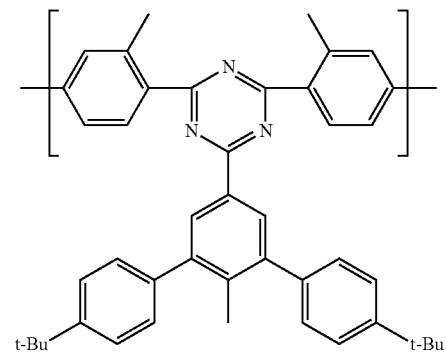
3C-009
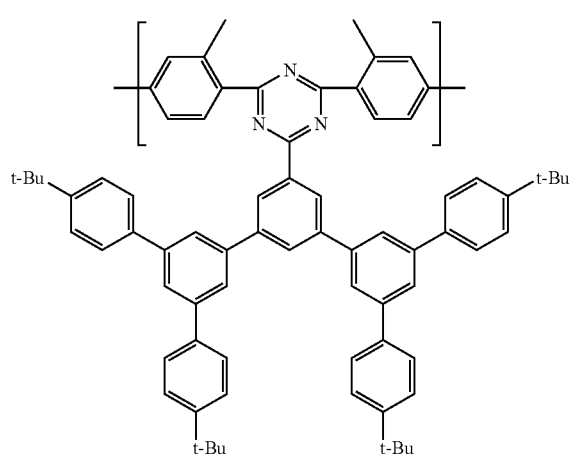
3C-010
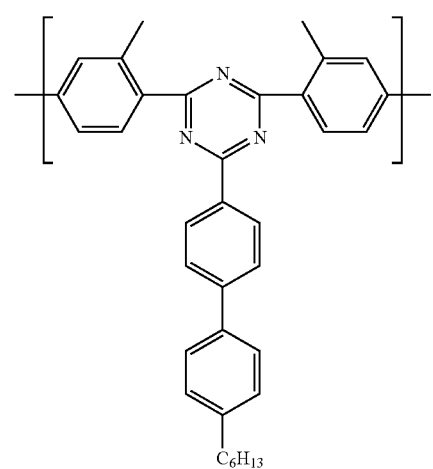
3C-011
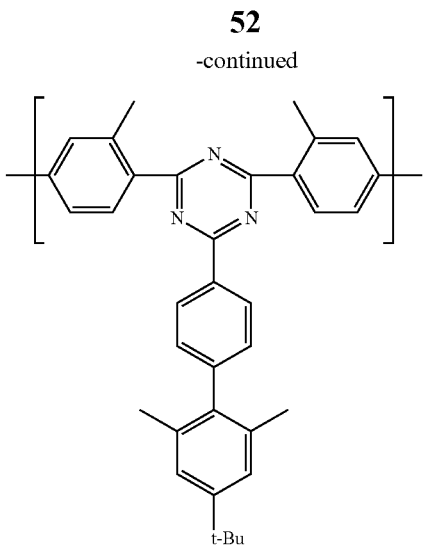
3C-012
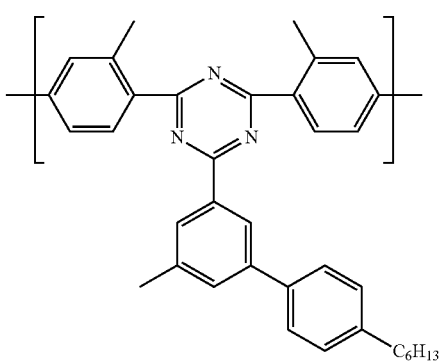
3C-301
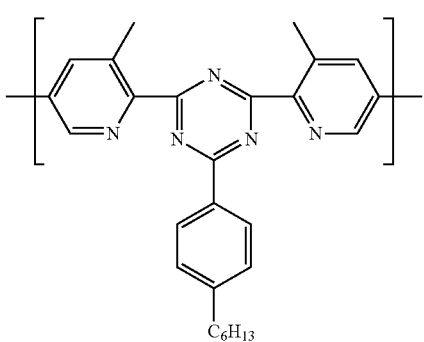
3C-302
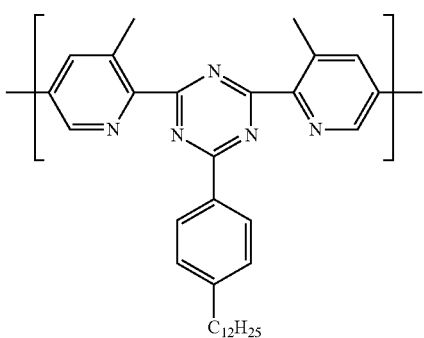

-continued

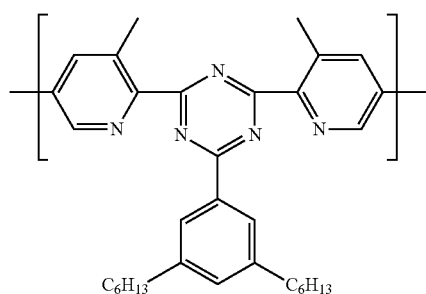

3C-303

The group represented by the formula (3) is preferably a divalent aromatic amine residue represented by the formula (5) described above since the driving voltage of a light emitting device using the polymer compound of the present embodiment decreases more. The polymer compound of the present embodiment in which the group represented by the formula (3) is a divalent aromatic amine residue represented by the formula (5) is particularly useful as a hole transporting material showing high $T_1$ energy level.

$Ar^{5a}$, $Ar^{5b}$, $Ar^{5c}$, $Ar^{5d}$ and $Ar^{5h}$ in the formula (5) represent preferably an arylene group, more preferably a 1,4-phenylene group (the formula 001) or a fluorene-2,7-diyl group (the formula 009), further preferably a 1,4-phenylene group (the formula 001).

$Ar^{5e}$, $Ar^{5f}$ and $Ar^{5g}$ in the formula (5) represent preferably an aryl group, more preferably a phenyl group substituted with an alkyl group. $R^A$ in the formula (5) is preferably an alkyl group.

The group represented by the formula (5) includes, for example, groups represented by the following formulae 5-001 to 5-006.

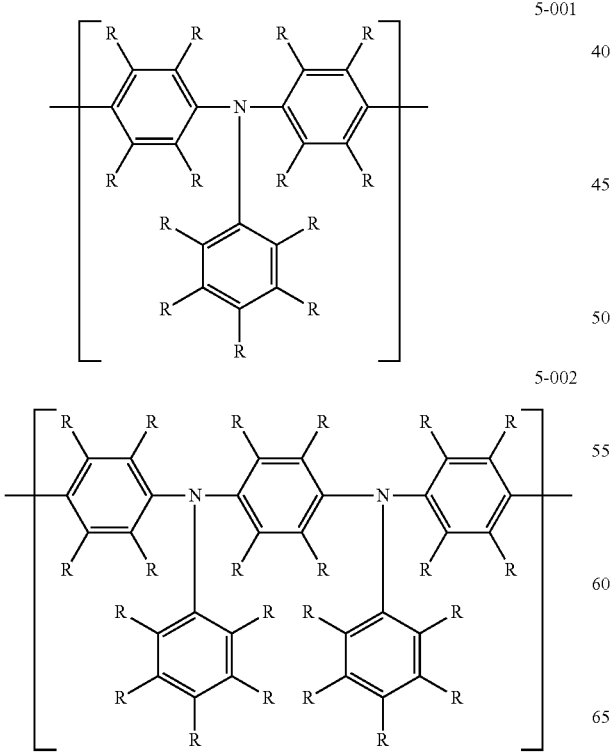

5-001

5-002

-continued

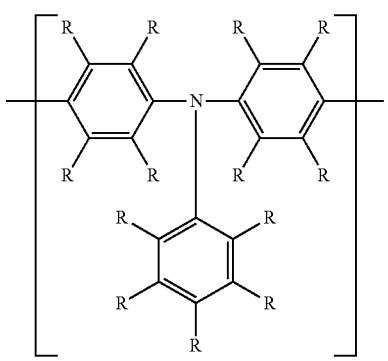

5-003

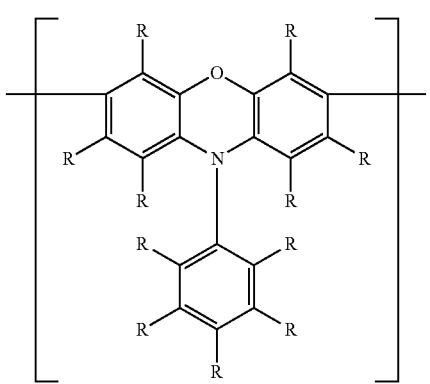

5-004

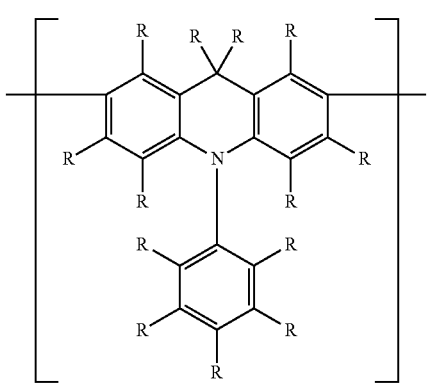

5-005

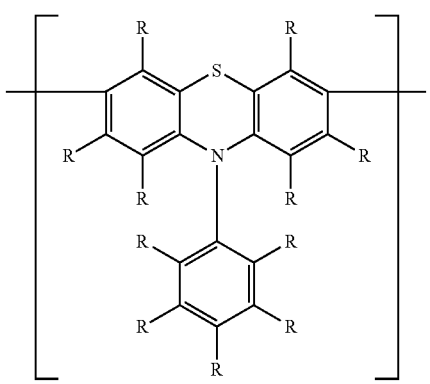

5-006

(wherein, R represents the same meaning as described above, and a hydrogen atom, an alkyl group or an aryl group is preferable.)

(Tg and Solubility of Polymer Compound)

The glass transition temperature (hereinafter, referred to as "Tg" in some cases) of the polymer compound of the present invention is preferably 60° C. or higher, more preferably 80° C. or higher, particularly preferably 100° C. or higher, since when the polymer compound of the present invention is used in production of a light emitting device, more stable shape of an organic film can be obtained, the preservation temperature range of the resultant light emitting device can be enlarged and the stability such as luminance life or the like of the resultant light emitting device can be improved. When the polymer compound of the present invention is used in the form of a composition with a phosphorescent compound described later, a metal complex as the phosphorescent compound has usually high glass transition temperature (Tg), thus, the glass transition temperature of the composition of the present embodiment is higher than the glass transition temperature of a single body of the polymer compound of the present invention.

For adjusting the glass transition temperature of the polymer compound of the present invention within the above-described preferable range, it is preferable to introduce a suitable substituent into a repeating unit contained in the polymer compound. The substituent is preferably an alkyl group.

Since a solution coating method is usually used when the polymer compound of the present invention is used for production of a light emitting device, if it is used together with a phosphorescent compound described later, it is preferable that the polymer compound manifests solubility in a solvent which is capable of dissolving the phosphorescent compound.

For allowing the polymer compound of the present invention to have suitable solubility, it is preferable to introduce a suitable substituent into a repeating unit contained in the polymer compound. The substituent is preferably an alkyl group.

(Structure of Polymer Compound)

The preferable structure of the polymer compound of the present invention will be illustrated below.

The polymer compound of the present invention in which a group obtained by mutually directly bonding one or more groups selected from the group consisting of the above-described arylene group, divalent aromatic heterocyclic group and divalent aromatic amine residue is contained as a repeating unit in the polymer chain is preferable since the luminance life of a light emitting device using a composition with a phosphorescent compound described later is more excellent.

In the polymer compound of the present embodiment, the content of a group represented by the formula (11) (may also be a group represented by the formula (1)) is preferably 20 mol % or more, more preferably 25 mol % or more, further preferably 30 mol % or more, with respect to the total content of repeating units contained in the polymer compound since the device life of a light emitting device using a composition with a phosphorescent compound described later is more excellent.

When the polymer compound of the present embodiment contains the above-described divalent aromatic amine residue as a repeating unit, its content is preferably 1 mol % or more and 50 mol % or less, more preferably 3 mol % or more and 30 mol % or less, further preferably 5 mol % or more and 20 mol % or less with respect to the total content of repeating units contained in the polymer compound since the current efficiency of alight emitting device using a composition with a phosphorescent compound described later is more excellent.

When the polymer compound of the present embodiment contains groups represented by the formula (3) as a repeating unit, it is preferable that the content of groups represented by the formula (3) is 50 mol % or less with respect to the total content of repeating units contained in the polymer compound and the groups represented by the formula (3) are not mutually substantially adjacent since the current efficiency of a light emitting device using a composition with a phosphorescent compound described later is more excellent. The reason for this is that the $T_1$ energy level of the polymer compound of the present embodiment tends to lower by mutually linking groups represented by the formula (3).

The term "not substantially adjacent" described above means that the proportion of mutual linkage of groups represented by the formula (3) with respect to linkage of all repeating units contained in the polymer compound is 10% or less, and the proportion is preferably 5% or less, more preferably 1% or less, further preferably 0%.

When the polymer compound of the present embodiment contains a group represented by the formula (2) as a repeating unit or when the polymer compound of the present embodiment contains a group represented by the formula (2) and a group represented by the formula (3) as a repeating unit, it is preferable that the content of a group represented by the formula (2) is 50 mol % or more with respect to the total content of repeating units contained in the polymer compound and groups represented by the formula (11), and a group represented by the formula (11) and a group represented by the formula (3) are not substantially adjacent (in other words, groups represented by the formula (11) are not mutually substantially adjacent, and a group represented by the formula (11) and a group represented by the formula (3) are not substantially adjacent), since the $T_1$ energy level of the polymer compound of the present embodiment is enhanced more and the driving voltage of a light emitting device using a composition with a phosphorescent compound described later is more excellent. The reason for this is that a chain constitution of mutual linkage of a group represented by the formula (11) and a group represented by the formula (2) provides a higher effect of reducing the driving voltage of a light emitting device using the polymer compound as compared with a chain constitution of mutual linkage of groups represented by the formula (11), and a chain constitution of mutual linkage of a group represented by the formula (11) and a group represented by the formula (2) provides a larger effect of enhancing the $T_1$ energy level of the polymer compound as compared with a chain constitution of mutual linkage of a group represented by the formula (11) and a group represented by the formula (3). Therefore, the polymer compound of the present embodiment preferably contains a chain constitution in which a group represented by the formula (2) is linked to both sides of a group represented by the formula (11).

This "not substantially adjacent" represents the same meaning as the above-described "no substantially adjacent".

It is preferable, from the above-described standpoint, that the polymer compound of the present embodiment is a polymer compound obtained by polymerization using as a raw material monomer a compound having a group obtained by mutually linking several specific groups, the polymer compound having this group as a repeating unit.

The polymer compound of the present embodiment may be any of a block copolymer, a random copolymer, an alternate copolymer and a graft copolymer, or may also be another embodiment, and it is preferable, from the above-described standpoint, that the polymer compound of the present embodiment is a copolymer obtained by copolymerizing several kinds of raw material monomers.

[Production Method of Polymer Compound]

The polymer compound of the present invention can be produced by a reaction of raw material monomers for introducing repeating units constituting the polymer compound and other constitutional units, and the polymer compound is preferably produced by reacting the raw material monomers so as to obtain the chain constitution of the polymer compound as described above. As the raw material monomer, use is made of a monomer having a structure in which two connecting bonds of each repeating unit or each constitutional unit linking to a polymer chain are replaced by a leaving group (hereinafter, referred to also as "polymerization active group") capable of forming a linkage by a polymerization reaction. The polymerization reaction can be conducted, for example, by copolymerizing raw material monomers by applying known polymerization methods such as cross coupling and the like.

For introducing a repeating unit represented by the formula (11), it is preferable to use a compound represented by the formula (M11) described above as a monomer.

For introducing a repeating unit represented by the formula (1), it is preferable to use a compound represented by the following formula (M1) as a monomer.

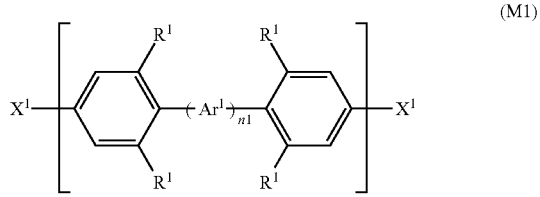

(M1)

[in the formula (M1), n1, Ar$^1$, R$^1$ and X$^1$ represent the same meaning as described above.]

The method of producing a compound represented by the formula (M11) will be illustrated below referring to a production method of a compound represented by the formula (M1) as an example. The compound represented by the formula (M1) can be produced, for example, by a method described in the following scheme 1 or scheme 2.

Scheme 1

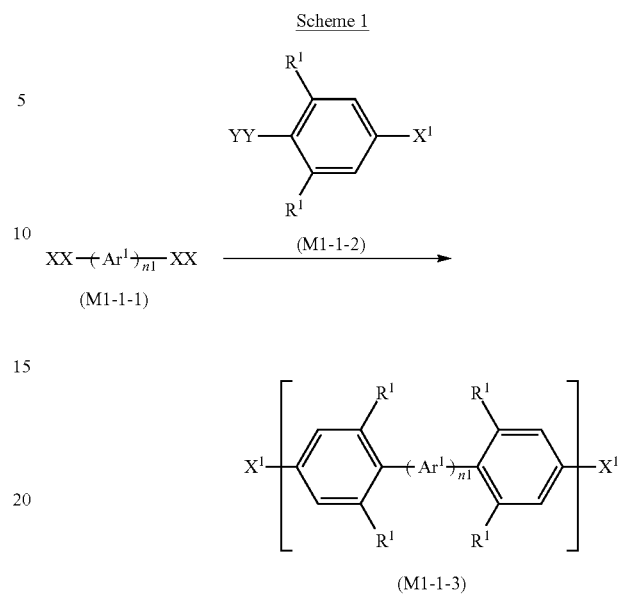

In the scheme 1,

XX and YY represent each independently a group selected from the above-described substituent group (a) or a group selected from the above-described substituent group (b). When the group represented by XX is a group selected from the substituent group (a), the group represented by YY is preferably a group selected from the substituent group (b), and when the group represented by XX is a group selected from the substituent group (b), the group represented by YY is preferably a group selected from the substituent group (a).

Ar$^1$, n1, R$^1$ and X$^1$ represent the same meaning as described above.

In the scheme 1, first, a compound represented by the formula (M1-1-1) and a compound represented by the formula (M1-1-2) are subjected to a cross coupling reaction such as the Suzuki coupling reaction, the Grignard reaction, the Stille coupling reaction and the like, to obtain a compound represented by the formula (M1-1-3). The compound represented by the formula (M1-1-3) is a compound represented by the formula (M1).

For obtaining a compound represented by the formula (M1-1-3) in good yield according to the scheme 1, when both XX and X$^1$ are a group selected from the substituent group (a) or when both XX and X$^1$ are a group selected from the substituent group (b), it is preferable that XX and X$^1$ are mutually different groups, when both YY and X$^1$ are a group selected from the substituent group (a) or when both YY and X$^1$ are a group selected from the substituent group (b), it is more preferable that YY and X$^1$ are mutually different groups, and when X$^1$ is a bromine atom, it is further preferable that XX is an iodine atom and Y is —B(OR$^{21}$)$_2$ or the group represented by XX is —B(OR$^{21}$)$_2$ and the group represented by YY is an iodine atom, it is particularly preferable that the group represented by XX is —B(OR$^{21}$)$_2$ and the group represented by YY is an iodine atom.

In the compound represented by the formula (M1-1-3), the group represented by X$^1$ which is a group selected from the substituent group (a) or a group selected from the substituent group (b) can be converted to another group selected from the substituent group (a) or another group selected from the substituent group (b) by a known method.

Scheme 2

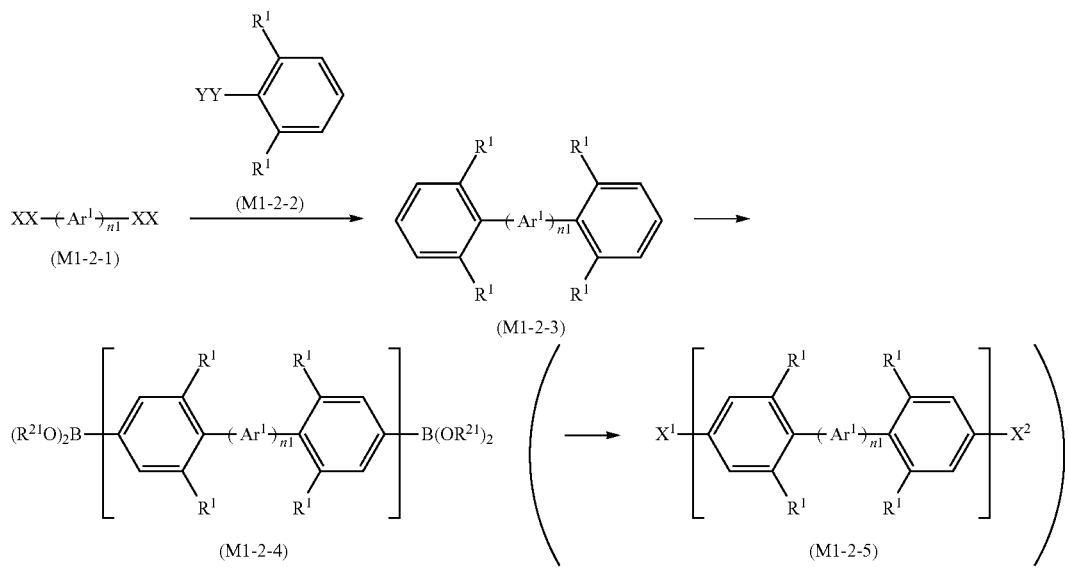

In the scheme 2,

XX, YY, Ar$^1$, n1, R$^1$, X$^1$ and R$^{21}$ represent the same meaning as described above.

In the scheme 2, first, a compound represented by the formula (M1-2-1) and a compound represented by the formula (M1-2-2) are subjected to a cross coupling reaction such as the Suzuki coupling reaction, the Grignard reaction, the Stille coupling reaction and the like, to obtain a compound represented by the formula (M1-2-3).

The compound represented by the formula (M1-2-3) can be converted to a compound represented by the formula (M1-2-4) by a known method such as, for example, a direct borylation reaction using an iridium complex as a catalyst, and the like. The compound represented by the formula (M1-2-4) is a compound represented by the formula (M1).

In the compound represented by the formula (M1-2-4), —B(OR$^{21}$)$_2$ can be converted to a halogen atom or the like by a known method such as a nucleophilic substitution reaction and the like, and further, it can be converted to a compound represented by the formula (M1-2-5) by using the other known method. The compound represented by the formula (M1-2-5) is a compound represented by the formula (M1).

Of the method represented by the above-described scheme 1 and the method represented by the above-described scheme 2, preferable is the method represented by the scheme 2 since generation of impurities derived from a side reaction in the first cross coupling step is generally small and it is easier to obtain a high purity compound represented by the formula (M1).

Likewise, for introducing a repeating unit represented by the formula (2), it is preferable to use a raw material monomer represented by the following formula (M2), and for introducing a repeating unit represented by the formula (3), it is preferable to use a raw material monomer represented by the following formula (M3).

$$X^2—Ar^2—X^2 \quad (M2)$$

(wherein,

X$^2$ represents a group selected from the above-described substituent group (a) or a group selected from the above-described substituent group (b). A plurality of X$^2$ may be mutually the same or different.

Ar$^2$ represents the same meaning as described above.)

$$X^3—Ar^3—X^3 \quad (M3)$$

(wherein,

X$^3$ represents a group selected from the above-described substituent group (a) or a group selected from the following substituent group (b). A plurality of X$^3$ may be mutually the same or different.

Ar$^3$ represents the same meaning as described above.)

For introducing a repeating unit represented by the formula (2B), it is preferable to use a compound represented by the following formulae (M2B) as a monomer.

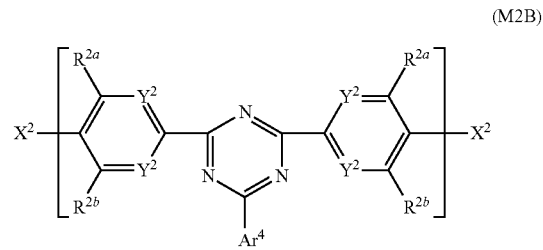

(M2B)

[in the formula (M2B),

Y$^2$ represents a carbon atom or a nitrogen atom, and the carbon atom may have an alkyl group, an aryl group, a monovalent aromatic heterocyclic group or an aralkyl group as a substituent. A plurality of Y$^2$ may be mutually the same or different.

R$^{2a}$ represents an alkyl group, an aryl group, a monovalent aromatic heterocyclic group or an aralkyl group, and these groups may have a substituent. A plurality of R$^{2a}$ may be mutually the same or different.

R$^{2b}$ represents a hydrogen atom, an alkyl group, an aryl group, a monovalent aromatic heterocyclic group or an aralkyl group, and these groups may have a substituent. A plurality of R$^{2b}$ may be mutually the same or different.

Ar⁴ represents an aryl group or a monovalent aromatic heterocyclic group, and these groups may have a substituent.

X² represents a group selected from the following substituent group (a) or a group selected from the following substituent group (b). A plurality of X² may be mutually the same or different.

(Substituent Group (a))

a chlorine atom, a bromine atom, an iodine atom and a group represented by —O—S(=O)₂R²⁰ (R²⁰ represents an alkyl group, or an aryl group which may have an alkyl group, an alkoxy group, a nitro group, a fluorine atom or a cyano group as a substituent.)

(Substituent Group (b))

a group represented by —B(OR²¹)₂ (R²¹ represents a hydrogen atom or an alkyl group. A plurality of R²¹ may be mutually the same or different and may be mutually linked to form a ring together with an oxygen atom to which they are linked.), a group represented by —BF₄Q¹ (Q¹ represents a monovalent cation of lithium, sodium, potassium, rubidium or cesium.), a group represented by —Sn(R²²)₃ (R²² represents a hydrogen atom or an alkyl group. A plurality of R²² may be mutually the same or different and may be mutually linked to form a ring together with a tin atom to which they are linked), a group represented by —MgY¹ (Y¹ represents a chlorine atom, a bromine atom or an iodine atom.) and a group represented by —ZnY² (Y² represents a chlorine atom, a bromine atom or an iodine atom.).]

The method of producing a compound represented by the formula (M2B) described above will be explained below.

The compound represented by the formula (M2B) can be produced, for example, by methods described in the following scheme 3, scheme 4 and scheme 5.

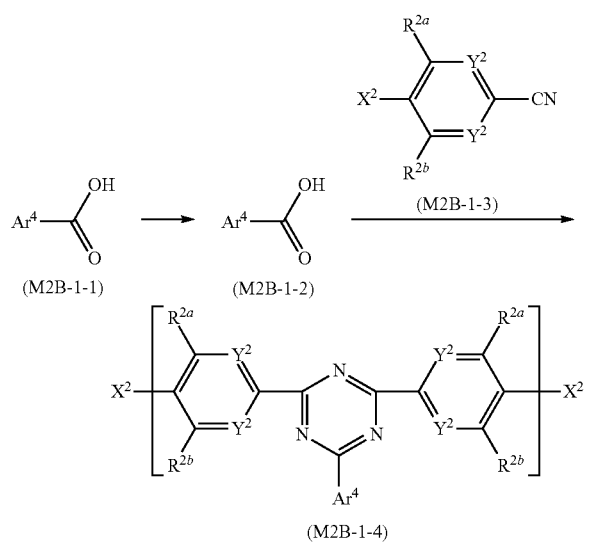

In the scheme 3,

Ar⁴, X², R²ᵃ and Y² represent the same meaning as described above.

In the scheme 3, first, a compound represented by the formula (M2B-1-1) is converted to a compound represented by the formula (M2B-1-2) using a reagent such as thionyl chloride and the like, further, a compound represented by the formula (M2B-1-3) is reacted in the presence of a Lewis acid such as antimony chloride, aluminum chloride and the like, then, these are reacted with ammonia water, ammonia gas, ammonium chloride or the like, thus, a compound represented by the formula (M2B-1-4) can be obtained. The compound represented by the formula (M2B-1-4) is a compound represented by the formula (M2B).

For obtaining a compound represented by the formula (M2B-1-4) in good yield according to the above-described scheme, the molar ratio of a compound represented by the formula (M2B-1-2) to a compound represented by the formula (M2B-1-3) ([the mole number of a compound represented by the formula (M2B-1-3)]/[the mole number of a compound represented by the formula (M2B-1-2)]) is preferably 1.9 or more and 2.0 or less.

In the compound represented by the formula (M2B-1-4), the group represented by X² which is a group selected from the substituent group (a) or a group selected from the substituent group (b) can be converted to another group selected from the substituent group (a) or another group selected from the substituent group (b) by a known method.

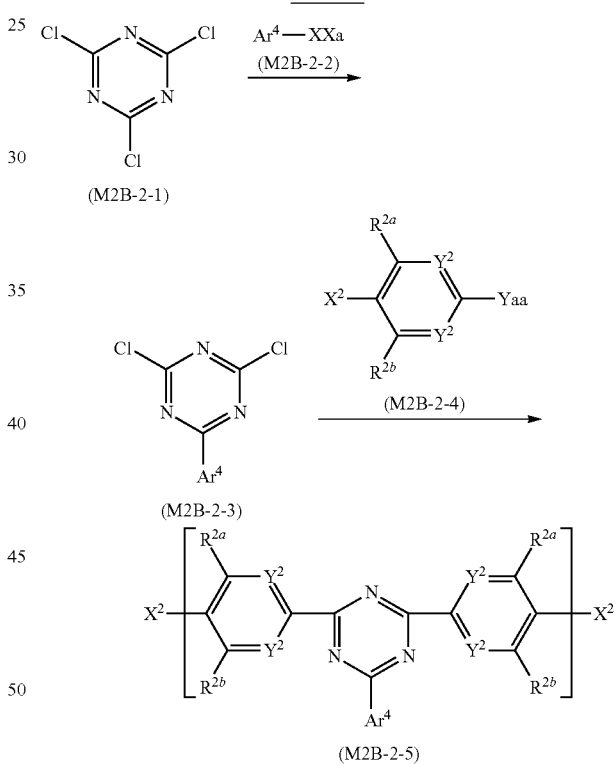

In the scheme 4,

XXa and YYa represent each independently a group selected from the above-described substituent group (b).

Ar⁴, X², R²ᵃ and Y² represent the same meaning as described above.

In the scheme 4, first, a compound represented by the formula (M2B-2-1) and a compound represented by the formula (M2B-2-2) are subjected to a cross coupling reaction such as the Suzuki coupling reaction, the Grignard reaction, the Stille coupling reaction and the like, to obtain a compound represented by the formula (M2B-2-3).

Further, a compound represented by the formula (M2B-2-3) and a compound represented by the formula (M2B-2-4)

are subjected to a cross coupling reaction such as the Suzuki coupling reaction, the Grignard reaction, the Stille coupling reaction and the like, to obtain a compound represented by the formula (M2B-2-5). The compound represented by the formula (M2B-2-5) is a compound represented by the formula (M2B).

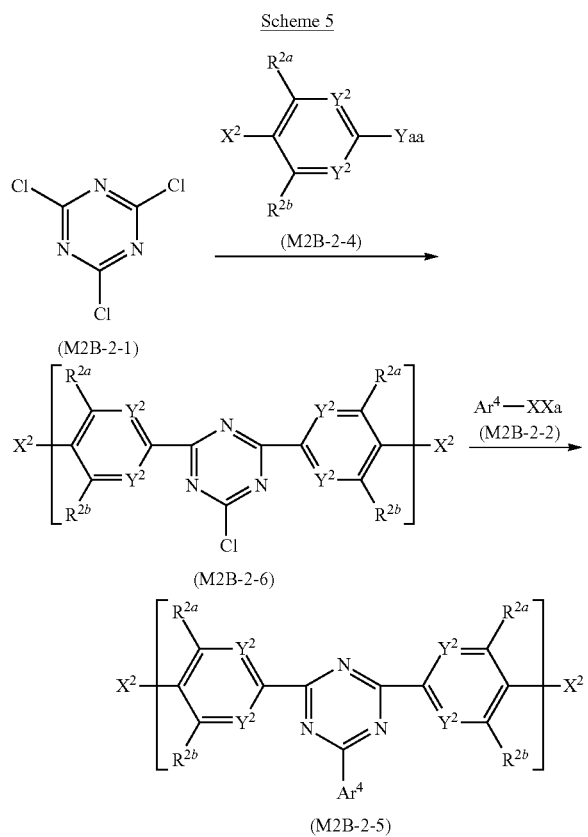

In the scheme 5,

XXa, YYa, Ar⁴, X², $R^{2a}$ and Y² represent the same meaning as described above.

In the scheme 5, first, a compound represented by the formula (M2B-2-1) and a compound represented by the formula (M2B-2-4) are subjected to a cross coupling reaction such as the Suzuki coupling reaction, the Grignard reaction, the Stille coupling reaction and the like, to obtain a compound represented by the formula (M2B-2-6).

Further, a compound represented by the formula (M2B-2-6) and a compound represented by the formula (M2B-2-2) are subjected to a cross coupling reaction such as the Suzuki coupling reaction, the Grignard reaction, the Stille coupling reaction and the like, to obtain a compound represented by the formula (M2B-2-5). The compound represented by the formula (M2B-2-5) is a compound represented by the formula (M2B).

In the compound represented by the formula (M2B-2-5), the group represented by X² which is a group selected from the substituent group (a) or a group selected from the substituent group (b) can be converted to another group selected from the substituent group (a) or another group selected from the substituent group (b) by a known method.

Of the method represented by the scheme 3, the method represented by the scheme 4 and the method represented by the scheme 5 described above, preferable is the method represented by the scheme 3 since generation of impurities derived from a side reaction is generally small and it is easier to obtain a high purity compound represented by the formula (M2B).

For introducing a repeating unit represented by the formula (3C), it is preferable to use a compound represented by the following formulae (M3C) as a monomer.

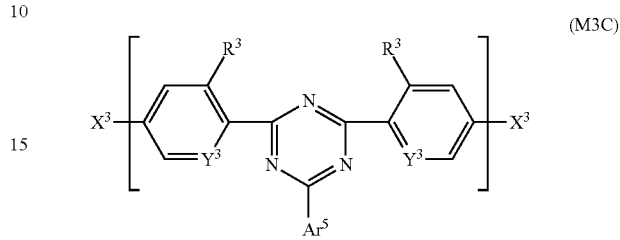

[in the formula (M3C),

Y³ represents a carbon atom or a nitrogen atom, and the carbon atom may have an alkyl group, an aryl group, a monovalent aromatic heterocyclic group or an aralkyl group as a substituent. A plurality of Y³ may be mutually the same or different.

Ar⁵ represents an aryl group or a monovalent aromatic heterocyclic group, and these groups may have a substituent.

R³ represents an alkyl group, an aryl group, a monovalent aromatic heterocyclic group or an aralkyl group. A plurality of R³ may be mutually the same or different.

X³ represents a group selected from the following substituent group (a) or a group selected from the following substituent group (b). A plurality of X³ may be mutually the same or different.

(Substituent Group (a))

a chlorine atom, a bromine atom, an iodine atom, and a group represented by —O—S(=O)₂R²⁰ (R²⁰ represents an alkyl group, or an aryl group which may have an alkyl group, an alkoxy group, a nitro group, a fluorine atom or a cyano group as a substituent.).

(Substituent Group (b))

a group represented by —B(OR²¹)₂ (R²¹ represents a hydrogen atom or an alkyl group. A plurality of R²¹ may be mutually the same or different and may be mutually linked to form a ring together with an oxygen atom to which they are linked.), a group represented by —BF₄Q¹ (Q¹ represents a monovalent cation of lithium, sodium, potassium, rubidium or cesium.), a group represented by —Sn(R²²)₃ (R²² represents a hydrogen atom or an alkyl group. A plurality of R²² may be mutually the same or different and may be mutually linked to form a ring together with a tin atom to which they are linked), a group represented by —MgY¹ (Y¹ represents a chlorine atom, a bromine atom or an iodine atom.) and a group represented by —ZnY² (Y² represents a chlorine atom, a bromine atom or an iodine atom.).]

The method of producing a compound represented by the formula (M3C) described above will be explained below.

The compound represented by the formula (M3C) can be produced, for example, by a method described in the following scheme 6, scheme 7 or scheme 8.

Scheme 6

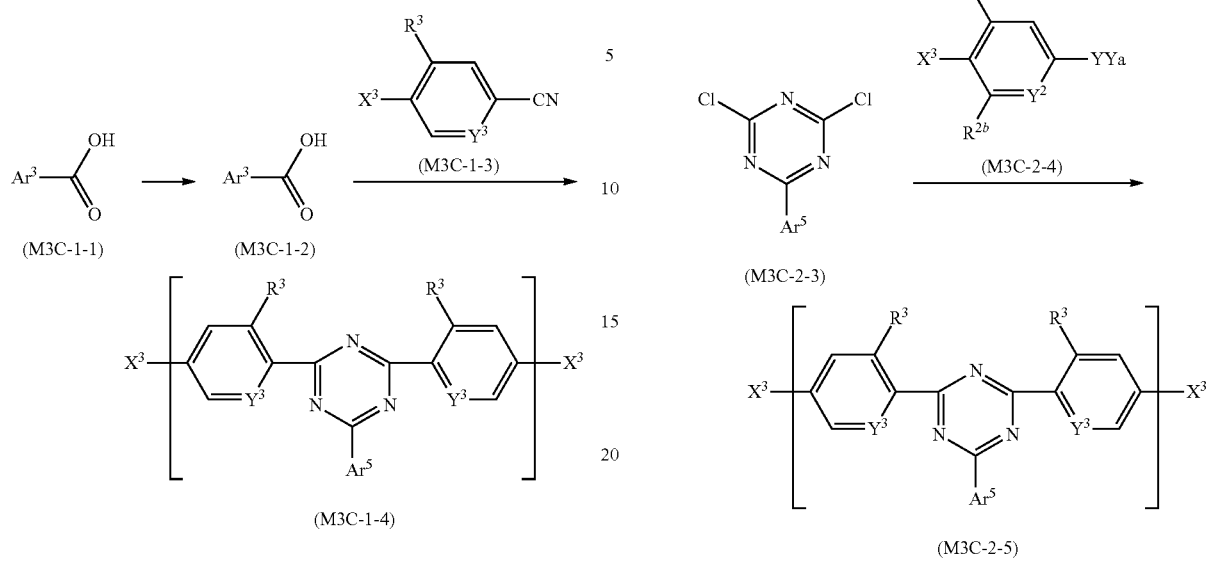

In the scheme 6, $Ar^5$, $X^3$, $R^3$ and $Y^3$ represent the same meaning as described above.

In the scheme 6, first, a compound represented by the formula (M3C-1-1) is converted to a compound represented by the formula (M3C-1-2) using a reagent such as thionyl chloride and the like, further, a compound represented by the formula (M3C-1-3) is reacted in the presence of a Lewis acid such as antimony chloride, aluminum chloride and the like, then, these are reacted with ammonia water, ammonia gas, ammonium chloride and the like, thus, a compound represented by the formula (M3C-1-4) can be obtained. The compound represented by the formula (M3C-1-4) is a compound represented by the formula (M3C).

For obtaining a compound represented by the formula (M3C-1-4) in good yield according to the above-described scheme, the molar ratio of a compound represented by the formula (M3C-1-2) and a compound represented by the formula (M3C-1-3) ([the mole number of a compound represented by the formula (M3C-1-3)]/[the mole number of a compound represented by the formula (M3C-1-2)]) is preferably 1.9 or more and 2.0 or less.

In the compound represented by the formula (M3C-1-4), the group represented by $X^3$ which is a group selected from the substituent group (a) or a group selected from the substituent group (b) can be converted to another group selected from the substituent group (a) or another group selected from the substituent group (b) by a known method.

Scheme 7

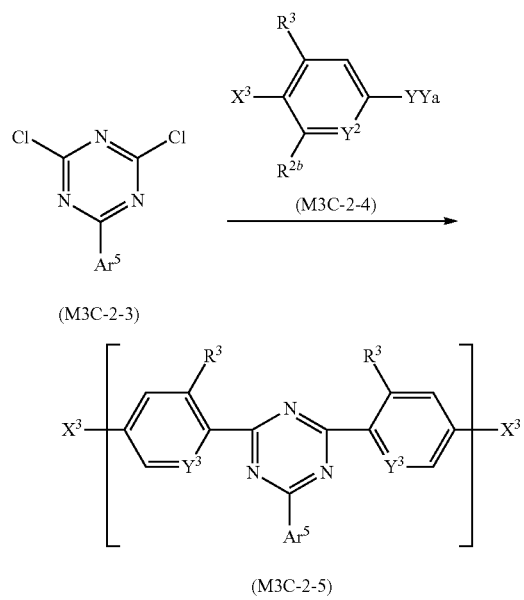

In the scheme 7, XXa, YYa, $Ar^5$, $X^3$, $R^3$ and $Y^3$ represent the same meaning as described above.

In the scheme 7, first, a compound represented by the formula (M3C-2-1) and a compound represented by the formula (M3C-2-2) are subjected to a cross coupling reaction such as the Suzuki coupling reaction, the Grignard reaction, the Stille coupling reaction and the like, to obtain a compound represented by the formula (M3C-2-3).

Further, a compound represented by the formula (M3C-2-3) and a compound represented by the formula (M3C-2-4) are subjected to a cross coupling reaction such as the Suzuki coupling reaction, the Grignard reaction, the Stille coupling reaction and the like, to obtain a compound represented by the formula (M3C-2-5). The compound represented by the formula (M3C-2-5) is a compound represented by the formula (M3C).

Scheme 8

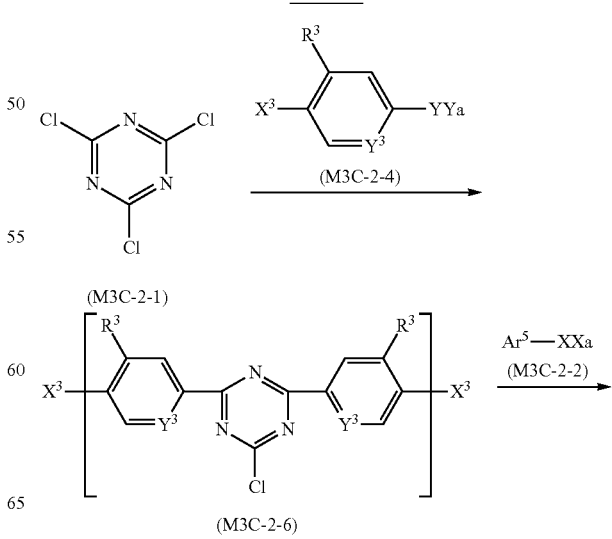

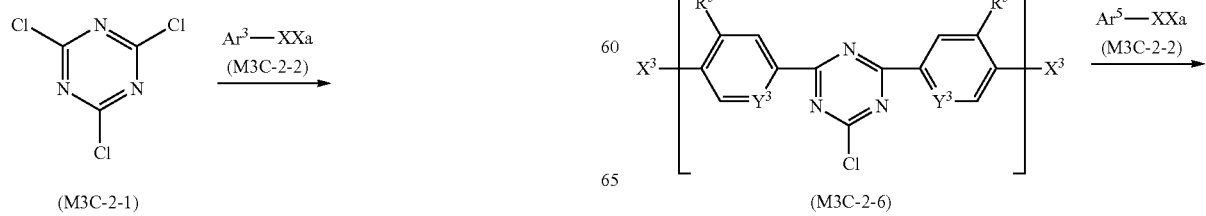

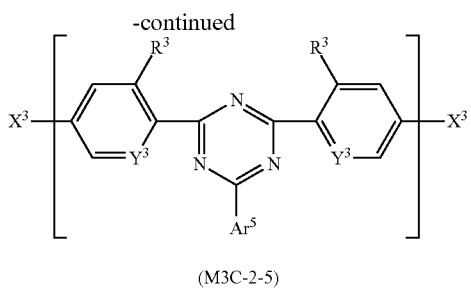

(M3C-2-5)

In the scheme 8, XXa, YYa, Ar⁵, $X^3$, $R^3$ and $Y^3$ represent the same meaning as described above.

In the scheme 8, first, a compound represented by the formula (M3C-2-1) and a compound represented by the formula (M3C-2-4) are subjected to a cross coupling reaction such as the Suzuki coupling reaction, the Grignard reaction, the Stille coupling reaction and the like, to obtain a compound represented by the formula (M3C-2-6).

Further, a compound represented by the formula (M3C-2-6) and a compound represented by the formula (M3C-2-2) are subjected to a cross coupling reaction such as the Suzuki coupling reaction, the Grignard reaction, the Stille coupling reaction and the like, to obtain a compound represented by the formula (M3C-2-5). The compound represented by the formula (M3C-2-5) is a compound represented by the formula (M3C).

In the compound represented by the formula (M3C-2-5), the group represented by $X^3$ which is a group selected from the substituent group (a) or a group selected from the substituent group (b) can be converted to another group selected from the substituent group (a) or another group selected from the substituent group (b) by a known method.

Of the methods represented by the scheme 6, the scheme 7 and the scheme 8 described above, preferable is the method represented by the scheme 6 since generation of impurities derived from a side reaction is generally small and it is easier to obtain a high purity compound represented by the formula (M3C).

The polymer compound of the present invention can be produced by polymerizing a raw material monomer mixture containing a raw material monomer represented by the formula (M11) (may also be a raw material monomer represented by the formula (M1), the same shall apply in the following descriptions unless otherwise stated) and a raw material monomer selected from the group consisting of a raw material monomer represented by the formula (M2), a raw material monomer represented by the formula (M3) and a raw material monomer for introducing the other constitutional unit, according to demand. In the polymerization, the raw material monomer mixture is, if necessary, dissolved in a solvent, an alkali, a catalyst or a ligand is appropriately used, and a known polymerization (polycondensation) reaction such as a cross coupling reaction and the like is caused.

In the method of producing the polymer compound of the present invention, the raw material monomer mixture is mixed so that the total mole number of a raw material monomer represented by the formula (M11), a raw material monomer represented by the formula (M2) and a raw material monomer represented by the formula (M3) is preferably 60 to 100 mol %, more preferably 70 to 100 mol %, when the total mole number thereof is 100 mol %.

It is preferable that polymerization active groups $X^1$, $X^2$ and $X^3$ which the raw material monomer as described above has on its both ends are combined as described below, from the standpoint of producing a polymer compound in which the content of groups represented by the formula (3) is 50% or less with respect to the total content of repeating units contained in the polymer compound and groups represented by the formula (3) are not mutually substantially adjacent, which is the preferable embodiment of the polymer compound of the present invention described above.

$X^3$ is a group selected from the substituent group (a) and part or all of $X^1$ and $X^2$ are a group selected from the substituent group (b);

$X^3$ is a group selected from the substituent group (b) and part or all of $X^1$ and $X^2$ are a group selected from the substituent group (a).

Of them, a combination in which $X^3$ is a group selected from the substituent group (a) and part or all of $X^1$ and $X^2$ are a group selected from the substituent group (b) is more preferable from the standpoint of easy progress of the polymerization reaction. According to a combination of them, polymerization using known various cross coupling reactions such as the Suzuki coupling reaction and the like is possible, and by this, it is made possible to produce a polymer compound which is the preferable embodiment of the polymer compound of the present invention described above.

Likewise, it is preferable that polymerization active groups $X^1$, $X^2$ and $X^3$ which the raw material monomer as described above has on its both ends are combined as described below, from the standpoint of producing a polymer compound in which the content of a group represented by the formula (2) is 50 mol % or more with respect to the total content of repeating units contained in the polymer compound and groups represented by the formula (11), and a group represented by the formula (11) and a group represented by the formula (3) are not substantially adjacent, which is the preferable embodiment of the polymer compound of the present invention described above.

$X^1$ and $X^3$ are a group selected from the substituent group (a) and part or all of $X^2$ are a group selected from the substituent group (b);

$X^1$ and $X^3$ are a group selected from the substituent group (b) and part or all of $X^2$ are a group selected from the substituent group (a).

Of them, a combination in which $X^1$ and $X^3$ are a group selected from the substituent group (a) and part or all of $X^2$ are a group selected from the substituent group (b) is more preferable from the standpoint of easy progress of the polymerization reaction. According to a combination of them, polymerization using known various cross coupling reactions such as the Suzuki coupling reaction and the like is possible, and by this, it is made possible to produce a polymer compound which is the preferable embodiment of the polymer compound of the present invention described above.

Here, the alkyl group as an example of $R^{20}$, $R^{21}$ and $R^{22}$ in a group represented by $-O-S(=O)_2R^{20}$ in the substituent group (a) and a group represented by $-B(OR^{21})_2$ and a group represented by d $Sn(R^{22})_3$ in the substituent group (b) has a number of carbon atoms of preferably 1 to 20, more preferably 1 to 15, further preferably 1 to 10.

The aryl group which may have an alkyl group, an alkoxy group, a nitro group, a fluorine atom or a cyano group as a substituent, which is one example of $R^{20}$, is preferably a phenyl group, a 4-tolyl group, a 4-methoxyphenyl group, a 4-nitrophenyl group, a 3-nitrophenyl group, a 2-nitrophenyl group or a 4-trifluoromethylphenyl group. When $R^{20}$, $R^{21}$ and $R^{22}$ are these groups, reactivity in polymerizing a raw material monomer is excellent and synthesis of a polymer compound tends to be easier.

The group represented by $-O-S(=O)_2R^{20}$ in the substituent group (a) includes, for example, a methanesulfonyloxy group, a trifluoromethanesulfonyloxy group, a phenylsulfonyloxy group, a 4-methylphenylsulfonyloxy group and a 4-trifluoromethylphenylsulfonyloxy group.

The group represented by $-B(OR^{21})_2$ in the substituent group (b) includes, for example, groups represented by the following formulae.

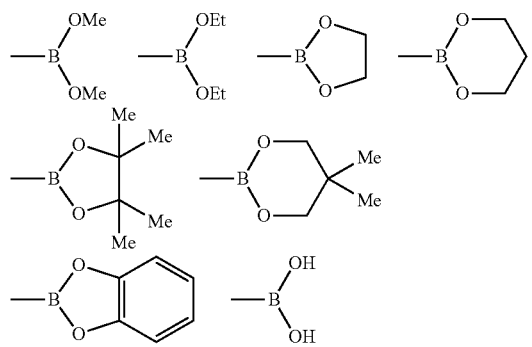

The group represented by $-BF_4Q^1$ in substituent group (b) includes, for example, a group represented by $-BF_4^-K^+$. Further, the group represented by $-Sn(R^{22})_3$ in the substituent group (b) includes, for example, a trimethylstannanyl group, a triethylstannanyl group and a tributylstannanyl group.

When compounds represented by the formulae (M11), (M2) and (M3) are used as raw material monomers and polymerized to produce a polymer compound, it is preferable to raise the purity of each raw material monomer before polymerization so at to obtain a polymer compound having higher purity. By producing a light emitting device using a high purity polymer compound, stability of the resulting current efficiency, light emission efficiency and luminance life is more excellent.

The purity of a compound represented by the formula (M11), a compound represented by the formula (M2) and a compound represented by the formula (M3) can be raised by, for example, performing purification by distillation, sublimation purification, recrystallization and the like. Each compound having higher purity is more desirable. For example, in analysis according to high performance liquid chromatography (HPLC) using a UV detector (detection wavelength: 254 nm), the area percentage value shown by the peak of each compound is preferably 98.5% or more, more preferably 99.0% or more, further preferably 99.5% or more.

The polymerization reaction using a compound represented by the formula (M11), a compound represented by the formula (M2) and a compound represented by the formula (M3) includes, for example, a method of polymerization by the Suzuki coupling reaction as a method according to an aryl coupling reaction (Chem. Rev., vol. 95, pp. 2457-2483 (1995)), a method of polymerization by the Grignard reaction (Bull. Chem. Soc. Jpn., vol. 51, p. 2091 (1978)), a method of polymerization with a Ni (0) catalyst (Progress in Polymer Science), vol. 17, pp. 1153 to 1205, 1992) and a method using the Stille coupling reaction (European Polymer Journal, vol. 41, pp. 2923-2933 (2005)).

Of them, a method of polymerization by the Suzuki coupling reaction and a method of polymerization with a Ni(0) catalyst are preferable as the polymerization method from the standpoint of easiness of production of a polymer compound and simplicity of operation in a polymerization reaction. Further, methods of polymerization by a cross coupling reaction such as the Suzuki coupling reaction, the Grignard reaction, the Stille coupling reaction and the like are preferable and a method of polymerization by the Suzuki coupling reaction is particularly preferable from the standpoint of control of the structure of a polymer compound containing a specific chain constitution described above as one of preferable embodiments of the present invention.

As the groups represented by polymerization active groups $X^1$, $X^2$ and $X^3$ which a compound represented by the formula (M11), a compound represented by the formula (M2) and a compound represented by the formula (M3) have, a suitable group may be selected depending on the kind of a polymerization reaction. For example, in the case of polymerization by the Suzuki coupling reaction, a bromine atom, an iodine atom or a chlorine atom is preferable in the substituent group (a) and a group represented by $-B(OR^{21})_2$ is preferable in the substituent group (b) as these groups, and it is more preferable to select a bromine atom and a group represented by $-B(OR^{21})_2$ from the substituent group (a) and the substituent group (b), respectively. When these groups are contained as the polymerization active group, synthesis of a compound represented by the formula (M11), a compound represented by the formula (M2) and a compound represented by the formula (M3) is easy, and additionally, handling in polymerization is also excellent.

The polymerization method includes a method in which a compound represented by the formula (M11), a compound represented by the formula (M2) and a compound represented by the formula (M3) (raw material monomers) having the substituent group (a) and the substituent group (b) described above as the polymerization active group, and the like, are reacted if necessary together with a suitable catalyst and a suitable base. In the case of selection of a method of polymerization by a cross coupling reaction such as the Suzuki coupling reaction, the Grignard reaction, the Stille coupling reaction and the like, the ratio of the mole number of a group contained in the substituent group (b) to the mole number of a group contained in the substituent group (a) in the whole raw material monomer (ratio when the total mole number of a group contained in the substituent group (a) is the denominator and the total mole number of a group contained in the substituent group (b) is the numerator, hereinafter described as ratio (b/a) in some cases) may be adjusted so as to obtain a polymer compound having desired molecular weight. The ratio (b/a) is preferably 0.90 to 1.10, more preferably 0.95 to 1.05, further preferably 0.98 to 1.02 from the standpoint of further raising the molecular weight of the polymer compound of the present embodiment. In contrast, when it is desired to control the existing proportion of a chain constitution by split addition or consecutive addition of a raw material monomer and the like, it is possible to control the molecular weight by conducting a polymerization reaction under condition wherein the above-described ratio (b/a) is set to a suitable value of less than 1, thereby generating a constitution in which both ends of a polymer compound is composed of a group contained in the substituent group (a) in the polymerization reaction, and it becomes possible to control the molecular weight further precisely by further adding a raw material monomer so that the ratio (b/a) approximates 1. Further, it is also possible to produce a block copolymer by later adding a raw material monomer as the different repeating unit from the raw material monomer added initially.

The polystyrene-equivalent number-average molecular weight (Mn) according to gel permeation chromatography (hereinafter, referred to as "GPC") of the polymer compound of the present invention is usually $1\times10^3$ to $1\times10^8$, preferably $1\times10^4$ to $1\times10^6$. The polystyrene-equivalent weight-average molecular weight (Mw) of the polymer compound of the present embodiment is usually $2\times10^3$ to $2\times10^8$, and, because of an improvement in film formability, preferably $2\times10^4$ to $2\times10^6$, more preferable $3\times10^4$ to $1\times10^6$, further preferably $5\times10^4$ to $5\times10^5$.

In the case of polymerization by the Suzuki coupling reaction, the catalyst includes, for example, transition metal complexes such as palladium complexes such as) [tetrakis(triphenylphosphine)]palladium(0) (Pd(PPh$_3$)$_4$), [tris(dibenzylideneacetone)]dipalladium (Pd$_2$(dba)$_3$), palladium(II) acetate (Pd(OAc)$_2$), dichlorobistriphenylphosphinepalladium(II) (PdCl$_2$(PPh$_3$)$_2$), dichlorobis[tris(2-methoxyphenyl)phosphine]palladium(II) (PdCl$_2$[P(2-MeOPh)$_3$]$_2$) and the like, and catalysts prepared by adding, if necessary, a ligand such as triphenylphosphine, tri(tert-butyl)phosphine, tris(2-methoxyphenyl)phosphine, tricyclohexylphosphine and the like to these transition metal complexes.

As these catalysts, those synthesized previously may be used, and those prepared in the reaction system may be used as they are. These catalysts may be used each singly or two or more of them may be used in combination. Further, these catalysts may be not only added in initiation of the polymerization, but also further added during the polymerization reaction.

When a catalyst is used, its use amount may be an effective amount as the catalyst. For example, the amount of a catalyst with respect to the sum of the mole numbers of raw material monomers to be used is preferably 0.00001 to 3 molar equivalent, more preferably 0.00005 to 0.5 molar equivalent, further preferably 0.0001 to 0.2 molar equivalent in terms of a transition metal.

In polymerization by the Suzuki coupling reaction, it is preferable to use a base as the catalyst. The base includes inorganic bases such as sodium carbonate, potassium carbonate, cesium carbonate, potassium fluoride, cesium fluoride, tripotassium phosphate and the like, and organic bases such as tetrabutylammonium fluoride, tetrabutylammonium chloride, tetrabutylammonium bromide, tetraethylammonium hydroxide, tetrabutylammonium hydroxide and the like. These bases may also be used in the form of an aqueous solution.

When a base is used, its amount is preferably 0.5 to 20 molar equivalent, more preferably 1 to 10 molar equivalent with respect to the sum of the mole numbers of raw material monomers to be used.

The polymerization reaction may be conducted in the absence of a solvent or in the presence of a solvent, and it is more preferable to conduct the polymerization reaction in the presence of an organic solvent. The organic solvent includes, for example, toluene, xylene, mesitylene, tetrahydrofuran, 1,4-dioxane, dimethoxyethane, N,N-dimethylacetamide and N,N-dimethylformamide. From the standpoint of suppression of side reactions, it is desired that the solvent is subjected to a deoxygenation treatment. The organic solvents may be used each singly or two or more of them may be used in combination.

The use amount of the organic solvent is adjusted so that the total concentration of raw material monomers in a solution is preferably 0.1 to 90 wt %, more preferably 1 to 50 wt %, further preferably 2 to 30 wt %.

The reaction temperature in the polymerization reaction is preferably 0 to 200° C., more preferably 20 to 150° C., further preferably 20 to 120° C. The reaction time is preferably 0.5 hours or more, more preferably 2 to 500 hours.

The polymerization reaction is preferably conducted under dehydrated condition when a group represented by —MgY$^1$ is used as the group contained in the substituent group (b). When the polymerization reaction is the Suzuki coupling reaction, the base to be used may be used in the form of an aqueous solution, and further, water may be added to an organic solvent and the resultant solution may be used as the solvent.

Further, it is preferable that the polymer compound of the present invention has a structure in which the polymerization active group in the polymerization reaction is removed by an operation such as an end treatment and the like or substituted with a stable group such as an unsubstituted phenyl group and the like from the standpoint of improvement of stability such as the luminance life or the like of a light emitting device. In the polymerization reaction, it is preferable to further use a compound represented by the formula (19) as an end capping reagent for avoiding retention of polymerization active groups (X$^1$, X$^2$, X$^3$ and the like) at the end of the resultant polymer compound. By conducting the reaction with adding such a compound, a polymer compound in which the end of the polymer compound is substituted with an aryl group or a monovalent aromatic heterocyclic group can be obtained. The compounds represented by the formula (19) (functioning as an end capping reagent) may be used singly or two or more of them may be used in combination, in polymerization in producing a polymer compound.)

$$X^{19a}\text{—}Ar^{19a} \tag{19}$$

[in the formula (19),

Ar$^{19a}$ represents an aryl group or a monovalent aromatic heterocyclic group, and these groups may have a substituent.

X$^{19a}$ represents a group selected from the above-described substituent group (a) or the above-described substituent group (b).]

Ar$^{19a}$ in the formula (19) represents preferably an aryl group, more preferably an aryl group which may have an alkyl group, an aryl group, a monovalent aromatic heterocyclic group or a substituted amino group as a substituent, further preferably an aryl group which may have an alkyl group or an aryl group as a substituent, particularly preferably a phenyl group which may have an alkyl group or an aryl group as a substituent.

The post treatment of the polymerization reaction can be conducted by a known method. It can be conducted, for example, by a method in which a reaction liquid obtained in the polymerization reaction is added to a lower alcohol such as methanol and the like to cause deposition of a precipitate, which is then filtrated and dried.

When thus obtained polymer compound contains impurities such as a catalyst and a base used in the polymerization reaction and residues thereof and the like, it is possible to perform a purification treatment according to a known purification method. Particularly when the polymer compound is used in a light emitting device, its purity exerts an influence on performances of the device such as a light emission property and the like, therefore, it is preferable that, after condensation polymerization, impurities are removed and the polymer compound is purified by a purification treatment such as precipitation fractionation, extraction fractionation, silica gel column chromatography, adsorption, washing and the like.

The compound represented by the formula (M1) includes, for example, compounds represented by the following formulae M301 to M-321, M401 to M403, M1-007 to M1-009 and M1-110 to M1 to 115, and from the standpoint of easiness of synthesis, compounds represented by the formulae M1-301, M1-303, M1-304, M1-309, M1-401 to M1-402, M1-007, M1-009, M1-111, M1-113 and M1-115 are preferable, compounds represented by the formulae M1-301, M1-304, M1-402, M1-111, M1-113 and M1-115 are more preferable.

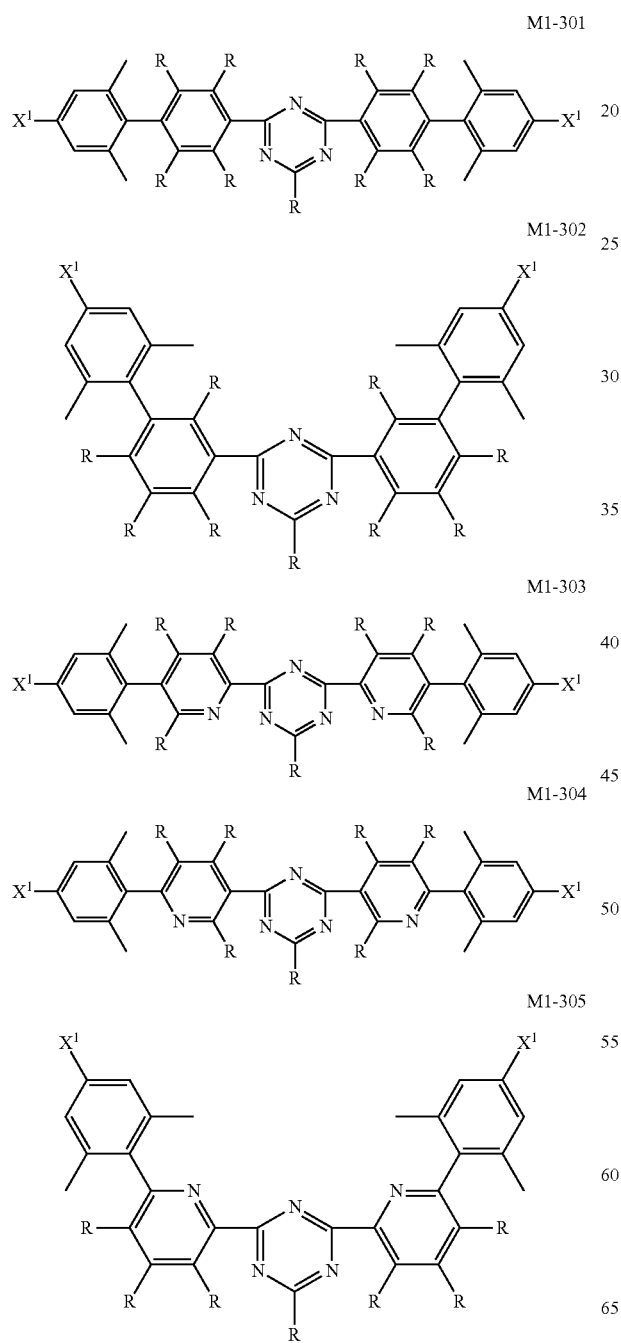

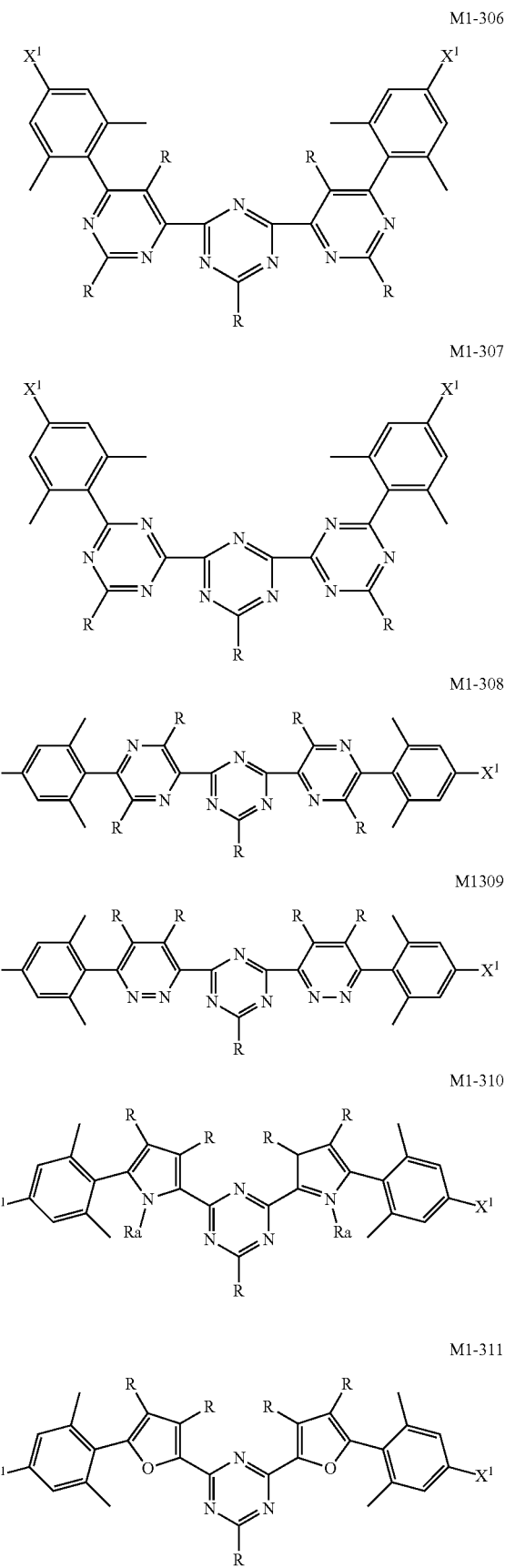

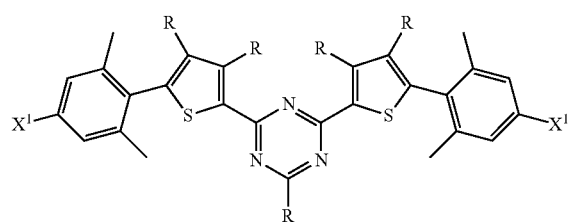
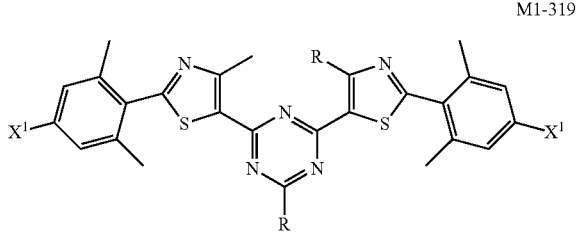
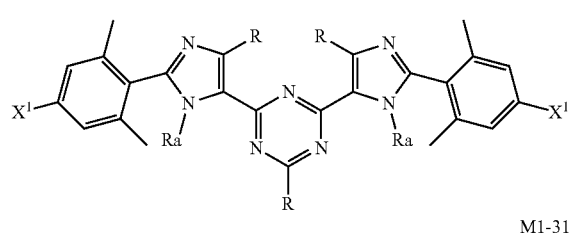
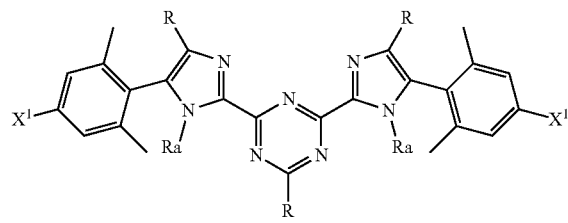
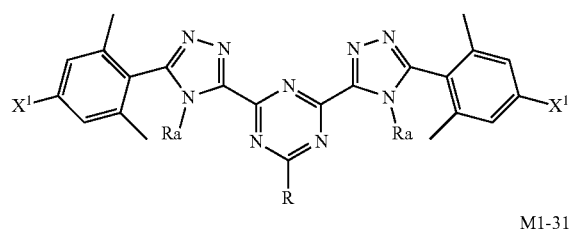
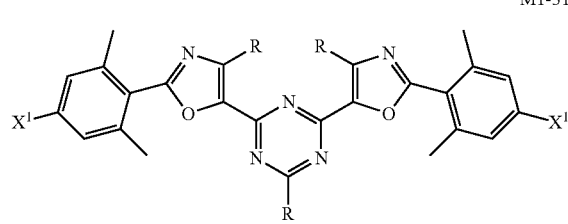

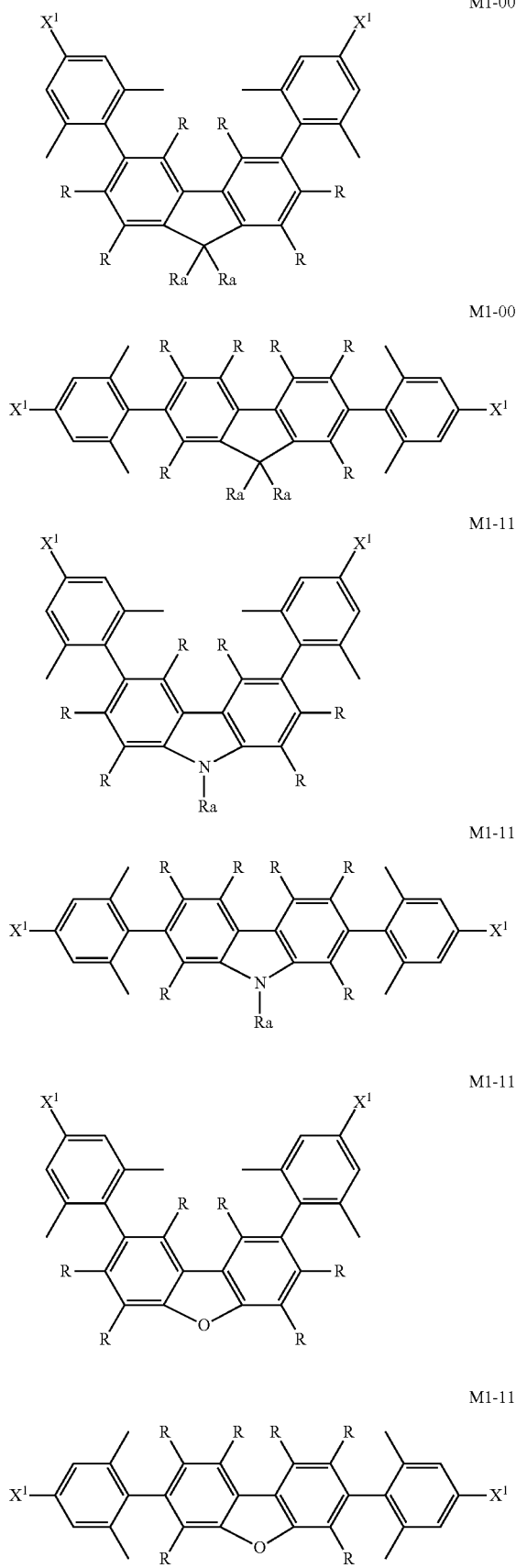
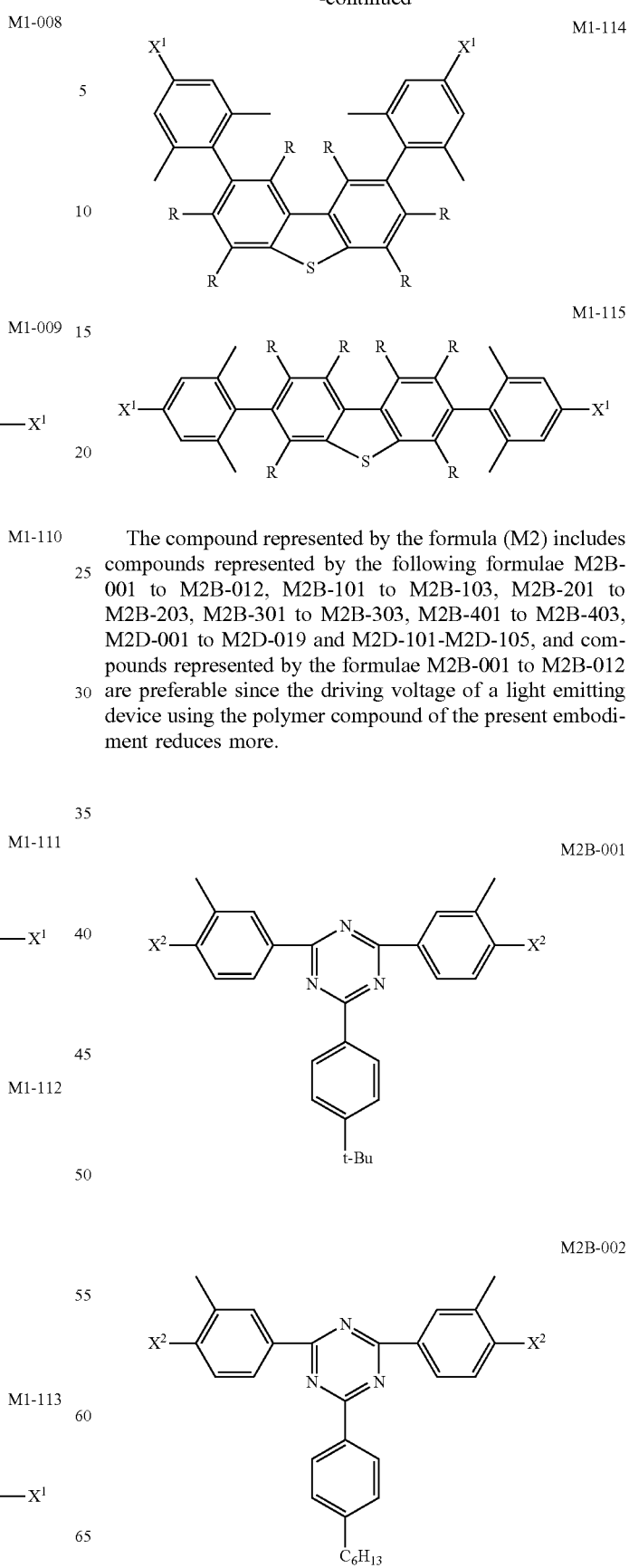
The compound represented by the formula (M2) includes compounds represented by the following formulae M2B-001 to M2B-012, M2B-101 to M2B-103, M2B-201 to M2B-203, M2B-301 to M2B-303, M2B-401 to M2B-403, M2D-001 to M2D-019 and M2D-101-M2D-105, and compounds represented by the formulae M2B-001 to M2B-012 are preferable since the driving voltage of a light emitting device using the polymer compound of the present embodiment reduces more.

M2B-003
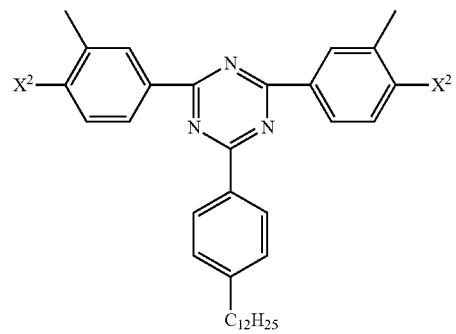
M2B-004
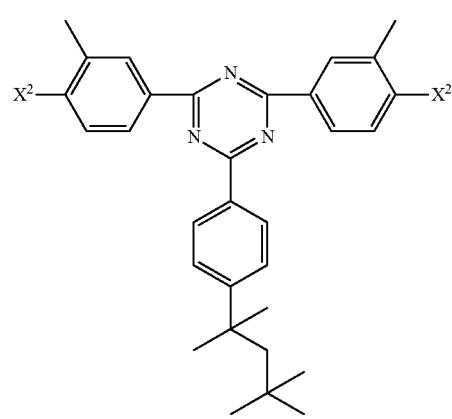
M2B-005
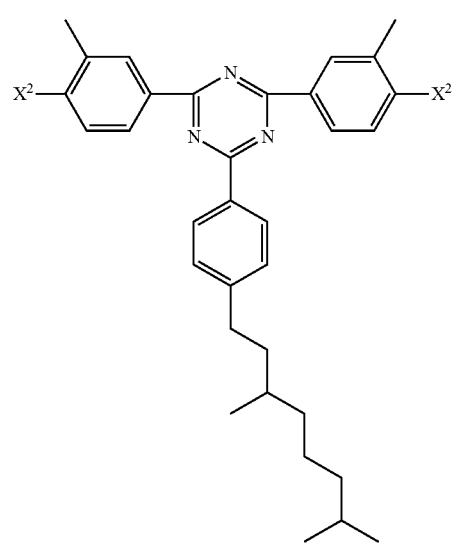
M2B-006
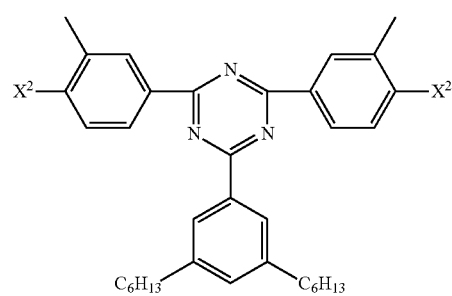
M2B-007
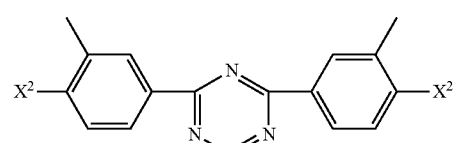
M2B-008
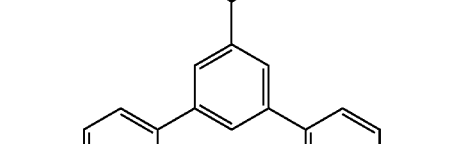
M2B-009
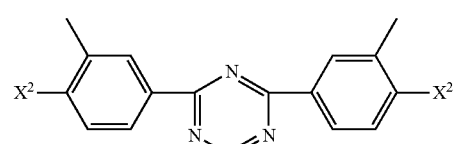
M2B-010
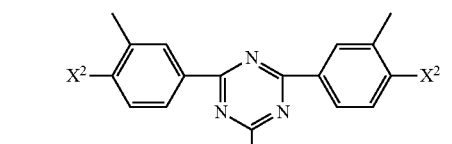

M2B-011
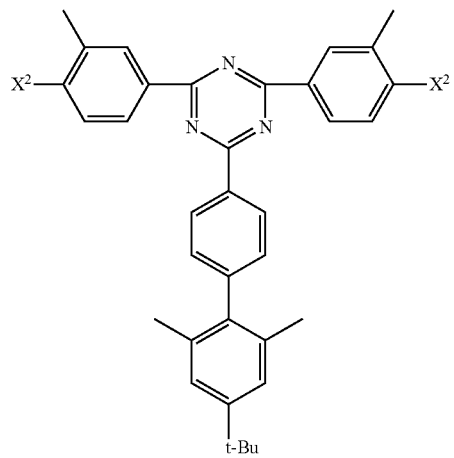
M2B-012
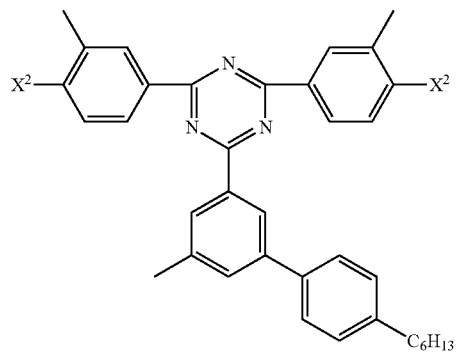
M2B-101
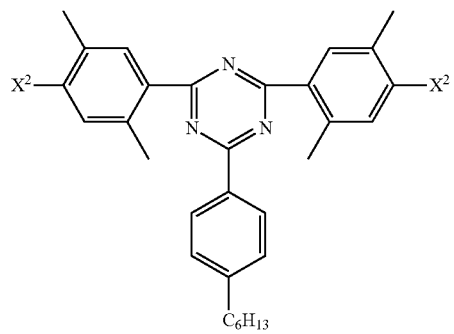
M2B-102
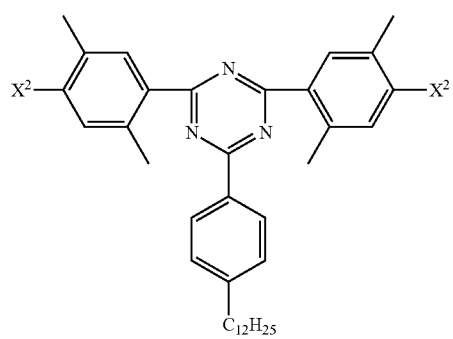
M2B-103
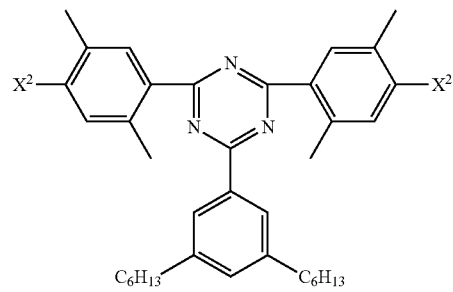
M2B-201
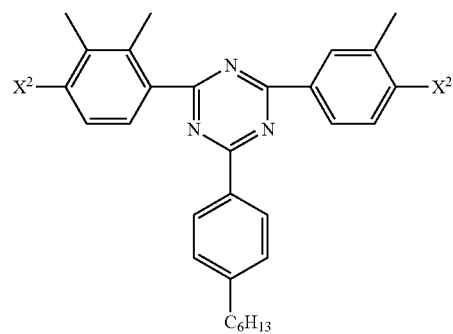
M2B-202
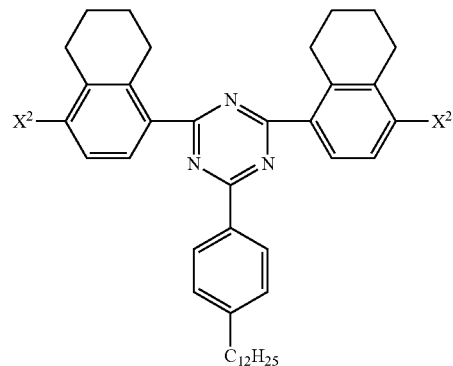
M2B-203
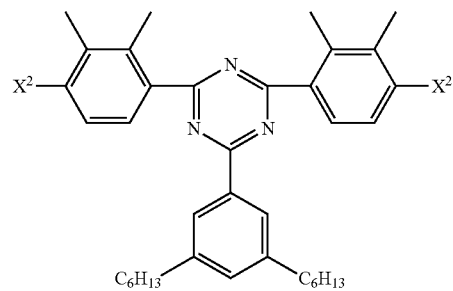

M2B-301
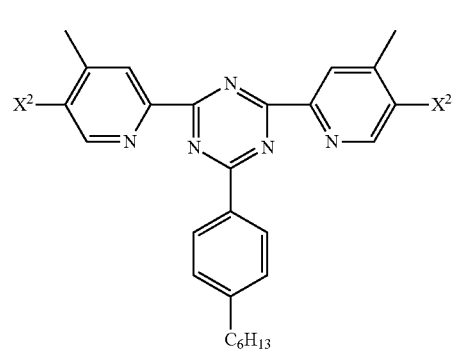
M2B-302
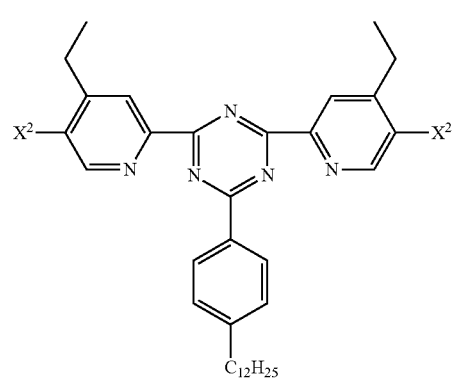
M2B-303
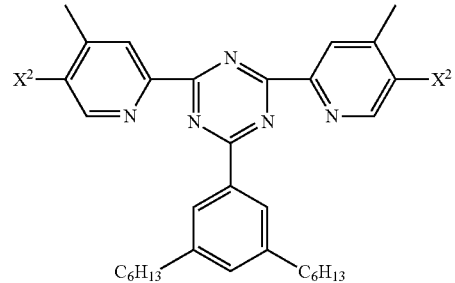
M2B-401
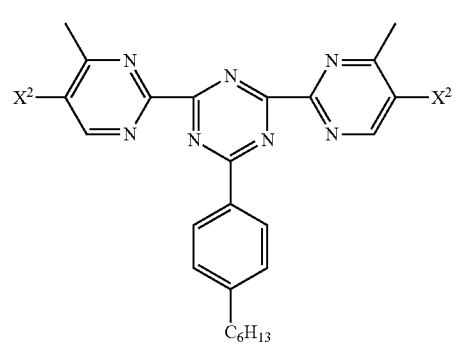
M2B-402
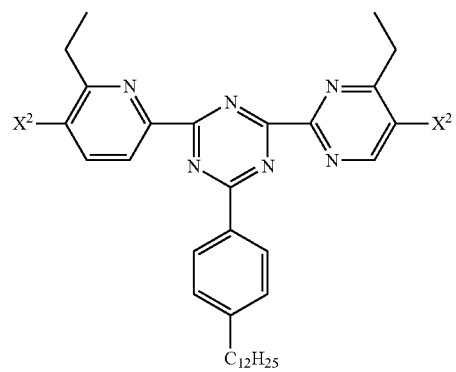
M2B-403
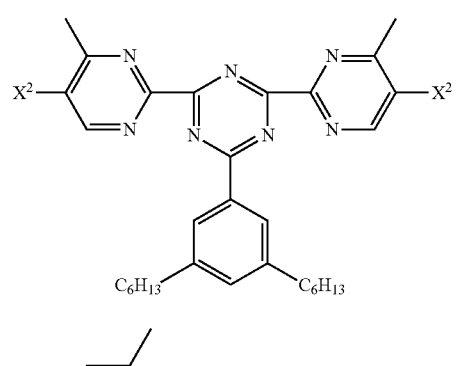
M2D-001
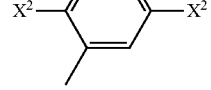
M2D-002
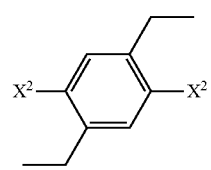
M2D-003
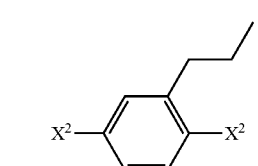
M2D-004
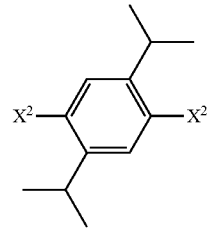

-continued
M2D-005
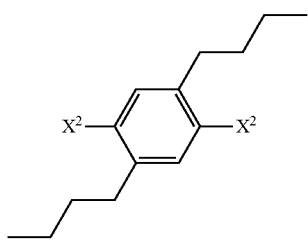
M2D-006
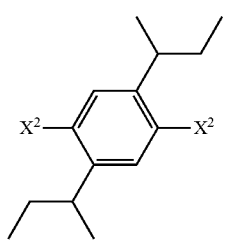
M2D-007
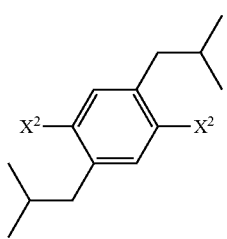
M2D-008
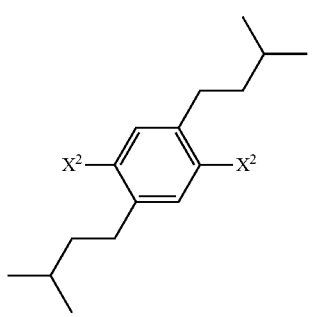
M2D-009
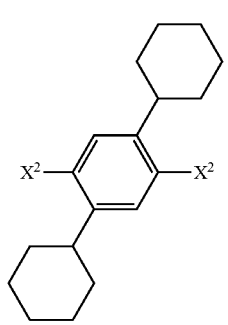
-continued
M2D-010
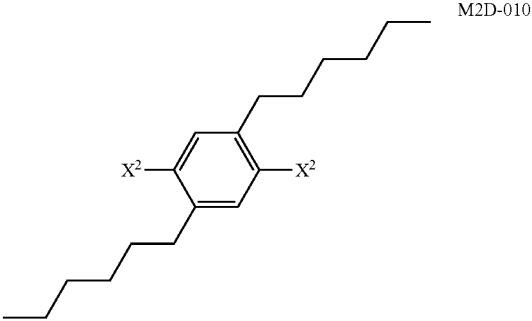
M2D-011
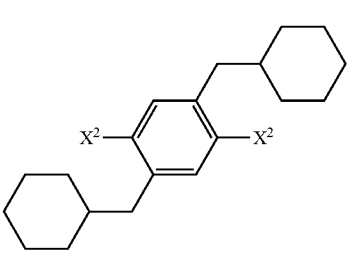
M2D-012
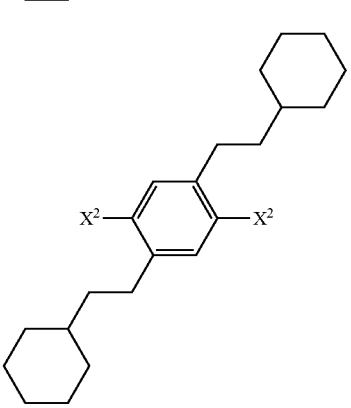
M2D-013
M2D-014

M2D-015 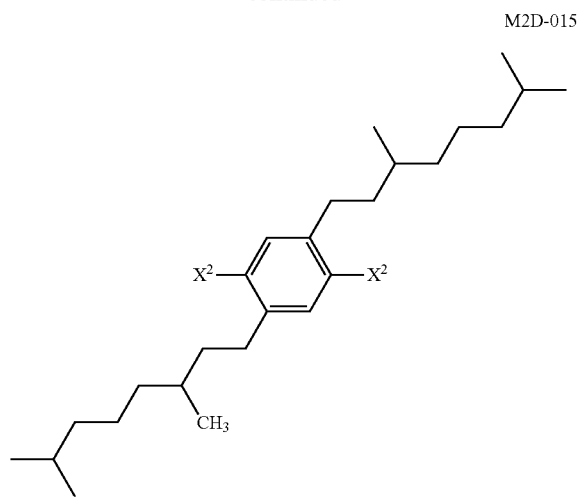
M2D-016 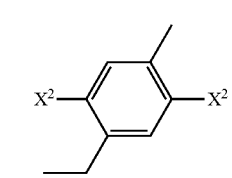
M2D-017 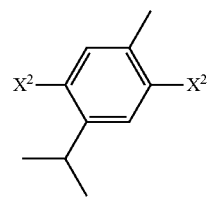
M2D-018 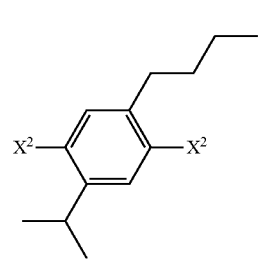
M2D-019 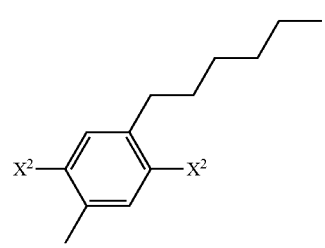
M2D-101 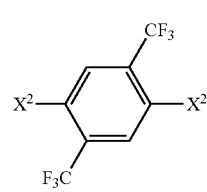
M2D-102 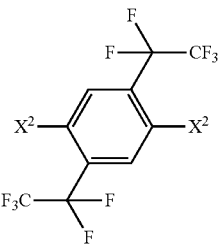
M2D-103 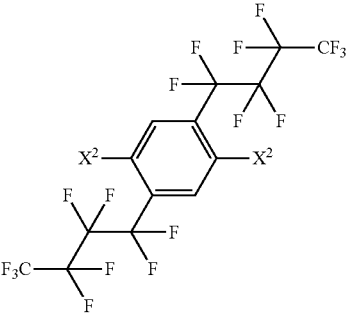
M2D-104 
M2D-105 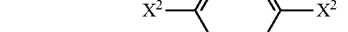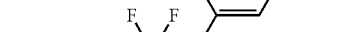
The compound represented by the formula (M3) includes compounds represented by the following formulae M3B-001 to M3B-012, M3B-301 to M3B-303, M3B-401 to M3B-403, M3C-001 to M3C-012, M3C-301 to M3C-303 and M5-001 to M5-006, and compounds represented by the formulae M3B-001 to M3B-012 are preferable, compounds represented by the formulae M3B-003 to M3B-010 are more preferable, from the standpoint of the luminance life of a light emitting device using the polymer compound of the present embodiment.
3B-001
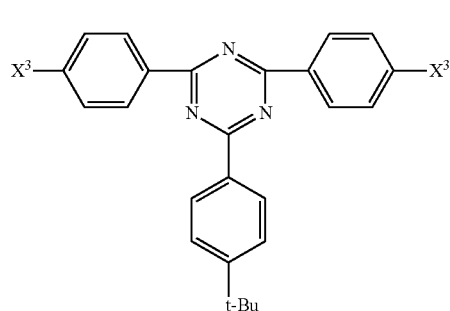
M3B-002
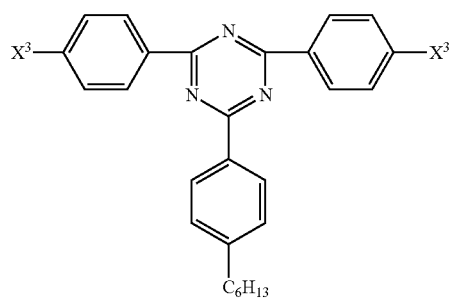
M3B-003
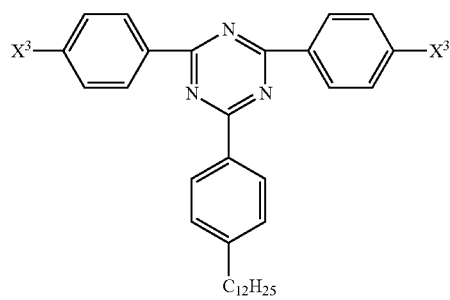
M3B-004
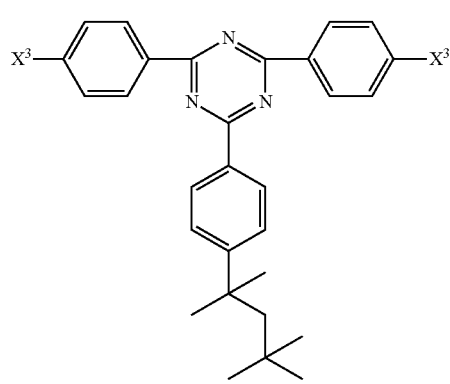
M3B-005
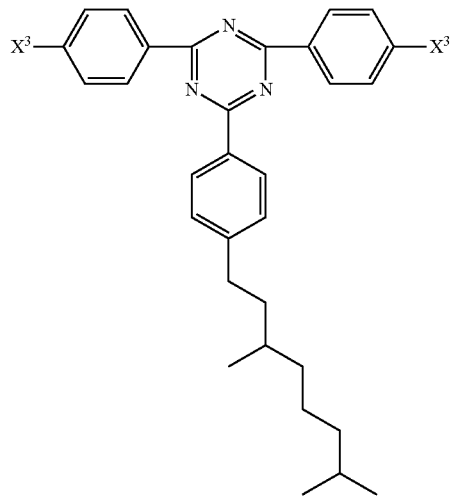
M3B-006
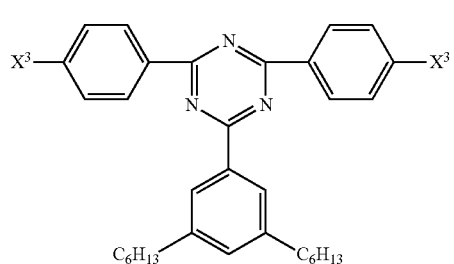
M3B-007
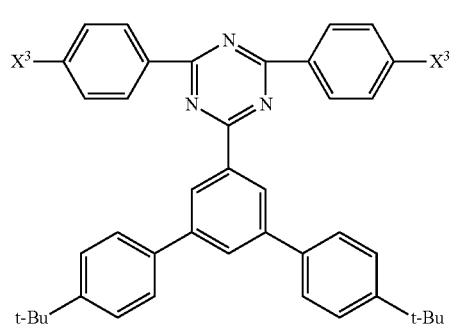
M3B-008
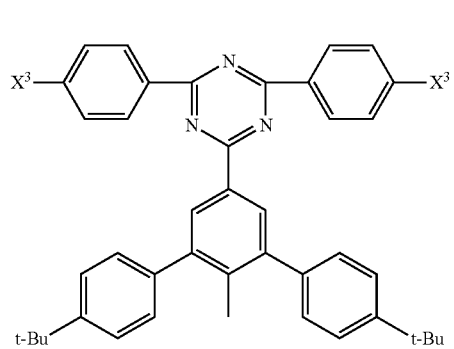

M3B-009
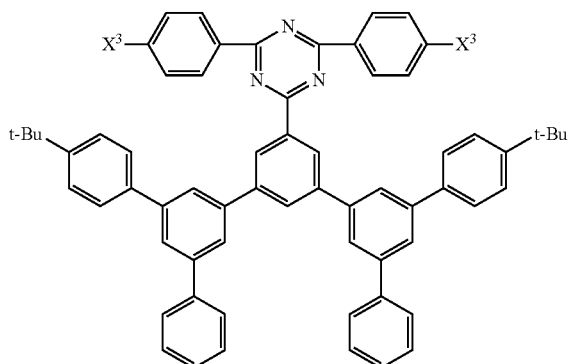
M3B-010
MB3-011
M3B-012
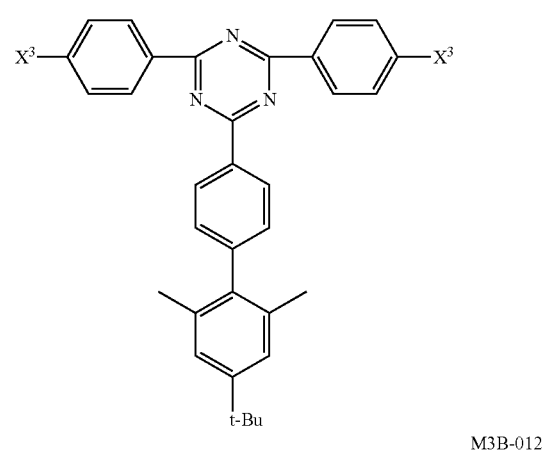
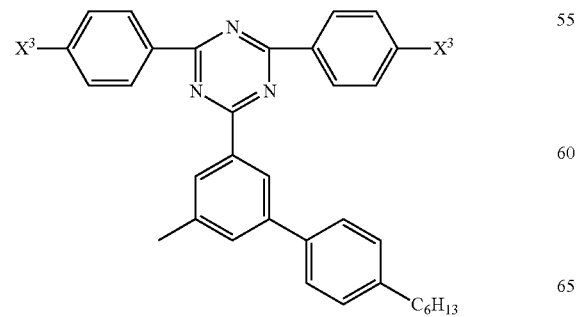
M3B-301
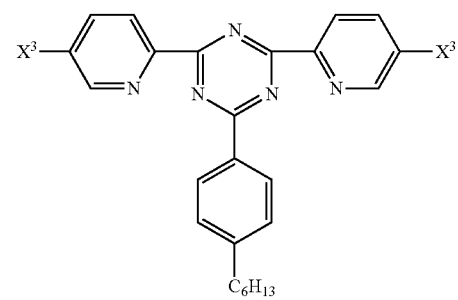
M3B-302
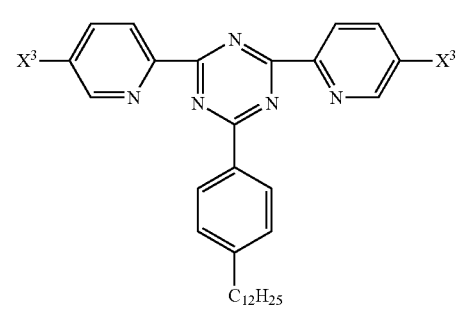
M3B-303
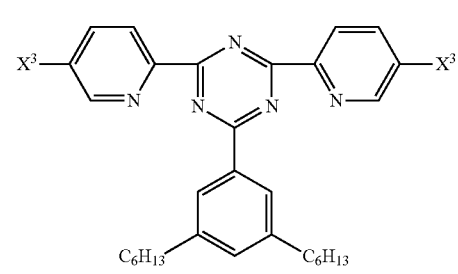
M3B-401
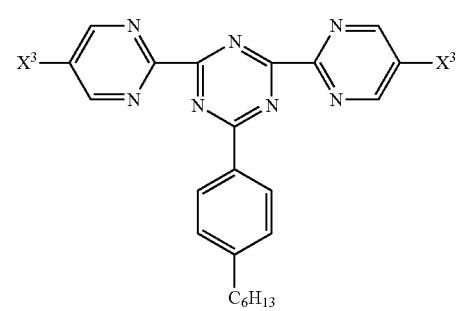
M3B-402
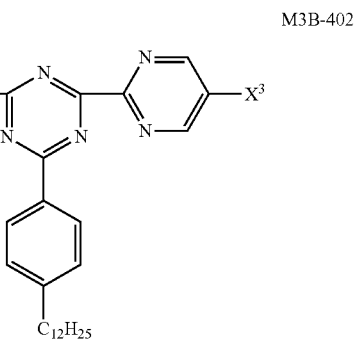

M3B-403
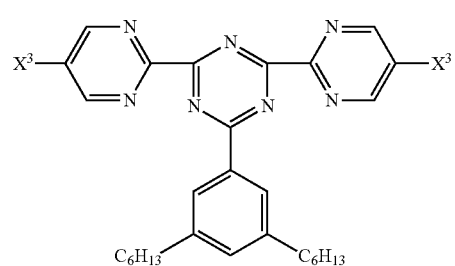
M3CB-001
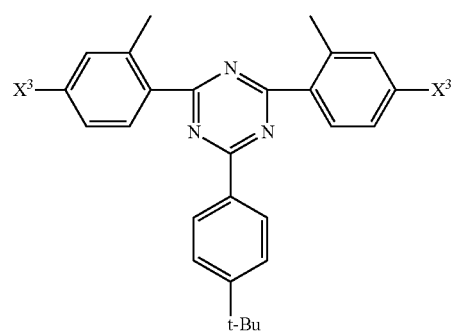
M3C-002
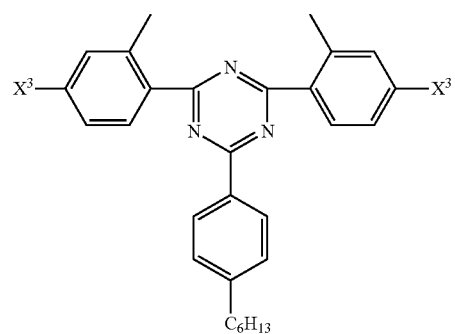
M3C-003
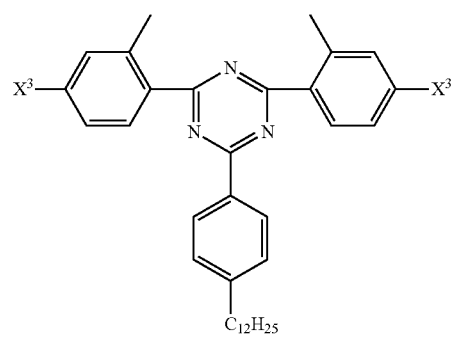
M3C-004
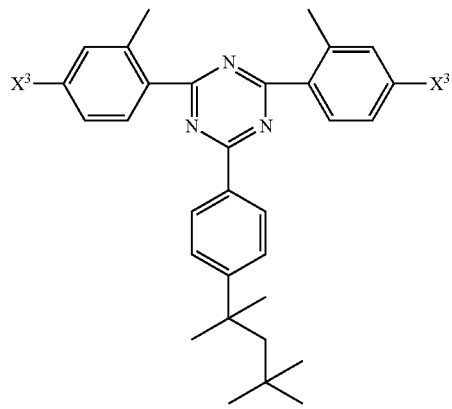
M3C-005
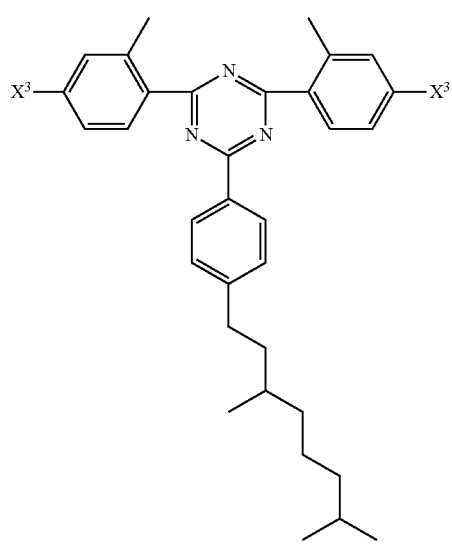
M3C-006
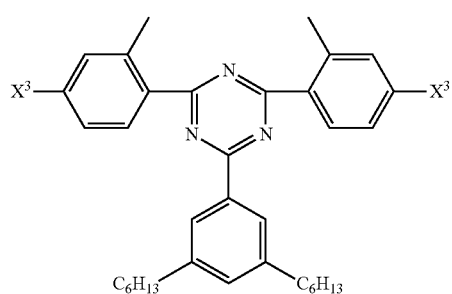
M3C-007
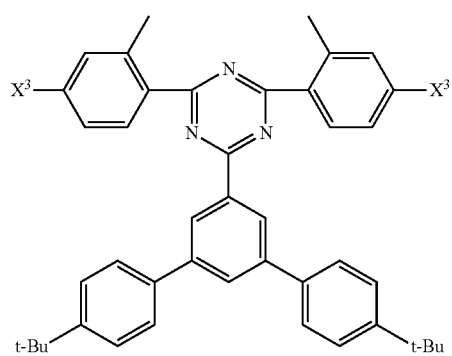

-continued
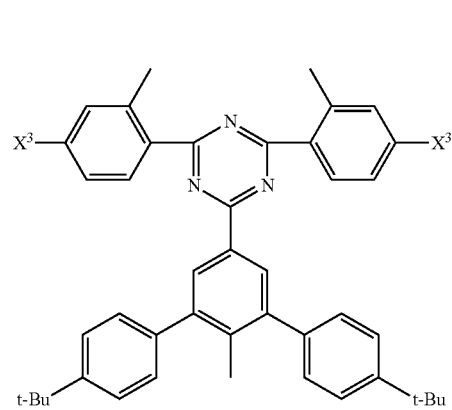
M3C-008
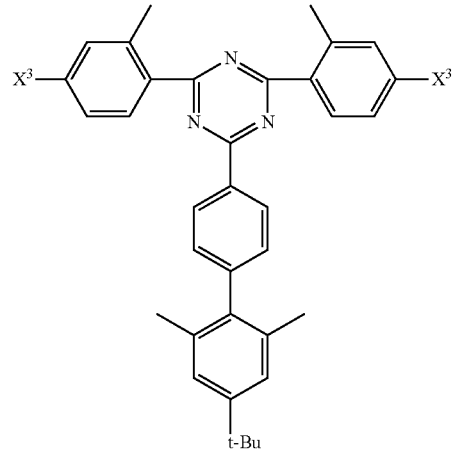
M3C-011
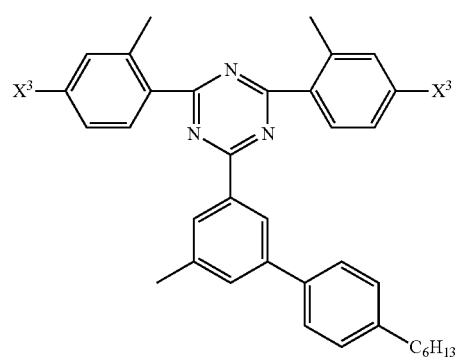
M3C-012
M3C-009
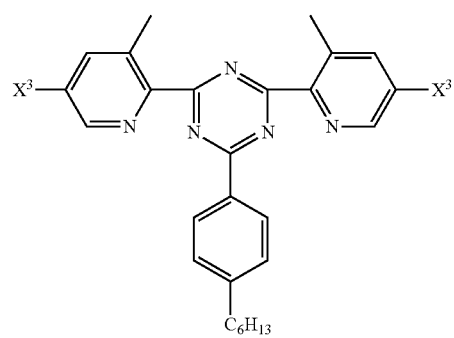
M3C-301
M3C-010
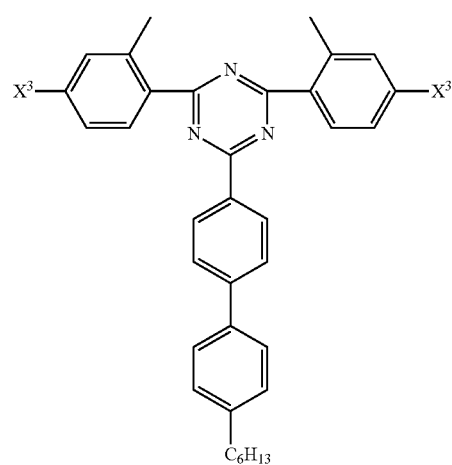
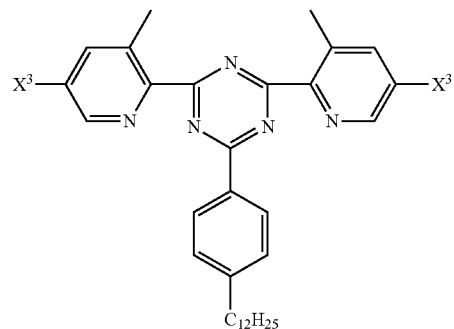
M3C-302

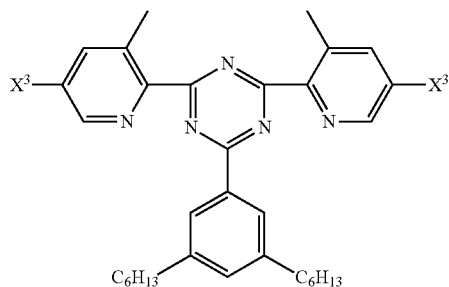

M3C-303

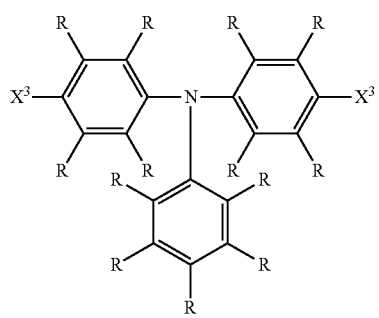

M5-001

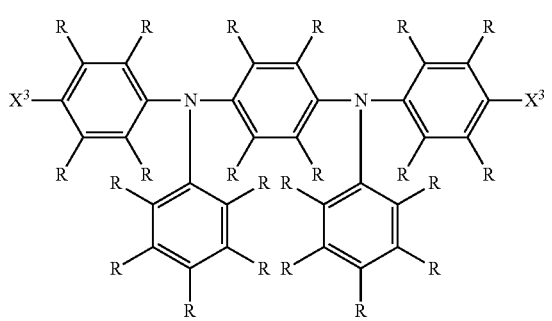

M5-002

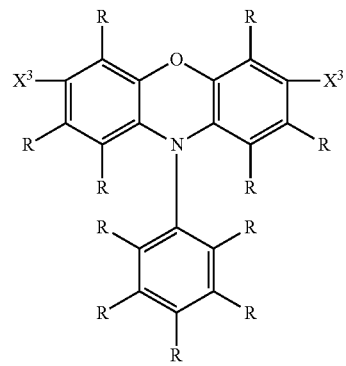

M5-004

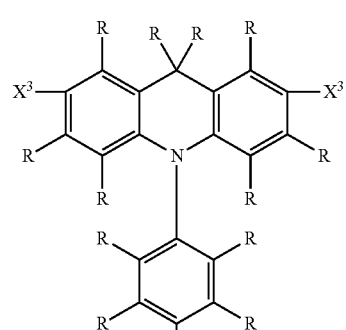

M5-005

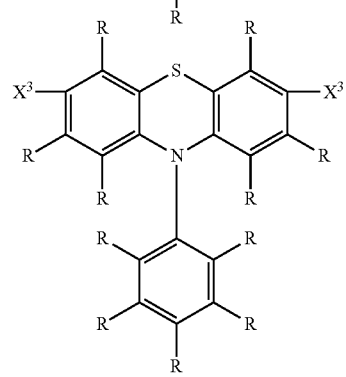

M5-006

Suitable embodiments of the polymer compound of the present invention are exemplified, together with combinations of raw material monomers suitable for producing the polymer compounds, in Table 1.

TABLE 1

| | | | | | | | | |
|---|---|---|---|---|---|---|---|---|
| | M1-301~M1-321 M1-401~M1-403 M1-007~M1-009 M1-110~M1-115 | | M2B-001~M2B-012 M2B-101~M2B-103 M2B-201~M2B-203 M2B-301~M2B-303 M2B-401~M2B-403 M2D-001~M2D-019 M2D-101~M2D-105 | | M3B-001~M3B-012 M3B-301~M3B-303 M3B-401~M3B-403 M3C-001~M3C-012 M3C-301~M3C-303 M5-001~M5-006 | | | |
| Compound | $X^1$: group a v | $X^1$: group b w | $X^2$: group a x | $X^2$: group b y | $X^3$: group a z | $X^3$: group b p | others q |
| EP-1 | 20~50 | 50 | | | | | 0~30 |
| EP-2 | 0.1~49.9 | | 0.1~49.9 | 50 | | | 0~30 |
| EP-3 | 0.1~49.9 | 50 | 0.1~49.9 | | | | 0~30 |
| EP-4 | 0.1~49.9 | 50 | | | 0.1~49.9 | | 0~30 |
| EP-5 | 0.1~49.9 | | | 50 | 0.1~49.9 | | 0~30 |
| EP-6 | 50 | 20~50 | | | | | 0~30 |
| EP-7 | | 0.1~49.9 | 50 | 0.1~49.9 | | | 0~30 |
| EP-8 | 50 | 0.1~49.9 | | 0.1~49.9 | | | 0~30 |

TABLE 1-continued

|  | | M2B-001~M2B-012 | | | | |
| --- | --- | --- | --- | --- | --- | --- |
|  | | M2B-101~M2B-103 | | M3B-001~M3B-012 | | |
|  | | M2B-201~M2B-203 | | M3B-301~M3B-303 | | |
|  | M1-301~M1-321 | M2B-301~M2B-303 | | M3B-401~M3B-403 | | |
|  | M1-401~M1-403 | M2B-401~M2B-403 | | M3C-001~M3C-012 | | |
|  | M1-007~M1-009 | M2D-001~M2D-019 | | M3C-301~M3C-303 | | |
|  | M1-110~M1-115 | M2D-101~M2D-105 | | M5-001~M5-006 | | |
| Compound | $X^1$: group a $v$ | $X^1$: group b $w$ | $X^2$: group a $x$ | $X^2$: group b $y$ | $X^3$: group a $z$ | $X^3$: group b $p$ | others $q$ |
| EP-9 | 50 | 0.1~49.9 | | | | 0.1~49.9 | 0~30 |
| EP-10 | | 0.1~49.9 | 50 | | | 0.1~49.9 | 0~30 |

(in the table, v, w, x, y, z, p and q represent each independently mole fraction. Of them, the mole fraction of raw material monomers represented by the above-described formulae M1-301 to M1-321, M1-401 to M1-403, M1-007 to M1-009 and M1-110 to M1-115 is represented by v and w, the mole fraction of raw material monomers represented by the above-described formulae M2B-001 to M2B-012, M2B-101 to M2B-103, M2B-201 to M2B-203, M2B-301 to M2B-303, M2B-401 to M2B-403, M2D-001 to M2D-019 and M2D-101 to M2D-105 is represented by x and y, the mole fraction of raw material monomers represented by the above-described formulae M3B-001 to M3B-012, M3B-301 to M3B-303, M3B-401 to M3B-403, M3C-001 to M3C-012, M3C-301 to M3C-303 and M5-001 to M5-006 is represented by z and p, and the mole fraction of the other raw material monomers is represented by q. Here, v, w, x, y, z, p and q satisfy $v + w + x + y + z + p + q = 100$ and $100 \geq v + w + x + y + z + p \geq 70$.)

[Composition]

The composition of the present invention comprises the polymer compound of the present invention and at least one material selected from the group consisting of a hole transporting material, an electron transporting material and a light emitting material. The composition of the present invention can be suitably used as a light emitting material, a hole transporting material or an electron transporting material. In the composition of the present embodiment, the polymer compounds of the present invention, hole transporting materials, electron transporting materials and light emitting materials may be used each singly or two or more of each of them may be used in combination.

Regarding the ratio of the composition of the present invention to "at least one material selected from the group consisting of a hole transporting material, an electron transporting material and a light emitting material" in the composition of the present embodiment, when the composition is used as a light emitting material, the proportion of "at least one material selected from the group consisting of a hole transporting material, an electron transporting material and a light emitting material" with respect to 100 parts by weight of the polymer compound of the present invention is preferably 0.01 to 400 parts by weight, more preferably 0.05 to 150 parts by weight, for each material. In the case of a composition containing a phosphorescent compound described later as a light emitting material, the proportion of the phosphorescent compound with respect to 100 parts by weight of the polymer compound of the present invention is preferably 0.01 to 80 parts by weight, more preferably 0.1 to 50 parts by weight, further preferably 1 to 40 parts by weight.

As the hole transporting material, compounds known as a hole transporting material of a light emitting device can be used. Examples thereof include polyvinylcarbazole and derivatives thereof, polysilane and derivatives thereof, polysiloxane derivatives having an aromatic amine structure in the side chain or main chain, pyrazoline derivatives, arylamine derivatives, stilbene derivatives, polyaniline and derivatives thereof, polythiophene and derivatives thereof, polyarylamine and derivatives thereof, polypyrrole and derivatives thereof, poly(p-phenylenevinylene) and derivatives thereof and poly(2,5-thienylenevinylene) and derivatives thereof. These derivatives may have an arylene group and a divalent aromatic heterocyclic group as a copolymerization component.

As the electron transporting material, compounds known as an electron transporting material of a light emitting device can be used. Examples thereof include oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, triaryltriazine and derivatives thereof, polyquinoline and derivatives thereof, polyquinoxaline and derivatives thereof and polyfluorene and derivatives thereof. These derivatives may have an arylene group and a divalent aromatic heterocyclic group as a copolymerization component.

As the light emitting material, compounds known as a light emitting material of a light emitting device can be used, and a phosphorescent compound described later is preferable from the standpoint of obtaining excellent light emission efficiency. As the light emitting material other than the phosphorescent compound, a fluorescent compound can be used. The fluorescent compound includes a small molecule fluorescent material and a polymer fluorescent material. The small molecule fluorescent material has the spectrum peak of fluorescence usually in the wavelength range of 400 to 700 nm. The molecular weight of the small molecule fluorescent material is preferably less than 3000, more preferably 100 to 2000, further preferably 100 to 1000.

As the small molecule fluorescent material, compounds known as a light emitting material of a light emitting device can be used. Examples thereof include dye materials such as naphthalene derivatives, anthracene and derivatives thereof, perylene and derivatives thereof, quinacridone derivatives, xanthene dyes, coumarin dyes, cyanine dyes, triphenylamine derivatives, oxadiazole derivatives, pyrazoloquinoline derivatives, distyrylbenzene derivatives, distyrylarylene derivatives, pyrrole derivatives, thiophene ring compounds, pyridine ring compounds, olligothiophene derivatives and the like; metal complex type materials such as metal complexes having Al, Zn, Be and the like or a rare earth metal such as Tb, Eu, Dy and the like as the center metal and having oxadiazole, thiadiazole, phenylpyridine, phenylbenzoimidazole, quinolone structure or the like as a ligand, such as alumiquinolinol complexes, benzoquinolinolberyllium complexes, benzooxazolyl zinc complexes, benzothiazole zinc complexes, azomethyl zinc complexes, porphyrin zinc complexes, europium complexes and the like.

The polymer fluorescent material includes materials obtained by increasing the molecular weight of the dyes and metal complex type light emitting materials exemplified as the above-described small molecule fluorescent material, such as, for example, polyparaphenylenevinylene derivatives, polythiophene derivatives, polyparaphenylene derivatives, polysilane derivatives, polyacetylene derivatives, polyfluorene derivatives, polyvinylcarbazole derivatives and the like.

[Phosphorescent Compound]

Next, the phosphorescent compound contained in a composition of a suitable embodiment will be explained.

As the phosphorescent compound to be used together with the polymer compound of the present invention, various phosphorescent compounds can be used since the polymer compound of the present invention usually has high $T_1$ energy level, and it is preferable to select a phosphorescent compound having $T_1$ energy level equivalent to or lower than $T_1$ of the polymer compound of the present invention, for obtaining more excellent current efficiency.

More specifically, the $T_1$ energy level of the polymer compound of the present invention (hereinafter, described as "TH") and the $T_1$ energy level of the phosphorescent compound (hereinafter, described as "TM") satisfy preferably the relation of $TH>TM-0.1$ (eV), more preferably the relation of $TH>TM$, further preferably the relation of $TH>TM+0.1$ (eV).

TH of the polymer compound of the present invention can be determined by measuring the phosphorescent spectrum of the polymer compound at 77K. Specifically, if the intensity of the maximum peak wavelength (wavelength of the largest intensity) in the phosphorescent spectrum of the polymer compound measured is 1.0, the value obtained by converting the wavelength at the shortest side showing an intensity of 0.1 into energy is defined as TH. TM of a phosphorescent compound can be determined by measuring the phosphorescent spectrum of the phosphorescent compound at room temperature. Specifically, if the intensity of the maximum peak wavelength (wavelength of the largest intensity) in the phosphorescent spectrum of the phosphorescent compound is 1.0, the value obtained by converting the wavelength at the shortest side showing an intensity of 0.1 into energy is defined as TM.

Examples of the phosphorescent compound to be used together with the polymer compound of the present invention are shown below, but the phosphorescent compound to be used together is not limited to them, and a phosphorescent compound is useful if TH of the polymer compound of the present invention and TM of the phosphorescent compound satisfy the above-described relation.

As the phosphorescent compound, known compounds such as triplet emission complexes and the like can be used, and examples thereof include metal complexes described in Nature, (1998), 395, 151, Appl. Phys. Lett. (1999), 75(1), 4, Proc. SPIE-Int. Soc. Opt. Eng. (2001), 4105 (Organic Light-Emitting Materials and Devices IV), 119, J. Am. Chem. Soc., (2001), 123, 4304, Appl. Phys. Lett., (1997), 71(18), 2596, Syn. Met., (1998), 94(1), 103, Syn. Met., (1999), 99 (2), 1361, Adv. Mater., (1999), 11(10), 852, Inorg. Chem., (2003), 42, 8609, Inorg. Chem., (2004), 43, 6513, Journal of the SID 11/1, 161 (2003), WO 2002/066552, WO 2004/020504, WO 2004/020448 and the like.

As the metal complex which is a phosphorescent compound, one in which the proportion of the sum of squares of the orbital coefficients of the outermost d orbital of a central metal with respect to the sum of squares of all atomic orbital coefficients is ⅓ or more is preferably applied from the standpoint of obtaining high emission quantum efficiency (namely, from the standpoint of obtaining excellent light emission efficiency in a light emitting device using the composition of the present embodiment). The metal complex as described above includes, for example, ortho metalated complexes in which the central metal is a transition metal belonging to the period V or the period VI.

The central metal of the metal complex which is a phosphorescent compound includes metals having an atomic number of 50 or more, showing spin-orbital interaction with the complex and which can cause intersystem crossing between the single state and the triplet state, and includes preferably ruthenium(II), rhodium(III), palladium(II), osmium(II), iridium(III) or platinum(II), more preferably platinum(II) or iridium(III), further preferably iridium(III).

As the phosphorescent compound, a phosphorescent compound represented by the following general formula (MM) is preferable.

$$M(L)_{ka}(Z)_{kb} \qquad (MM)$$

In the formula (MM),

M represents a metal atom selected from the group consisting of ruthenium, rhodium, palladium, osmium, iridium and platinum.

L represents a neutral or 1 to 3-valent anionic ligand capable of making polydentate coordination by forming at least two bonds selected from the group consisting of a coordinate bond and a covalent bond between L and a metal atom represented by M. When there are a plurality of L, these may be mutually the same or different.

Z represents a counter anion. When there are a plurality of Z, these may be mutually the same or different.

ka represents an integer of 1 or more, kb represents an integer of 0 or more. Here, ka+kb are so present as to satisfy the valency of a metal atom M The phosphorescent compound represented by the formula (MM) has totally neutral valency.

M in the formula (MM) is preferably platinum(II) or iridium(III), more preferably iridium(III).

L in the formula (MM) includes a ligand bonding at a nitrogen atom and an oxygen atom to a metal atom by a coordinate bond or a covalent bond such as 8-quinolinol and derivatives thereof, benzoquinolinol and derivatives thereof and the like, a ligand bonding at a nitrogen atom and a carbon atom by a coordinate bond or a covalent bond such as 2-phenyl-pyridine and derivatives thereof and the like, a ligand bonding at an oxygen atom by a coordinate bond or a covalent bond such as acetylacetone and derivatives thereof and the like, a ligand bonding at a nitrogen atom by a coordinate bond such as 2,2'-bipyridyl and derivatives thereof and the like, a ligand bonding at a phosphorus atom and a carbon atom by a coordinate bond or a covalent bond, and the like, and preferable is a ligand bonding at a nitrogen atom and a carbon atom by a coordinate bond or a covalent or a ligand bonding at a nitrogen atom by a coordinate bond, more preferable is a monoanionic ortho metalated ligand bonding at a nitrogen atom and a carbon atom by a coordinate bond or a covalent bond or a 2-valent or 3-valent ortho metalated ligand formed by mutually bonding the monoanionic ortho metalated ligands, further preferable is a monoanionic ortho metalated ligand bonding at a nitrogen atom and a carbon atom by a coordinate bond or a covalent bond.

L in the formula (MM) may be used singly or two or more ligands L may be used in combination as described above, and when used singly, the phosphorescent compound represented by the formula (MM) is a homoleptic complex, and when two or more ligands are used in combination, the phosphorescent compound represented by the formula (MM) is a heteroleptic complex.

The monoanionic ortho metalated ligand bonding at a nitrogen atom and a carbon atom by a coordinate bond or a covalent bond, which is a preferable example of L in the formula (MM), is exemplified below.

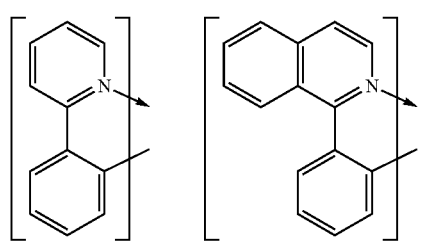

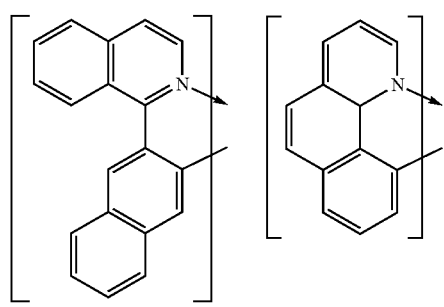

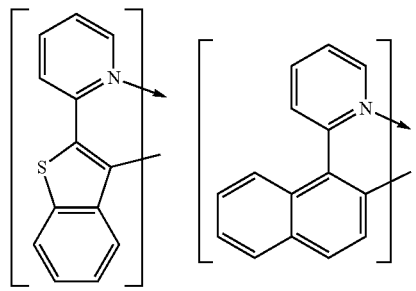

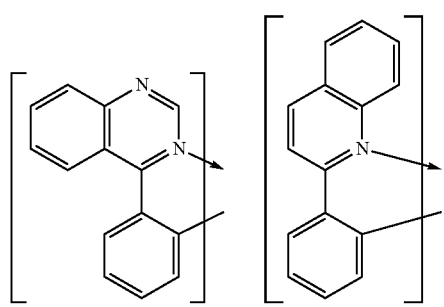

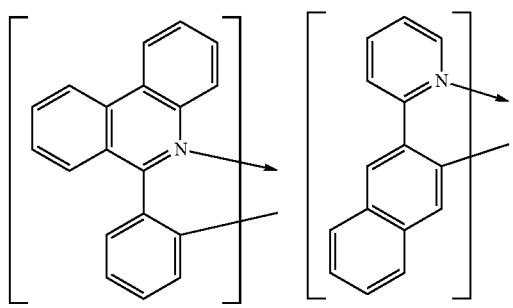

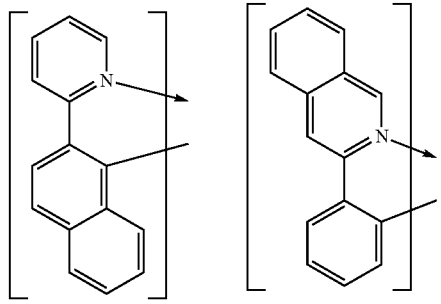

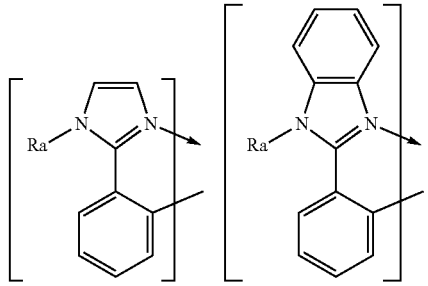

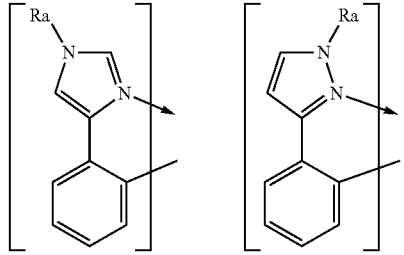

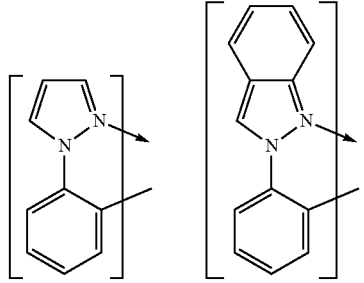

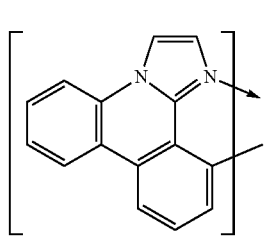

-continued

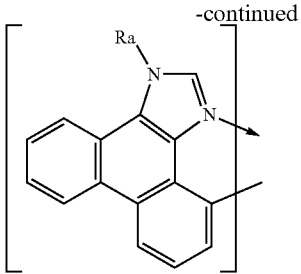

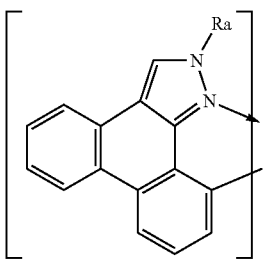

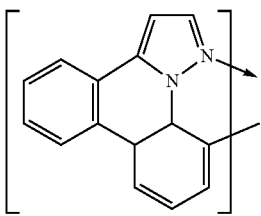

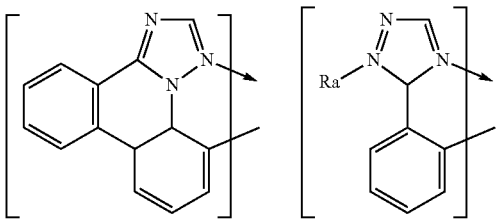

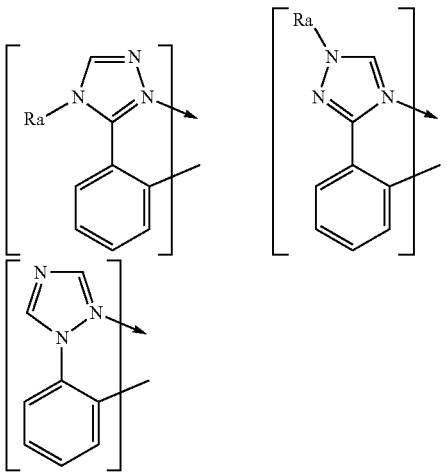

(wherein, Ra represents the same meaning as described above.)

Any hydrogen atom in the monoanionic ortho metalated ligand exemplified above may be substituted with an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom or a cyano group. When there are a plurality of the substituents, these may be the same or different and may be usually linked to form a ring structure together with an atom to which they are linked.

When a composition composed of the polymer compound of the present invention and a phosphorescent compound is used in production of a light emitting device, the composition is contained in an organic layer constituting the light emitting device, thus, it is preferable that the phosphorescent compound shows high compatibility with the polymer compound of the present invention (namely, phase separation scarcely occurs, and coating film formability is excellent).

In the phosphorescent compound to be used together with the polymer compound of the present invention, it is preferable to introduce a suitable substituent into a ligand held in the phosphorescent compound. As the substituent, an alkyl group, an alkoxy group, an aryl group, a monovalent aromatic heterocyclic group or an aralkyl group is preferable. The total number of atoms other than a hydrogen atom in the substituent is preferably 3 or more, more preferably 5 or more, further preferably 7 or more, particularly preferably 10 or more. It is preferable that the substituents are introduced into all ligands held in the phosphorescent compound. In this case, the substituents may be the same or different for every ligand.

As the above-described substituent, a dendron composed of an aryl group which may have a substituent or a monovalent aromatic heterocyclic group which may have a substituent is preferable. The dendron is a branching structure, and is a regular dendritic branched structure having a branching point at an atom or a ring (dendrimer structure). By introducing a dendron as a substituent into a ligand, the phosphorescent compound can be a phosphorescent compound having highly-condensed functionality endowed with, for example, functionality such as charge transportability and the like, and effects such as emission color adjustment and the like, in addition to the above-described improvement in coating film formability. A highly branched macro molecule having a dendron as a substituent is called a dendrimer in some cases, and described, for example, in WO 02/066575, WO 02/066552 and WO 02/067343 and designed and synthesized intending various functions.

Typical dendrons are exemplified below.

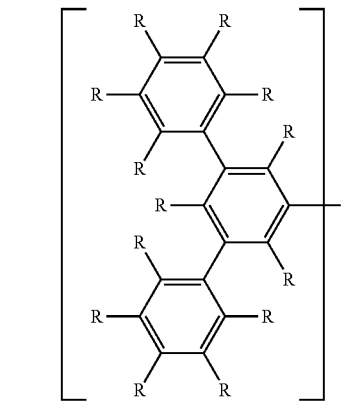

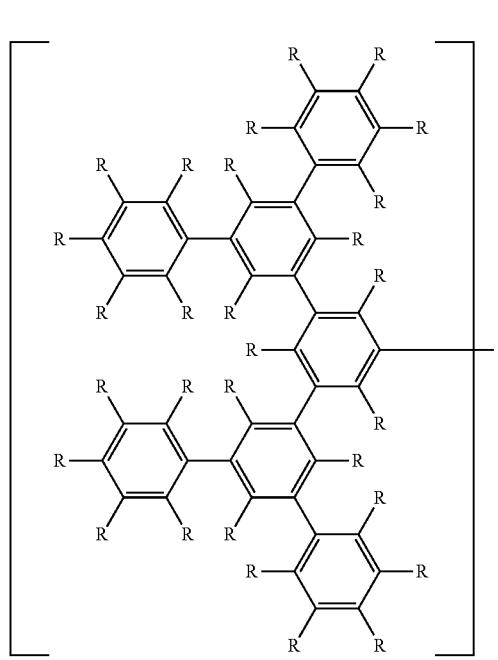
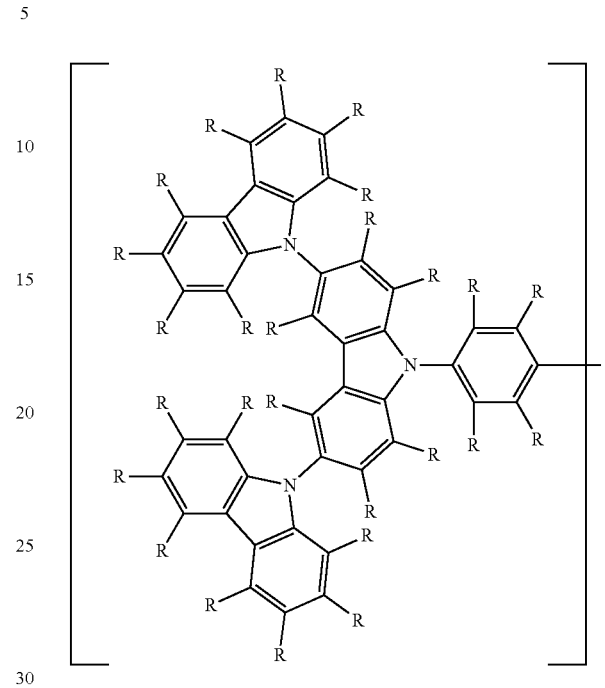
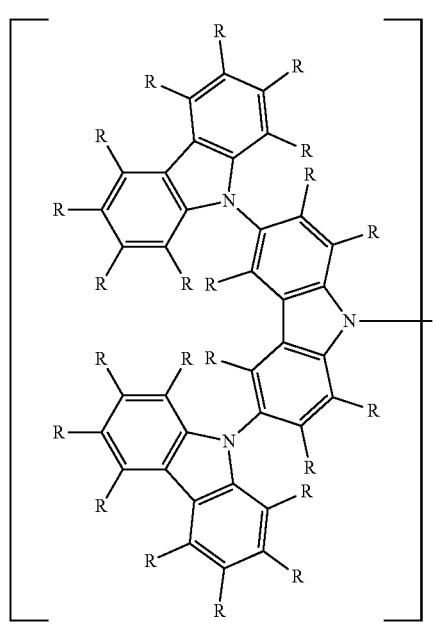
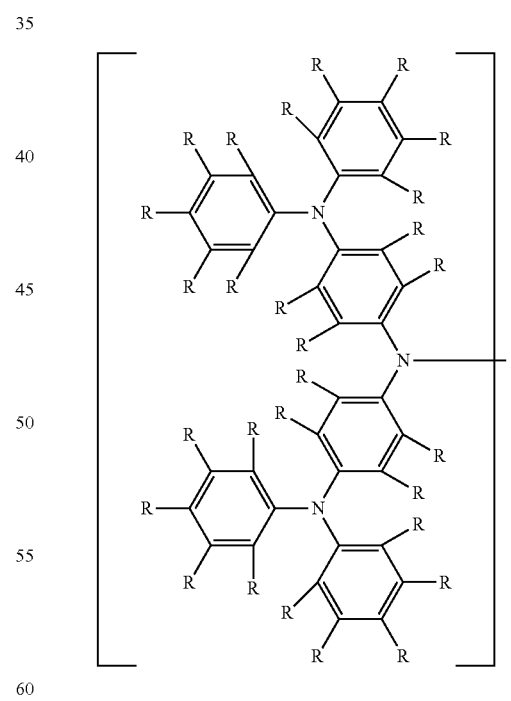

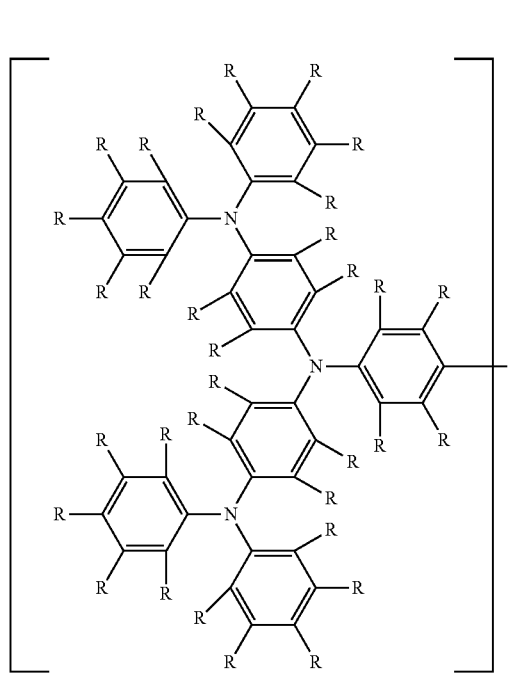
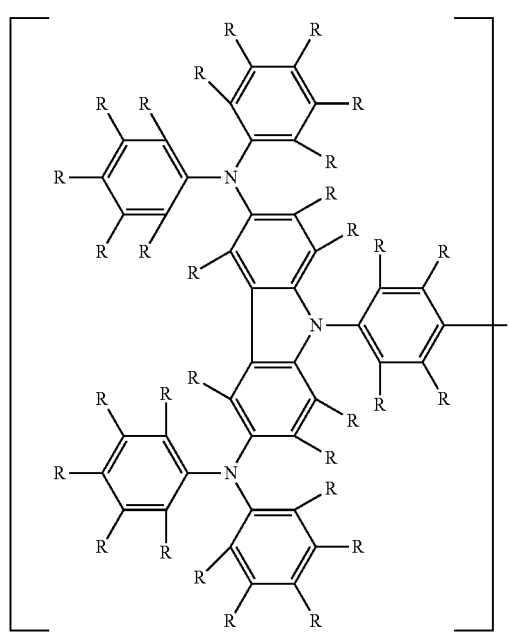
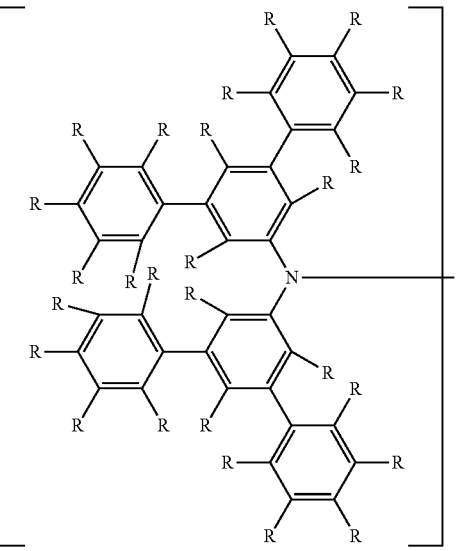
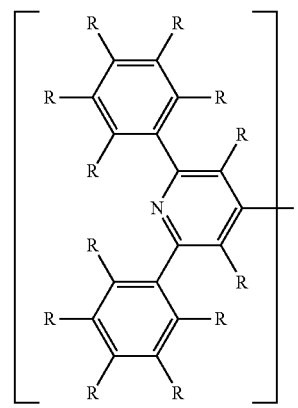
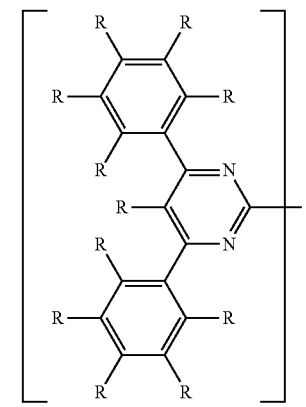

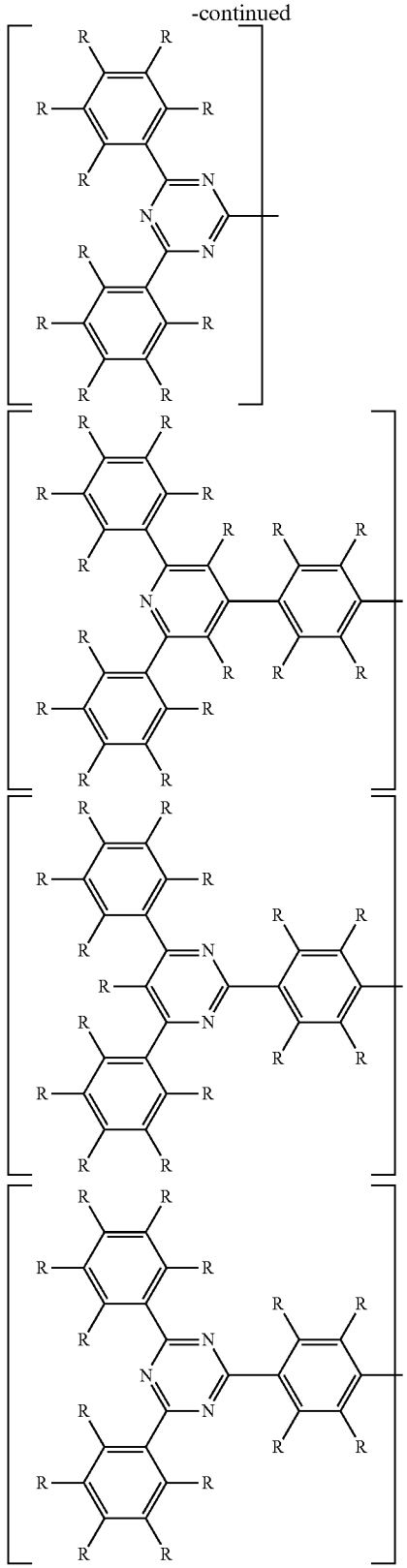

(wherein, R represents the same meaning as described above.)

Z in the formula (MM) includes, for example, conjugated bases of Broensted acids. Examples of the conjugated bases of Broensted acids include a fluoride ion, a chloride ion, a bromide ion, an iodide ion, a sulfate ion, a nitrate ion, a carbonate ion, a perchlorate ion, a tetrafluoroborate ion, a tetrakis(pentafluorophenyl)borate ion, a hexafluorophosphate ion, a methanesulfonate ion and a trifluoroacetate ion.

As the phosphorescent compound represented by the formula (MM), phosphorescent compounds in which M is iridium(III), L is a monoanionic ortho metalated ligand bonding at a nitrogen atom and a carbon atom to M by a coordinate bond or a covalent bond, ka is 3 and kb is 0 are preferable.

The phosphorescent compound represented by the formula (MM) includes preferably phosphorescent compounds represented by the following general formulae (Ir-1) to (Ir-3).

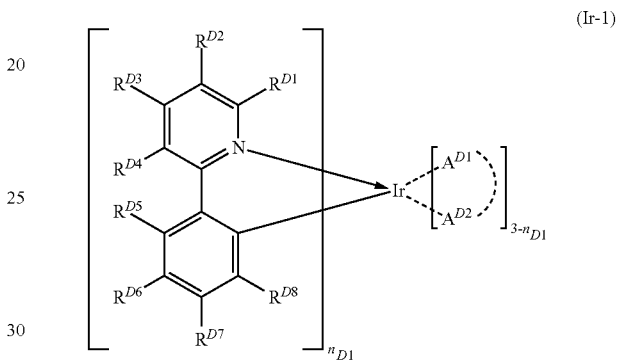

(Ir-1)

[in the formula (Ir-1),
$R^{D1}$, $R^{D2}$, $R^{D3}$, $R^{D4}$, $R^{D5}$, $R^{D6}$, $R^{D7}$ and $R^{D8}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D1}$, $R^{D2}$, $R^{D3}$, $R^{D4}$, $R^{D5}$, $R^{D6}$, $R^{D7}$ and $R^{D8}$ is a group represented by the following general formula (dend-A) or (dend-B).

-$A^{D1}$---$A^{D2}$- represents an anionic bidentate ligand, $A^{D1}$ and $A^{D2}$ represent each independently a carbon atom, an oxygen atom or a nitrogen atom bonding to an iridium atom.

$n_{D1}$ represents 1, 2 or 3.]

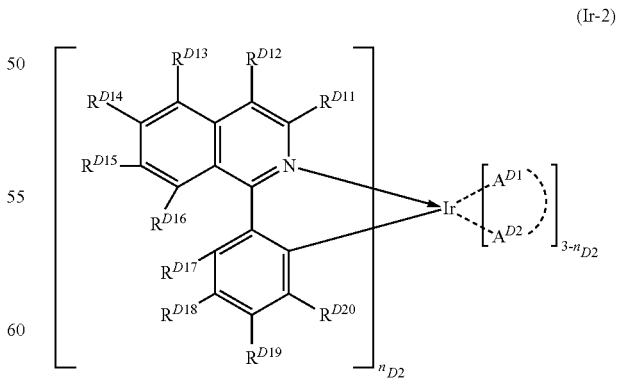

(Ir-2)

[in the formula (Ir-2),
$R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ is a group represented by the following general formula (dend-A) or (dend-B).

-$A^{D1}$---$A^{D2}$- represents an anionic bidentate ligand, $A^{D1}$ and $A^{D2}$ represent each independently a carbon atom, an oxygen atom or a nitrogen atom bonding to an iridium atom.

$n_{D2}$ represents 1, 2 or 3.]

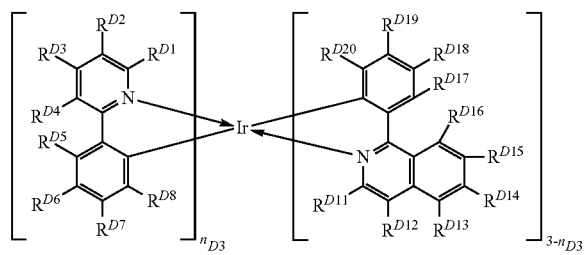

(Ir-3)

[in the formula (Ir-3), $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D1}$, $R^{D2}$, $R^{D3}$, $R^{D4}$, $R^{D5}$, $R^{D6}$, $R^{D7}$, $R^{D8}$, $R^{11}$, $R^{D12}$, $R^{D13}$, $R^{D14}$, $R^{D15}$, $R^{D16}$, $R^{D17}$, $R^{D18}$, $R^{D19}$ and $R^{D20}$ is a group represented by the following general formula (dend-A) or (dend-B).

-$A^{D1}$---$A^{D2}$- represents an anionic bidentate ligand, $A^{D1}$ and $A^{D2}$ represent each independently a carbon atom, an oxygen atom or a nitrogen atom bonding to an iridium atom.

$n_{D3}$ represents 1 or 2.]

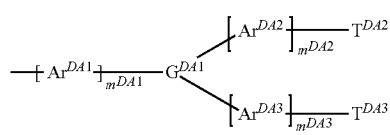

(Dend-A)

[in the formula (Dend-A), $G^{DA1}$ represents a nitrogen atom, a trivalent aromatic hydrocarbon group or a trivalent aromatic heterocyclic group.

$Ar^{DA1}$, $Ar^{DA2}$ and $Ar^{DA3}$ represent each independently an arylene group or a divalent aromatic heterocyclic group.

$T^{DA2}$ and $T^{DA3}$ represent each independently an aryl group or a monovalent aromatic heterocyclic group.

$m^{DA1}$, $m^{DA2}$ and $m^{DA3}$ represent each independently an integer of 0 or more.]

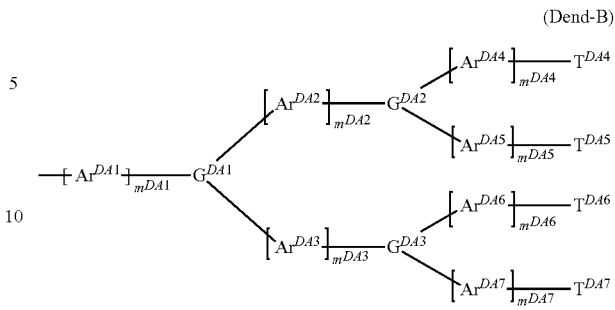

(Dend-B)

[in the formula (Dend-B), $G^{DA1}$, $G^{DA2}$ and $G^{DA3}$ represent each independently a nitrogen atom, a trivalent aromatic hydrocarbon group or a trivalent aromatic heterocyclic group.

$Ar^{DA1}$, $Ar^{DA2}$, $Ar^{DA3}$, $Ar^{DA4}$, $Ar^{DA5}$, $Ar^{DA6}$ and $Ar^{DA7}$ represent each independently an arylene group or a divalent aromatic heterocyclic group.

$T^{DA4}$, $T^{DA5}$, $T^{DA6}$ and $T^{DA7}$ represent each independently an aryl group or a monovalent aromatic heterocyclic group.

$m^{DA1}$, $m^{DA2}$, $m^{DA3}$, $m^{DA4}$, $m^{DA5}$, $m^{DA6}$ and $m^{DA7}$ represent each independently an integer of 0 or more.]

$G^{DA1}$ is preferably a group represented by the following formulae (GDA-11) to (GDA-15). $G^{DA2}$ is preferably a group represented by the following formulae (GDA-21) to (GDA-25). $G^{DA3}$ is preferably a group represented by the following formulae (GDA-31) to (GDA-35).

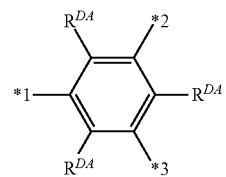

(GDA-11)

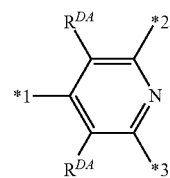

(GDA-12)

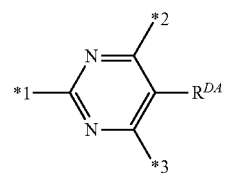

(GDA-13)

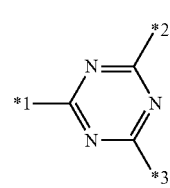

(GDA-14)

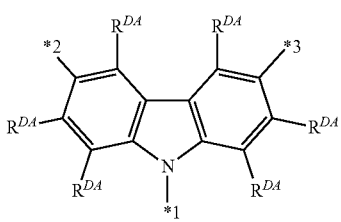
(GDA-15)

[in the formulae,

*1, *2 and *3 represent a linkage to Ar$^{DA1}$, Ar$^{DA2}$ and Ar$^{DA3}$, respectively R$^{DA}$ represents a hydrogen atom, an alkyl group, an alkoxy group, an aryl group or a monovalent aromatic heterocyclic group, and these groups may have a substituent. When there are a plurality of R$^{DA}$, these may be mutually the same or different.]

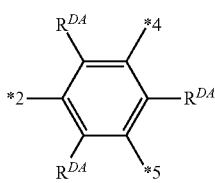
(GDA-21)

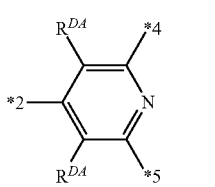
(GDA-22)

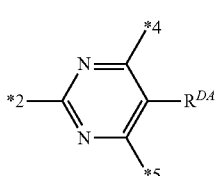
(GDA-23)

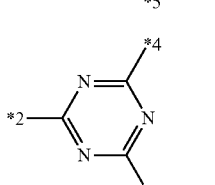
(GDA-24)

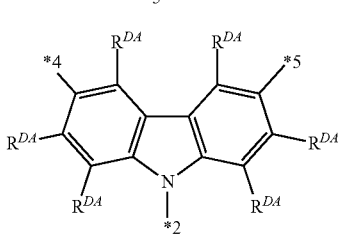
(GDA-25)

[in the formulae,

*2, *4 and *5 represent a linkage to Ar$^{DA2}$, Ar$^{DA4}$ and Ar$^{DA5}$, respectively R$^{DA}$ represents a hydrogen atom, an alkyl group, an alkoxy group, an aryl group or a monovalent aromatic heterocyclic group, and these groups may have a substituent. When there are a plurality of R$^{DA}$, these may be mutually the same or different.]

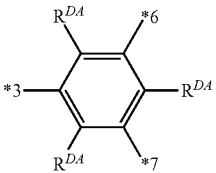
(GDA-31)

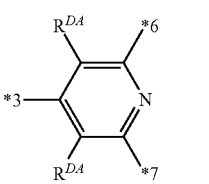
(GDA-32)

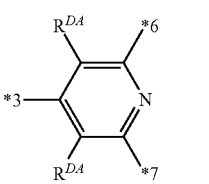
(GDA-33)

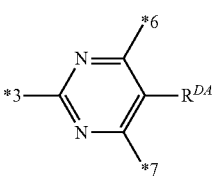
(GDA-34)

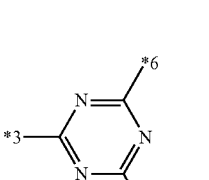

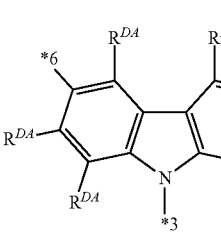
(GDA-35)

[in the formulae,

*3, *6 and *7 represent a linkage to Ar$^{DA3}$, Ar$^{DA6}$ and Ar$^{DA7}$, respectively.

R$^{DA}$ represents a hydrogen atom, an alkyl group, an alkoxy group, an aryl group or a monovalent aromatic heterocyclic group, and these groups may have a substituent. When there are a plurality of R$^{DA}$, these may be mutually the same or different.]

R$^{DA}$ represents preferably a hydrogen atom, an alkyl group or an alkoxy group, more preferably a hydrogen atom or an alkyl group, further preferably a hydrogen atom.

Ar$^{DA1}$, Ar$^{DA2}$, Ar$^{DA3}$, Ar$^{DA4}$, Ar$^{DA5}$, Ar$^{DA6}$ and Ar$^{DA7}$ are preferably a group represented by the following formulae (ArDA-1) to (ArDA-3). When there are a plurality of each of Ar$^{DA1}$, Ar$^{DA2}$, Ar$^{DA3}$, Ar$^{DA4}$, Ar$^{DA5}$, Ar$^{DA6}$ and Ar$^{DA7}$, these may each be mutually the same or different.

(ArDA-1)

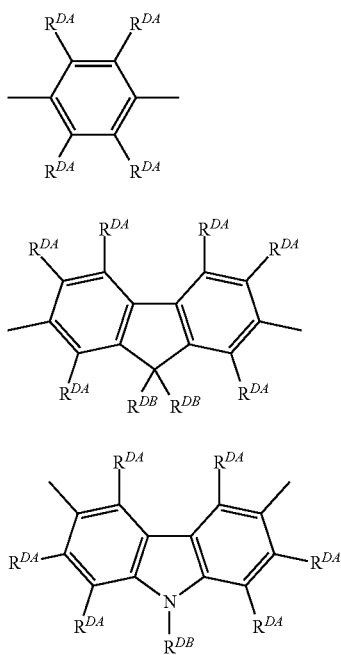

(ArDA-2)

(ArDA-3)

[in the formulae, $R^{DA}$ represents the same meaning as described above.

$R^{DB}$ represents a hydrogen atom, an alkyl group, an alkoxy group, an aryl group or a monovalent aromatic heterocyclic group. When there are a plurality of $R^{DB}$, these may be mutually the same or different.]

$R^{DB}$ represents preferably an alkyl group, an aryl group or a monovalent aromatic heterocyclic group, more preferably an aryl group or a monovalent aromatic heterocyclic group, further preferably an aryl group.

$T^{DA2}$, $T^{DA3}$, $T^{DA4}$, $T^{DA5}$, $T^{DA6}$ and $T^{DA7}$ are preferably a group represented by the following formulae (TD-1) to (TD-3).

(TDA-1)

(TDA-2)

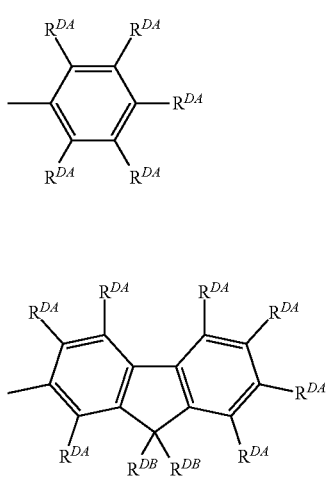

(TDA-3)

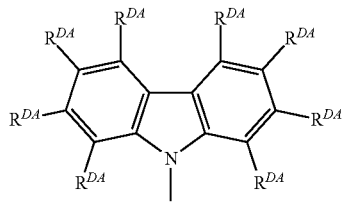

[in the formulae, $R^{DA}$ and $R^{DB}$ represent the same meaning as described above.].

$m^{DA1}$, $m^{DA2}$, $m^{DA3}$, $m^{DA4}$, $m^{DA5}$, $m^{DA6}$ and $m^{DA7}$ represent usually an integer of 10 or less, preferably an integer of 5 or less, more preferably 0 or 1, further preferably 0.

The group represented by the formula (Dend-A) is preferably a group represented by the following formula (Dend-A1), (Dend-A2) or (Dend-A3), more preferably a group represented by the formula (Dend-A1) or (Dend-A3), further preferably a group represented by the formula (Dend-A1).

(Dend-A1)

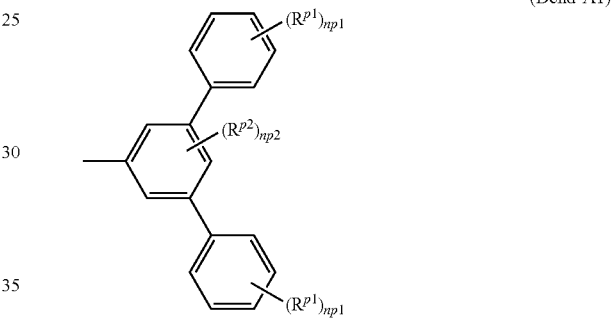

(Dend-A2)

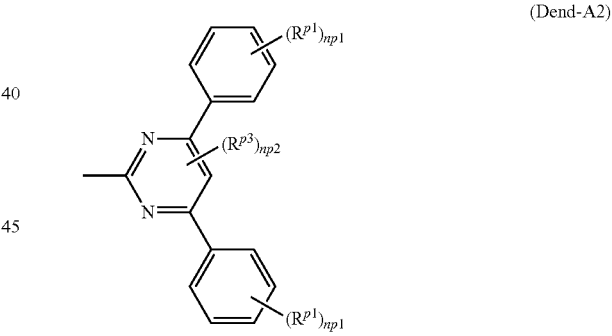

(Dend-A3)

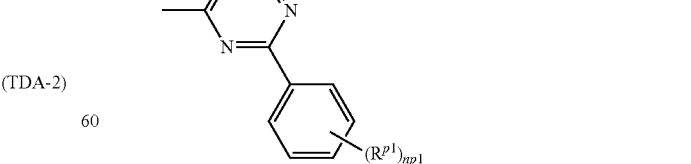

[in the formulae (Dend-A1) to (Dend-A3), $R^{p1}$, $R^{p2}$ and $R^{p3}$ represent each independently an alkyl group, an alkoxy group, an aryl group, an aryloxy group, a monovalent aromatic heterocyclic group or halogen atom.

When there are a plurality of each of $R^{p1}$ and $R^{p2}$, these may each be mutually the same or different.

np1 represents an integer of 0 to 5, np2 represents an integer of 0 to 3, and np3 represents 0 or 1. When there are a plurality of np1, these may be mutually the same or different.]

The group represented by the formula (Dend-B) is preferably a group represented by the following formula (Dend-B1), (Dend-B2) or (Dend-B3), more preferably a group represented by the formula (Dend-B1) or (Dend-B3), further preferably a group represented by the formula (Dend-B1).

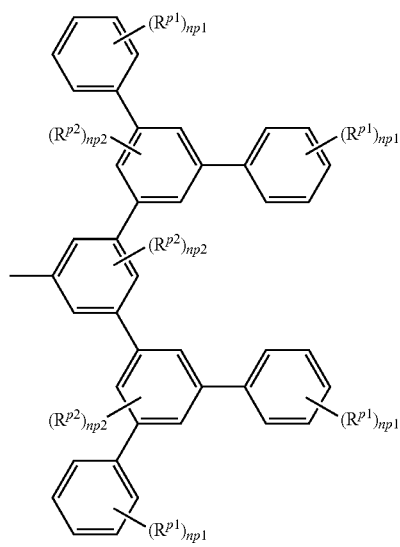

(Dend-B1)

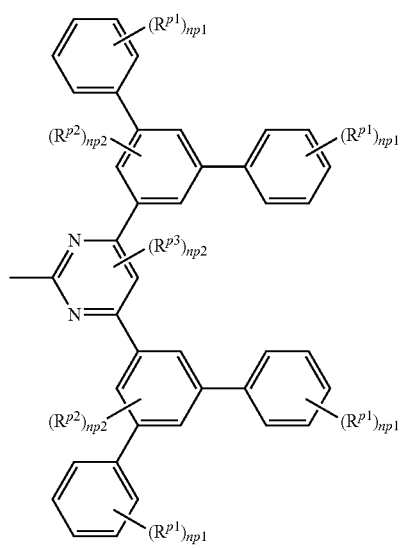

(Dend-B2)

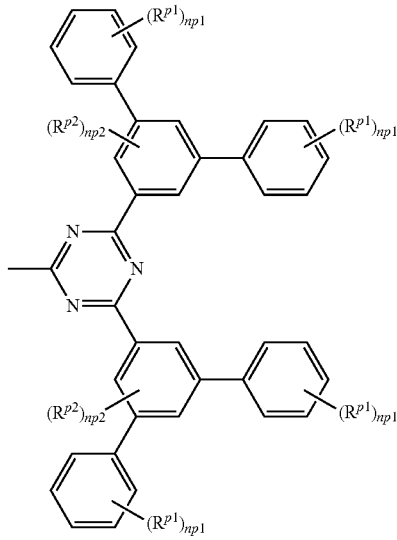

(Dend-B3)

[in the formulae (Dend-B1) to (Dend-B3), $R^{p1}$, $R^{p2}$ and $R^{p3}$ represent each independently an alkyl group, an alkoxy group, an aryl group, an aryloxy group, a monovalent aromatic heterocyclic group or halogen atom. When there are a plurality of each of $R^{p1}$ and $R^{p2}$, these may each be mutually the same or different.

np1 represents an integer of 0 to 5, np2 represents an integer of 0 to 3, and np3 represents 0 or 1. When there are a plurality of each of np1 and np2, these may each be mutually the same or different.]

$R^{p1}$, $R^{p2}$ and $R^{p3}$ represent preferably an alkyl group, an aryl group or a monovalent aromatic heterocyclic group, more preferably an alkyl group.

np1 represents preferably 0 or 1, more preferably 1. np2 represents preferably 0 or 1, more preferably 0. np3 represents preferably 0.

The anionic bidentate ligand represented by -$A^{D1}$---$A^{D2}$- includes, for example, ligands represented by the following formulae.

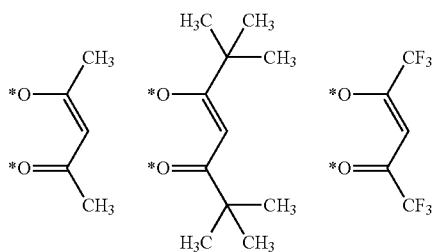

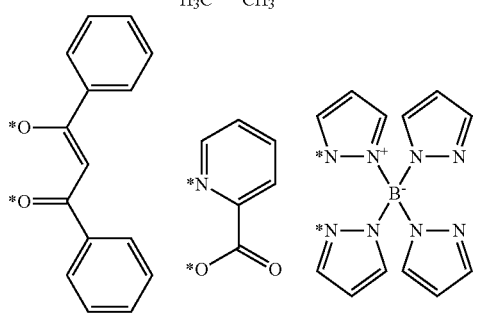

[in the formulae, * represents a bond to an iridium atom.]

The phosphorescent compound represented by the formulae Ir-1 is preferably a phosphorescent compound represented by the following formulae Ir-11 to Ir-13. The phosphorescent compound represented by the formulae Ir-2 is preferably a phosphorescent compound represented by the following formula Ir-21. The phosphorescent compound represented by the formula Ir-3 is preferably a phosphorescent compound represented by the following formulae Ir-31 to Ir-33.

Ir-11
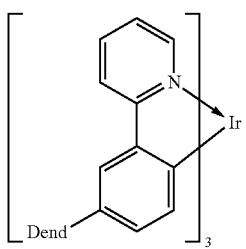

Ir-12
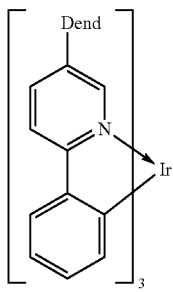

Ir-13
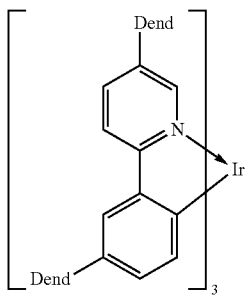

Ir-21
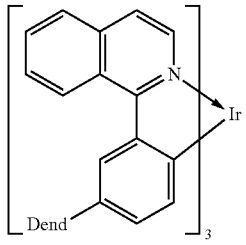

Ir-31
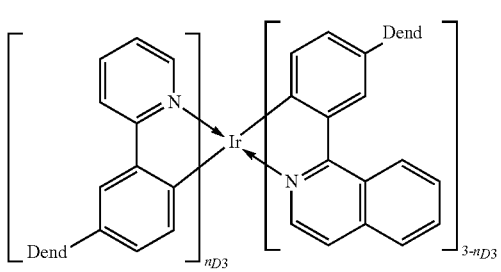

Ir-32
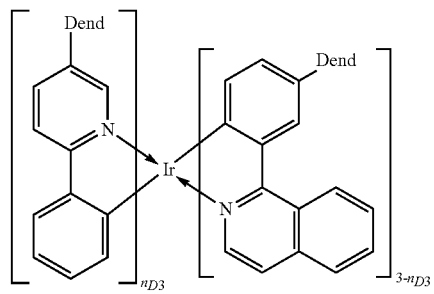

Ir-33
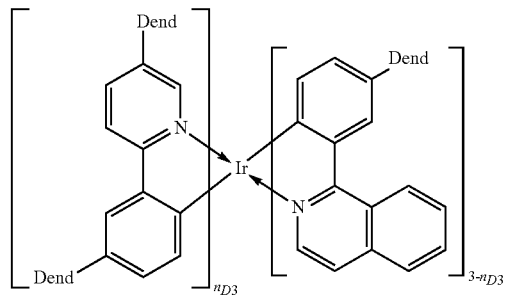

[in the formulae (Ir-11) to (Ir-31), (Ir-21) and (Ir-31) to (Ir-33), Dend represents a group represented by the above-described formula (Dend-A) or (Dend-B). $n_{D3}$ represents the same meaning as described above.]

A composition comprising a phosphorescent compound represented by the formula (Ir-1), (Ir-2) or (Ir-3) and a polymer compound containing as a repeating unit a group represented by the following general formula (IB) is useful for production of a light emitting device excellent in luminance life.

As the phosphorescent compound represented by the formula (MM), compounds represented by the following formulae Ir-1a to Ir-24a, Ir-1b to Ir-29b, Ir-1c to Ir-14c and Ir-1d to Ir-19d are exemplified, and because of more excellent luminance life of alight emitting device using the composition of the present embodiment, compounds represented by the formulae Ir-2a to Ir-6a, Ir-10a to Ir-13a, Ir-17a to Ir-24a, Ir-2b to Ir-6b, Ir-10b to Ir-13b, Ir-18b to Ir-29b, Ir-1c to Ir-14c and Ir-1d to Ir-19d are preferable, compounds represented by the formulae Ir-10a to Ir-13a, Ir-17a to Ir-24a, Ir-10b to Ir-13b, Ir-18b to Ir-29b, Ir-1c, Ir-5c, Ir-8c, Ir-10c to Ir-14c, Ir-1d to Ir-2d, Ir-6d to Ir-12d and Ir-15d to Ir-19d are more preferable. In the following examples, Rp described as a substituent which a dendron portion has is preferably an alkyl group or an alkoxy group, more preferably an alkyl group, and from the standpoint of easiness of synthesis and easiness of dissolution in an organic solvent when the resultant compound is used for fabrication of a light emitting device, alkyl groups such as a tert-butyl group, a hexyl group, an ethylhexyl group and the like are particularly preferable.

Ir-1a 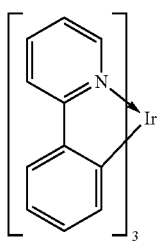
Ir-2a 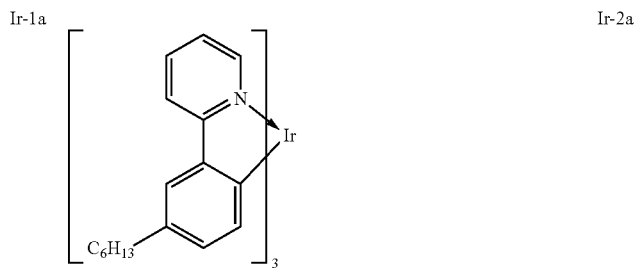
Ir-3a 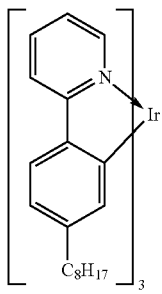
Ir-4a 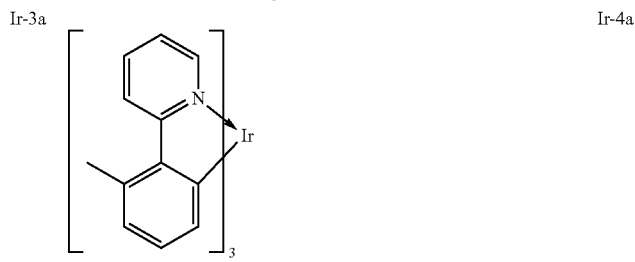
Ir-5a 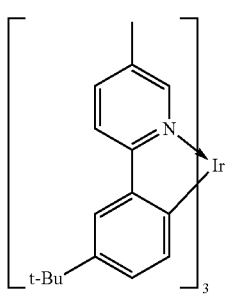
Ir-6a 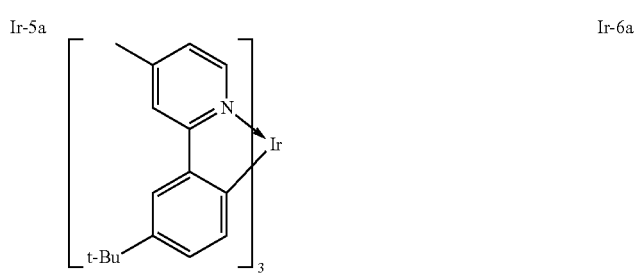
Ir-7a 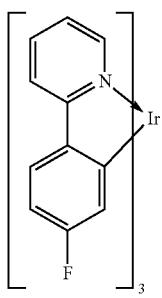
Ir-8a 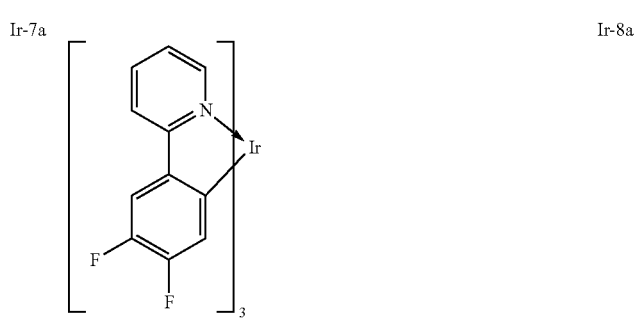
Ir-9a 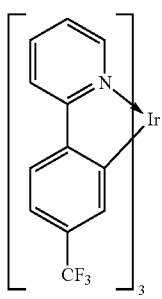
Ir-10a 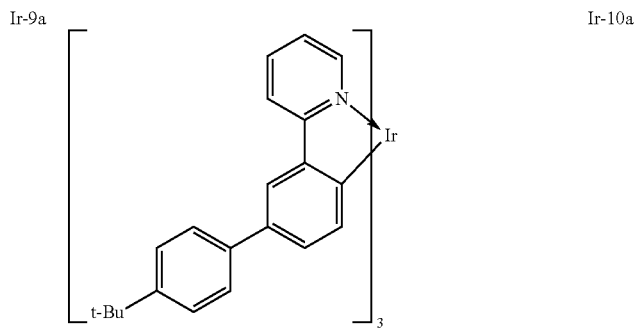

-continued
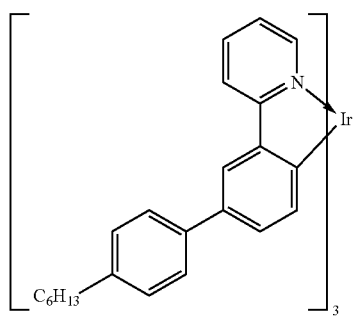
Ir-11a
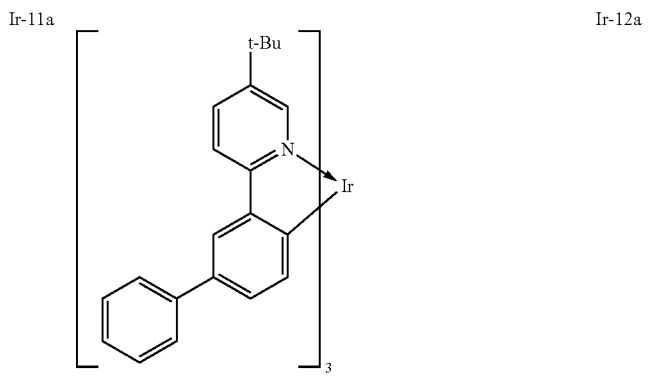
Ir-12a
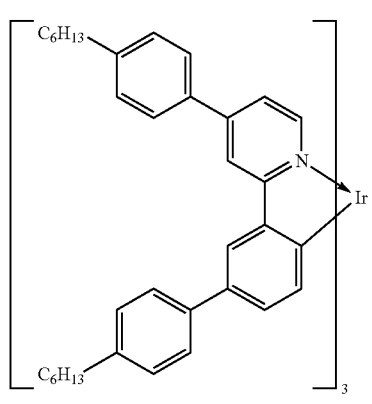
Ir-13a
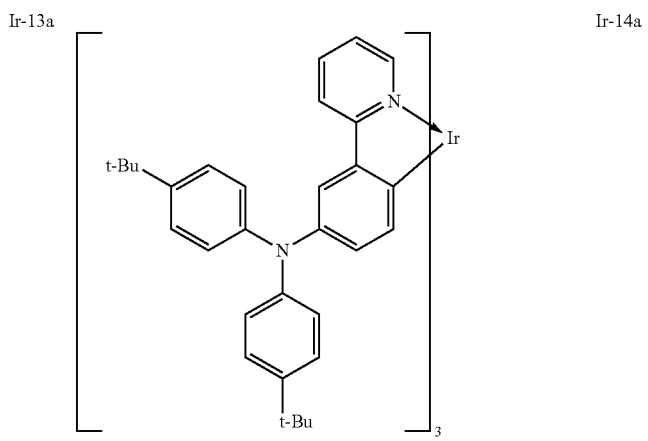
Ir-14a
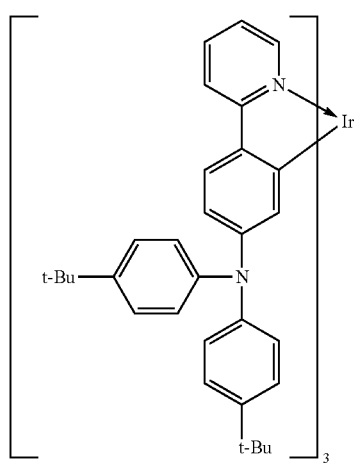
Ir-15a
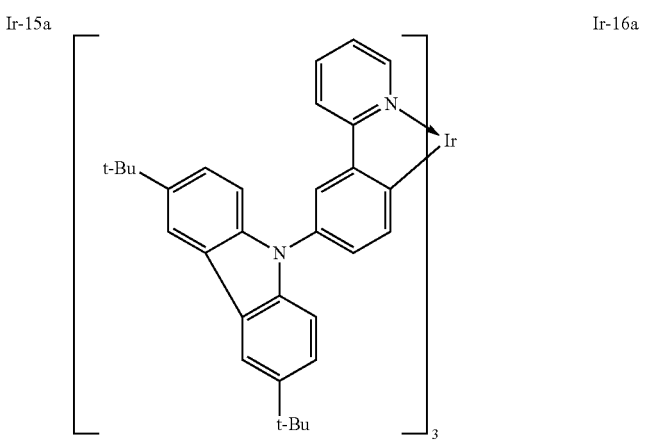
Ir-16a -continued
Ir-17a
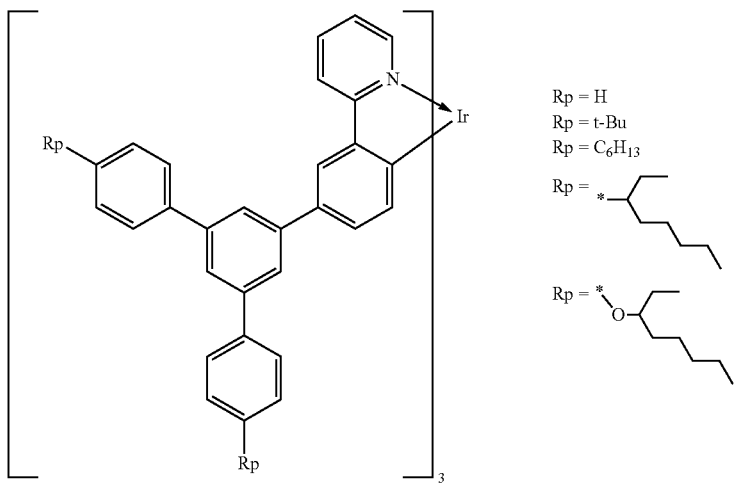
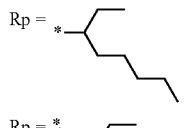
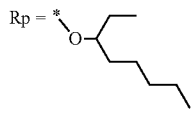
Ir-18a
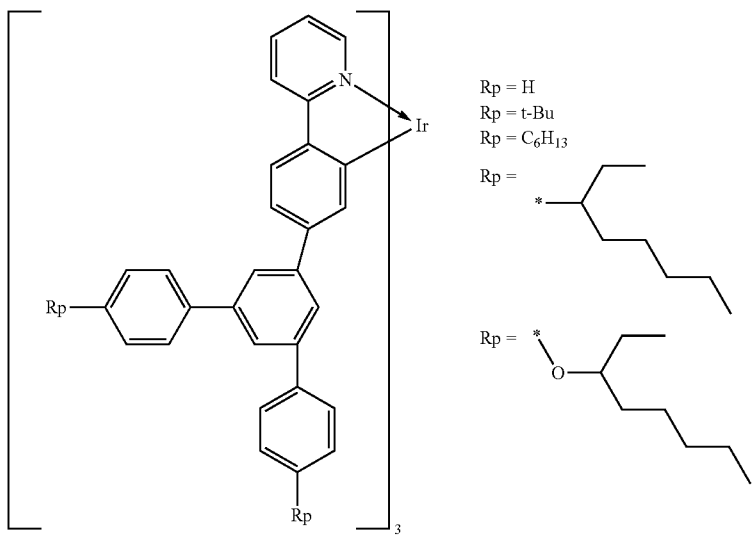
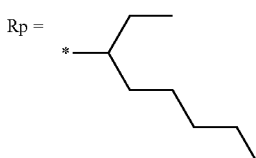
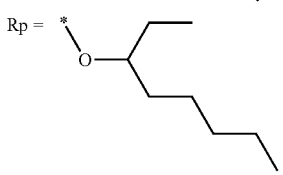
Ir-19a
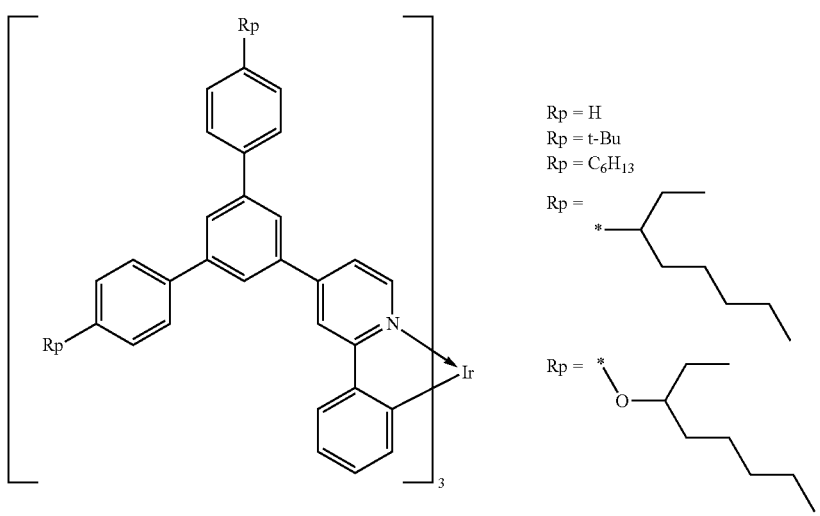
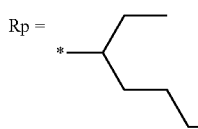
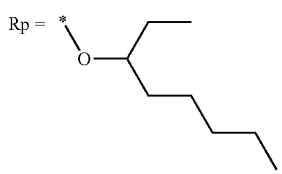

-continued
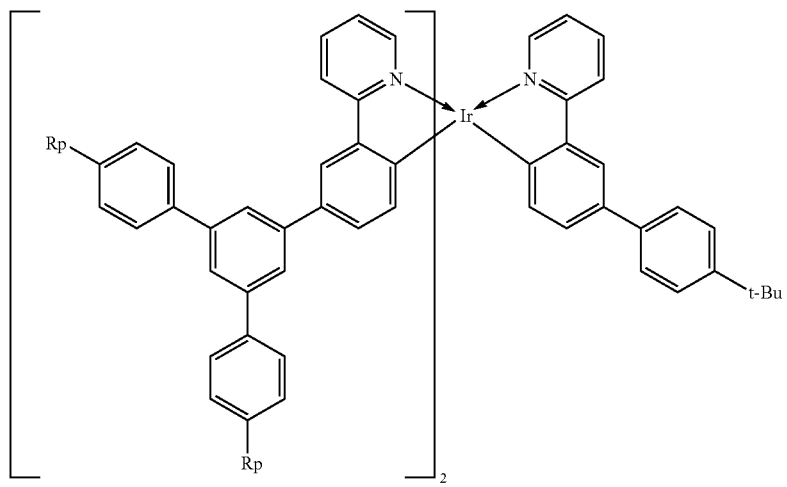
Ir-20a
Rp = H
Rp = t-Bu
Rp = C$_6$H$_{13}$
Rp =
Rp =
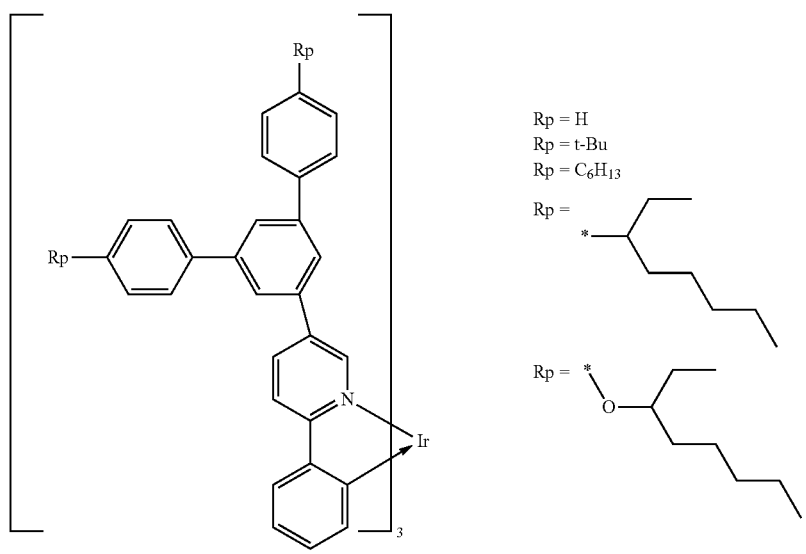
Ir-21a
Rp = H
Rp = t-Bu
Rp = C$_6$H$_{13}$
Rp =
Rp =
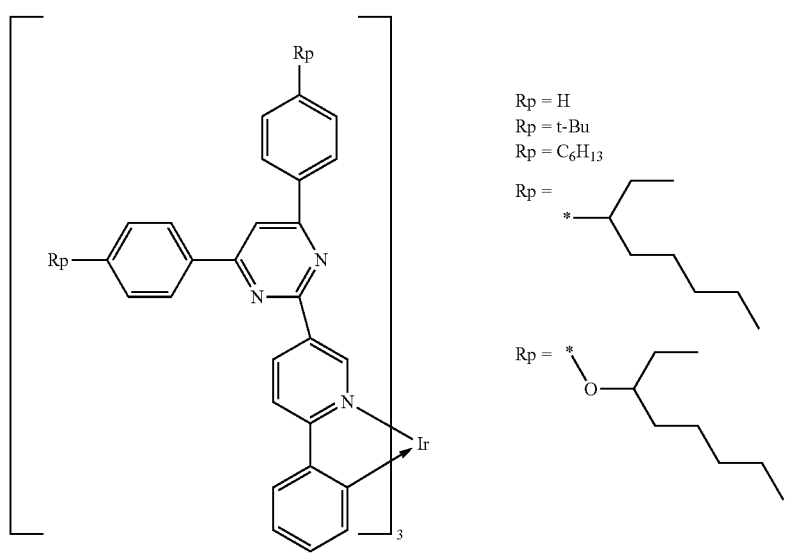
Ir-22a
Rp = H
Rp = t-Bu
Rp = C$_6$H$_{13}$
Rp =
Rp =

-continued
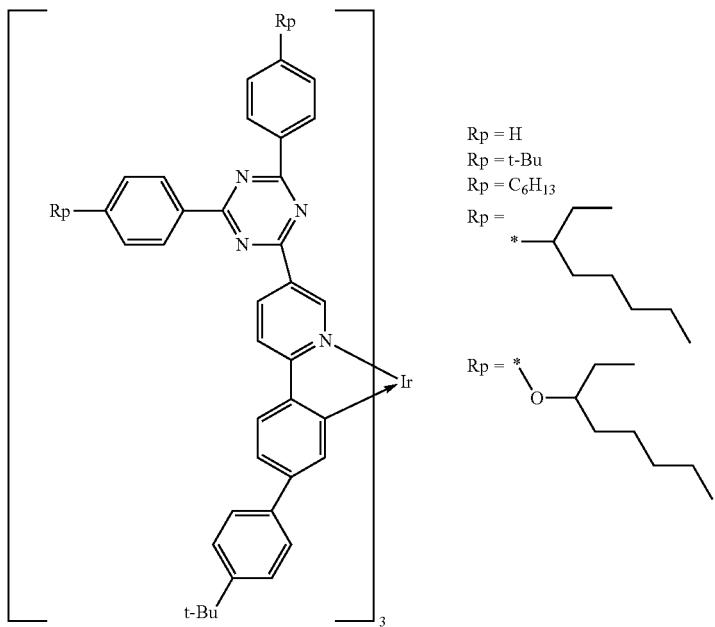
Ir-23a
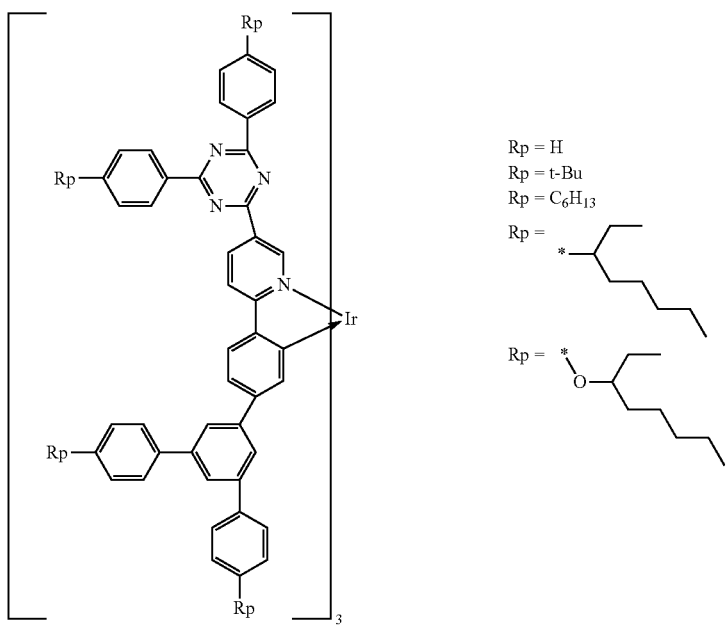
Ir-24a
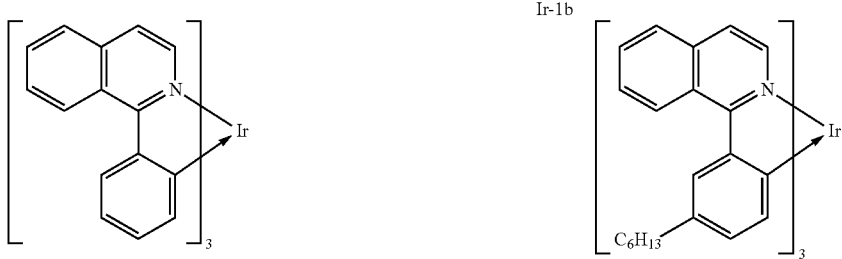

-continued
| | |
|---|---|
| Ir-3b 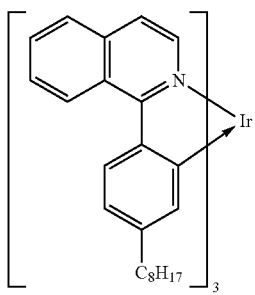 | Ir-4b 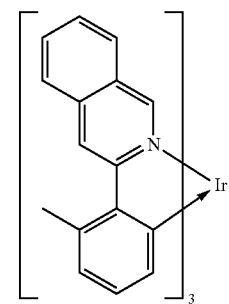 |
| Ir-5b 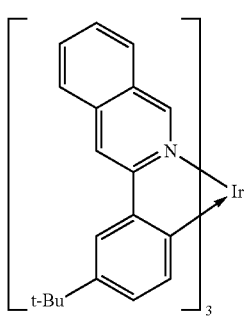 | Ir-6b 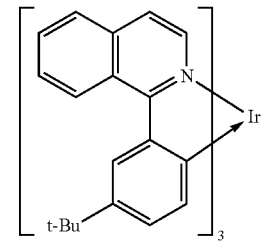 |
| Ir-7b 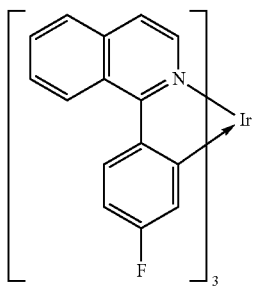 | Ir-8b 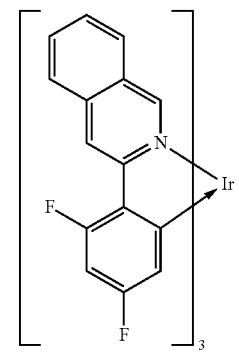 |
| Ir-9b 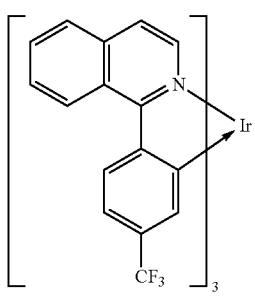 | Ir-10b 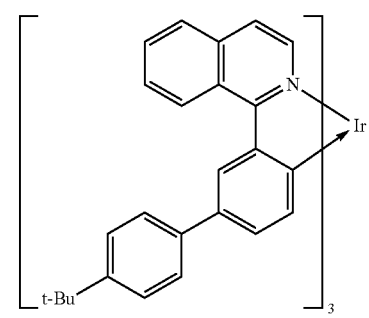 |
| Ir-11b 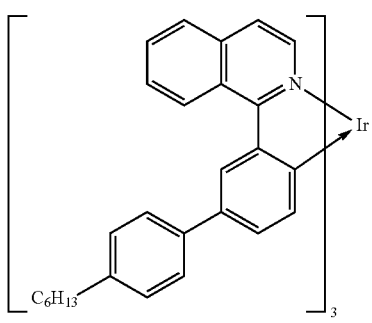 | Ir-12b 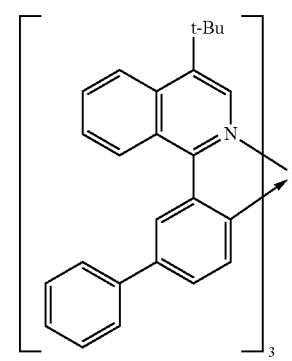 |

-continued
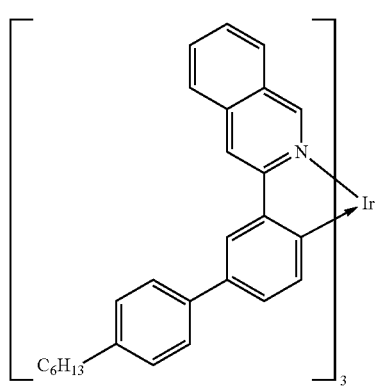
Ir-13b
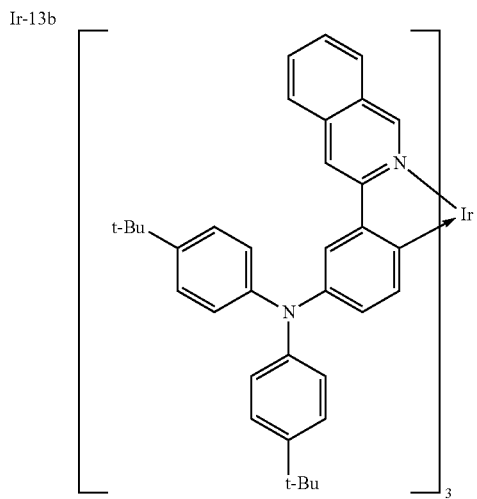
Ir-14b
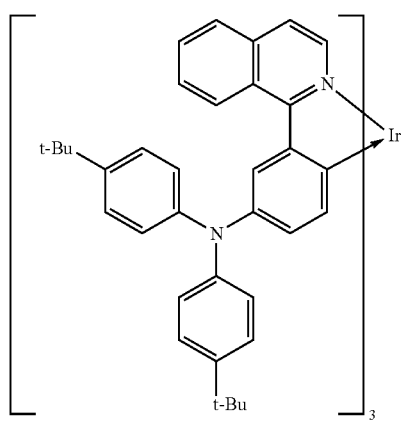
Ir-15b
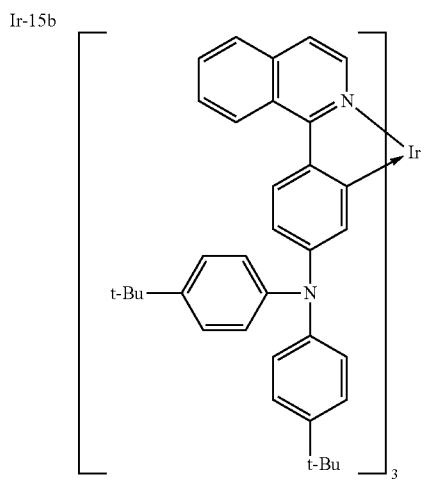
Ir-16b
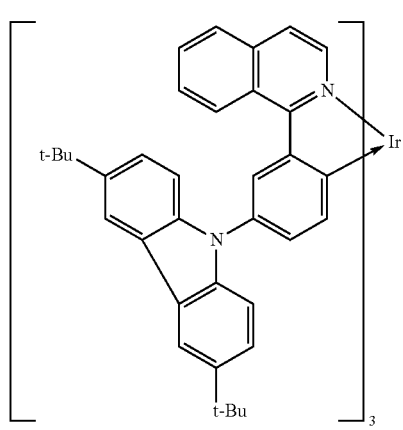
Ir-17b -continued
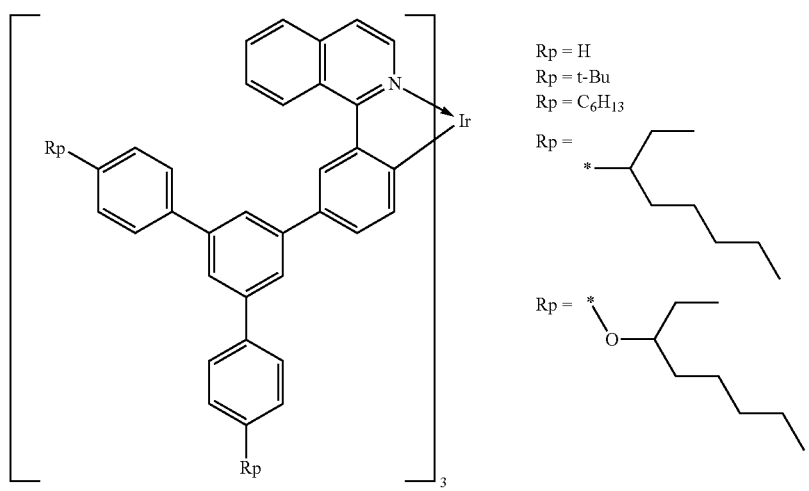
Ir-18a
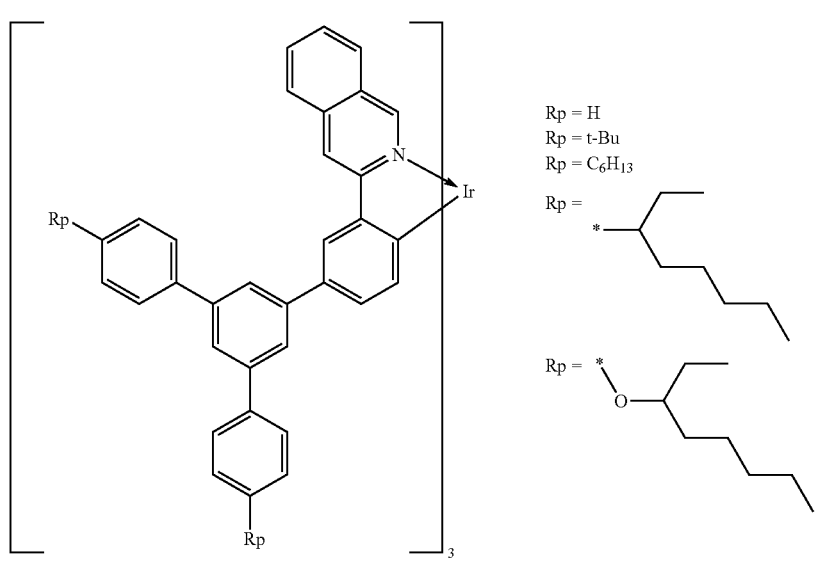
Ir-19b
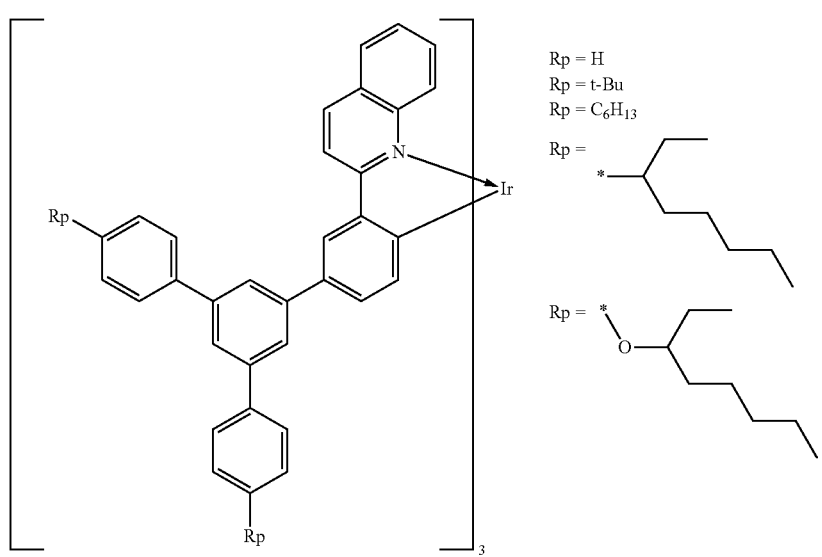
Ir-20b -continued
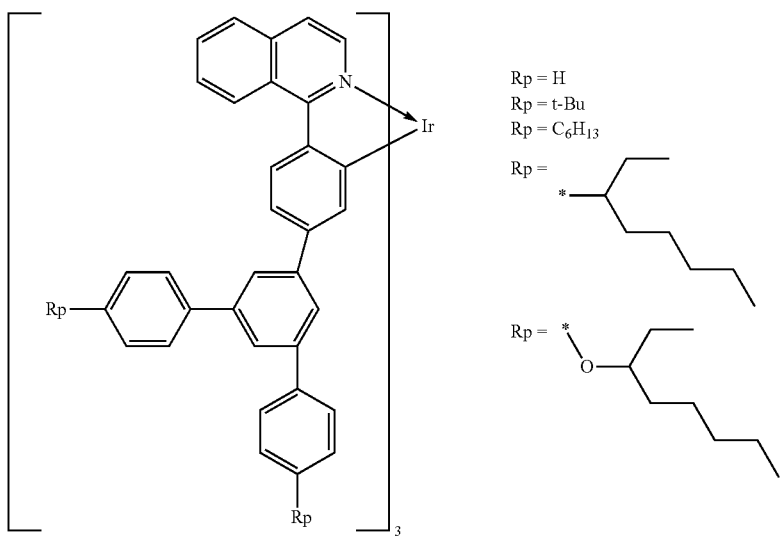
Ir-21b
Rp = H
Rp = t-Bu
Rp = C_6H_{13}
Rp =
Rp =
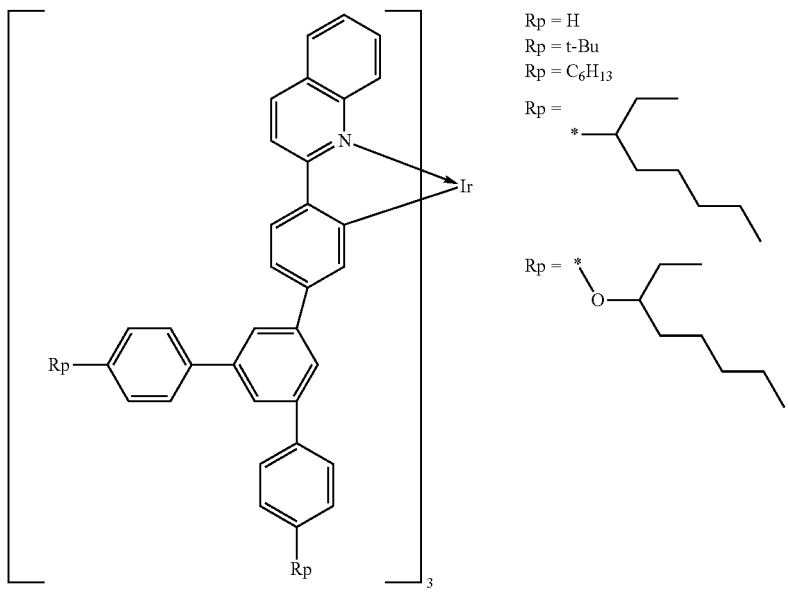
Ir-22b
Rp = H
Rp = t-Bu
Rp = C_6H_{13}
Rp =
Rp =
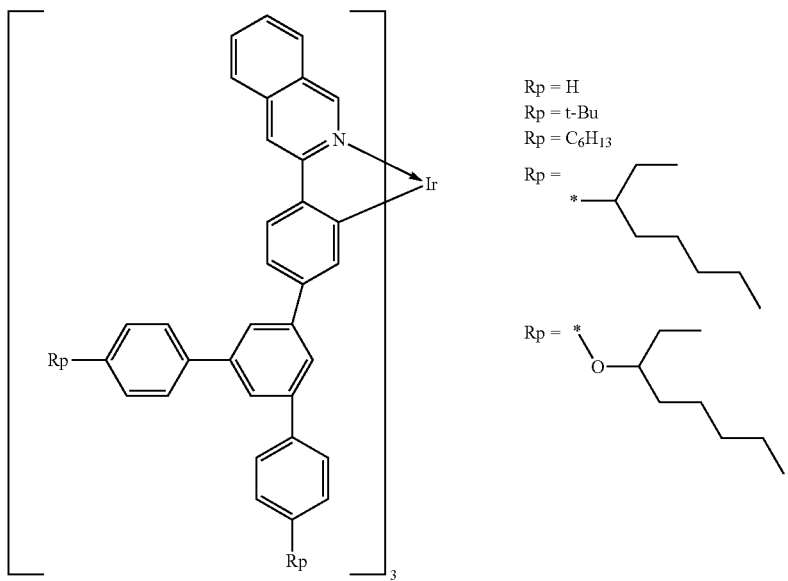
Ir-23b
Rp = H
Rp = t-Bu
Rp = C_6H_{13}
Rp =
Rp =

-continued
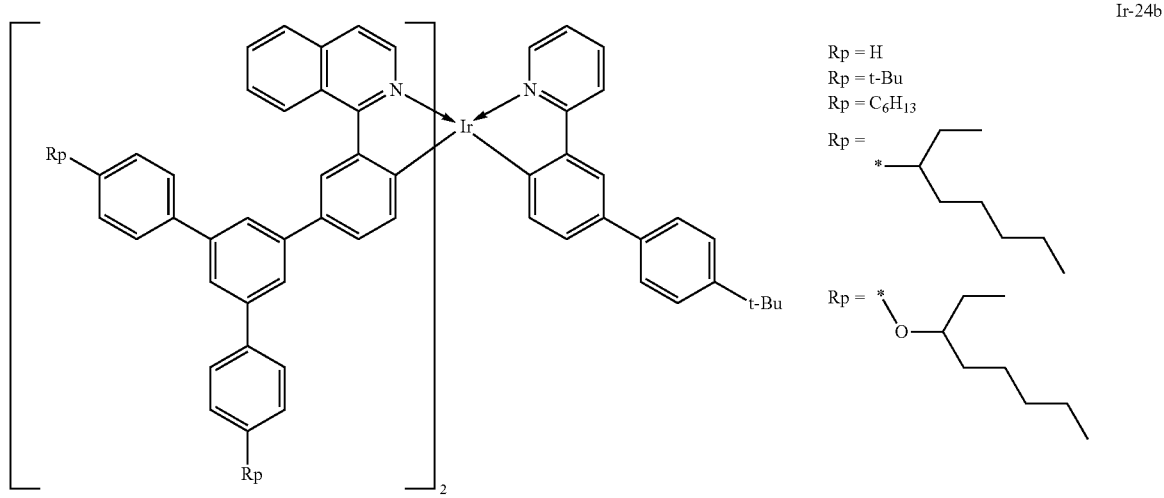
Ir-24b
Rp = H
Rp = t-Bu
Rp = C₆H₁₃
Rp =
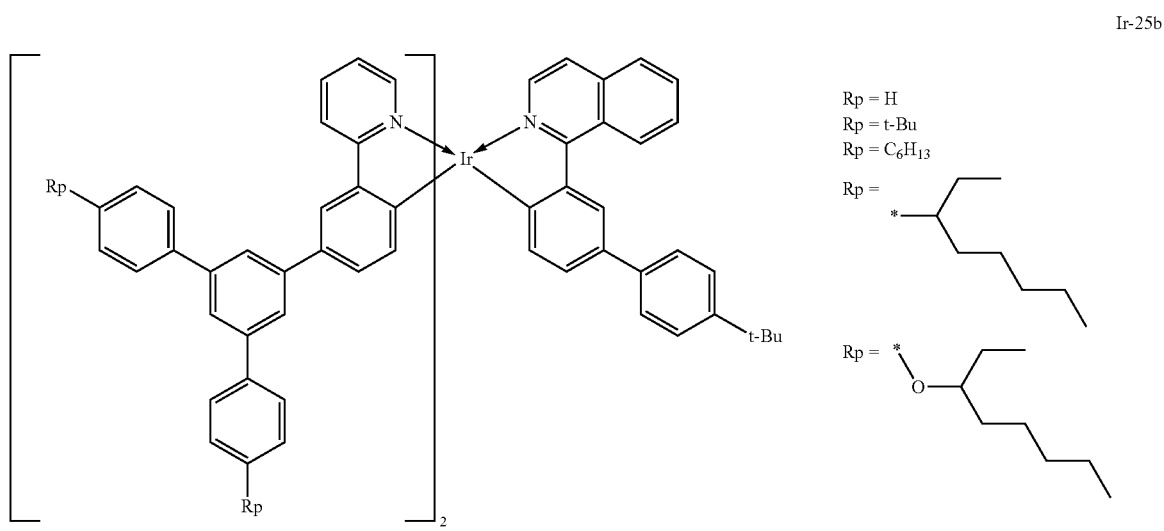
Ir-25b
Rp = H
Rp = t-Bu
Rp = C₆H₁₃
Rp =
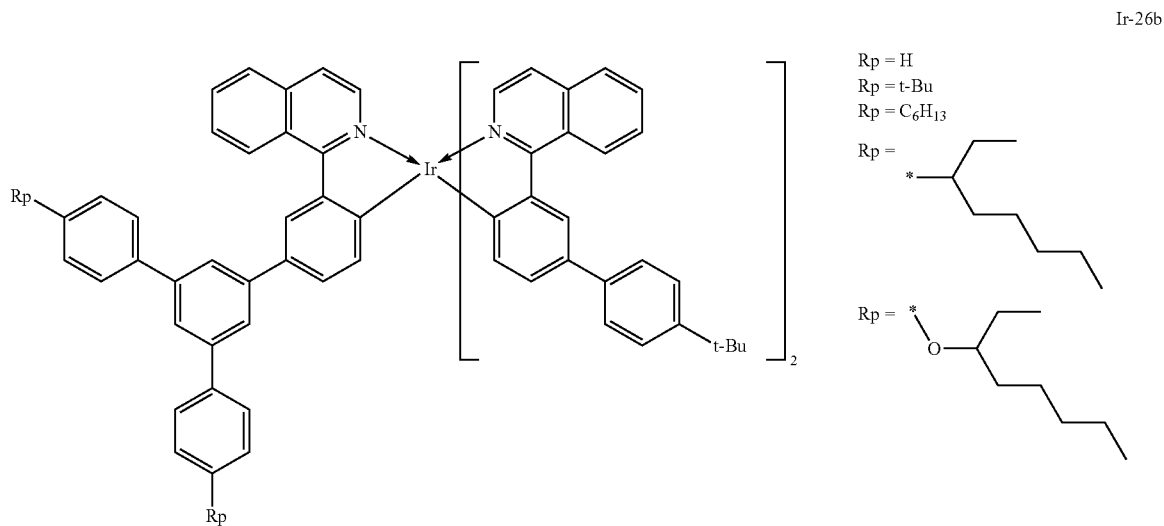
Ir-26b
Rp = H
Rp = t-Bu
Rp = C₆H₁₃
Rp =

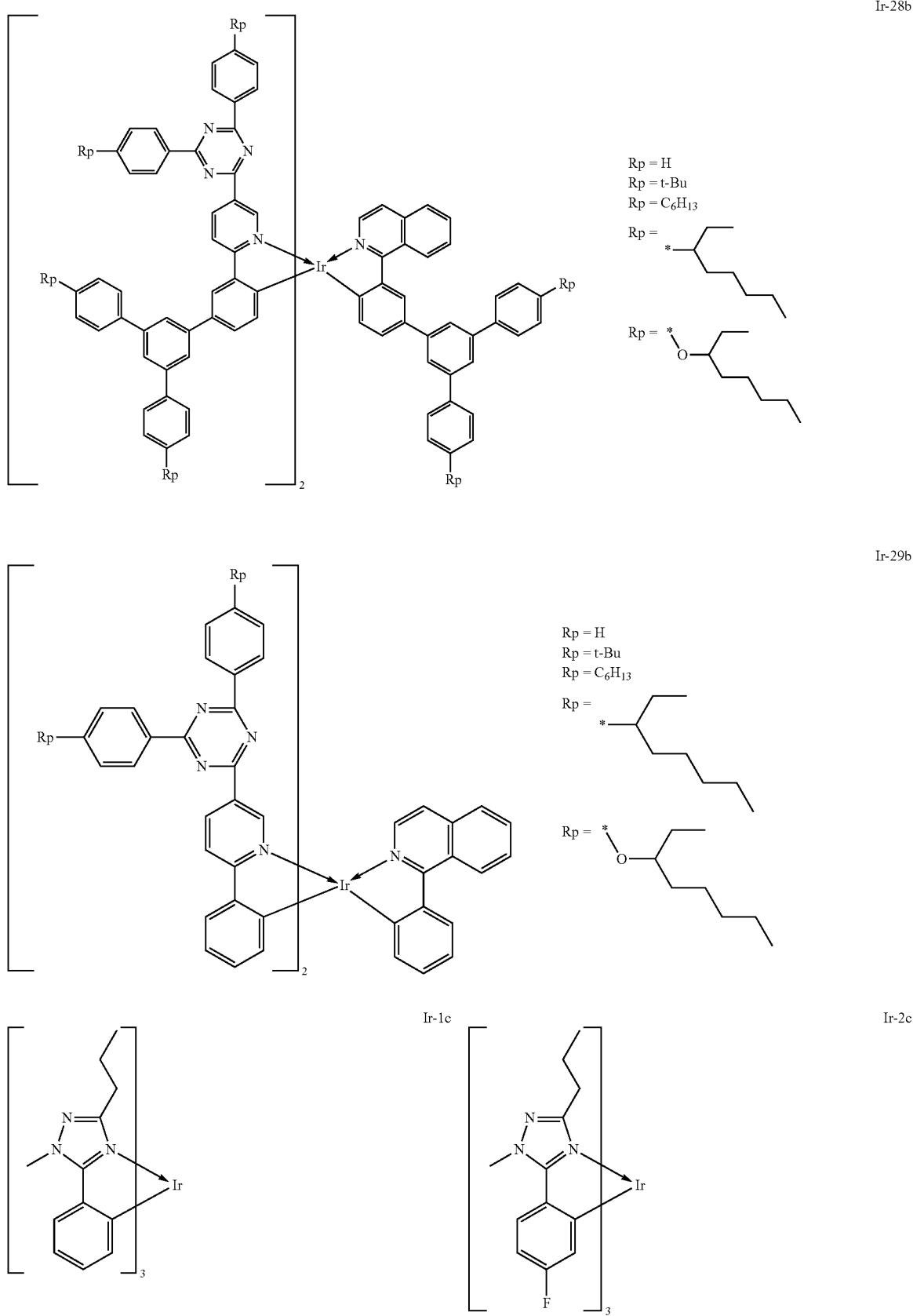

-continued
Ir-3c
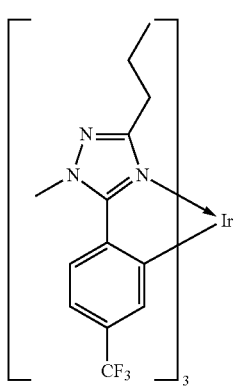
Ir-4c
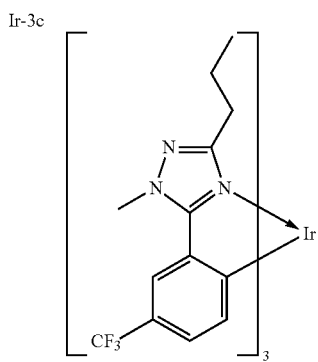
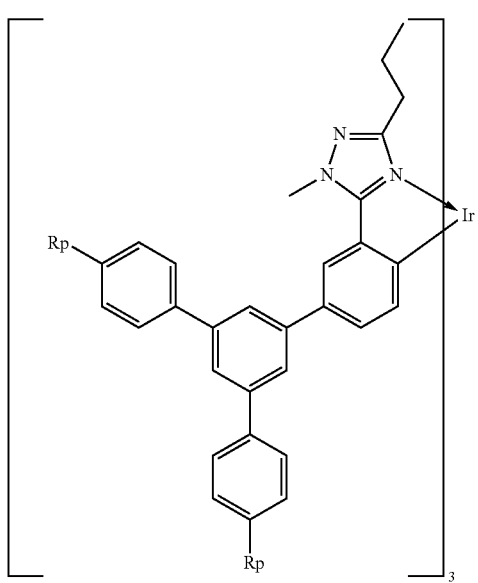
Ir-5c
Rp = H
Rp = t-Bu
Rp = C$_6$H$_{13}$
Rp = 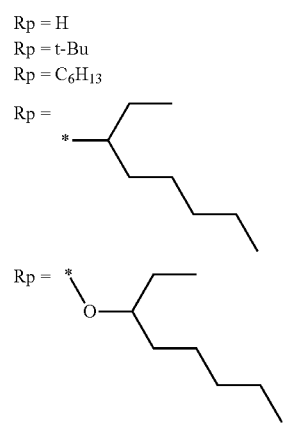
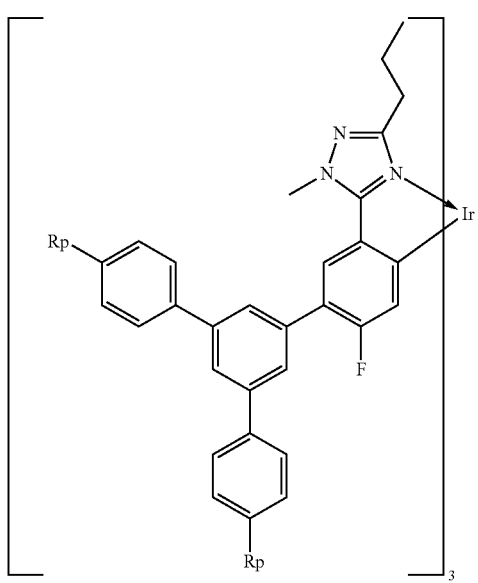
Ir-6c
Rp = H
Rp = t-Bu
Rp = C$_6$H$_{13}$
Rp = 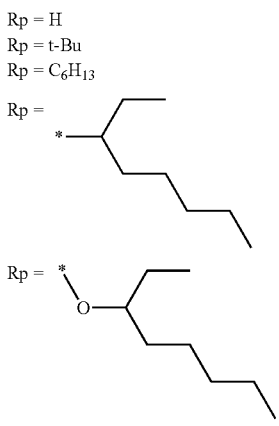

-continued
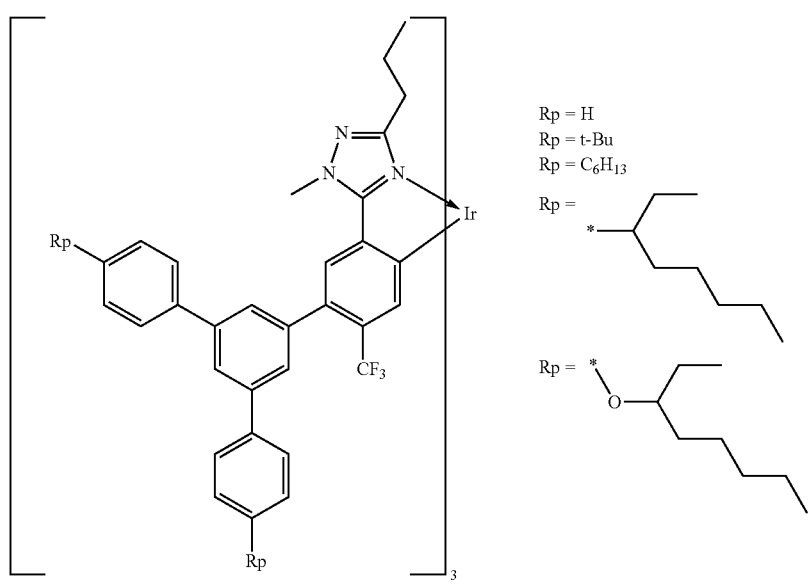
Ir-7c
Rp = H
Rp = t-Bu
Rp = C₆H₁₃
Rp = 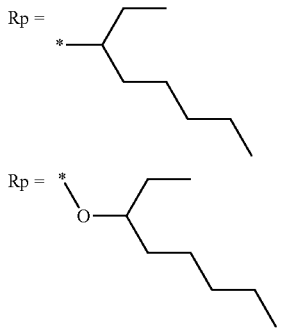
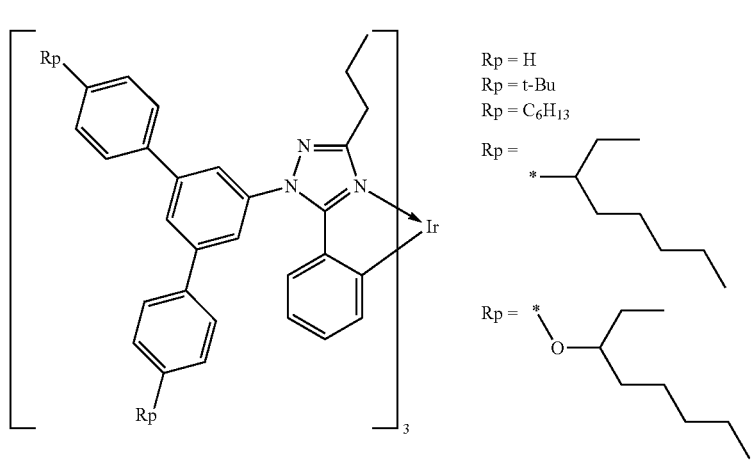
Ir-8c
Rp = H
Rp = t-Bu
Rp = C₆H₁₃
Rp = 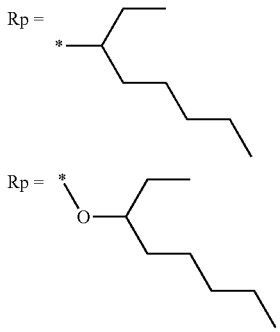
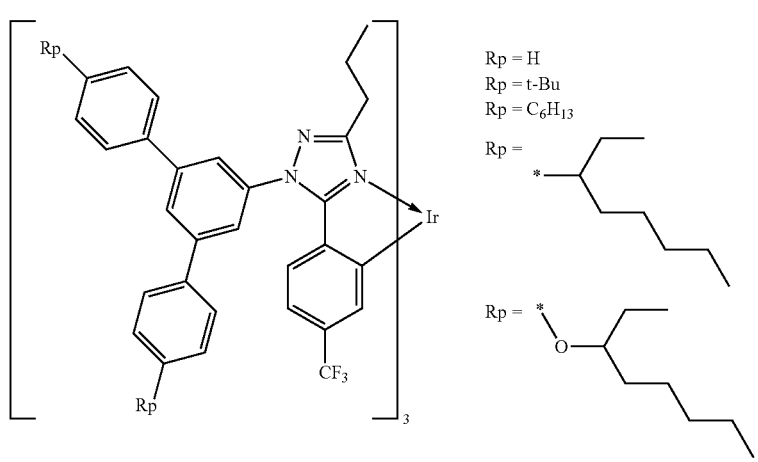
Ir-9c
Rp = H
Rp = t-Bu
Rp = C₆H₁₃
Rp = 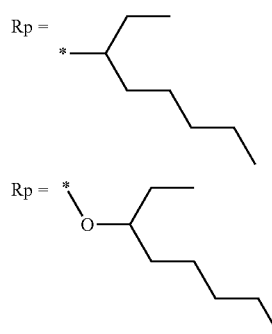

-continued
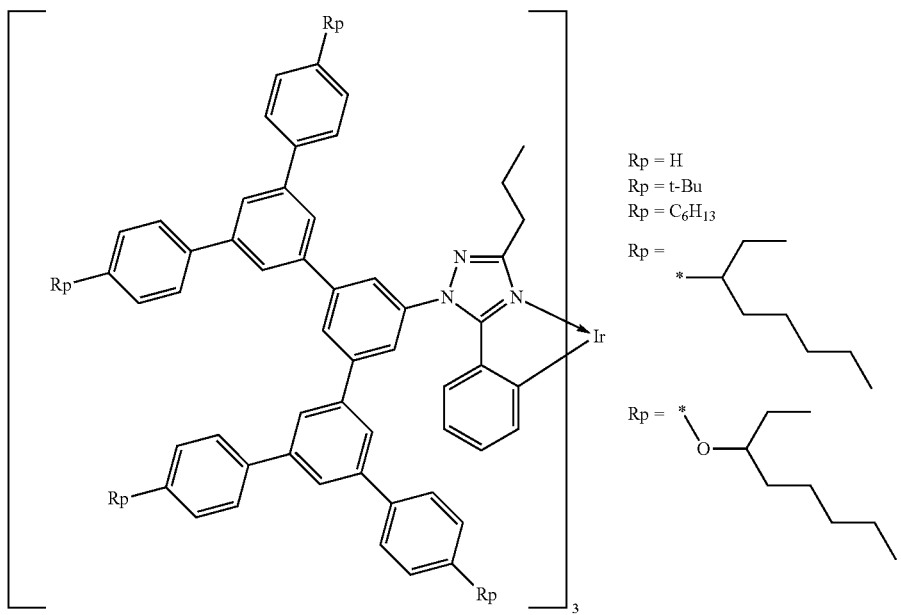
Ir-10c
Rp = H
Rp = t-Bu
Rp = C$_6$H$_{13}$
Rp = 
Rp = 
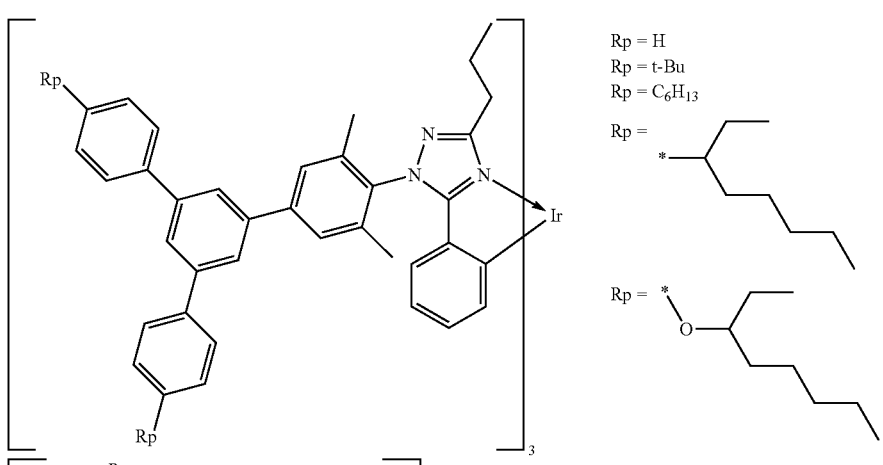
Ir-11c
Rp = H
Rp = t-Bu
Rp = C$_6$H$_{13}$
Rp = 
Rp = 
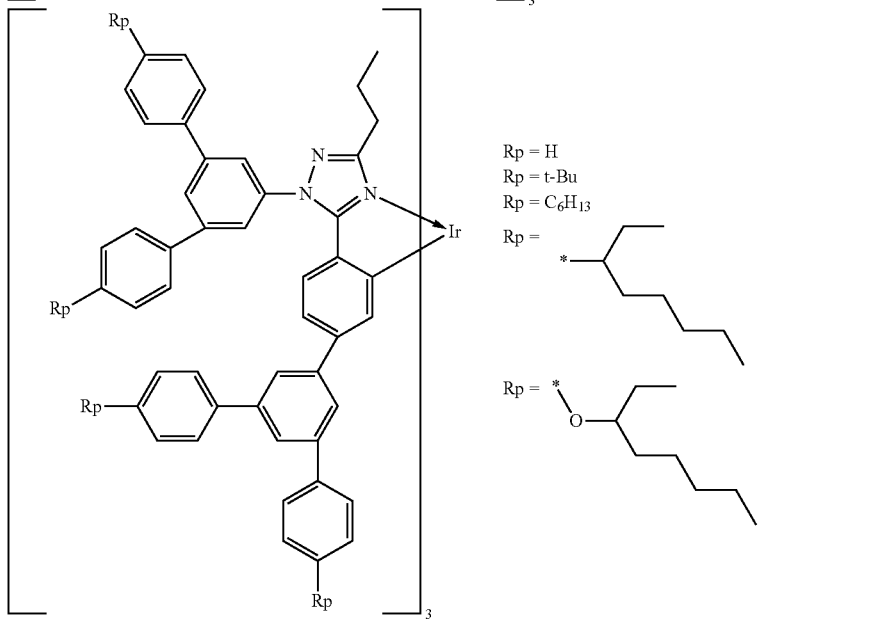
Ir-12c
Rp = H
Rp = t-Bu
Rp = C$_6$H$_{13}$
Rp = 
Rp =

-continued
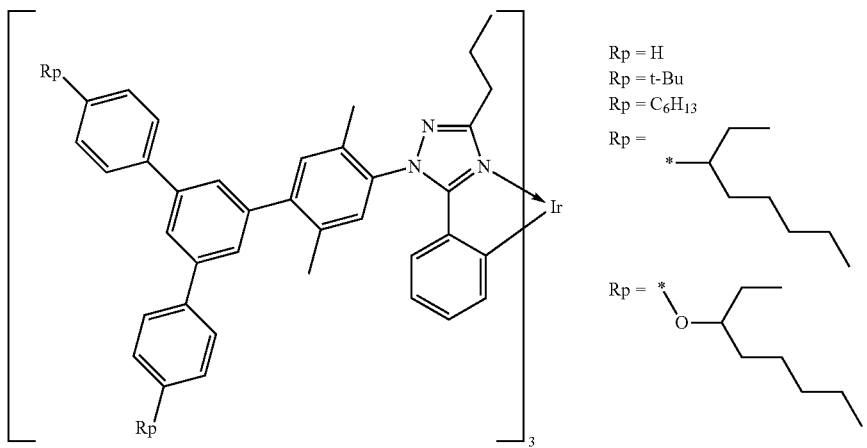
Ir-13c
Rp = H
Rp = t-Bu
Rp = C$_6$H$_{13}$
Rp = 
Rp = 
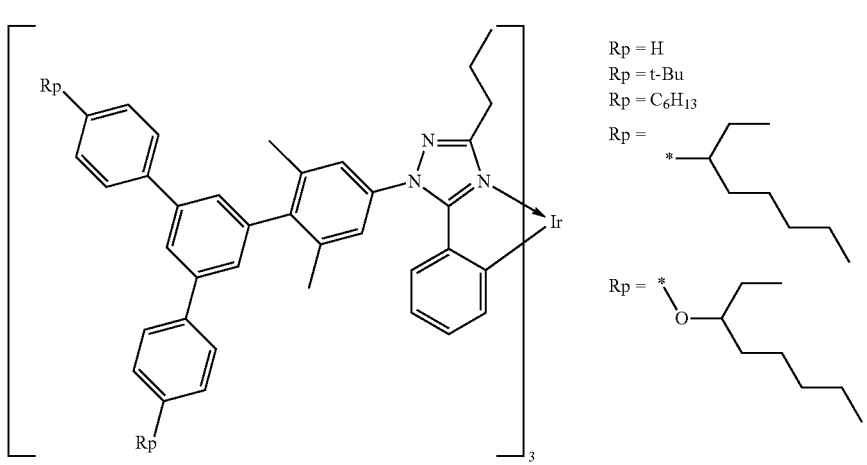
Ir-14c
Rp = H
Rp = t-Bu
Rp = C$_6$H$_{13}$
Rp = 
Rp = 
Ir-1d
Ir-2d
Ir-3d
Ir-4d)

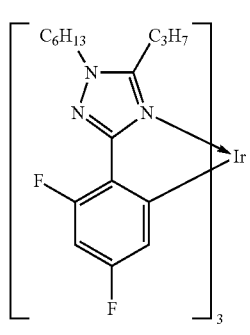 Ir-5d
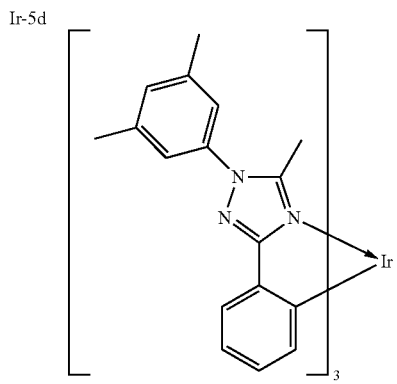 Ir-6d
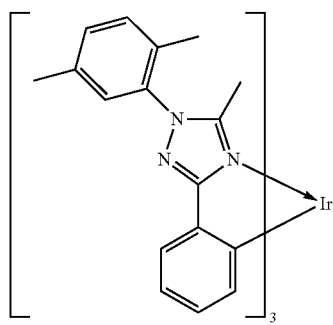 Ir-7d
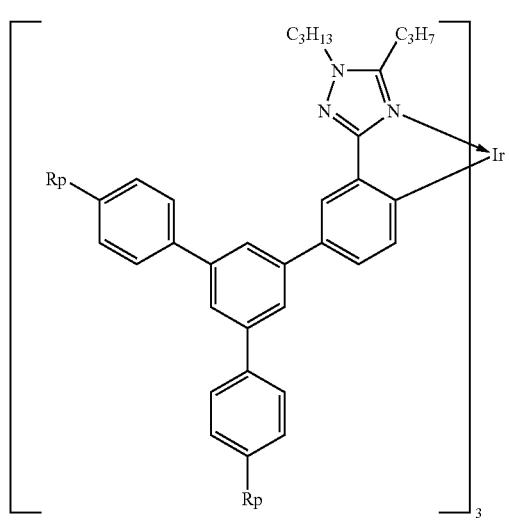 Ir-8d
Rp = H
Rp = t-Bu
Rp = C₆H₁₃
Rp = 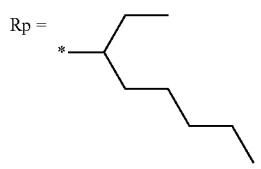
Rp = 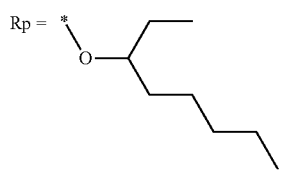

-continued
Ir-9d
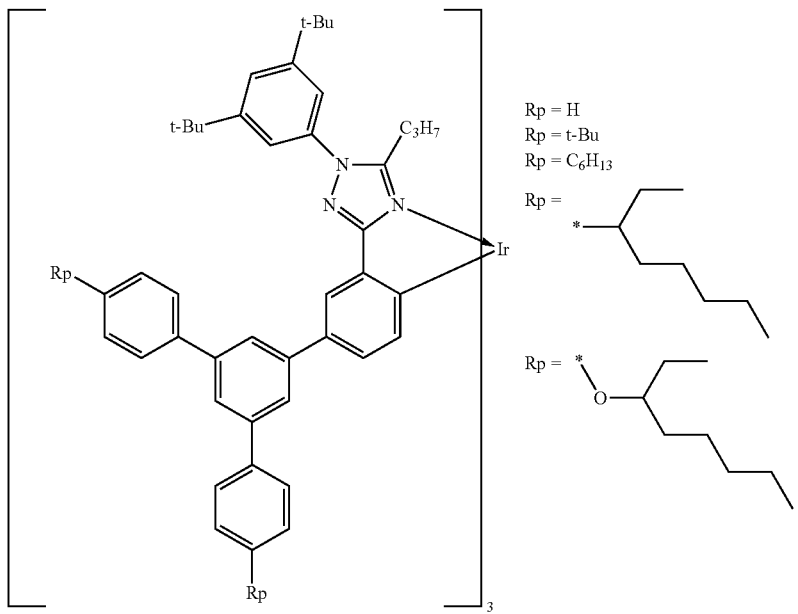
Ir-10d
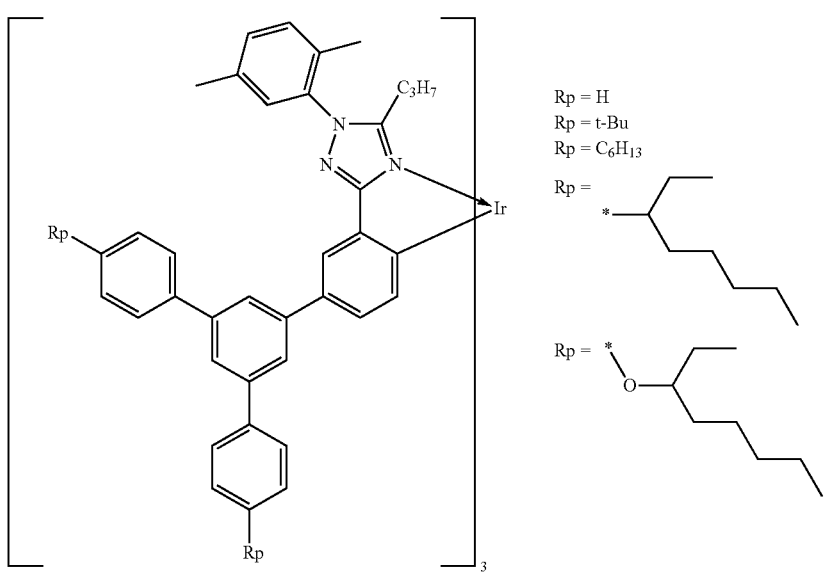

-continued
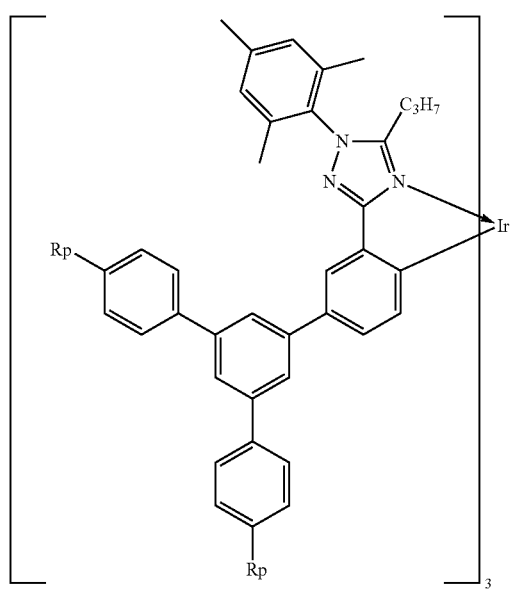
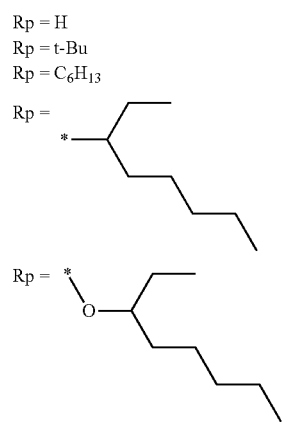
Ir-11d
Rp = H
Rp = t-Bu
Rp = C$_6$H$_{13}$
Rp =
Rp =
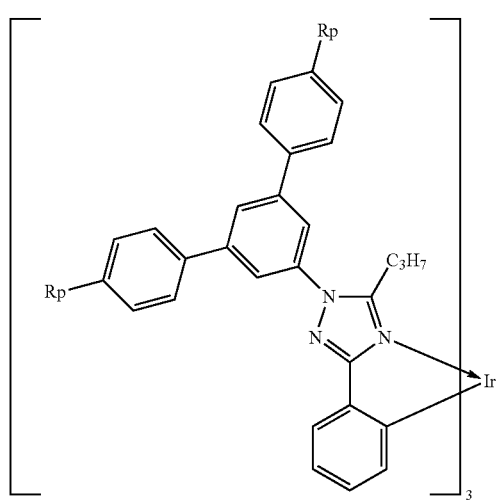
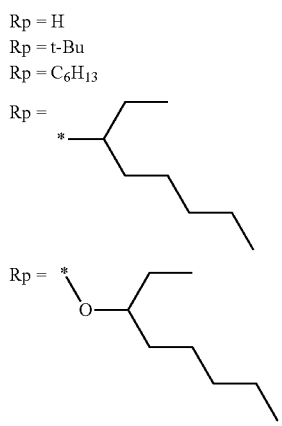
Ir-12d
Rp = H
Rp = t-Bu
Rp = C$_6$H$_{13}$
Rp =
Rp =
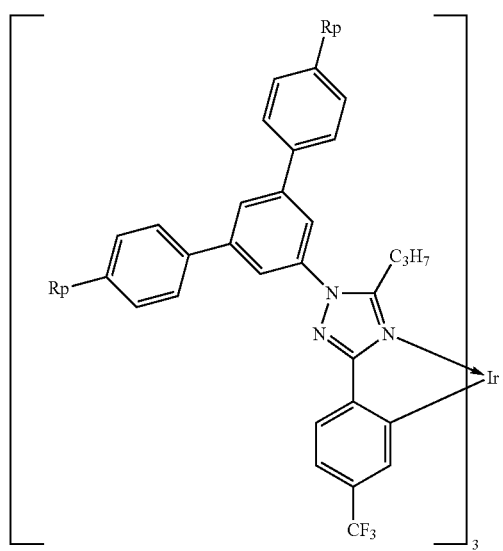
Ir-13d
Rp = H
Rp = t-Bu
Rp = C$_6$H$_{13}$
Rp =
Rp =

-continued
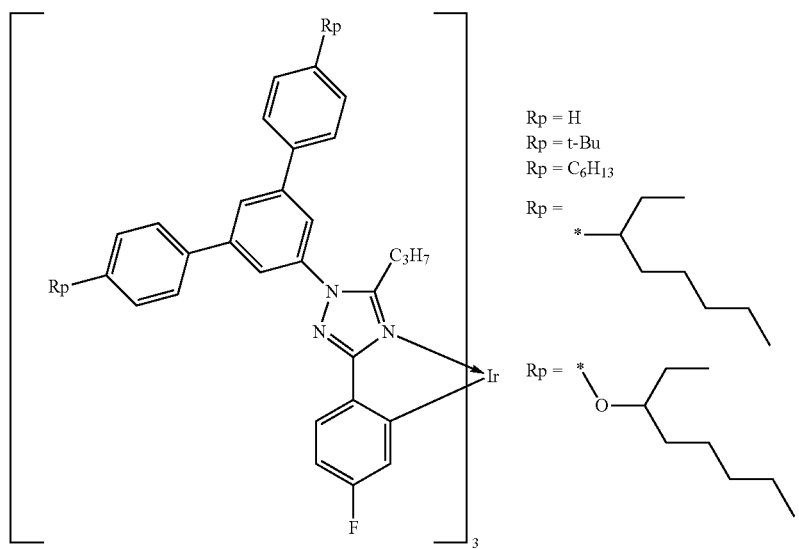
Ir-14d
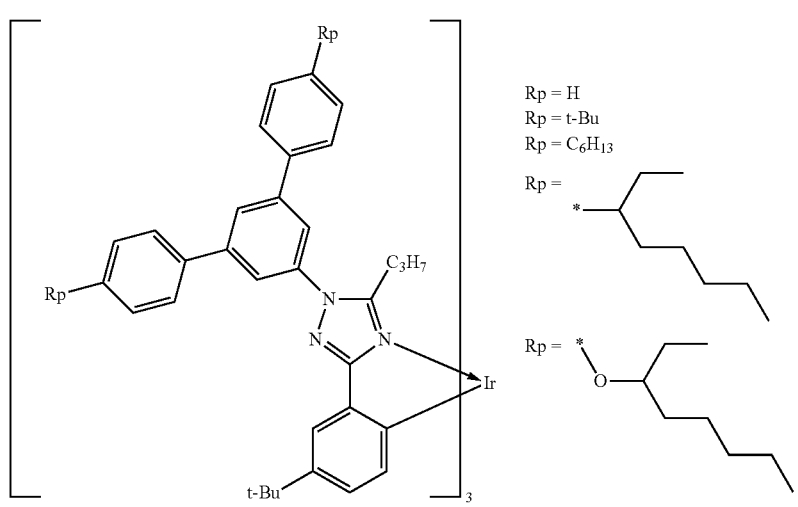
Ir-15d
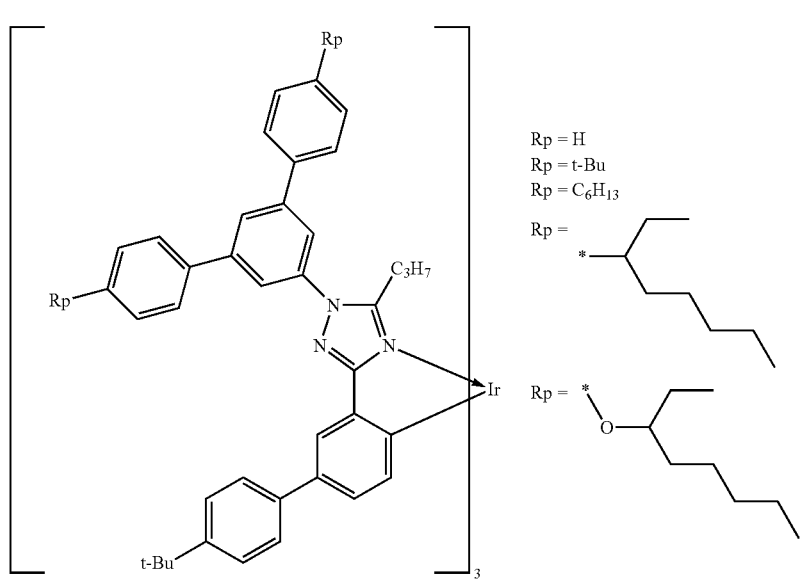
Ir-16d

-continued
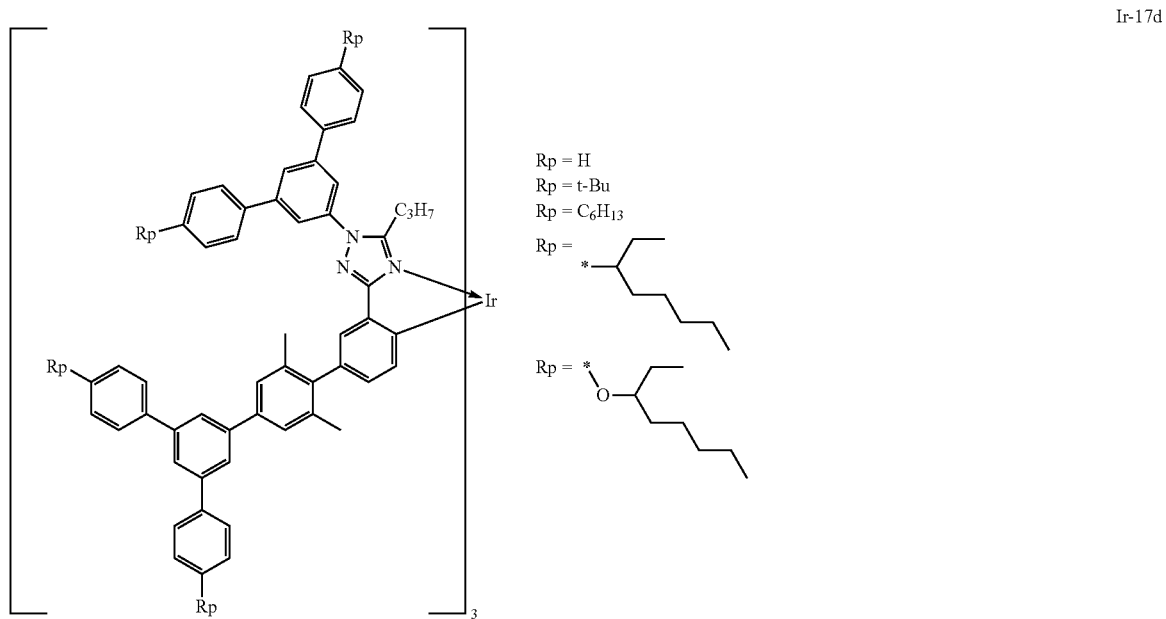
Ir-17d
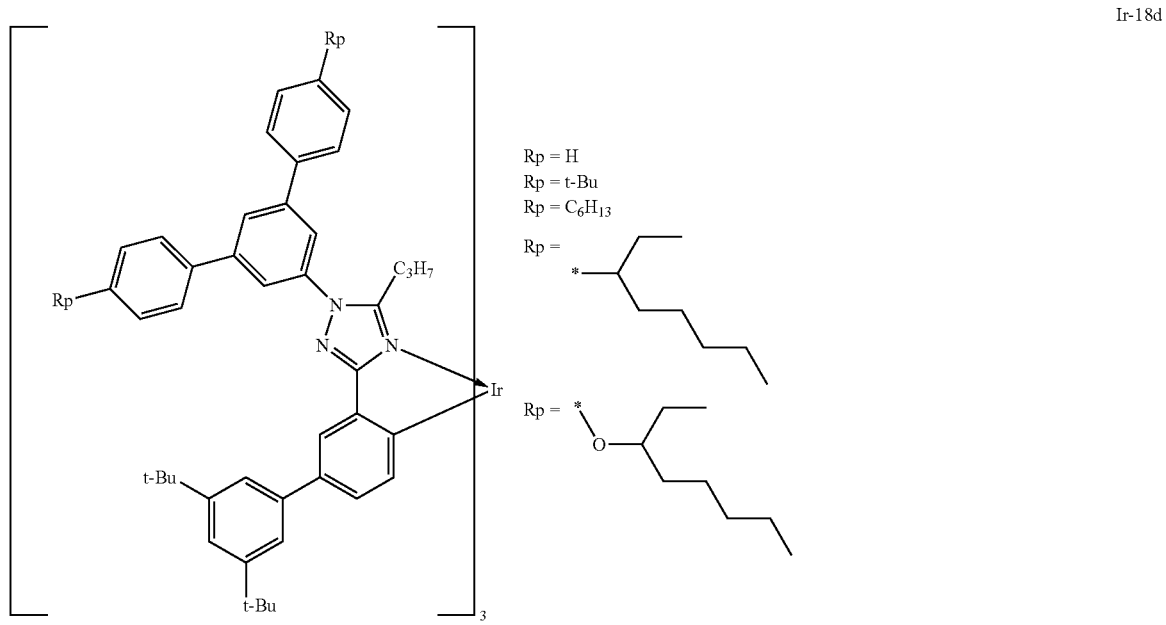
Ir-18d

-continued

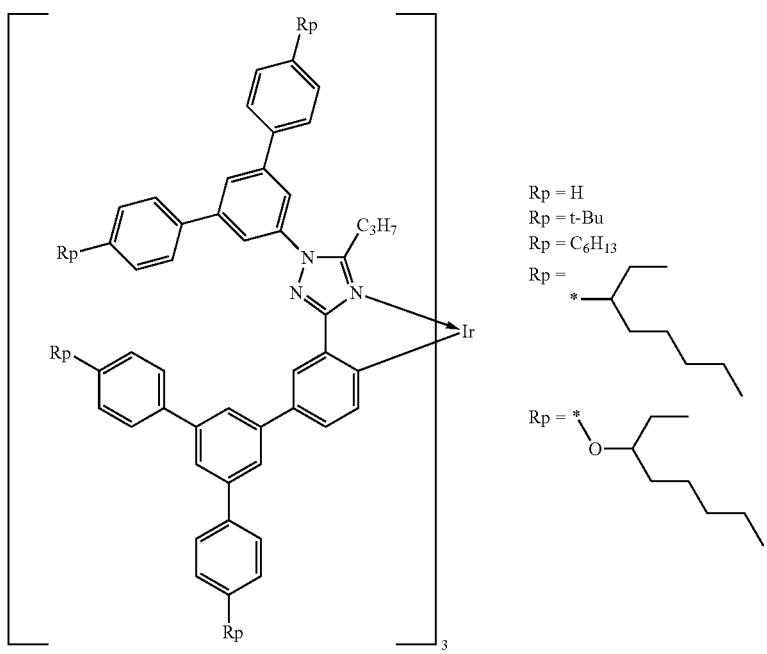

Ir-19d

Rp = H
Rp = t-Bu
Rp = C$_6$H$_{13}$
Rp =

Rp =

The polymer compound of the present invention can provide more excellent light emission efficiency as compared with a composition using a conventional polymer compound particularly when a composition of the polymer compound with a phosphorescent compound showing light emission spectrum of short wavelength is prepared, and its effect is remarkable particularly when the peak at the shortest wavelength side of the light emission spectrum of the phosphorescent compound is 490 nm or less. Therefore, L in the formula (MM) is preferably a ligand represented by the following formulae L-1e to L-15e since a phosphorescent compound showing light emission spectrum of short wavelength can be obtained.

-continued

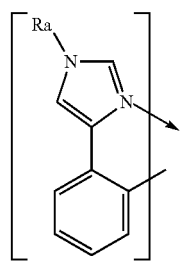

L-3e

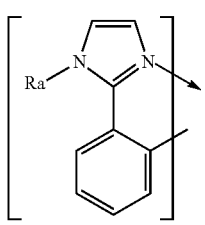

L-1e

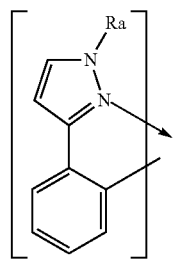

L-4e

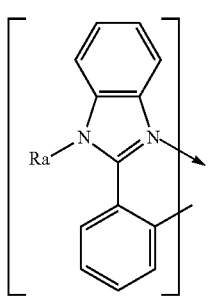

L-2e

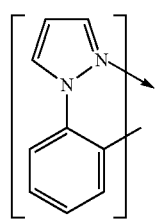

L-5e

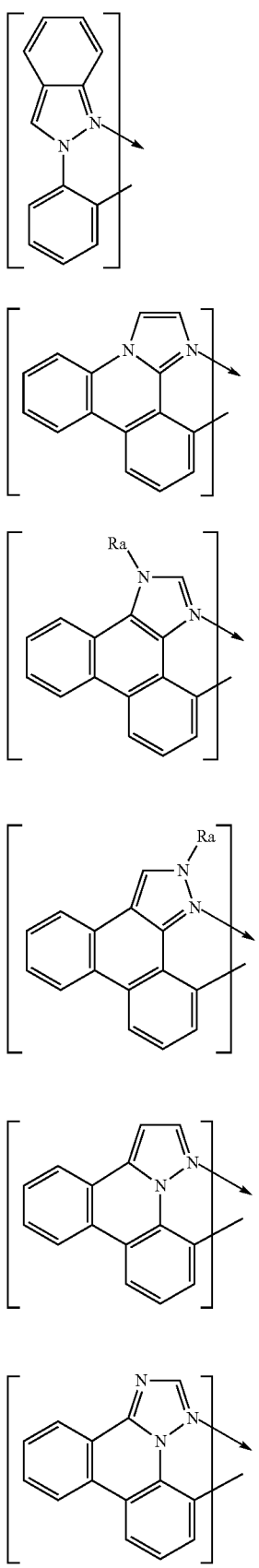

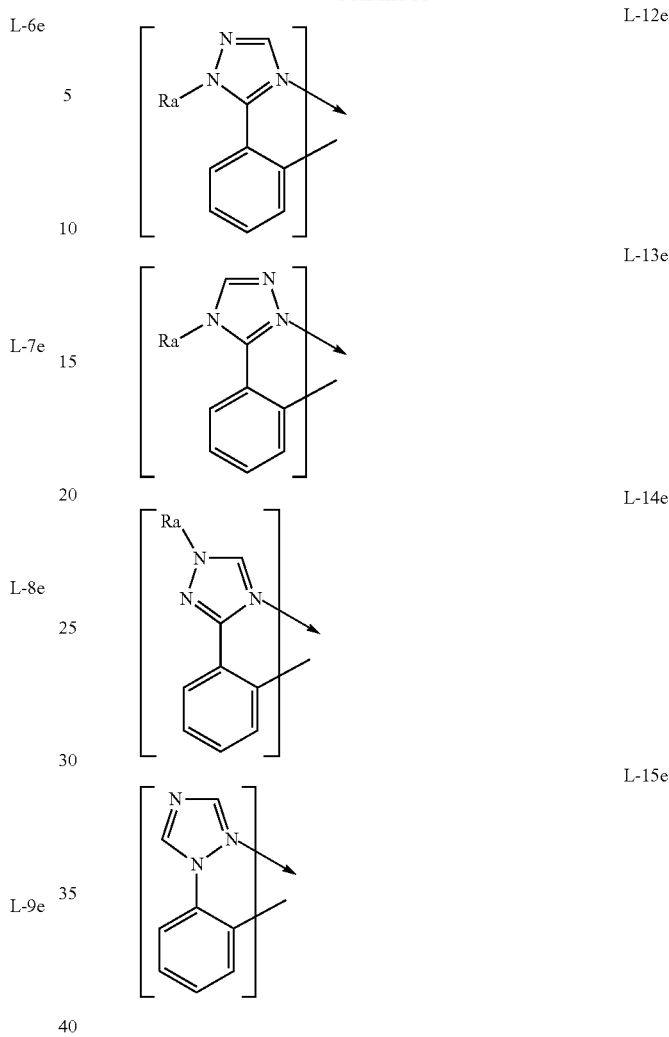

(wherein, Ra represents the same meaning as described above.)

Any hydrogen atom in each ligand exemplified above may be substituted with an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom or a cyano group. When there are a plurality of the substituents, these may be the same or different and may be mutually linked to form a ring structure together with an atom to which they are linked.

More preferable examples of the phosphorescent compound include, for example, compounds represented by the formulae Ir-1c to Ir-14c and Ir-1d to Ir-19d.

[Liquid Composition]

The polymer compound of the present invention may be dissolved or dispersed in a solvent (preferably, organic solvent) to prepare a liquid composition (solution or dispersion) of the present invention. Such a liquid composition is called also an ink or varnish. When the liquid composition of the present invention is used for forming an organic layer constituting a light emitting device, it is preferable that the liquid composition is a solution.

The liquid composition may contain at least one selected from the group consisting of a hole transporting material, an electron transporting material and a light emitting material in addition to the polymer compound of the present invention. To the liquid composition, other substances may be added providing the effect of the present invention is not prevented. The other substances include an antioxidant, a viscosity modifier, a surfactant and the like.

Here, the solvent is not particularly restricted providing it dissolves or disperses the polymer compound of the present invention, and includes the following organic solvents.

Aromatic hydrocarbon solvents: toluene, xylene (isomers or mixtures thereof), 1,2,3-trimethylbenzene, 1,2,4-trimethylbenzene, mesitylene (1,3,5-trimethylbenzene), ethylbenzene, propylbenzene, isopropylbenzene, butylbenzene, isobutylbenzene, 2-phenylbutane, tert-butylbenzene, pentylbenzene, neopentylbenzene, isoamylbenzene, hexylbenzene, cyclohexylbenzene, heptylbenzene, octylbenzene, 3-propyltoluene, 4-propyltoluene, 1-methyl-4-propylbenzene, 1,4-diethylbenzene, 1,4-dipropylbenzene, 1,4-di-tert-butylbenzene, indane, tetralin (1,2,3,4-tetrahydronaphthalene) and the like.

Aliphatic hydrocarbon solvents: n-pentane, n-hexane, cyclohexane, methylcyclohexane, n-heptane, n-octane, n-nonane, n-decane, decalin and the like.

Aromatic ether solvents: anisole, ethoxybenzene, propoxybenzene, butyloxybenzene, pentyloxybenzene, cyclopentyloxybenzene, hexyloxybenzene, cyclohexyloxybenzene, heptyloxybenzene, octyloxybenzene, 2-methylanisole, 3-methylanisole, 4-methylanisole, 4-ethylanisole, 4-propylanisole, 4-butylanisole, 4-pentylanisole, 4-hexylanisole, diphenyl ether, 4-methylphenoxybenzene, 4-ethylphenoxybenzene, 4-propylphenoxybenzene, 4-butylphenoxybenzene, 4-pentylphenoxybenzene, 4-hexylphenoxybenzene, 4-phenoxytoluene, 3-phenoxytoluene, 1,3-dimethoxybenzene, 2,6-dimethylanisole, 2,5-dimethylanisole, 2,3-dimethylanisole, 3,5-dimethylanisole and the like.

Aliphatic ether solvents: tetrahydrofuran, dioxane, dioxolane and the like.

Ketone solvents: acetone, methyl ethyl ketone, methyl isobutyl ketone, cyclohexanone, acetophenone and the like.

Ester solvents: ethyl acetate, butyl acetate, methyl benzoate, ethyl cellosolve acetate and the like.

Chlorine-based solvents: methylene chloride, chloroform, 1,2-dichloroethane, 1,1,2-trichloroethane, chlorobenzene, o-dichlorobenzene and the like.

Alcohol solvents: methanol, ethanol, propanol, isopropanol, cyclohexanol, phenol and the like.

Poly-hydric alcohols and derivatives thereof: ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol and the like.

Aprotic polar solvents: dimethyl sulfoxide, N-methyl-2-pyrrolidone, N,N-dimethylformamide, N,N-dimethylacetamide and the like.

These organic solvents may be used singly or two or more of them may be used as a mixed solvent. When a mixed solvent is used, it is preferable that two or three or more solvents selected from the above-described solvent groups are combined, and it may also be permissible that several solvents in the same solvent group exemplified above are combined or each one or more solvents from different solvent groups are combined. The composition ratio can be determined in view of the physical property of each solvent and the solubility of a polymer compound or the like.

When several solvents are selected from the same solvent group and combined, examples thereof include several solvents from the aromatic hydrocarbon solvent, several solvents from the aromatic ether solvent, and the like. When each one or more solvents are selected from different solvent groups and combined, examples thereof include the following combinations. An aromatic hydrocarbon solvent and an aliphatic hydrocarbon solvent, an aromatic hydrocarbon solvent and an aromatic ether solvent, an aromatic hydrocarbon solvent and an aliphatic ether solvent, an aromatic hydrocarbon solvent and an aprotic polar solvent, an aromatic ether solvent and an aprotic polar solvent, and the like.

Further, it is also possible to add water to a single solvent or a mixed solvent.

Of these organic solvents, a single solvent or mixed solvent containing one or more organic solvents having a structure containing a benzene ring, having a melting point of 0° C. or lower and having a boiling point of 100° C. or higher is preferable from the standpoint of viscosity, film formability and the like, and particularly, a single solvent or mixed solvent containing one or more solvents selected from the group consisting of aromatic hydrocarbon solvents and aromatic ether solvents is preferable.

The organic solvents may be used singly or two or more of them may be used as a mixed solvent, and from the standpoint of control of film formability, a mixed solvent is preferably used. The organic solvent may be purified by a method such as washing, distillation, contact with an adsorbent and the like before use, if necessary.

With the above-described liquid composition, an organic film containing the polymer compound of the present invention can be produced easily. Specifically, an organic film containing the polymer compound of the present invention is obtained by coating the above-described liquid composition on a substrate, and distilling off the organic solvent by heating, blast, pressure reduction and the like. In distillation off of an organic solvent, conditions can be varied depending on the organic solvent to be used, and examples thereof include an atmosphere temperature of about 50 to 150° C. (heating) or a pressure-reduced atmosphere of about $10^{-3}$ Pa.

For coating, coating methods such as a spin coat method, a casting method, a micro gravure coat method, a gravure coat method, a bar coat method, a roll coat method, a wire bar coat method, a dip coat method, a slit coat method, a capillary coat method, a spray coat method, a screen printing method, a flexo printing method, an offset printing method, an inkjet printing method, a nozzle coat method and the like can be used.

The suitable viscosity of the above-described liquid composition varies depending on a printing method, and it is preferably 0.5 to 1000 mPa·s, more preferably 0.5 to 500 mPa·s at 25° C. In the case of a method in which a liquid composition passes through a discharge device such as an inkjet printing method and the like, the viscosity at 25° C. is preferably 0.5 to 50 mPa·s, more preferably 0.5 to 20 mPa·s for preventing curved flying and clogging in discharging. Though the concentration of the polymer compound of the present invention in the liquid composition is not particularly restricted, it is preferably 0.01 to 10 wt %, more preferably 0.1 to 5 wt %.

[Organic Film]

The organic film of the present invention contains the polymer compound of the present invention, and examples thereof include organic films such as a luminous film, an electric conductive film, an organic semiconductor film or the like. These organic films may contain components constituting the composition of the present invention described above appropriately in combination depending on its application.

The organic film can be fabricated by a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method, a capillary coat method, a nozzle coat method and the like, using the polymer compound of the present invention as it is or in the form of the inventive composition or inventive liquid composition described above.

For example, when an organic film is formed using the solution described above, it is preferable to perform baking at a temperature of 100° C. or higher (for example, 130° C. to 160° C.), though varying depending on the glass transition temperature of the polymer compound of the present invention contained in the solution.

When the organic film is a luminous film, it has a light emission quantum yield of preferably 30% or more, more preferably 40% or more, further preferably 50% or more, particularly preferably 60% or more, from the standpoint of successfully obtaining the luminance and light emission voltage of a light emitting device.

When the organic film is an electric conductive film, it has a surface resistivity of preferably 1 kΩ/sq. or less, more preferably 100 Ω/sq. or less, further preferably 10 Ω/sq. or less. In the case of an electric conductive film, by doping with a Lewis acid, an ionic compound or the like, electric conductivity can be enhanced. "Ω/sq." is a unit showing surface resistivity.

Further, when the organic film is an organic semiconductor film, one larger parameter of electron mobility or hole mobility of the film is preferably $10^{-5}$ cm$^2$/V/s or more, more preferably $10^{-3}$ cm$^2$/V/s or more, further preferably $10^{-1}$ cm$^2$/V/s or more. For example, by forming this organic semiconductor film on a Si substrate carrying a gate electrode and an insulation film made of SiO$_2$ and the like formed thereon, and forming a source electrode and a drain electrode with Au and the like, an organic transistor can be fabricated.

[Light Emitting Device]

The light emitting device of the present invention contains an anode and a cathode, and an organic layer containing the polymer compound of the present invention disposed between the anode and the cathode. The light emitting device may be composed of one organic layer or may be composed of two or more organic layers. When composed of two or more organic layers, at least one of them may advantageously contain the polymer compound of the present invention.

The organic layer containing the polymer compound of the present invention described above can function as a light emitting layer, a hole transporting layer or an electron block layer in a light emitting device. Therefore, in the light emitting device of the present invention, it is preferable that at least one of these layers is constituted of an organic layer containing the polymer compound of the present invention described above. Particularly, it is preferable that a light emitting layer is a light emitting device constituted of an organic layer containing the polymer compound of the present invention described above, in the light emitting device of the present invention. In addition to the anode, the cathode and the organic layer functioning as a light emitting layer (hereinafter, referred to simply as "light emitting layer"), the light emitting device may contain other layers between them. Each layer may be composed of one layer or composed of two or more layers. The materials and compounds constituting each layer may be used singly or two or more of them may be used in combination.

The layer to be disposed between an anode and a light emitting layer includes a hole injection layer, a hole transporting layer, an electron block layer and the like. When only one layer is disposed between an anode and a light emitting layer, it is a hole injection layer. When two or more layers are disposed between an anode and a light emitting layer, the layer next to an anode is a hole injection layer and other layers are hole transporting layers.

The hole injection layer is a layer having a function of improving hole injection efficiency from an anode. The hole transporting layer is a layer having a function of improving hole injection from a hole injection layer or a layer nearer to an anode. When these layers have a function of blocking transportation of electrons, these layers are called also an electron block layer. Whether the subject layer has a function of blocking transportation of electrons can be confirmed by fabricating a device allowing only electron current and measuring generation of a decrease in its current value.

The layer disposed between a cathode and a light emitting layer includes an electron injection layer, an electron transporting layer, a hole block layer and the like. When only one layer is disposed between a cathode and a light emitting layer, it is an electron injection layer. When two or more layers are disposed between a cathode and a light emitting layer, the layer next to a cathode is an electron injection layer and other layers are electron transporting layers.

The electron injection layer is a layer having a function of improving electron injection efficiency from a cathode. The electron transporting layer is a layer having a function of improving electron injection from an electron injection layer or a layer nearer to a cathode. When these layers have a function of blocking transportation of holes, these layers are called also a hole block layer. Whether the subject layer has a function of blocking transportation of holes can be confirmed by fabricating a device allowing only hole current and measuring generation of a decrease in its current value.

The structure of the light emitting device having a constitution having layers described above includes the following structures a) to d). "/" in the following structures means adjacent lamination of layers (the same shall apply hereinafter).

a) anode/light emitting layer/cathode
b) anode/hole transporting layer/light emitting layer/cathode
c) anode/light emitting layer/electron transporting layer/cathode
d) anode/hole transporting layer/light emitting layer/electron transporting layer/cathode Of hole transporting layers and electron transporting layers disposed adjacent to an electrode (cathode, anode), those having a function of improving charge (hole, electron) injection efficiency from an electrode and having an effect of lowering the driving voltage of a device are called a charge injection layer (hole injection layer, electron injection layer) in some cases.

Further, for improving close adherence with an electrode (cathode, anode) and improving charge injection from an electrode, a charge injection layer and an insulation layer may be disposed next to an electrode. In an interface of a charge transporting layer and a light emitting layer, a thin buffer layer may be further provided for improving close adherence in an interface between layers and preventing mixing of constituent materials. The order and number of layers to be laminated, and the thickness of each layer may be adjusted in view of light emission efficiency and device life.

The structure of the light emitting device in which a charge injection layer is further provided includes, for example, the following structures e) to p).
e) anode/charge injection layer/light emitting layer/cathode
f) anode/light emitting layer/charge injection layer/cathode
g) anode/charge injection layer/light emitting layer/charge injection layer/cathode
h) anode/charge injection layer/hole transporting layer/light emitting layer/cathode
i) anode/hole transporting layer/light emitting layer/charge injection layer/cathode
j) anode/charge injection layer/hole transporting layer/light emitting layer/charge injection layer/cathode
k) anode/charge injection layer/light emitting layer/charge transporting layer/cathode
l) anode/light emitting layer/electron transporting layer/charge injection layer/cathode
m) anode/charge injection layer/light emitting layer/electron transporting layer/charge injection layer/cathode
n) anode/charge injection layer/hole transporting layer/light emitting layer/charge transporting layer/cathode
o) anode/hole transporting layer/light emitting layer/electron transporting layer/charge injection layer/cathode
p) anode/charge injection layer/hole transporting layer/light emitting layer/electron transporting layer/charge injection layer/cathode The constitution of each layer in the light emitting device having structures a) to p) described above is, for example, as described below.

(Anode)

The anode is usually transparent or semi-transparent and constituted of film of a metal oxide, a metal sulfide or a metal having high electric conductivity, and particularly, the anode is preferably constituted of a material of high transmission. As the material of the anode, use is made of films fabricated using electric conductive inorganic compounds composed of indium oxide, zinc oxide, tin oxide, and composite thereof: indium.tin.oxide (ITO), indium.zinc.oxide and the like; NESA and the like, gold, platinum, silver, copper and the like. Of them, ITO, indium.zinc.oxide and tin oxide are preferable. For fabrication of the anode, a vacuum vapor-deposition method, methods such as a sputtering method, an ion plating method, a plating method and the like can be used. As the anode, organic transparent electric conductive films made of polyaniline and its derivatives, polythiophene and its derivatives, and the like may be used.

The thickness of the anode can be selected in view of light transmission and electric conductivity. For example, it is preferably 10 nm to 10 µm, more preferably 20 nm to 1 µm, further preferably 40 nm to 500 nm.

(Hole Injection Layer)

The material used in the hole injection layer includes phenyl amine compounds, starburst type amine compounds, phthalocyanine compounds, oxides such as vanadium oxide, molybdenum oxide, ruthenium oxide, aluminum oxide and the like, amorphous carbon, electric conductive polymers such as polyaniline and derivatives thereof, polythiophene and derivatives thereof, and the like.

When the hole injection layer is an electric conductive polymer or the polymer compound of the present embodiment described above, the hole injection layer may be doped with anions such as a polystyrenesulfonic ion, an alkylbenzenesulfonic ion, a camphor sulfonic ion and the like, if necessary, for improving the electric conductivity thereof.

(Hole Transporting Layer)

The material used in the hole transporting layer includes compounds exemplified as the hole transporting material. When the material used in the hole transporting layer is a small molecule compound, the small molecule compound is preferably dispersed in a polymer binder in use. When the polymer compound of the present embodiment described above is used in the hole transporting layer, it is preferable that the polymer compound has a group represented by the above-described formula (5) as a repeating unit.

Among them, preferable as the hole transporting material to be used in the hole transporting layer are polyvinylcarbazole and derivatives thereof, polysilane and derivatives thereof, polysiloxane derivatives having an aromatic amine in its side chain or main chain, and polyarylamine and derivatives thereof, and in addition, the polymer compound of the present embodiment.

As the method of formation of the hole transporting layer, film formation using a mixed solution with a polymer binder is used when the material used in the hole transporting layer is a small molecule compound, and film formation using a solution containing a polymer compound is used when the material is a polymer compound.

The solvent used for film formation using a solution may advantageously be one which dissolves materials used in the hole transporting layer. The solvent includes chlorine-based solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, ester solvents such as ethyl acetate, butyl acetate, ethylcellosolve acetate and the like.

For film formation using a solution, coating methods using a solution such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method and the like can be used.

As the polymer binder to be combined with a small molecule compound, those not extremely disturbing charge transportation are preferable, and those showing no strong absorption against visible light are suitable. The polymer binder as described above includes polycarbonate, polyacrylate, polymethyl acrylate, polymethyl methacrylate, polystyrene, polyvinyl chloride, polysiloxane and the like.

The thickness of the hole transporting layer can be selected in view of driving voltage and light emission efficiency. The thickness of the hole transporting layer is preferably 1 nm to 1 µm, more preferably 2 nm to 500 nm, further preferably 5 nm to 200 nm.

(Light Emitting Layer)

The light emitting layer is formed of an organic compound emitting fluorescence or phosphorescence (may be any of small molecule compound or polymer compound), and a dopant aiding this if necessary. In the light emitting layer in the light emitting device of the present embodiment, the polymer compound of the present embodiment described above and a phosphorescent compound are preferably contained. When the light emitting material is a small molecule compound, it is preferably dispersed in a polymer binder in use.

To the light emitting layer, a dopant may be added for improving light emission efficiency and changing light emission wavelength. The dopant includes anthracene derivatives, perylene derivatives, coumarin derivatives, rubrene derivatives, quinacridone derivatives, squalium derivatives, porphyrin derivatives, styryl dyes, tetracene derivatives, pyrazolone derivatives, decacyclene, phenoxazone and the like.

The thickness of the light emitting layer can be selected in view of driving voltage and light emission efficiency, and, for example, it is preferably 2 to 200 nm.

For forming the light emitting layer, there can be used a method in which a solution containing a light emitting material is coated on or above a substrate, a vacuum vapor deposition method, a transfer method and the like. In the case of performing film formation using a solution, the same solvents as exemplified in film formation using a solution of a hole transporting layer can be used. For coating a solution containing a light emitting material on or above a substrate, there can be used printing methods such as a spin coat method, a dip coat method, an inkjet printing method, a flexo printing method, a gravure printing method, a slit coat method and the like. When the light emitting material is a small molecule compound showing a sublimation property, film formation can be conducted also by a vacuum vapor deposition method. Use can be made also of a method of forming a light emitting layer at a desired position, by laser transfer or thermal transfer.

(Electron Transporting Layer)

As the material to be used in the electron transporting layer, there are mentioned the polymer compound of the present embodiment described above, the electron transporting material described above and the like. When the polymer compound of the present embodiment described above is used in the electron transporting layer, it is preferable that the polymer compound of the present embodiment contains as a repeating unit at least one group selected from the group consisting of a group represented by the above-described formula (2B), a group represented by the above-described formula (3B) and a group represented by the above-described formula (3C).

Of them, preferable as the electron transporting material used in the electron transporting layer are the polymer compound of the present embodiment described above, oxadiazole derivatives, benzoquinone and derivatives thereof, anthraquinone and derivatives thereof, metal complexes of 8-hydroxyquinoline and derivatives thereof, polyquinoline and derivatives thereof, polyquinoxaline and derivatives thereof, and polyfluorene and derivatives thereof.

For forming the electron transporting layer, a vacuum vapor deposition method using a powder and a method of film formation in the form of a solution or in melted state are used when the material used in the electron transporting layer is a small molecule compound. In contrast, a method of film formation in the form of a solution or in melted state is used when the material used in the electron transporting layer is a polymer compound. In film formation in the form of a solution or in melted state, a polymer binder may also be used together. Film formation using a solution can be conducted in the same manner as for formation of a hole transporting layer using a solution as described above.

The thickness of the electron transporting layer can be adjusted in view of driving voltage and light emission efficiency. The thickness of the electron transporting layer is preferably 1 nm to 1 μm, more preferably 2 nm to 500 nm, further preferably 5 nm to 200 nm.

(Electron Injection Layer)

The constitution of the electron injection layer can be appropriately selected according to the kind of a light emitting layer. Examples thereof include an electron injection layer having a single layer structure composed of a Ca layer, and an electron injection layer having a lamination structure composed of a Ca layer and a layer formed of one or two or more materials selected from the group consisting of metals belonging to group I and group II of the periodic table of elements and having a work function of 1.5 to 3.0 eV excluding Ca, and oxides, halides and carbonates of the metals. As the metals belonging to group I of the periodic table of elements and having a work function of 1.5 to 3.0 eV and oxides, halides and carbonates thereof, listed are lithium, lithium fluoride, sodium oxide, lithium oxide, lithium carbonate and the like. As the metals belonging to group II of the periodic table of elements and having a work function of 1.5 to 3.0 eV excluding Ca, and oxides, halides and carbonates thereof, listed are strontium, magnesium oxide, magnesium fluoride, strontium fluoride, barium fluoride, strontium oxide, magnesium carbonate and the like.

The electron injection layer can be formed by a vapor deposition method, a sputtering method, a printing method and the like. The thickness of the electron injection layer is preferably 1 nm to 1 μm.

(Electrode)

As the material of the cathode, materials having a small work function and providing easy injection of electrons into a light emitting layer are preferable. For example, use is made of metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like, alloys composed of two or more of these metals, or alloys composed of at least one of them and at least one of gold, silver, platinum, copper, manganese, titanium, cobalt, nickel, tungsten and tin, and, graphite or graphite intercalation compounds, and the like. The alloy includes a magnesium-silver alloy, a magnesium-indium alloy, a magnesium-aluminum alloy, an indium-silver alloy, a lithium-aluminum alloy, a lithium-magnesium alloy, a lithium-indium alloy, a calcium-aluminum alloy, and the like.

When the cathode has a laminated structure consisting of two or more layers, preferable is a laminated structure composed of a metal, a metal oxide, a metal fluoride or an alloy thereof and of a metal such as aluminum, silver, chromium and the like.

The cathode can be formed by, for example, a vacuum vapor deposition method, a sputtering method, a lamination method of thermally press-binding a metal film, and the like. The thickness of the cathode can be selected in view of electric conductivity and durability. For example, it is preferably 10 nm to 10 μm, more preferably 20 nm to 1 μm, further preferably 50 nm to 500 nm.

(Protective Layer)

After fabrication of the cathode, a protective layer for protecting a light emitting device may be further formed on its top. Particularly, for use of a light emitting device stably for a long period of time, it is preferable to install a protective layer and/or a protective cover, for protecting the light emitting device from outside.

As the constituent material of the protective layer, polymer compounds, metal oxides, metal fluorides, metal borides and the like can be used. As the protective cover, a metal plate, a glass plate, and a plastic plate having a surface which has been subjected to a low water permeation treatment, and the like can be used. As the protective method of a light emitting device using a protective cover, a method in which the protective cover is pasted to a device substrate with a thermosetting resin or a photo-curing resin to attain sealing is used. When a space is kept using a spacer, blemishing of a device can be prevented easily. If an inert gas such as nitrogen, argon and the like is filled in this space, oxidation of a cathode can be prevented. Further, by placing a drying agent such as barium oxide and the like in this space, it becomes easy to suppress moisture adsorbed in a production process or a small amount of water invaded through a hardened resin from imparting a damage to the device. It is preferable to adopt at least one strategy among these methods, in a light emitting device.

The light emitting device of the suitable embodiment explained above can be used as a planar light source, a display (segment displays, dot matrix display), back light of a liquid crystal display, or the like.

For example, for obtaining light emission in the form of plane using a light emitting device, a planar anode and a planar cathode may advantageously be placed so as to overlap. For obtaining light emission in the form of pattern, there are a method in which a mask having a window in the form of pattern is placed on the surface of the planar light emitting device, a method in which an organic layer in non-light emitting parts is formed with extremely large thickness to give substantially no light emission, and a method in which either an anode or a cathode, or both electrodes are formed in the form of pattern. By forming a pattern by any of these methods, and placing several electrodes so that on/off is independently possible, a display of segment type is obtained which can display digits, letters, simple marks and the like.

Further, for providing a dot matrix device, it may be advantageous that both an anode and a cathode are formed in the form of stripe, and placed so as to cross. By using a method in which several polymer compounds showing different emission colors are painted separately or a method in which a color filter or a fluorescence conversion filter is used, partial color display and multi-color display are made possible. In the case of a dot matrix device, passive driving is possible, and active driving may be carried out by combining with TFT and the like.

The planar light emitting device described above is of self emitting and thin type, and can be suitably used as a planar light source for back light of a liquid crystal display, or as a planar light source for illumination, and the like. These display devices can be used as a display of a computer, a television, a portable terminal, a cellular telephone, a car navigation, a view finder of a video camera, and the like. Further, if a flexible substrate is used, it can also be used as a curved light source or display.

EXAMPLES

The present invention will be illustrated further in detail by examples below, but the present invention is not limited to the following examples.

[Measurement Method]

In the examples below, measurement of number-average molecular weight and weight-average molecular weight, high performance liquid chromatography (HPLC), measurement of NMR, measurement of LC/MS, measurement of glass transition temperature and measurement of triplet energy were carried out as described below.

(Measurement of Number-Average Molecular Weight and Weight-Average Molecular Weight)

Polystyrene-equivalent number-average molecular weight (Mn) and polystyrene-equivalent weight-average molecular weight (Mw) were determined by GPC (manufactured by Shimadzu. Corp., trade name: LC-10Avp). In this operation, the polymer compound to be measured was dissolved in tetrahydrofuran so as to give a concentration of about 0.05 wt % and the solution was injected in an amount of 10 µL into GPC. Tetrahydrofuran was used as the mobile phase of GPC and allowed to flow at a flow rate of 2.0 ml/min. PLgel MIXED-B (manufactured by Polymer Laboratories Ltd.) was used as the column. As the detector, a UV-VIS detector (manufactured by Shimadzu. Corp., trade name: SPD-10Avp) was used.

(High Performance Liquid Chromatography (HPLC))

The value of HPLC area percentage was used as an index of the purity of a compound. This value is a value at 254 nm by high performance liquid chromatography (HPLC, manufactured by Shimadzu Corp., trade name: LC-20A). In this procedure, the compound to be measured was dissolved in tetrahydrofuran or chloroform so as to give a concentration of 0.01 to 0.2 wt %, and the solution was injected in an amount of 1 to 10 µL into HPLC depending on the concentration. As the mobile phase of HPLC, acetonitrile and tetrahydrofuran were used and allowed to flow at a flow rate of 1 ml/min in gradient mode of acetonitrile/tetrahydrofuran=100/0 to 0/100 (volume ratio). As the column, Kaseisorb LC ODS 2000 (manufactured by Tokyo Chemical Industry Co., Ltd.) or an ODS column having the equivalent performance was used. As the detector, a photodiode array detector (manufactured by Shimadzu. Corp., trade name: SPD-M20A) was used.

(Measurement of NMR)

A measurement sample (5 to 20 mg) was dissolved in about 0.5 ml of an organic solvent, and measurement of NMR was performed using NMR (manufactured by Varian, Inc., trade name: MERCURY300).

(Measurement of LC/MS)

A measurement sample was dissolved in a suitable organic solvent (chloroform, tetrahydrofuran, ethyl acetate, toluene and the like) so as to give a concentration of 1 to 10 mg/mL, and LC/MS was measured by LC/MS (manufactured by Agilent Technologies, trade name: 1100LCMSD) and the measured value was analyzed. As the mobile phase of LC-MS, ion exchanged water, acetonitrile, tetrahydrofuran or a mixed solution thereof was used, and, if necessary, acetic acid was added. As the column, L-column 2 ODS (3 µm) (manufactured by Chemicals Evaluation and Research Institute, Japan, internal diameter: 4.6 mm, length: 250 mm, particle diameter: 3 µm) was used.

(Measurement of Energy Level of $T_1$)

TH of a polymer compound was determined by measuring the phosphorescence spectrum of the polymer compound at 77K. Specifically, a toluene solution of the polymer compound (concentration: $8 \times 10^{-4}$ wt %) was used as the measurement sample. As the exciting light source, a xenon lamp was used, and the measurement sample was irradiated with exciting light (exciting wavelength: 300 nm) dispersed using a diffraction grating, and a multi-channel spectrometer manufactured by Hamamatsu Photonics Co., Ltd. (trade name: PMA-12) was used as the detector and the phosphorescence spectrum of the polymer compound was measured. When the intensity of the maximum peak wavelength (wavelength of the largest intensity) in the phosphorescent spectrum of the polymer compound was 1.0, the value obtained by converting the wavelength at the shortest side showing an intensity of 0.1 into energy was calculated as TM.

TM of the phosphorescent compound was determined by measuring the phosphorescence spectrum of the phosphorescent compound at room temperature. Specifically, a toluene solution of the phosphorescent compound (concentration: $8 \times 10^{-4}$ wt %) was used as the measurement sample. As the exciting light source, a xenon lamp was used, and the measurement sample was irradiated with exciting light (exciting wavelength: 300 nm) dispersed using a diffraction grating, and a multi-channel spectrometer manufactured by Hamamatsu Photonics Co., Ltd. (trade name: PMA-12) was used as the detector and the phosphorescence spectrum of the phosphorescent compound was measured. When the intensity of the maximum peak wavelength (wavelength of the largest intensity) in the phosphorescent spectrum of the phosphorescent compound was 1.0, the value obtained by converting the wavelength at the shortest side showing an intensity of 0.1 into energy was calculated as TM.

[Synthesis of Raw Material Monomer]

Compounds CC1 to CC16 shown below were synthesized by a known method or a synthesis method described later, and subjected to a purification operation such as recrystallization, silica gel column chromatography, sublimation and the like, and those showing a purity of 99.5% or more in terms of the HPLC area percentage value were used as raw material monomers in synthesis of a polymer compound or as raw material compounds in synthesis of a raw material monomer.

Compound CC8 was a mixture of stereoisomers (specifically, stereoisomers are present at a bond represented by a wavy line in the chemical formula) and, and the total value of the mixture of stereoisomers was used as the HPLC area percentage value.

CC1
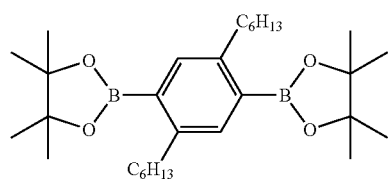

CC2
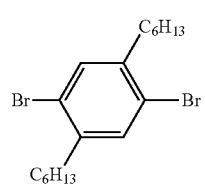

CC3
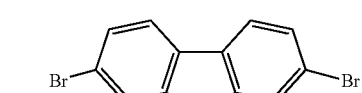

CC4
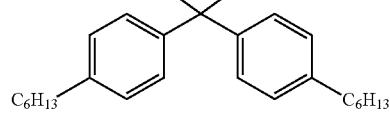

CC5
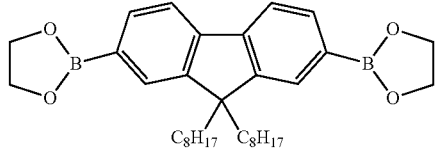

CC6
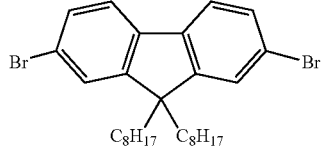

CC7
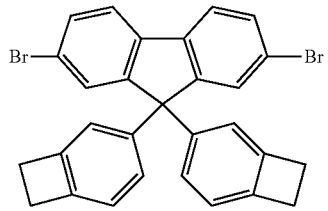

CC8
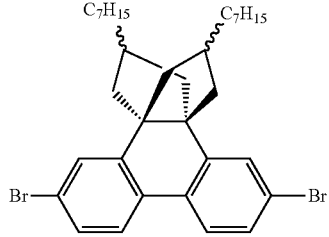

CC9
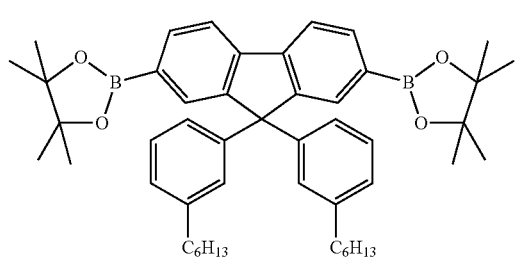

CC10
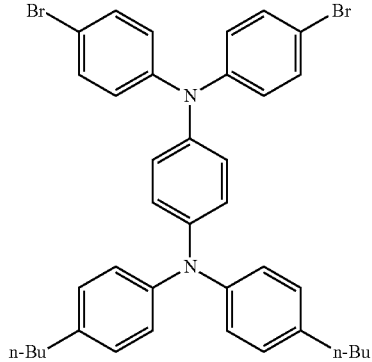

-continued

CC11
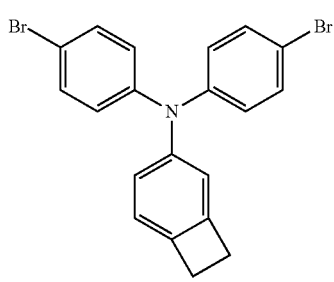

CC12
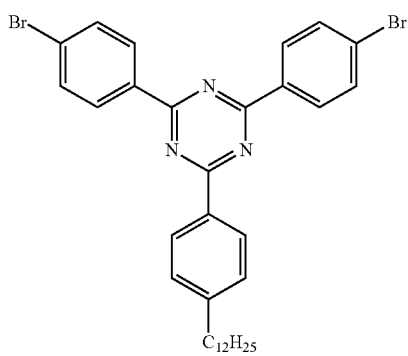

CC13
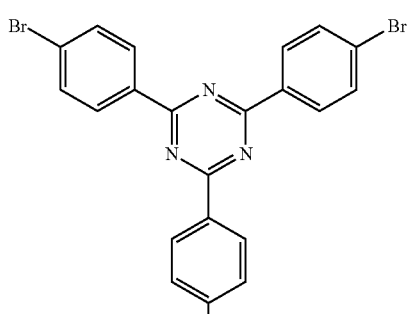

CC14
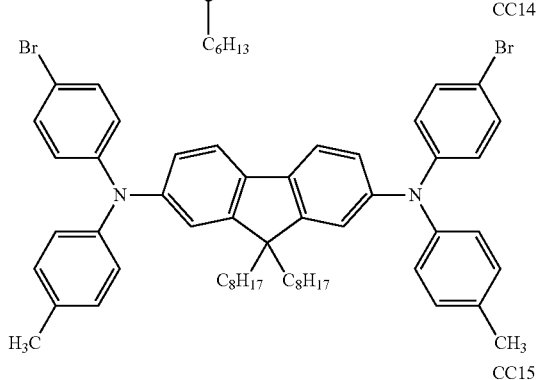

CC15
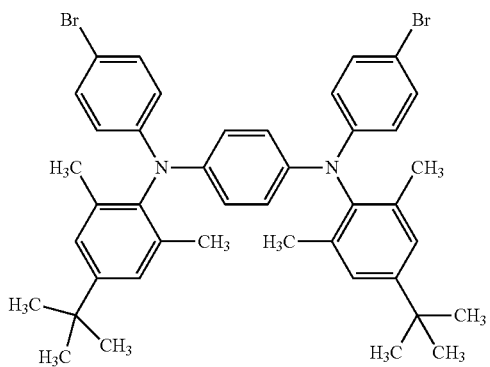

CC16
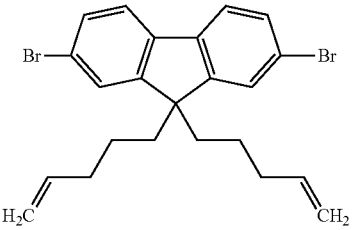

Example 1

(Synthesis of Compound MM1)

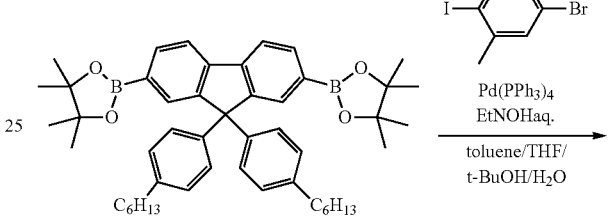

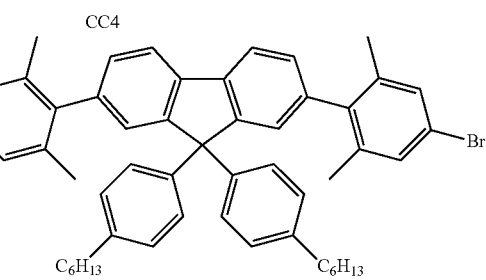

Into a 300 ml three-necked flask were added a compound CC4 (7.4 g, 10 mmol), 2-iodo-5-bromo-m-xylene (9.3 g, 30 mmol) and tetrakistriphenylphosphinepalladium(0) (0.23 g, 0.04 mmol), and a gas in the three-necked flask was purged with an argon gas. Thereafter, toluene (60 ml), tetrahydrofuran (30 ml), tert-butanol (40 ml) and ion exchanged water (20 ml), each previously bubbled with an argon gas for 10 minutes to remove dissolved oxygen, were added at room temperature, thereafter, a 20 wt % tetraethyl ammonium hydroxide aqueous solution (30 g, 8 mmol) was further added, and the mixture was stirred at 50° C. for 12 hours. To the resultant reaction solution were added ion exchanged water and toluene, and the mixture was stirred, allowed to stand still, then, the liquid was separated. The resultant organic layer was dried over anhydrous sodium sulfate, and an inorganic salt was filtrated. The solvent was distilled off under reduced pressure from the resultant filtrate, then, acetonitrile was added, and the mixture was stirred at 70° C. for 30 minutes, cooled down to room temperature, and the deposited solid was isolated by filtration. The resultant solid was purified by medium pressure silica gel column chromatography (hexane/chloroform=15/1 (v/v (denoting volume ratio, the same shall apply hereinafter))), further purified by recrystallization (chloroform/acetonitrile=4/7 (v/v)), and dried under reduced pressure, to obtain the targeted compound MM1 (4.72 g) as a white solid. The yield was 55%. The resultant compound MM1 showed a HPLC area percentage value of 99.99% or more. If necessary, the above-described operations were repeated.

$^1$H-NMR (300 MHz, CDCl$_3$): δ (ppm)=7.82 (d, 2H), 7.23 (m, 4H), 7.17 (s, 2H), 7.12-7.07 (m, 6H), 6.99-6.95 (m, 4H), 2.52 (t, 4H), 1.59-1.45 (m, 4H), 1.32-1.18 (m, 12H), 0.85 (t, 6H).

LC/MS (ESI-MS (posi)): 850 [M]$^+$

Example 2

(Synthesis of Compound MM2)

3,2-dioxaborolane (30.5 g, 164 mmol) was dropped slowly over a period of about 20 minutes, then, the dry ice/methanol bath was removed, and the mixture was stirred for 4 hours while slowly heating up to room temperature. Thereafter, the internal temperature was cooled down to −30° C. again using a dry ice/methanol bath, then, a hydrogen chloride diethyl ether solution was slowly dropped until the reaction solution showed pH 6 to 7. Thereafter, the dry ice/methanol bath was removed, the temperature was slowly raised up to room temperature, then, volatile components were removed by vacuum concentration. Thereafter, chloroform was added, the mixture was washed with ion exchanged water three times, then, the resultant organic layer was dried over anhydrous sodium sulfate, and an inorganic salt was filtrated. The resultant filtrate was concentrated under reduced pressure, and purified by silica gel column chromatography

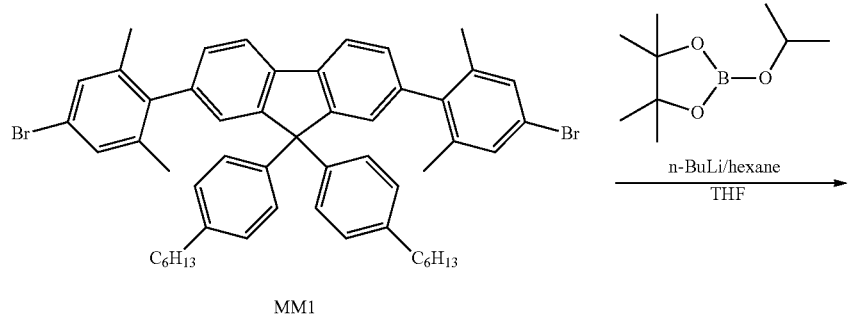

MM1

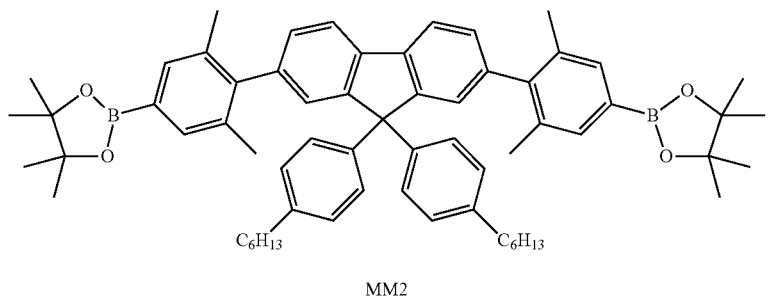

MM2

A gas in a 500 ml three-necked flask was purged with an argon gas, then, a compound MM1 (35.0 g, 41 mmol) and tetrahydrofuran (commercially available dehydrated grade, 250 ml) were added, the compound MM1 was dissolved, then, the solution was cooled sufficiently by a dry ice/methanol bath (−78° C.). Thereafter, a hexane solution of n-butyllithium (2.73 mol/L, 33 ml, 90 mmol) was dropped slowly under stirring, then, the mixture was further stirred for 3 hours. Thereafter, 2-isopropoxy-4,4,5,5-tetramethyl-1, (hexane/ethyl acetate=7/1 (v/v)), hexane was further added, and the mixture was stirred with heating, and hot-filtrated to obtain a solid. The resultant solid was dried under reduced pressure, to obtain the targeted compound MM2 (20.8 g) as a white solid. The yield was 54%. The resultant compound indicated a HPLC area percentage value of 99.8% or more.

$^1$H-NMR (CDCl$_3$, 300 MHz): δ (ppm)=7.82 (d, 2H), 7.55 (s, 4H), 7.21 (d, 2H), 7.14-7.08 (mult, 6H), 6.98-6.93 (mult, 4H), 2.51 (t, 4H), 2.00 (s, 12H), 1.57-1.46 (mult, 4H), 1.35 (s, 24H), 1.27-1.20 (mult, 12H), 0.85 (t, 6H).

Example 3

(Synthesis of Compound MM3)

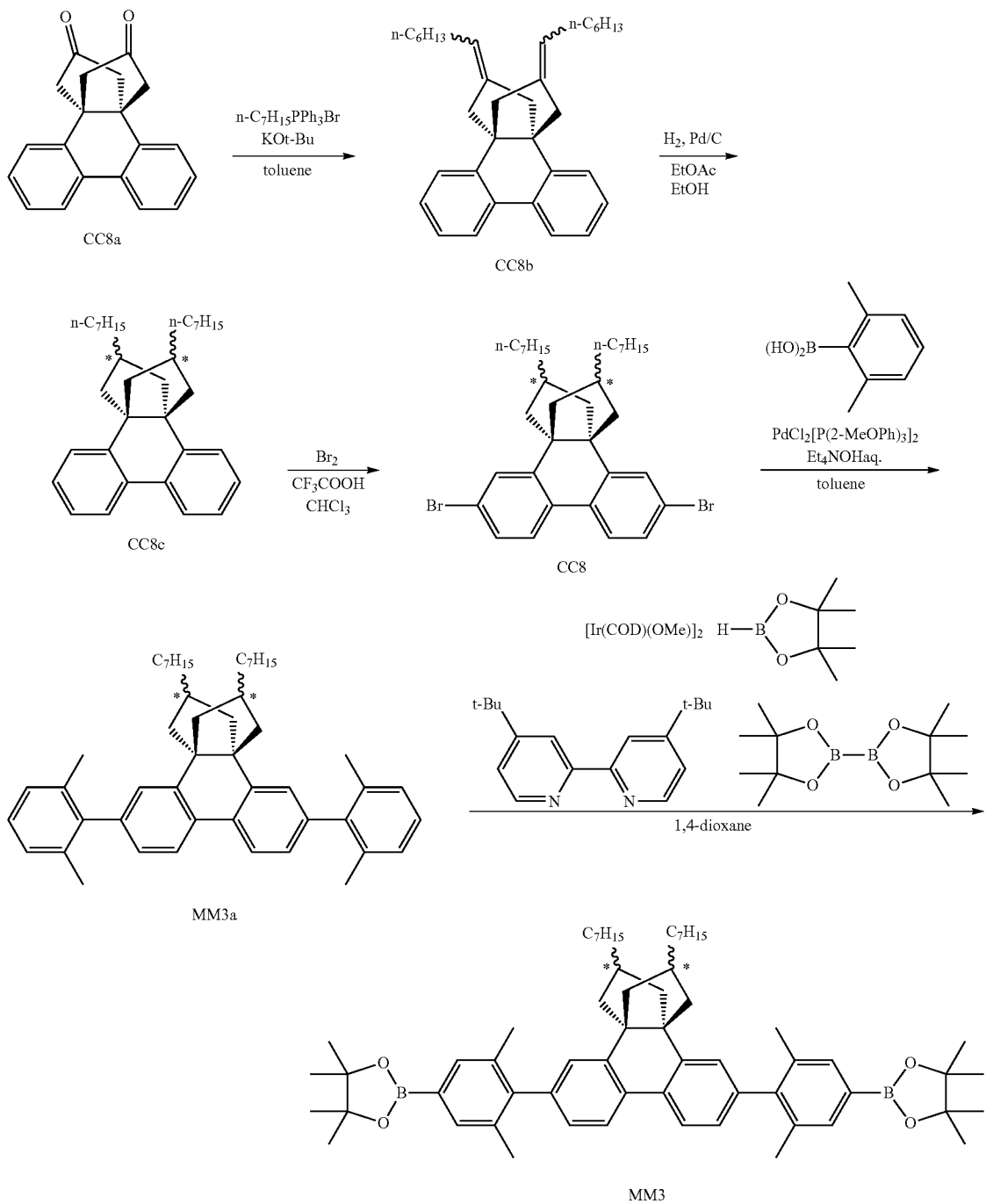

(in the formulae, a wavy line means that a compound having this wavy line is a mixture of geometric isomers or a mixture of stereoisomers containing a diastereomer. * means that a carbon atom appended with this is an asymmetric carbon atom.)

(First Step)

Into a 1 L four-necked flask equipped with a stirrer was charged heptyltriphenylphosphonium bromide (115.0 g), and a gas in the flask was purged with an argon gas. Thereafter, toluene (375 g) was added, and the mixture was cooled to 5° C. or lower. Thereafter, potassium tert-butoxide (29.2 g) was added, the temperature was raised up to room temperature, then, the mixture was stirred for 3 hours while keeping temperature at room temperature. To a red slurry generated in the resultant reaction solution was added a compound CC8a (15.0 g), and the mixture was stirred for 12 hours while keeping temperature at room temperature. To the resultant reaction solution was added acetic acid (10.0 g)

and the mixture was stirred for 15 minutes, then, filtrated to obtain the filtrate and the residue. Thereafter, the resultant residue was washed with toluene several times, to obtain the washed solution. Thereafter, the filtrate obtained above and the washed solution obtained after washing several times were combined and concentrated, and hexane was added to this, to find generation of a slurry. This slurry was stirred for 1 hour while thermally insulating at 50° C. The resultant mixture was cooled down to room temperature, and filtrated to obtain the filtrate and the residue. Thereafter, the resultant residue was washed with hexane several times, to obtain the washed solution. Thereafter, the filtrate obtained above and the washed solution obtained after washing several times were combined and concentrated to obtain a coarse product. The resultant coarse product was purified using a silica gel column (developing solvent: hexane), to obtain a compound CC8b (21.7 g) as a colorless transparent liquid.

LC-MS (ESI, positive, KCl added): [M+K]$^+$ 491.

$^1$H-NMR (CDCl$_3$, 300 MHz): δ (ppm)=0.87 (6H, t), 1.20-1.36 (16H, m), 1.82-1.97 (4H, m), 2.57-2.81 (8H, m), 5.20 (2H, br), 7.23-7.32 (4H, m), 7.41-7.48 (2H, m), 7.87-7.90 (2H, m).

(Second Step)

Into a 1 L four-necked flask equipped with a stirrer was added a compound CC8b (21.7 g), then, ethyl acetate (152.4 g) and ethanol (151.6 g) were added, and a gas in the four-necked flask was purged with a nitrogen gas. Thereafter, 5 wt % Pd/C (about 50 wt % hydrous product) (4.3 g) was added, then, a gas in the four-necked flask was purged with a hydrogen gas, and the mixture was stirred for 27 hours while thermally insulating at 40° C. under a hydrogen gas atmosphere. The resultant mixture was cooled down to room temperature, filtrated by a filtering apparatus pre-coated with Celite, to obtain the filtrate and the residue. The resultant residue was washed with ethyl acetate several times, to obtain the washed solution. Thereafter, the filtrate obtained above and the washed solution obtained after washing several times were combined and concentrated to obtain a coarse product. This coarse product was purified using a silica gel column (developing solvent: hexane), to obtain a compound CC8c (21.7 g) as a colorless transparent liquid.

LC-MS (APPI, positive): [M]$^+$ 456.

$^1$H-NMR (CDCl$_3$, 300 MHz): δ (ppm)=0.66-0.98 (6H, m), 1.00-2.22 (34H, m), 7.13-7.50 (6H, m), 7.80-7.98 (2H, m).

(Third Step)

Into a 500 ml four-necked flask equipped with a stirrer were charged a compound CC8c (21.7 g), chloroform (261.1 g) and trifluoroacetic acid (44 g), and the gas in the four-necked flask was purged with an argon gas. Thereafter, the whole body of the four-necked flask was light-shielded, and a mixture was bromine (19.0 g) and chloroform (65.3 g) was dropped at room temperature over a period of 15 minutes, then, the temperature was raised up to 35° C. Thereafter, the mixture was stirred at 35° C. for 7 hours, then, cooled down to 15° C. or lower. To the resultant reaction solution was added a 10 wt % sodium sulfite aqueous solution (109 g), and the temperature was raised up to room temperature. The aqueous layer was separated from the resultant reaction solution, and the organic layer was washed with water, a 5 wt % sodium hydrogen carbonate aqueous solution and water in this order. The resultant organic layer was dried over magnesium sulfate, filtrated, and the filtrate was concentrated to obtain a coarse product. The resultant coarse product was recrystallized from a mixture of ethanol and hexane twice. The resultant solid was dissolved in hexane, and purified using a silica gel column (developing solvent: hexane), and to the resultant hexane solution was added activated carbon (2.1 g), and the mixture was stirred for 1 hour while thermally insulating at 45° C. The resultant mixture was cooled down to room temperature, and filtrated by a filtering apparatus pre-coated with Celite. The resultant residue was washed with hexane several times, and the filtrates after washing several times were combined and partially concentrated, to obtain a hexane solution. To the resultant hexane solution was added ethanol, to cause recrystallization, to obtain a compound CC8 (18.8 g) as a white solid.

LC-MS (ESI, negative, KCl added): [M+Cl]$^-$ 648.

$^1$H-NMR (CDCl$_3$, 300 MHz): δ (ppm)=0.66-0.98 (6H, m), 1.00-2.20 (34H, m), 7.22-7.78 (6H, m).

From the measurement results of $^1$H-NMR, it was confirmed that the compound CC8 was a mixture of stereoisomers (CC8-1:CC8-2:CC8-3=51:39:10) (molar ratio). The total HPLC area percentage value of the resultant stereoisomers was 99.8% or more.

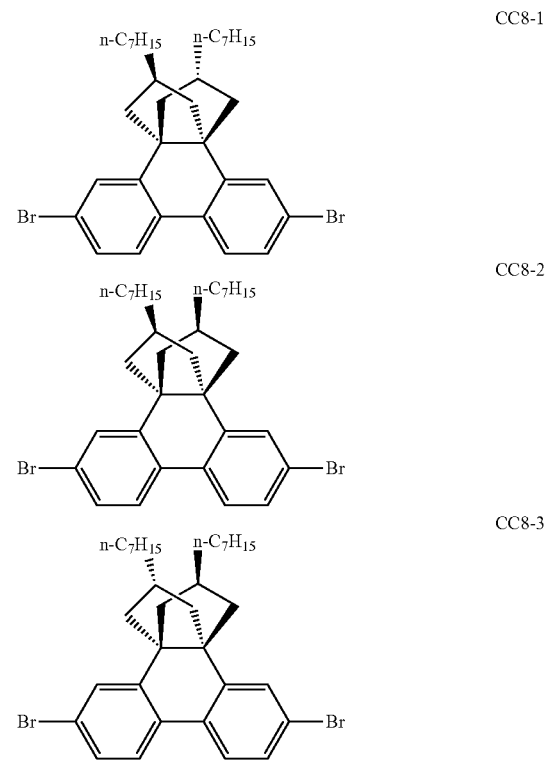

(Fourth Step)

To a 500 ml flask were added a compound CC8 (24.6 g, 40 mmol), 2,6-dimethylbenzeneboronic acid (15.0 g, 100 mmol), dichlorobis(tri(2-methoxyphenyl)phosphine)palladium(II) (0.71 g, 0.8 mmol), toluene (commercially available dehydrated grade, 200 ml) and 20 wt % tetraethyl ammonium hydroxide aqueous solution (118 g, 160 mmol), the mixture was bubbled with an argon gas for 15 minutes, then, the mixture was stirred for 1.5 hours while heating in an oil bath set at 110° C. Thereafter, the mixture was cooled down to room temperature, allowed to pass through a Celite pad to remove solid components, then, diluted with toluene, the aqueous layer was removed by liquid separation, and the resultant organic layer was washed with ion exchanged water twice, and with 15 wt % saline once. To the resultant organic layer was added activated white earth (manufactured by Wako Pure Chemical Industries, Ltd., 25 g) and the mixture was stirred at room temperature for 1 hour, then, filtrated by passing through a silica gel pad and a Celite pad, to remove solid components. The resultant filtrate was concentrated under reduced pressure, and recrystallized (toluene/ethanol), and the resultant solid was dried under reduced pressure, to obtain a compound MM3a (26.6 g) as a white solid. The yield was 99% or more. The resultant compound indicated a HPLC area percentage value of 99.9% or more. The compound MM3a is a mixture of isomers since the compound CC8 is a mixture of isomers, and the gained amount, yield and HPLC area percentage value described above were the total value of the mixture of isomers.

(Fifth Step)
(Preparation of Catalyst Solution)

A gas in a 100 ml two-necked flask was purged with an argon gas, then, bis(1,5-cyclooctadiene)di-μ-methoxydi-iridium(I) ([Ir(OMe) (1,5-cod)]$_2$, 0.245 g, 0.37 mmol), 1,4-dioxane (20 ml) and 4,4,5,5-tetramethyl-1,3,2-dioxaborolane (0.89 ml, 6.2 mmol) were added, and the mixture was stirred for 15 minutes, then, a solution prepared by dissolving 4,4'-di-tert-butyl-2,2'-bipyridyl (0.225 g, 0.84 mmol) in 1,4-dioxane (16 ml) was further added, and the mixture was stirred for 15 minutes, to obtain a catalyst solution.

(Reaction)

Into a 300 ml three-necked flask were added the compound MM3a (24.6 g, 37 mmol) synthesized above, bis(pinacol)diboron (28.2 g, 111 mmol) and 1,4-dioxane (74 ml), the mixture was bubbled with an argon gas for 15 minutes, then, the mixture was heated by an oil bath at 80° C. Thereafter, the catalyst solution prepared above was added, then, the mixture was stirred for 26 hours while heating by an oil bath at 120° C. Thereafter, the mixture was cooled down to room temperature, hexane (300 ml) and activated carbon (10 g) were added, the mixture was stirred at room temperature for 1.5 hours, then, allowed to pass through a silica gel pad and a Celite pad to remove solid components, and concentrated under reduced pressure, the operations were repeated three time in total, then, recrystallized (toluene/acetonitrile). To the resultant solid was added acetonitrile, and the mixture was stirred for 3 hours while heating by an oil bath at 90° C., cooled down to room temperature, and the resultant solid was isolated by filtration. Thereafter, the resultant solid was purified by medium pressure silica gel column chromatography (hexane/toluene=100/0 to 0/100: gradient). Thereafter, to the resultant solid was added acetonitrile and the mixture was stirred for 3 hours while heating by an oil bath at 90° C., cooled down to room temperature, and the resultant solid was isolated by filtration, and the operations were repeated. The resultant solid was dried under reduced pressure, to obtain the targeted compound MM3 (15.5 g) as a white solid. The yield was 46%. The resultant compound MM3 indicated a HPLC area percentage value of 99.5% or more. The compound MM3 is a mixture of isomers since the compound MM3a is a mixture of isomers, and the gained amount, yield and HPLC area percentage value described above were the total value of the mixture of isomers.

$^1$H-NMR (300 MHz, CDCl$_3$): δ (ppm)=7.98-7.93 (m, 2H), 7.61 (s, 4H), 7.23-7.10 (m, 2H), 7.07-6.98 (m, 2H), 2.24-2.22 (m, 4H), 2.15-2.09 (m, 12H), 1.80-1.57 (m, 4H), 1.50-1.10 ((m, 26H)+(s, 24H)), 0.90-0.80 (m, 6H).

Example 4

(Synthesis of Compound MM4)

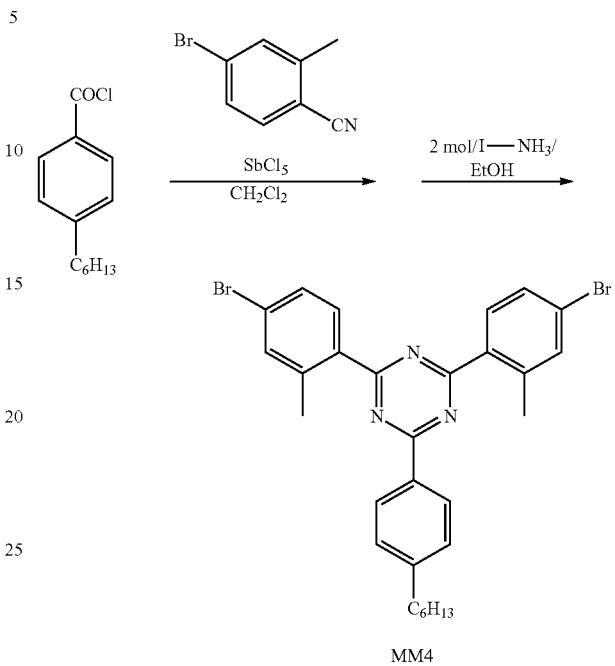

A gas in a reaction vessel was purged with an argon gas, then, 4-hexylbenzoyl chloride (4.49 g, 20 mmol), 4-bromo-2-methylbenzonitrile (7.84 g, 40 mmol) and dichloromethane (80 ml) were mixed, and the mixture was bubbled with an argon gas to remove an oxygen gas in the reaction solution, then, cooled down to 0° C., and antimony pentachloride (5.98 g, 20 mmol) was slowly added over a period of 30 minutes. Thereafter, the mixture was stirred at room temperature for 30 minute, then, stirred for 3 hours under reflux with heating while heating at 50° C. Thereafter, the resultant reaction solution was added slowly to a 2 mol/l ammonia-ethanol solution (300 ml) cooled by an ice water bath, and stirred at room temperature for 1 hour, and allowed to stand still overnight, then, the resultant solution was concentrated under reduced pressure, chloroform (500 ml) was added, the mixture was washed with ion exchanged water (400 ml) twice, and dried over anhydrous magnesium sulfate. Thereafter, an inorganic salt was filtrated, and the resultant filtrate was concentrated, to obtain about 12 g of an oily substance. The resultant oily substance was purified by medium pressure silica gel column chromatography (φ5 cm×30 cm, hexane/chloroform=100/0 to 90/10 (v/v)), to obtain the targeted compound MM4 (4.22 g). The resultant compound indicated a HPLC area percentage value of 82.6%. The above-described operations were repeated, to obtain the targeted compound MM4 (8.92 g). The resultant compound indicated a HPLC area percentage value of 87.3%.

The compound MM4 obtained by the above-described operations was purified by medium pressure silica gel column chromatography (hexane/chloroform=80/20 (v/v)), to obtain the targeted compound MM4 (4.99 g). The resultant compound indicated a HPLC area percentage value of 99.82%. To the resultant compound MM4 was added methanol (250 ml), and the mixture was stirred while heating at 50° C., then, cooled down to room temperature, the resultant solid was isolated by filtration, and dried under reduced pressure at 40° C., to obtain the targeted compound MM4 (4.38 g) as a white solid. The resultant compound indicated a HPLC area percentage value of 99.6% or more.

$^1$H-NMR (300 MHz, THF-d8): δ (ppm)=8.59 (d, 2H), 8.27 (d, 2H), 7.57 (m, 4H), 7.40 (d, 2H), 2.84 (s, 6H), 2.74 (t, 2H), 1.71 (t, 2H), 1.39 (m, 6H), 0.92 (t, 3H).

$^{13}$C-NMR (75 MHz, THF-d8): δ (ppm)=175.3, 173.1, 150.4, 143.6, 137.1, 136.6, 135.7, 134.9, 131.4, 131.0, 130.8, 127.4, 37.9, 33.8, 33.3, 31.1, 24.6, 23.7, 15.5.

TLC/MS: [M+H]+=580.11.

Example 5

(Synthesis of Compound MM5)

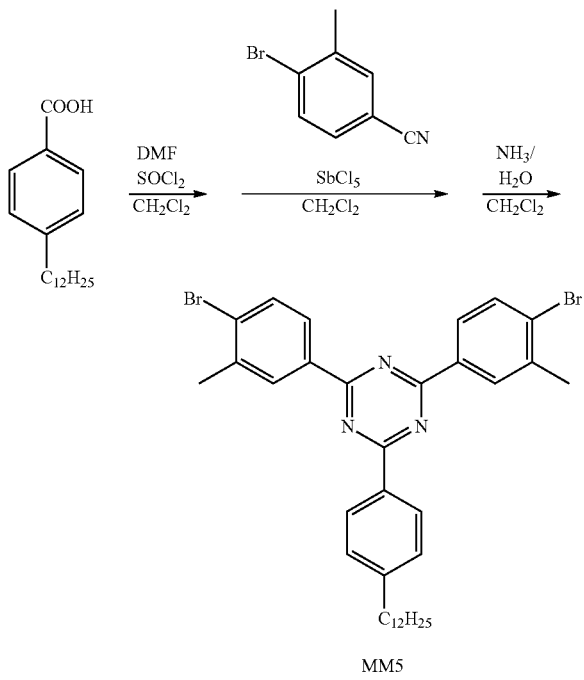

MM5

A gas in the reaction vessel was purged with an argon gas, then, 4-dodecylbenzoic acid (14.52 g), dichloromethane (90 ml), thionyl chloride (6.00 g) and N,N'-dimethylformamide (dMF) (about 60 mg) were stirred for 1 hour under reflux with heating, then, molecular sieves 3 Å (manufactured by Wako Pure Chemical Industries, Ltd., 30 g) were added, and the mixture was cooled by an ice bath down to 0° C. Thereafter, antimony pentachloride (14.7 g) was dropped over a period of 10 minutes, and the mixture was stirred at 0° C. for 1 hour. Thereafter, 4-bromo-3-methylbenzonitrile (19.6 g, 100 mmol) dissolved in dichloromethane (60 ml) was dropped at the same temperature over a period of 1 hour. Thereafter, the mixture was stirred at room temperature for 30 minutes, and stirred for 2 hours under reflux with heating. Thereafter, the mixture was cooled down to −15° C., and a 25% ammonia aqueous solution (22 g) was dropped. Thereafter, the mixture was stirred at room temperature for 1 hour, and allowed to stand still at room temperature. Thereafter, chloroform (500 ml) was added, and the mixture was stirred for 1 hour while heating at 45° C., then, hot-filtrated to remove solid components, and the resultant filtrate was washed with ion exchanged water (200 ml) four times, dried over anhydrous sodium sulfate, the resultant solid was filtrated, then, the resultant solid was concentrated under reduced pressure, to obtain an orange oily substance. The resultant orange oily substance was purified by performing recrystallization (chloroform/ethanol), medium pressure silica gel column chromatography (hexane/chloroform=96/4 (v/v)), recrystallization (chloroform/hexane), recrystallization (ethyl acetate) and recrystallization (chloroform/hexane, conducted twice) in series, and the resultant solid was dried under reduced pressure, to obtain the targeted compound MM5 (8.42 g) as a white solid. The resultant compound indicated a HPLC area percentage value of 99.6% or more.

$^1$H-NMR (300 MHz, THF-d8): δ (ppm)=8.63 (d, 4H), 8.43 (d, 2H), 7.73 (d, 2H), 7.40 (d, 2H), 2.76 (t, 2H), 2.55 (s, 6H), 1.71 (m, 2H), 1.31 (m, 18H), 0.90 (t, 3H).

$^{13}$C-NMR (75 MHz, THF-d$_8$): δ (ppm)=173.7, 172.9, 150.3, 140.2, 137.6, 135.5, 134.6, 132.9, 131.7, 131.0, 130.7, 129.8, 38.0, 34.0, 33.3, 31.8, 31.74, 31.72, 31.71, 31.6, 31.43, 31.41, 24.7, 24.3, 15.6.

Example 6

(Synthesis of Compound MM6)

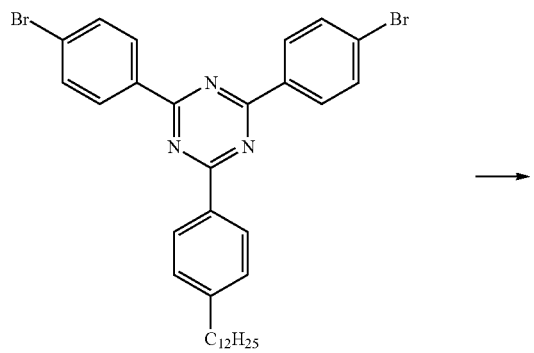

CC12

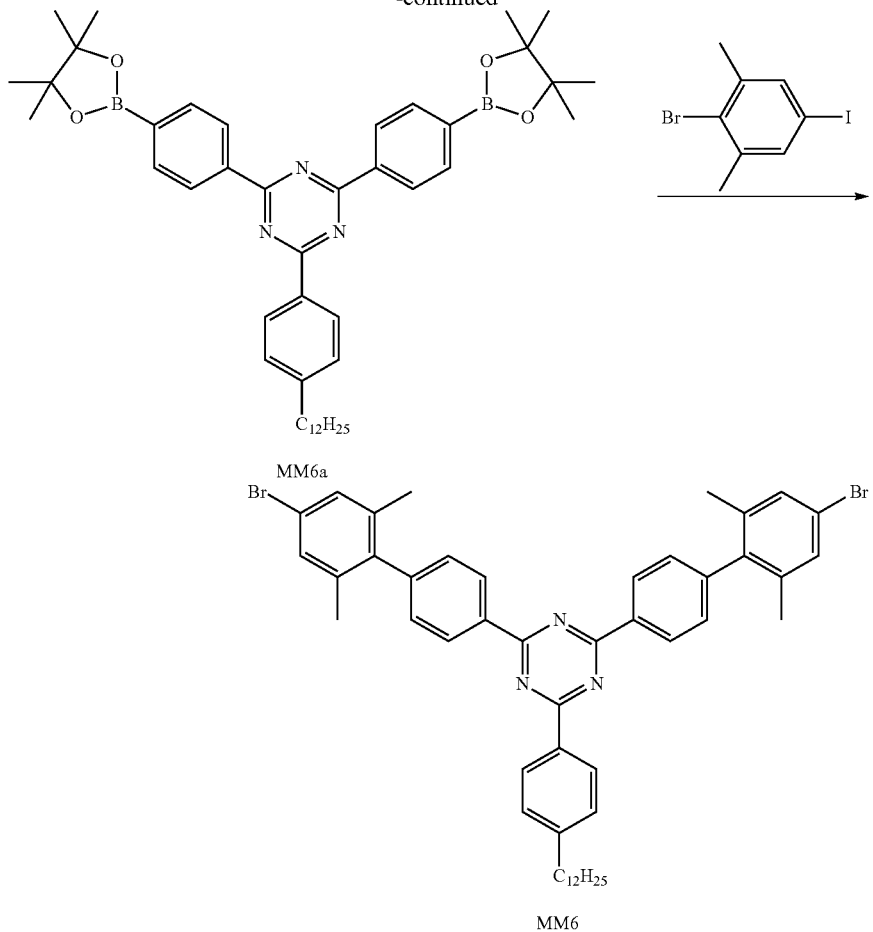

(First Step)

A gas in a reaction vessel was changed to an argon gas atmosphere, then, a mixture of a compound CC12 (41.77 g, 120 mmol), bis(pinacol)diboron (91.9 g, 362 mmol), a dichloromethane complex (1:1) of [1,1'-bis(diphenylphosphino)ferrocene]dichloropalladium(II) (Pd (dppf) $Cl_2 \cdot CH_2Cl_2$, CAS number: 95464-05-4, manufactured by Sigma-Aldrich Co. LLC, 5.096 g, 6.24 mmol), potassium acetate (70.67 g, 720 mmol) and 1,4-dioxane (commercially available dehydrated product, 500 ml) was stirred for about 8 hours while heating by an oil bath at 80° C., then, diluted with toluene (500 ml), then, allowed to pass through a Celite and silica gel pad to remove insoluble materials, then, the solvent was distilled off, to obtain a solid. To the resultant solid was added methanol (750 ml), the mixture was well stirred, then, the solid was isolated by filtration, and dried under reduced pressure, to obtain a solid (57 g). The resultant solid was dissolved in hexane, activated carbon was added to this, and the mixture was stirred for 1 hour while heating by an oil bath at 60° C., then, insoluble materials were removed by filtration through Celite, then, the solvent was distilled off, to obtain a white solid. To the resultant solid was added methanol (750 ml), and the mixture was stirred for 1 hour while heating at 50° C., then, cooled down to room temperature, the deposited solid was isolated by filtration, and dried under reduced pressure, to obtain a compound MM6a (40.59 g). The yield was 76%. The resultant compound MM6a indicated a HPLC area percentage value (UV254 nm) of 99.9% or more.

$^1$H-NMR (300 MHz, $CDCl_3$): δ (ppm)=8.75 (d, 2H), 8.68 (d, 2H), 8.06 (d, 2H), 7.39 (d, 2H), 2.73 (t, 2H), 1.71-1.60 (m, 2H), 1.50-1.20 (m, 46H), 0.88 (t, 3H).

TLC/MS (dART, posi): [M+H]%=730.49

(Second Step)

A gas in a reaction vessel was changed to an argon gas atmosphere, then, a mixture of a compound MM6a (25.54 g, 35 mmol), 5-iodo-2-bromo-m-xylene (32.65 g, 105 mmol), toluene (210 ml), tert-butanol (140 ml), tetrahydrofuran (105 ml), ion exchanged water (70 ml), a 20 wt % tetraethyl ammonium hydroxide aqueous solution (103.1 g, 140 mmol) and tetrakis(triphenylphosphine)palladium(0) (2.45 g, 2.12 mmol) was stirred for 40 hours while heating by an oil bath set at 40° C., then, cooled down to room temperature, toluene (140 ml) and ion exchanged water (140 ml) were added, and the organic layer was obtained by liquid separation. The resultant organic layer was washed with 5 wt % saline, then, dried over anhydrous magnesium sulfate, the resultant solid was removed by filtration, then, the solvent was distilled off by concentration under reduced pressure, to obtain a brown oily substance (37 g). The resultant brown oily substance was diluted with toluene, then, allowed to pass through a silica gel short column, and the solvent was distilled off by concentration under reduced pressure, to obtain a yellow oily substance. The resultant yellow oily substance was purified by medium pressure silica gel column chromatography (hexane), a fraction containing the targeted compound was concentrated under reduced pressure, then, purified by recrystallization (a mixed solvent of toluene and methanol), and the resultant solid was dried under reduced pressure, to obtain a compound MM6 (6.15 g). The yield was 21%. The resultant compound MM6 indicated a HPLC area percentage value of 99.9% or more.

$^1$H-NMR (300 MHz, CD$_2$Cl$_2$): δ (ppm)=8.86 (d, J=8.3 Hz, 4H), 8.72 (d, J=8.3 Hz, 2H), 7.43 (d, J=8.3 Hz, 2H), 7.37 (d, J=8.3 Hz, 4H), 7.32 (s, 4H), 2.75 (t, J=7.7 Hz, 2H), 2.07 (s, 12H), 1.75-1.66 (mult, 2H), 1.42-1.22 (mult, 18H), 0.88 (t, J=6.6 Hz, 3H).

TLC/MS (dART, posi): [M+H]$^+$=842.27

Example 7

(Synthesis of Compound MM7)

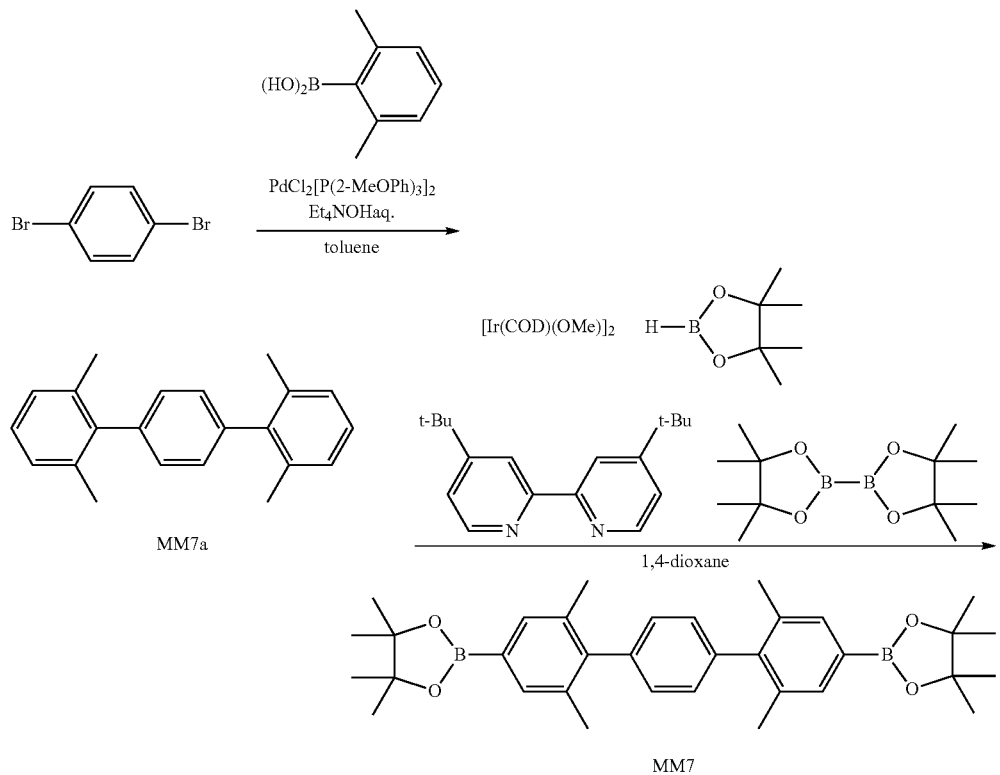

(First Step)

Into a 1 L flask were added 1,4-dibromobenzene (20.8 g, 88 mmol), 2,6-dimethylbenzeneboronic acid (33.0 g, 220 mmol), dichlorobis(tri(2-methoxyphenyl)phosphine)palladium(II) (1.55 g, 1.8 mmol), toluene (commercially available dehydrated grade, 440 ml) and a 20 wt % tetraethyl ammonium hydroxide aqueous solution (259 g, 352 mmol), and the mixture was bubbled with an argon gas for 15 minutes, then, stirred for 3 hours while heating by an oil bath set at 105° C. Thereafter, the mixture was cooled down to room temperature, diluted with toluene, the aqueous layer was removed by liquid separation, and the resultant organic layer was washed with ion exchanged water three times, with 15 wt % saline once. To the resultant organic layer was added activated white earth (manufactured by Wako Pure Chemical Industries, Ltd., 25 g), and the mixture was stirred at room temperature for 30 minutes, then, solid components were removed by filtration through a Celite pad. The resultant filtrate was concentrated under reduced pressure, purified by recrystallization (toluene/ethanol), and the resultant solid was dried under reduced pressure, to obtain a compound MM7a (24.4 g) as a white solid. The yield was 97%. The resultant compound MM7a indicated a HPLC area percentage value (UV254 nm) of 99.9% or more.

$^1$H-NMR (300 MHz, CDCl$_3$): δ (ppm)=7.20-7.14 (m, 10H), 2.09 (s, 12H).

$^{13}$C-NMR (75 MHz, CDCl$_3$): δ (ppm)=142.12, 139.59, 136.47, 129.31, 127.54, 127.28, 21.09.

(Second Step)

A gas in a 100 ml two-necked flask was changed to an argon gas atmosphere, then, [Ir(COD)(OMe)]$_2$ (0.464 g, 0.7 mmol), 1,4-dioxane (70 ml) and 4,4,5,5-tetramethyl-1,3,2-dioxaborolane (1.7 ml, 11.8 mmol) were added and stirred for 15 minutes, then, 4,4'-di-tert-butyl-2,2'-bipyridyl (0.426 g, 1.59 mmol) was further added, and the mixture was stirred for 15 minutes to obtain a catalyst solution.

Into a 500 ml three-necked flask were added a compound MM7a (20.0 g, 70 mmol), bis(pinacol)diboron (53.3 g, 210 mmol) and 1,4-dioxane (140 ml), the mixture was bubbled with an argon gas for 15 minutes, then, heated by an oil bath at 60° C. Thereafter, the whole amount of the catalyst solution prepared above was added to this, and the mixture was stirred for 6 hours while heating by an oil bath at 120° C. Thereafter, the mixture was cooled down to room temperature, and the deposited solid was isolated by filtration. The resultant solid was dissolved in chloroform, the solution was allowed to pass through a silica gel short column, then, purified by recrystallization (chloroform/acetonitrile), and the resultant solid was dried under reduced pressure, to obtain the targeted compound MM7 (30.8 g) as a white solid. The yield was 82%. The resultant compound MM7 indicated a HPLC area percentage value (UV254 nm) of 99.6% or more.

$^1$H-NMR (300 MHz, CDCl$_3$): δ (ppm)=7.61 (s, 4H), 7.18 (s, 4H), 2.10 (s, 12H), 1.37 (s, 24H).

$^{13}$C-NMR (75 MHz, CDCl$_3$): δ (ppm)=145.23, 139.58, 135.90, 133.93, 129.01, 84.01, 25.13, 20.84.

Example 8

(Synthesis of Compound MM8)

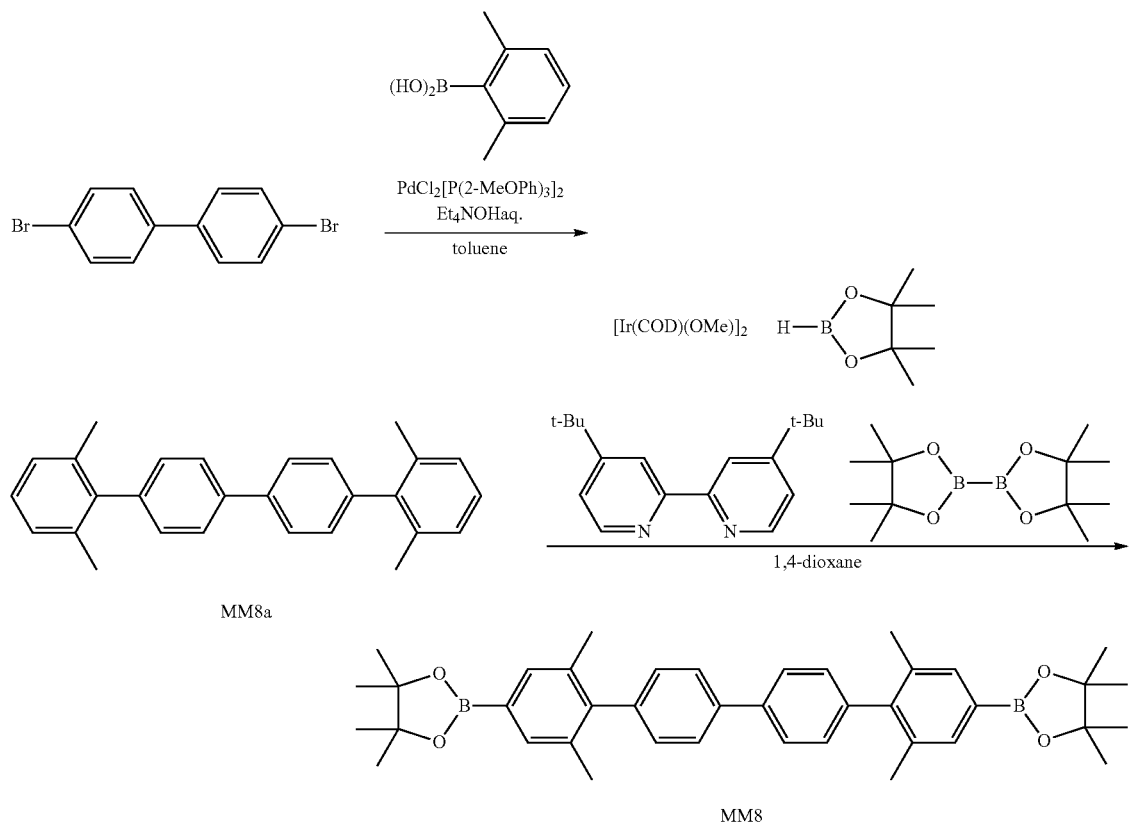

(First Step)

Into a 500 ml flask were added 4,4'-dibromobiphenyl (12.5 g, 40 mmol), 2,6-dimethylbenzeneboronic acid (15.0 g, 100 mmol), dichlorobis(tri(2-methoxyphenyl)phosphine)palladium(II) (0.35 g, 0.4 mmol), toluene (commercially available dehydrated grade, 200 ml) and a 20 wt % tetraethyl ammonium hydroxide aqueous solution (118 g, 160 mmol), the mixture was bubbled with an argon gas for 15 minutes, then, stirred for 2 hours while heating by an oil bath set at 105° C. Thereafter, the mixture was cooled down to room temperature, diluted with toluene, the aqueous layer was removed by liquid separation, and the resultant organic layer was washed with ion exchanged water twice, with 15 wt % saline once. To the resultant organic layer was added activated white earth (manufactured by Wako Pure Chemical Industries, Ltd., 25 g), and the mixture was stirred at room temperature for 1.5 hours, then, solid components were removed by filtration through a Celite pad. The resultant filtrate was concentrated under reduced pressure and purified by recrystallization (ethanol), and the operations were repeated twice, and the resultant solid was dried under reduced pressure, to obtain a compound MM8a (12.8 g) as a white solid. The yield was 88%. The resultant compound MM8a indicated a HPLC area percentage value (UV254 nm) of 99.8% or more.

(Second Step)

A gas in a 100 ml two-necked flask was changed to an argon gas atmosphere, then, [Ir(COD)(OMe)]$_2$ (0.232 g, 0.35 mmol), 1,4-dioxane (36 ml) and 4,4,5,5-tetramethyl-1,3,2-dioxaborolane (0.85 ml, 5.9 mmol) were added, stirred for 15 minutes, then, 4,4'-di-tert-butyl-2,2'-bipyridyl (0.213 g, 0.8 mmol) was further added, and the mixture was stirred for 15 minutes to obtain a catalyst solution.

Into a 500 ml three-necked flask were added a compound MM8a (12.7 g, 35 mmol), bis(pinacol)diboron (26.7 g, 105 mmol) and 1,4-dioxane (70 ml), the mixture was bubbled with an argon gas for 15 minutes, then, heated by an oil bath at 100° C. Thereafter, the whole amount of the catalyst solution prepared above was added to this, then, the mixture was stirred for 15 hours while heating by an oil bath at 110° C. Thereafter, the mixture was cooled down to room temperature, acetonitrile (100 ml) was added, and the deposited solid was isolated by filtration. The resultant solid was dissolved in chloroform, the solution was allowed to pass through a silica gel short column, then, purified by recrystallization (chloroform/acetonitrile), and further, purified by recrystallization (toluene/acetonitrile), and the resultant solid was dried under reduced pressure, to obtain the targeted compound MM8 (16.5 g) as a white solid. The yield was 77%. The resultant compound MM8 indicated a HPLC area percentage value (UV254 nm) of 99.5% or more.

$^1$H-NMR (300 MHz, CDCl$_3$): δ (ppm)=7.74 (d, 4H), 7.60 (s, 4H), 7.22 (d, 4H), 2.10 (s, 12H), 1.37 (s, 24H).

$^{13}$C-NMR (75 MHz, CDCl$_3$): δ (ppm)=144.96, 140.27, 139.31, 135.89, 134.00, 133.97, 129.53, 127.25, 25.15, 25.10, 20.97.

Example 9

(Synthesis of Compound MM9)

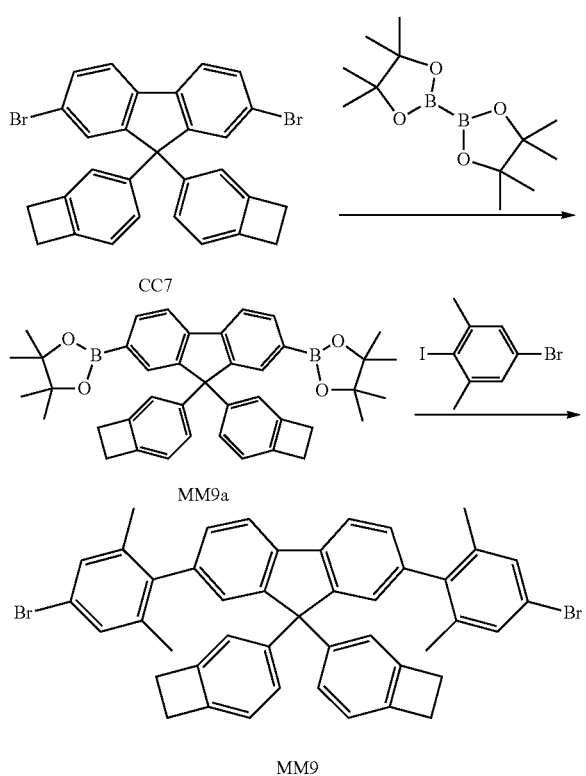

(First Step)

A gas in a reaction vessel was changed to a nitrogen gas atmosphere, then, a compound CC7 (96.41 g, 182 mmol), bis(pinacol)diboron (139.3 g, 547 mmol), a dichloromethane complex (1:1) of [1,1'-bis(diphenylphosphino)ferrocene]dichloropalladium(II) (Pd (dppf)Cl$_2$·CH$_2$Cl$_2$, CAS number: 95464-05-4, manufactured by Sigma-Aldrich Co. LLC, 14.9 g, 18.3 mmol), potassium acetate (107.5 g, 1095 mmol) and 1,4-dioxane (commercially available dehydrated product, 550 ml) were added, and the mixture was stirred for about 6 hours while heating by an oil bath at 80° C., then, toluene (850 ml) was further added, and insoluble materials were removed by passing through a Celite and silica gel pad, then, the solvent was distilled off to obtain a solid. The resultant solid was dissolved in toluene, then, activated carbon was added, and the mixture was stirred for 1 hour while heating by an oil bath at 60° C. Thereafter, insoluble materials were removed by filtration through Celite and the solvent was distilled off, and the operations were repeated twice, to obtain a white solid. The resultant solid was purified by recrystallization (acetonitrile) and the resultant solid was dried under reduced pressure, to obtain a compound MM9a (113.7 g). The yield was 91%. The resultant compound MM9a indicated a HPLC area percentage value (UV254 nm) of 98.7%.

$^1$H-NMR (300 MHz, CDCl$_3$): δ (ppm)=7.81 (s, 2H), 7.80 (d, 2H), 7.75 (d, 2H), 7.12 (d, 2H), 6.89 (d, 2H), 6.86 (s, 2H), 3.07 (d, 8H), 1.31 (s, 24H).

LC/MS (ESI, posi): [M+K]$^+$=661.3

(Second Step)

A gas in a reaction vessel was changed to a nitrogen gas atmosphere, then, a compound MM9a (107.7 g, 171 mmol), 5-iodo-2-bromo-m-xylene (159.5 g, 513 mmol), toluene (1000 ml), tert-butanol (700 ml), tetrahydrofuran (500 ml), ion exchanged water (350 ml), a 20 wt % tetraethyl ammonium hydroxide aqueous solution (500 g, 682 mmol) and tetrakis(triphenylphosphine)palladium(0) (5.0 g, 4.3 mmol) were added, and the mixture was stirred for 64 hours while heating by an oil bath set at 50° C. Thereafter, the mixture was cooled down to room temperature, toluene (680 ml) and ion exchanged water (680 ml) were added, and the aqueous layer was removed by liquid separation. The resultant organic layer was washed with ion exchanged water and 10 wt % saline in series, then, dried over anhydrous magnesium sulfate, the resultant solid was removed by filtration, then, the solvent was distilled off by concentration under reduced pressure, to obtain a yellow oily substance (212 g). The resultant yellow oily substance was purified by recrystallization (ethyl acetate/acetonitrile), and further purified by silica gel column chromatography (hexane/chloroform), and a fraction containing the targeted compound was concentrated under reduced pressure, then, purified by recrystallization (toluene/acetonitrile), the resultant solid was dried under reduced pressure, to obtain a compound MM9 (81 g). The yield was 61%. The resultant compound MM9 indicated a HPLC area percentage value (UV254 nm) of 99.8%.

$^1$H-NMR (300 MHz, CDCl$_3$): δ (ppm)=7.81 (d, 2H), 7.24 (s, 4H), 7.17 (s, 2H), 7.11 (d, 2H), 7.03 (d, 2H), 6.87 (s, 2H), 6.83 (d, 2H), 3.06 (d, 8H), 1.98 (s, 12H).

LC/MS (ESI, posi): [M+K]$^+$=773.1

Example 10

(Synthesis of Compound MM10)

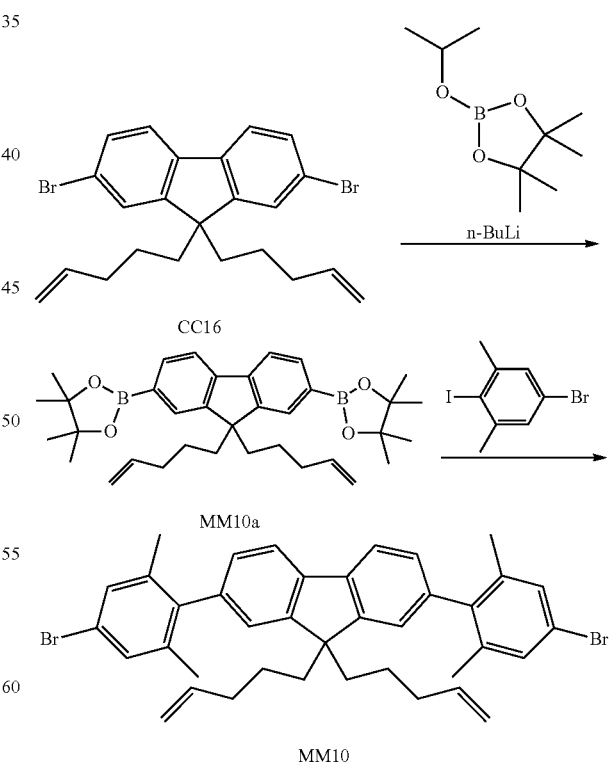

(First Step)

A gas in a reaction vessel was changed to a nitrogen gas atmosphere, then, a compound CC16 (85.6 g, 186 mmol)

and tetrahydrofuran (commercially available dehydrated grade, 1900 ml) were added, the compound CC16 was dissolved in tetrahydrofuran, then, the solution was sufficiently cooled by a dry ice/methanol bath (−78° C.). Thereafter, a hexane solution of n-butyllithium (1.6 mol/L, 256 ml, 409 mmol) was dropped while stirring, then, the mixture was stirred further for 1 hour. Thereafter, 2-isopropoxy-4,4,5,5-tetramethyl-1,3,2-dioxaborolane (96.9 g, 521 mmol) was dropped into this, then, the dry ice/methanol bath was removed, and the mixture was stirred for 3 hours while heating up to 0° C. Thereafter, hydrochloric acid (1 mol/L) was dropped while cooling the resultant reaction solution by an ice bath until the reaction solution showed a pH of 6 to 7. Thereafter, toluene was added to this, the ice bath was removed, the temperature was slowly raised up to room temperature, then, the aqueous layer was removed by liquid separation. The resultant organic layer was washed with ion exchanged water and 10 wt % saline in series, then, the resultant organic layer was dried over anhydrous sodium sulfate, and an inorganic salt was filtrated. The resultant filtrate was concentrated under reduced pressure, to obtain a solid. To the resultant solid was added acetonitrile, the mixture was stirred, then, the solid was filtrated, and the operations were repeated three times. The resultant solid was dried under reduced pressure, to obtain the targeted compound MM10a (92.2 g) as a white solid. The yield was 89%. The resultant compound indicated a HPLC area percentage value (UV254 nm) of 95.6%.

$^1$H-NMR (300 MHz, CDCl$_3$): δ (ppm)=7.81 (d, 2H), 7.74 (s, 2H), 7.71 (d, 2H), 5.58-5.47 (m, 2H), 4.81 (d, 2H), 4.77 (s, 2H), 2.05-2.00 (m, 4H), 1.82-1.75 (Q, 4H), 1.39 (s, 24H), 0.70-0.60 (m, 4H).

LC/MS (ESI, posi): [M+K]$^+$=593.3

(Second Step)

A gas in a reaction vessel was changed to a nitrogen gas atmosphere, then, a compound MM10a (87.0 g, 157 mmol), 5-iodo-2-bromo-m-xylene (146 g, 471 mmol), toluene (950 ml), tert-butanol (630 ml), tetrahydrofuran (480 ml), ion exchanged water (320 ml), a 20 wt % tetraethyl ammonium hydroxide aqueous solution (460 g, 625 mmol) and tetrakis(triphenylphosphine)palladium(0) (3.6 g, 3.1 mmol) were added, and the mixture was stirred for 22 hours while heating by an oil bath set at 50° C. Thereafter, the mixture was cooled down to room temperature, toluene (620 ml) and ion exchanged water (620 ml) were added, and the aqueous layer was removed by liquid separation. The resultant organic layer was washed with ion exchanged water and 10 wt % saline in series, then, dried over anhydrous magnesium sulfate, the resultant solid was removed by filtration, the solvent was distilled off by concentration under reduced pressure, then, the residue was purified by silica gel column chromatography (hexane/chloroform), a fraction containing the targeted compound was concentrated under reduced pressure, then, purified by recrystallization (toluene/acetonitrile), and further purified by recrystallization (chloroform/acetonitrile), and the resultant solid was dried under reduced pressure, to obtain a compound MM10 (51 g). The yield was 49%. The resultant compound MM10 indicated a HPLC area percentage value (UV254 nm) of 99.5% or more.

$^1$H-NMR (300 MHz, CDCl$_3$): δ (ppm)=7.77 (d, 2H), 7.29 (s, 4H), 7.09 (s, 2H), 7.06 (d, 2H), 5.58-4.45 (m, 2H), 4.83 (d, 2H), 4.78 (s, 2H), 2.04 (s, 12H), 2.04-1.95 (m, 4H), 1.83-1.76 (Q, 4H), 0.82-0.72 (m, 4H).

LC/MS (ESI, nega): [M+Cl]$^-$=701.1

[Production of Polymer Compound]

Example 11

(Synthesis of Polymer Compound P1)

A gas in a reaction vessel was changed to a nitrogen gas atmosphere, then, a mixture of a compound CC1 (2.1095 g), a compound MM1 (2.1659 g), a compound CC12 (1.0760 g) and toluene (80 ml) was heated at about 80° C., then, bis[tris(2-methoxyphenyl)phosphine]palladium dichloride (7.45 mg) and a 20 wt % tetraethyl ammonium hydroxide aqueous solution (15.0 g) were added, and the mixture was stirred for about 5.5 hours under reflux of an argon gas. Thereafter, 2-isopropylphenylboronic acid (0.1402 g), bis[tris(2-methoxyphenyl)phosphine]palladium dichloride (3.78 mg) and a 20 wt % tetraethyl ammonium hydroxide aqueous solution (15.0 g) were added, and the mixture was further stirred for about 17.5 hours under reflux of an argon gas. Thereafter, a solution prepared by dissolving sodium N,N-diethyldithiocarbamate trihydrate (1.19 g) in ion exchanged water (23 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P1 (3.335 g). The polymer compound P1 had a polystyrene-equivalent number-average molecular weight (Mn) and a polystyrene-equivalent weight-average molecular weight (Mw) of Mn=7.6×10$^4$ and Mw=2.2×10$^5$, respectively. The polymer compound P1 had a TH of 2.73 eV.

The polymer compound P1 is estimated to be a polymer compound having the following repeating units and mole fractions and in which a repeating unit of (PA) and a repeating unit selected from (PB) are alternately polymerized, based on the charging ratios of raw material monomers.

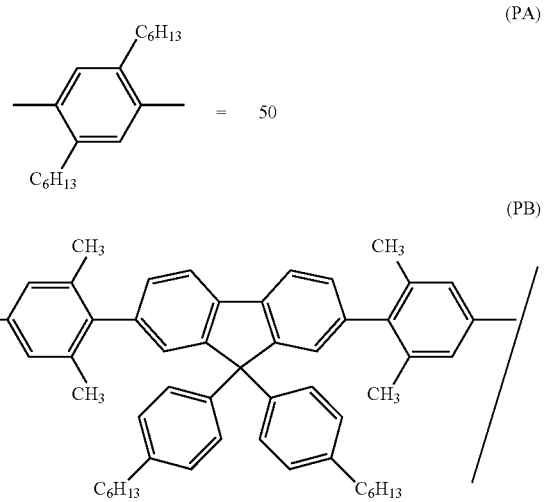

-continued

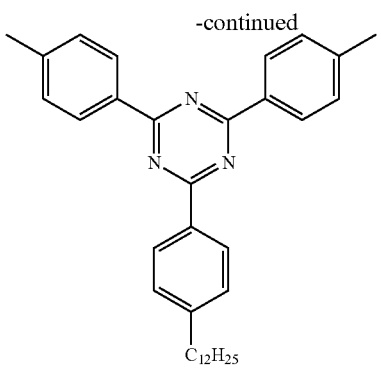

= 30/20

Example 12

(Synthesis of Polymer Compound P2)

A gas in a reaction vessel was changed to a nitrogen gas atmosphere, then, a mixture of a compound CC1 (0.8156 g), a compound MM1 (0.9771 g), a compound MM4 (0.2845 g) and toluene (31 ml) was heated at about 80° C., then, bis[tris(2-methoxyphenyl)phosphine]palladium dichloride (1.40 mg) and 20 wt % tetraethyl ammonium hydroxide aqueous solution (5.8 g) were added, and the mixture was stirred for about 8 hours under reflux of an argon gas. Thereafter, phenylboronic acid (0.0403 g), bis[tris(2-methoxyphenyl)phosphine]palladium dichloride (1.37 mg) and a 20 wt % tetraethyl ammonium hydroxide aqueous solution (5.8 g) were added, and the mixture was further stirred for about 16 hours under reflux of an argon gas. Thereafter, a solution prepared by dissolving sodium N,N-diethyldithiocarbamate trihydrate (0.46 g) in ion exchanged water (9 ml) was added, and the mixture was stirred for about 4 hours while heating at 85° C. The resultant organic layer was washed with 3.6 wt % hydrochloric acid twice, with 2.5 wt % ammonia water twice and with ion exchanged water five times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P2 (1.290 g). The polymer compound P2 had a polystyrene-equivalent number-average molecular weight (Mn) and a polystyrene-equivalent weight-average molecular weight (Mw) of $Mn=7.5\times10^4$ and $Mw=2.1\times10^5$, respectively. The polymer compound P2 had a TH of 2.75 eV.

The polymer compound P2 is estimated to be a polymer compound having the following repeating units and mole fractions and in which a repeating unit of (PA) and a repeating unit selected from (PB) are alternately polymerized, based on the charging ratios of raw material monomers.

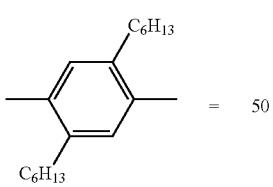

(PA)

= 50

-continued

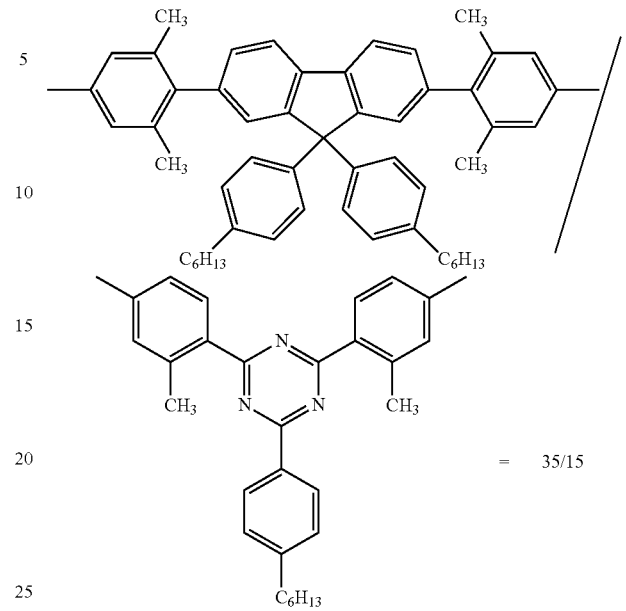

= 35/15

Example 13

(Synthesis of Polymer Compound P3)

A gas in a reaction vessel was changed to a nitrogen gas atmosphere, then, a mixture of a compound CC1 (2.4290 g), a compound MM1 (2.4940 g), a compound MM5 (1.2936 g) and toluene (94 ml) was heated at about 80° C., then, bis[tris(2-methoxyphenyl)phosphine]palladium dichloride (8.56 mg) and a 20 wt % tetraethyl ammonium hydroxide aqueous solution (17.2 g) were added, and the mixture was stirred for about 9 hours under reflux of an argon gas. Thereafter, phenylboronic acid (0.1201 g), bis[tris(2-methoxyphenyl)phosphine]palladium dichloride (4.30 mg) and a 20 wt % tetraethyl ammonium hydroxide aqueous solution (17.2 g) were added, and the mixture was further stirred for about 14 hours under reflux of an argon gas. Thereafter, a solution prepared by dissolving sodium N,N-diethyldithiocarbamate trihydrate (1.37 g) in ion exchanged water (26 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P3 (3.769 g). The polymer compound P3 had a polystyrene-equivalent number-average molecular weight (Mn) and a polystyrene-equivalent weight-average molecular weight (Mw) of $Mn=8.2\times10^4$ and $Mw=2.4\times10^5$, respectively. The polymer compound P3 had a TH of 2.77 eV.

The polymer compound P3 is estimated to be a polymer compound having the following repeating units and mole fractions and in which a repeating unit of (PA) and a repeating unit selected from (PB) are alternately polymerized, based on the charging ratios of raw material monomers.

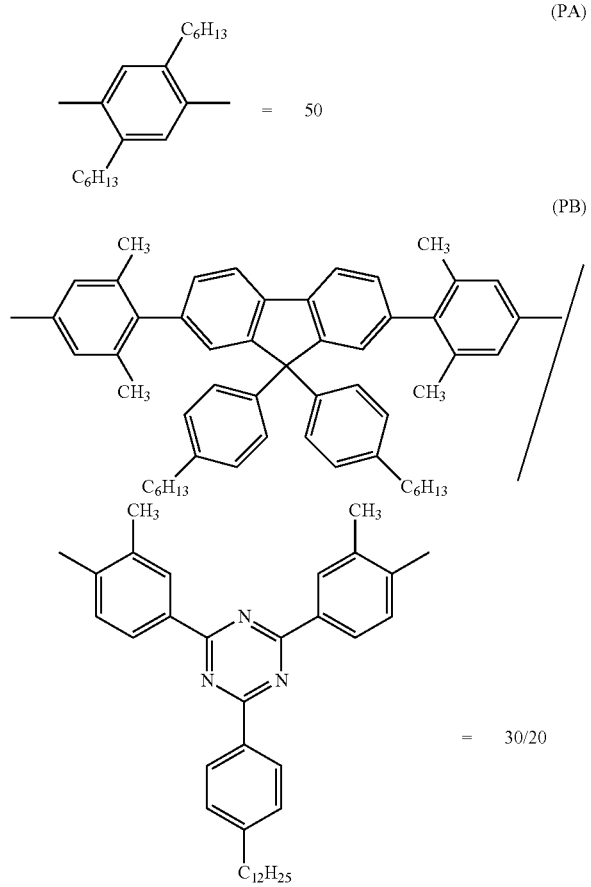

Example 14

(Synthesis of Polymer Compound P4)

A gas in a reaction vessel was changed to a nitrogen gas atmosphere, then, a mixture of a compound CC1 (1.2759 g), a compound MM1 (2.1834 g) and toluene (55 ml) was heated at about 80° C., then, bis[tris(2-methoxyphenyl)phosphine]palladium dichloride (2.34 mg) and a 20 wt % tetraethyl ammonium hydroxide aqueous solution (9.1 g) were added, and the mixture was stirred for about 4 hours under reflux of an argon gas. Thereafter, 2-isopropylphenylboronic acid (0.0630 g), bis[tris(2-methoxyphenyl)phosphine]palladium dichloride (2.17 mg) and a 20 wt % tetraethyl ammonium hydroxide aqueous solution (9.1 g) were added, and the mixture was further stirred for about 15.5 hours under reflux. Thereafter, a solution prepared by dissolving sodium N,N-diethyldithiocarbamate trihydrate (0.72 g) in ion exchanged water (14 ml) was added, and the mixture was stirred for about 5 hours while heating at 85° C. The resultant organic layer was washed with 3.6 wt % hydrochloric acid twice, with 2.5 wt % ammonia water twice and with ion exchanged water five times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P4 (2.279 g). The polymer compound P4 had a polystyrene-equivalent number-average molecular weight (Mn) and a polystyrene-equivalent weight-average molecular weight (Mw) of $Mn=7.4\times10^4$ and $Mw=2.3\times10^5$, respectively. The polymer compound P4 had a TH of 2.73 eV.

The polymer compound P4 is estimated to be a polymer compound having the following repeating units and mole fractions and in which a repeating unit of (PA) and a repeating unit selected from (PB) are alternately polymerized, based on the charging ratios of raw material monomers.

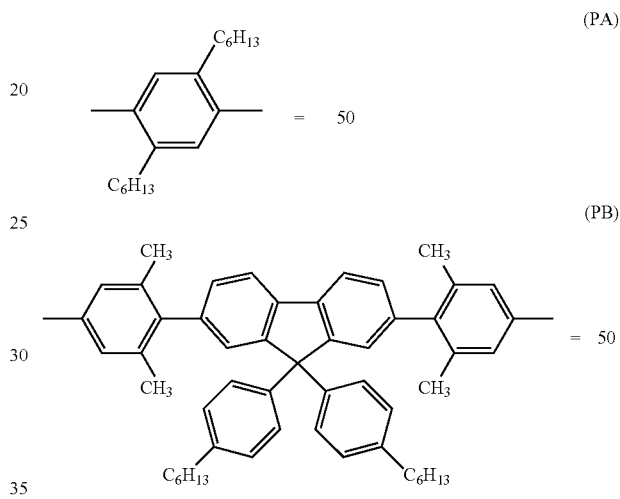

Example 15

(Synthesis of Polymer Compound P5)

A gas in a reaction vessel was changed to a nitrogen gas atmosphere, then, a mixture of a compound MM2 (0.8774 g), a compound MM1 (0.4109 g), a compound MM5 (0.2951 g) and toluene (37 ml) was heated at about 80° C., then, bis[tris(2-methoxyphenyl)phosphine]palladium dichloride (2.53 mg) and a 20 wt % tetraethyl ammonium hydroxide aqueous solution (6.5 g) were added, and the mixture was stirred for about 6.5 hours under reflux of an argon gas. Thereafter, phenylboronic acid (0.0229 g), bis[tris(2-methoxyphenyl)phosphine]palladium dichloride (1.26 mg) and a 20 wt % tetraethyl ammonium hydroxide aqueous solution (6.5 g) were added, and the mixture was further stirred for about 16 hours under reflux. Thereafter, a solution prepared by dissolving sodium N,N-diethyldithiocarbamate trihydrate (0.26 g) in ion exchanged water (5 ml) was added, and the mixture was stirred for about 5 hours while heating at 85° C. The resultant organic layer was washed with 3.6 wt % hydrochloric acid twice, with 2.5 wt % ammonia water twice and with ion exchanged water seven times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P5 (1.084 g). The polymer compound P5 had a polystyrene-equivalent number-average molecular weight (Mn) and a polystyrene-equivalent weight-average molecular weight (Mw) of Mn=$9.9 \times 10^4$ and Mw=$2.8 \times 10^5$, respectively. The polymer compound P5 had a TH of 2.69 eV.

The polymer compound P5 is estimated to be a polymer compound having the following repeating units and mole fractions and in which a repeating unit of (PA) and a repeating unit selected from (PB) are alternately polymerized, based on the charging ratios of raw material monomers.

stirred for about 4 hours under reflux of an argon gas. Thereafter, bromobenzene (0.5756 g), palladium acetate (1.0 mg) and tris(2-methoxyphenyl)phosphine (5.7 mg) were added, and the mixture was further stirred for about 4 hours under reflux. Thereafter, a solution prepared by dissolving sodium N,N-diethyldithiocarbamate trihydrate (1.58 g) in ion exchanged water (16 ml) was added, and the mixture was stirred for about 3 hours while heating at 85° C. The resultant organic layer was washed with ion exchanged water twice, with 3 wt % acetic acid twice and with ion exchanged water twice, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P6 (2.878 g). The polymer compound P6 had a polystyrene-equivalent number-average molecular weight (Mn) and a polystyrene-equivalent weight-average molecular weight (Mw) of Mn=$1.9 \times 10^5$ and Mw=$4.8 \times 10^5$, respectively. The polymer compound P6 had a TH of 2.60 eV.

The polymer compound P6 is estimated to be a polymer compound having the following repeating units and mole fractions and in which a repeating unit of (PA) and a repeating unit selected from (PB) are alternately polymerized, based on the charging ratios of raw material monomers.

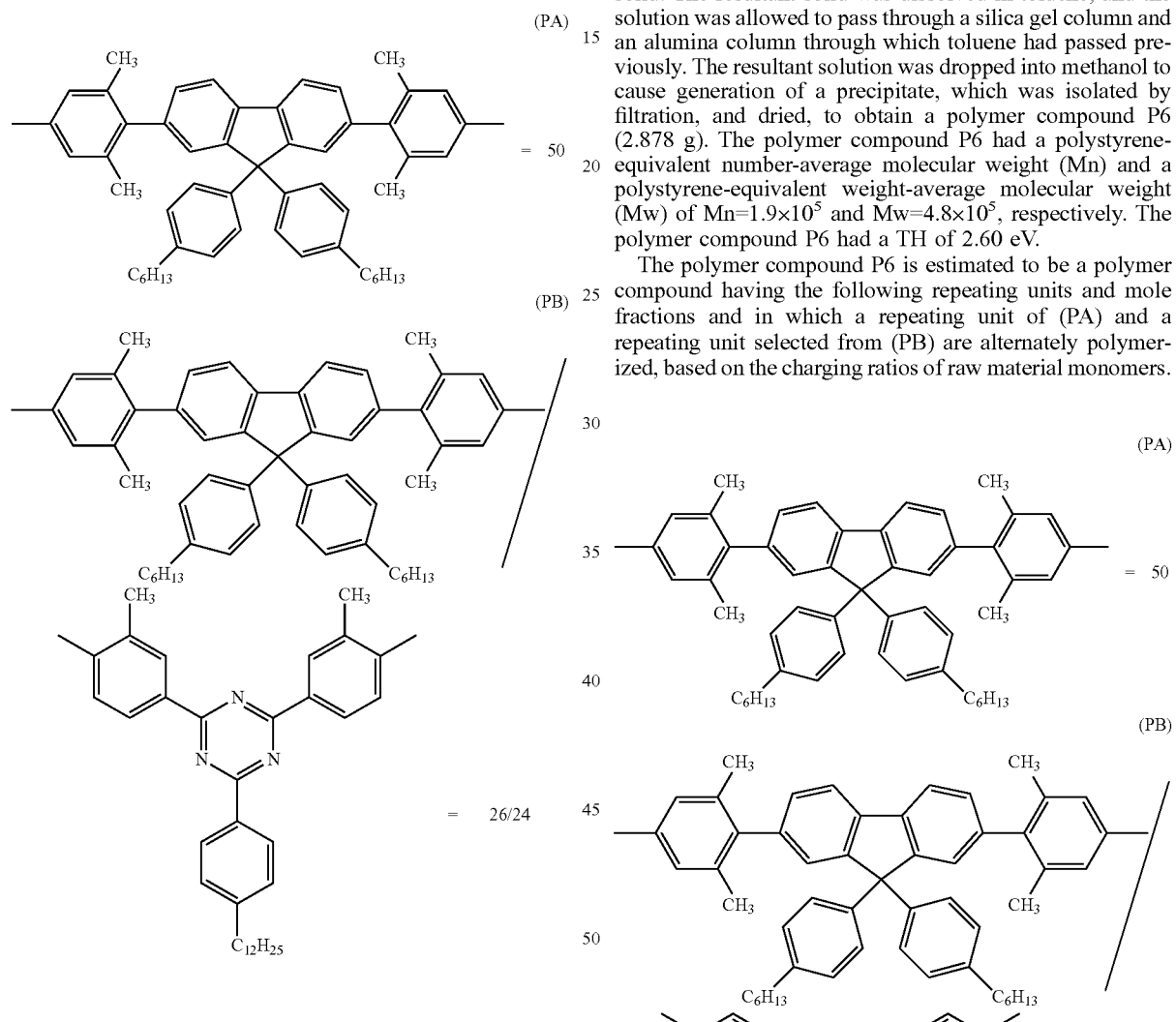

Example 16

(Synthesis of Polymer Compound P6)

A gas in a reaction vessel was changed to a nitrogen gas atmosphere, then, a mixture of a compound MM2 (2.4621 g), a compound MM1 (1.3304 g), a compound CC13 (0.5734 g) and toluene (52 ml) was heated at about 80° C., then, palladium acetate (2.0 mg), tris(2-methoxyphenyl) phosphine (10.3 mg) and a 20 wt % tetraethyl ammonium hydroxide aqueous solution (9.0 g) were added, and the mixture was stirred for about 21 hours under reflux of an argon gas. Thereafter, phenylboronic acid (0.3189 g), palladium acetate (1.0 mg) and tris(2-methoxyphenyl)phosphine (5.5 mg) were added, and the mixture was further

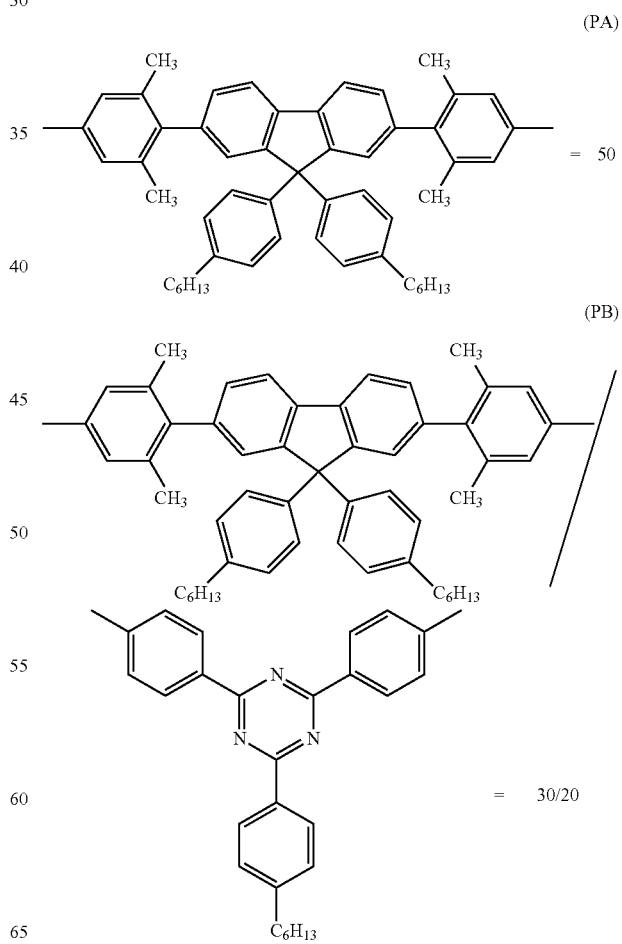

Example 17

(Synthesis of Polymer Compound P7)

A gas in a reaction vessel was changed to a nitrogen gas atmosphere, then, a mixture of a compound MM2 (1.8939 g), a compound CC14 (1.5485 g), a compound CC11 (0.1287 g) and toluene (71 ml) was heated at about 80° C., then, bis[tris(2-methoxyphenyl)phosphine]palladium dichloride (1.73 mg) and a 20 wt % tetraethyl ammonium hydroxide aqueous solution (6.9 g) were added, and the mixture was stirred for about 7 hours under reflux of an argon gas. Thereafter, phenylboronic acid (0.0244 g), bis[tris(2-methoxyphenyl)phosphine]palladium dichloride (1.72 mg) and a 20 wt % tetraethyl ammonium hydroxide aqueous solution (6.9 g) were added, and the mixture was further stirred for about 17 hours under reflux of an argon gas. Thereafter, a solution prepared by dissolving sodium N,N-diethyldithiocarbamate trihydrate (1.11 g) in ion exchanged water (33 ml) was added, and the mixture was stirred for about 3 hours while heating at 85° C. The resultant organic layer was washed with ion exchanged water twice, with 3 wt % acetic acid water twice and with ion exchanged water twice, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P7 (2.42 g). The polymer compound P7 had a polystyrene-equivalent number-average molecular weight (Mn) and a polystyrene-equivalent weight-average molecular weight (Mw) of Mn=4.9×10$^4$ and Mw=2.2×10$^5$, respectively. The polymer compound P7 had a TH of 2.42 eV.

The polymer compound P7 is estimated to be a polymer compound having the following repeating units and mole fractions and in which a repeating unit of (PA) and a repeating unit selected from (PB) are alternately polymerized, based on the charging ratios of raw material monomers.

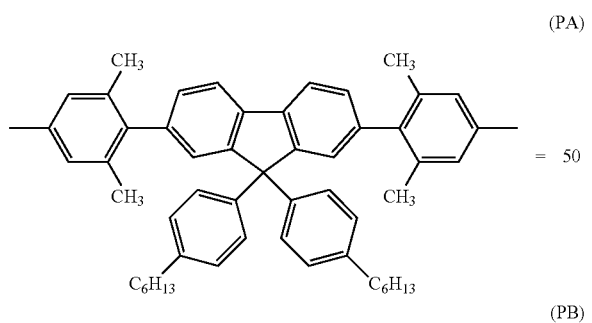

(PA)

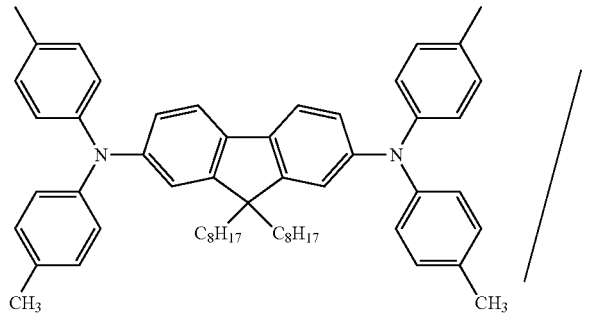

(PB)

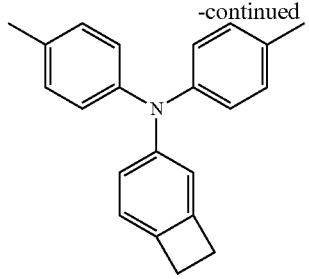

= 42.5/7.5

Example 18

(Synthesis of Polymer Compound P8)

A gas in a reaction vessel was changed to a nitrogen gas atmosphere, then, a mixture of a compound MM3 (1.8339 g), a compound CC14 (1.5485 g), a compound CC11 (0.1585 g) and toluene (70 ml) was heated at about 80° C., then, bis[tris(2-methoxyphenyl)phosphine]palladium dichloride (1.77 mg) and a 20 wt % tetraethyl ammonium hydroxide aqueous solution (6.9 g) were added, and the mixture was stirred for about 7 hours under reflux of an argon gas. Thereafter, phenylboronic acid (0.0244 g), bis[tris(2-methoxyphenyl)phosphine]palladium dichloride (1.75 mg) and a 20 wt % tetraethyl ammonium hydroxide aqueous solution (6.9 g) were added, and the mixture was further stirred for about 16.5 hours under reflux of an argon gas. Thereafter, a solution prepared by dissolving sodium N,N-diethyldithiocarbamate trihydrate (1.11 g) in ion exchanged water (33 ml) was added, and the mixture was stirred for about 2 hours while heating at 85° C. The resultant organic layer was washed with ion exchanged water twice, with 3 wt % acetic acid water twice and with ion exchanged water twice, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P8 (1.61 g). The polymer compound P8 had a polystyrene-equivalent number-average molecular weight (Mn) and a polystyrene-equivalent weight-average molecular weight (Mw) of Mn=5.9×10$^4$ and Mw=2.3×10$^5$, respectively.

The polymer compound P8 is estimated to be a polymer compound having the following repeating units and mole fractions and in which a repeating unit of (PA) and a repeating unit selected from (PB) are alternately polymerized, based on the charging ratios of raw material monomers.

(PA)

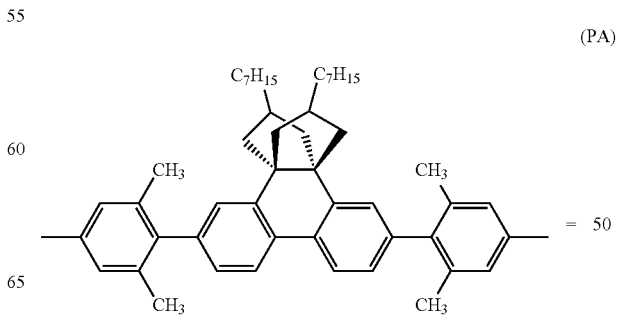

= 50

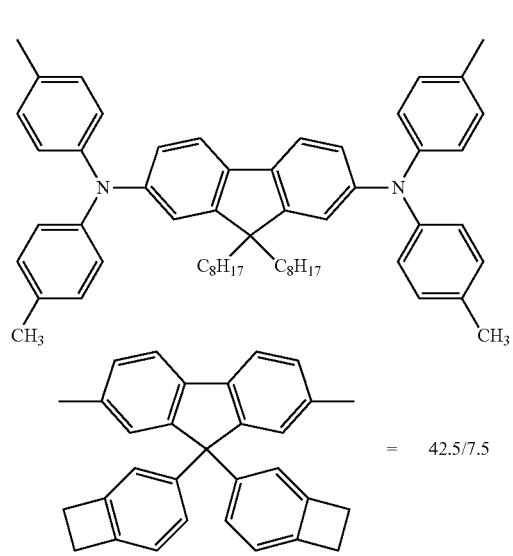

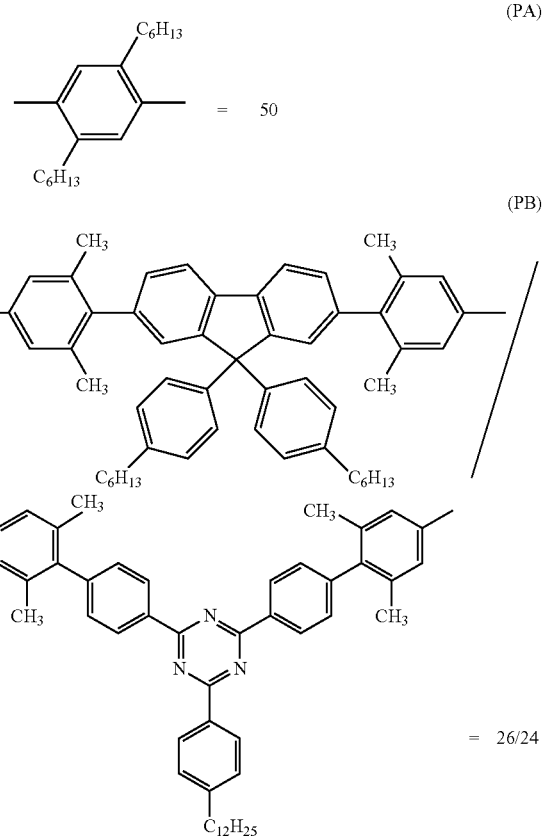

Example 19

(Synthesis of Polymer Compound P11)

A gas in a reaction vessel was changed to a nitrogen gas atmosphere, then, a mixture of a compound CC1 (1.9934 g), a compound MM1 (1.7739 g), a compound MM6 (1.6200 g) and toluene (84 ml) was heated at about 80° C., then, bis[tris(2-methoxyphenyl)phosphine]palladium dichloride (7.11 mg) and a 20 wt % tetraethyl ammonium hydroxide aqueous solution (14.1 g) were added, and the mixture was stirred for about 4 hours under reflux of an argon gas. Thereafter, phenylboronic acid (0.0985 g), bis[tris(2-methoxyphenyl)phosphine]palladium dichloride (3.52 mg) and a 20 wt % tetraethyl ammonium hydroxide aqueous solution (14.1 g) were added, and the mixture was further stirred for about 19 hours under reflux of an argon gas. Thereafter, a solution prepared by dissolving sodium N,N-diethyldithiocarbamate trihydrate (1.13 g) in ion exchanged water (21 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P11 (3.210 g). The polymer compound P11 had a polystyrene-equivalent number-average molecular weight (Mn) and a polystyrene-equivalent weight-average molecular weight (Mw) of $Mn=9.8 \times 10^4$ and $Mw=2.7 \times 10^5$, respectively. The polymer compound P11 had a TH of 2.79 eV.

The polymer compound P11 is estimated to be a polymer compound having the following repeating units and mole fractions and in which a repeating unit of (PA) and a repeating unit selected from (PB) are alternately polymerized, based on the charging ratios of raw material monomers.

Example 20

(Synthesis of Polymer Compound P12)

A gas in a reaction vessel was changed to a nitrogen gas atmosphere, then, a mixture of a compound CC1 (1.7141 g), a compound MM1 (2.0533 g), a compound CC12 (0.6557 g) and toluene (67 ml) was heated at about 80° C., then, bis[tris(2-methoxyphenyl)phosphine]palladium dichloride (9.14 mg) and a 20 wt % tetraethyl ammonium hydroxide aqueous solution (12.2 g) were added, and the mixture was stirred for about 10 hours under reflux of an argon gas. Thereafter, 2-isopropylphenylboronic acid (0.1140 g), bis[tris(2-methoxyphenyl)phosphine]palladium dichloride (2.94 mg) and a 20 wt % tetraethyl ammonium hydroxide aqueous solution (12.2 g) were added, and the mixture was further stirred for about 14 hours under reflux of an argon gas. Thereafter, a solution prepared by dissolving sodium N,N-diethyldithiocarbamate trihydrate (0.97 g) in ion exchanged water (18 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P12 (2.633 g). The polymer compound P12 had a polystyrene-equivalent number-average molecular weight (Mn) and a polystyrene-equivalent weight-average molecular weight (Mw) of Mn=$1.1 \times 10^5$ and Mw=$3.2 \times 10^5$, respectively. The polymer compound P12 had a TH of 2.73 eV.

The polymer compound P12 is estimated to be a polymer compound having the following repeating units and mole fractions and in which a repeating unit of (PA) and a repeating unit selected from (PB) are alternately polymerized, based on the charging ratios of raw material monomers.

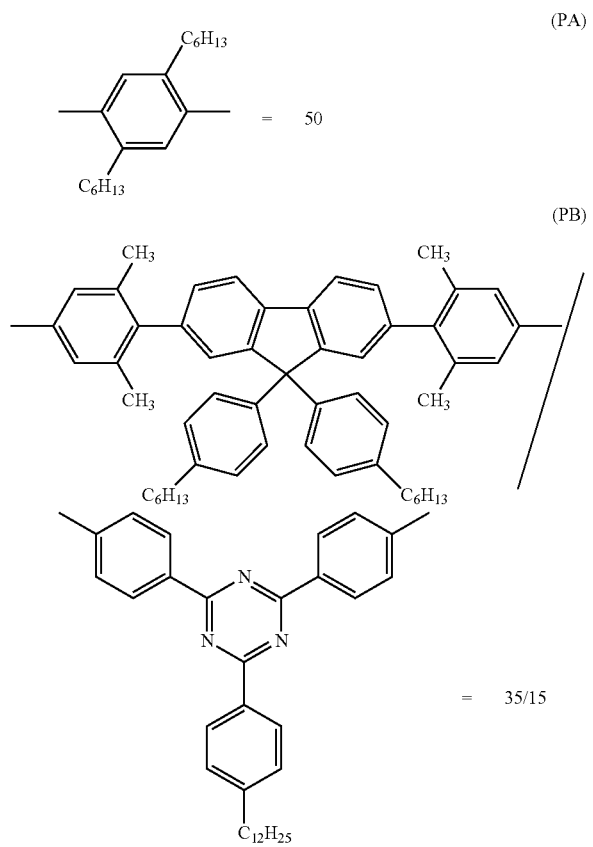

Example 21

(Synthesis of Polymer Compound P13)

A gas in a reaction vessel was changed to a nitrogen gas atmosphere, then, a mixture of a compound MM7 (1.0767 g), a compound CC2 (0.5255 g), a compound MM6 (0.5906 g) and toluene (35 ml) was heated at about 80° C., then, bis[tris(2-methoxyphenyl)phosphine]palladium dichloride (1.79 mg) and a 20 wt % tetraethyl ammonium hydroxide aqueous solution (8.8 g) were added, and the mixture was stirred for about 5 hours under reflux of an argon gas. Thereafter, phenylboronic acid (0.0493 g), bis[tris(2-methoxyphenyl)phosphine]palladium dichloride (1.76 mg) and a 20 wt % tetraethyl ammonium hydroxide aqueous solution (8.8 g) were added, and the mixture was further stirred for about 18 hours under reflux of an argon gas. Thereafter, a solution prepared by dissolving sodium N,N-diethyldithiocarbamate trihydrate (0.56 g) in ion exchanged water (11 ml) was added, and the mixture was stirred for about 2 hours while heating at 85° C. The resultant organic layer was washed with 3.6 wt % hydrochloric acid twice, with 2.5 wt % ammonia water twice and with ion exchanged water five times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P13 (1.190 g). The polymer compound P13 had a polystyrene-equivalent number-average molecular weight (Mn) and a polystyrene-equivalent weight-average molecular weight (Mw) of Mn=$9.7 \times 10^4$ and Mw=$2.6 \times 10^5$, respectively. The polymer compound P13 had a TH of 2.78 eV.

The polymer compound P13 is estimated to be a polymer compound having the following repeating units and mole fractions and in which a repeating unit of (PA) and a repeating unit selected from (PB) are alternately polymerized, based on the charging ratios of raw material monomers.

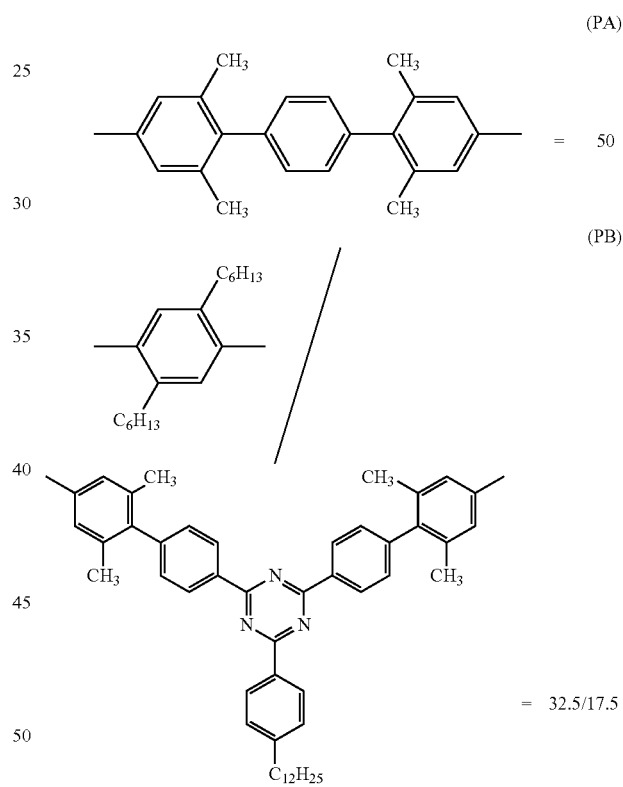

Example 22

(Synthesis of Polymer Compound P14)

A gas in a reaction vessel was changed to a nitrogen gas atmosphere, then, a mixture of a compound MM8 (1.0753 g), a compound CC2 (0.4244 g), a compound MM6 (0.5906 g) and toluene (36 ml) was heated at about 80° C., then, bis[tris(2-methoxyphenyl)phosphine]palladium dichloride (1.55 mg) and a 20 wt % tetraethyl ammonium hydroxide aqueous solution (7.7 g) were added, and the mixture was stirred for about 4 hours under reflux of an argon gas. Thereafter, phenylboronic acid (0.0431 g), bis[tris(2-methoxyphenyl)phosphine]palladium dichloride (1.59 mg)

and a 20 wt % tetraethyl ammonium hydroxide aqueous solution (7.7 g) were added, and the mixture was further stirred for about 19 hours under reflux of an argon gas. Thereafter, a solution prepared by dissolving sodium N,N-diethyldithiocarbamate trihydrate (0.49 g) in ion exchanged water (9 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P14 (1.160 g). The polymer compound P14 had a polystyrene-equivalent number-average molecular weight (Mn) and a polystyrene-equivalent weight-average molecular weight (Mw) of $Mn=1.5\times10^5$ and $Mw=3.9\times10^5$, respectively. The polymer compound P14 had a TH of 2.74 eV.

The polymer compound P14 is estimated to be a polymer compound having the following repeating units and mole fractions and in which a repeating unit of (PA) and a repeating unit selected from (PB) are alternately polymerized, based on the charging ratios of raw material monomers.

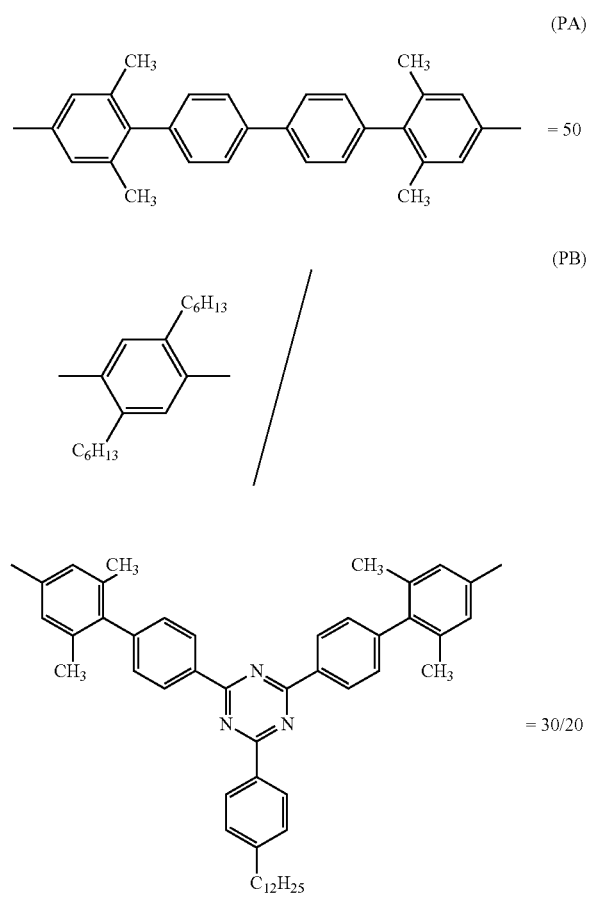

Example 23

(Synthesis of Polymer Compound P15)

A gas in a reaction vessel was changed to a nitrogen gas atmosphere, then, a mixture of a compound MM3 (1.1004 g), a compound CC2 (0.1940 g), a compound MM6 (0.6075 g) and toluene (38 ml) was heated at about 80° C., then, bis[tris(2-methoxyphenyl)phosphine]palladium dichloride (1.09 mg) and a 20 wt % tetraethyl ammonium hydroxide aqueous solution (7.4 g) were added, and the mixture was stirred for about 5 hours under reflux of an argon gas. Thereafter, phenylboronic acid (0.0296 g), bis[tris(2-methoxyphenyl)phosphine]palladium dichloride (1.10 mg) and a 20 wt % tetraethyl ammonium hydroxide aqueous solution (7.4 g) were added, and the mixture was further stirred for about 20 hours under reflux of an argon gas. Thereafter, a solution prepared by dissolving sodium N,N-diethyldithiocarbamate trihydrate (0.34 g) in ion exchanged water (6 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P15 (1.213 g). The polymer compound P15 had a polystyrene-equivalent number-average molecular weight (Mn) and a polystyrene-equivalent weight-average molecular weight (Mw) of $Mn=7.0\times10^4$ and $Mw=1.9\times10^5$, respectively. The polymer compound P15 had a TH of 2.70 eV.

The polymer compound P15 is estimated to be a polymer compound having the following repeating units and mole fractions and in which a repeating unit of (PA) and a repeating unit selected from (PB) are alternately polymerized, based on the charging ratios of raw material monomers.

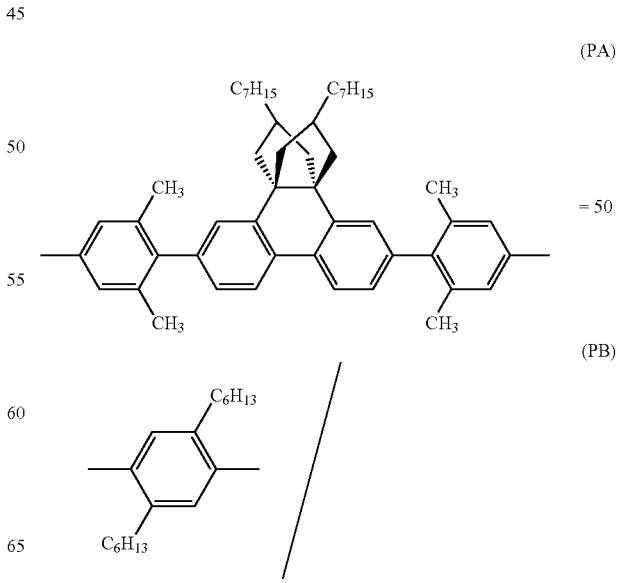

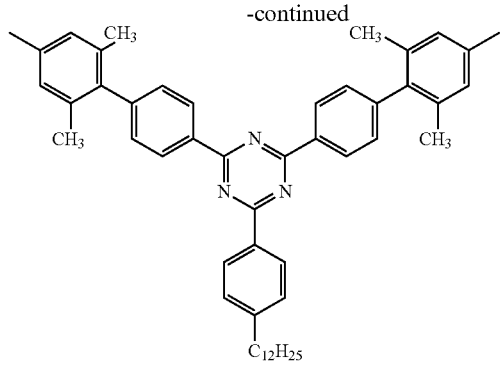

= 20/30

Example 24

(Synthesis of Polymer Compound P16)

A gas in a reaction vessel was changed to a nitrogen gas atmosphere, then, a mixture of a compound CC1 (1.1213 g), a compound CC14 (1.2297 g), a compound MM9 (0.3315 g), a compound MM10 (0.3008 g) and toluene (44 ml) was heated at about 80° C., then, bis[tris(2-methoxyphenyl)phosphine]palladium dichloride (2.00 mg) and a 20 wt % tetraethyl ammonium hydroxide aqueous solution (10.0 g) were added, and the mixture was stirred for about 6 hours under reflux of an argon gas. Thereafter, phenylboronic acid (0.0554 g), bis[tris(2-methoxyphenyl)phosphine]palladium dichloride (2.03 mg) and a 20 wt % tetraethyl ammonium hydroxide aqueous solution (10.0 g) were added, and the mixture was further stirred for about 17 hours under reflux of an argon gas. Thereafter, a solution prepared by dissolving sodium N,N-diethyldithiocarbamate trihydrate (0.63 g) in ion exchanged water (12 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P16 (1.651 g). The polymer compound P16 had a polystyrene-equivalent number-average molecular weight (Mn) and a polystyrene-equivalent weight-average molecular weight (Mw) of Mn=$4.6\times10^4$ and Mw=$7.0\times10^5$, respectively. The polymer compound P16 had a TH of 2.44 eV.

The polymer compound P16 is estimated to be a polymer compound having the following repeating units and mole fractions and in which a repeating unit of (PA) and a repeating unit selected from (PB) are alternately polymerized, based on the charging ratios of raw material monomers.

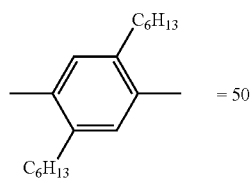

= 50

(PA)

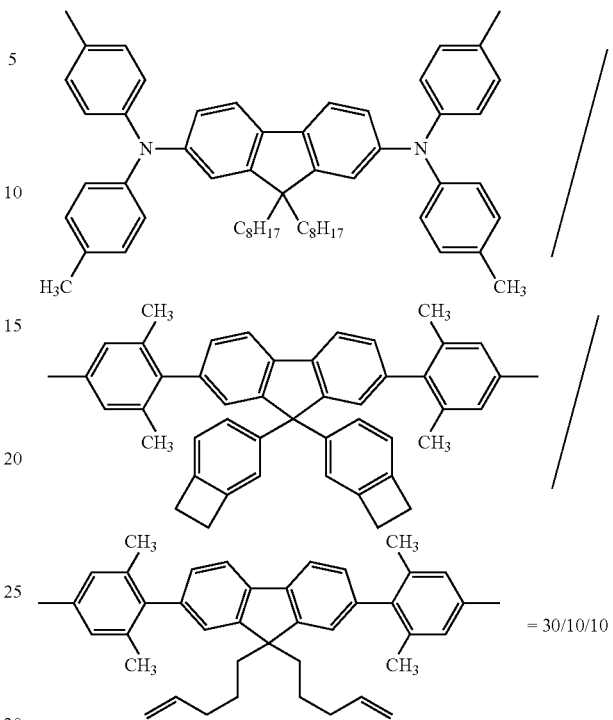

Comparative Example 1

(Synthesis of Polymer Compound CP1)

A gas in a reaction vessel was changed to a nitrogen gas atmosphere, then, a mixture of a compound CC1 (2.8707 g), a compound CC3 (3.7127 g) and toluene (90 ml) was heated at about 80° C., then, bis[tris(2-methoxyphenyl)phosphine]palladium dichloride (5.05 mg) and a 20 wt % tetraethyl ammonium hydroxide aqueous solution (20.4 g) were added, and the mixture was stirred for about 4.5 hours under reflux of an argon gas. Thereafter, 2,5-dimethylphenylboronic acid (0.1745 g), bis[tris(2-methoxyphenyl)phosphine]palladium dichloride (5.07 mg) and a 20 wt % tetraethyl ammonium hydroxide aqueous solution (20.4 g) were added, and the mixture was further stirred for about 17.5 hours under reflux of an argon gas. Thereafter, a solution prepared by dissolving sodium N,N-diethyldithiocarbamate trihydrate (1.62 g) in ion exchanged water (31 ml) was added, and the mixture was stirred for about 2 hours while heating at 85° C. The resultant organic layer was washed with 3.6 wt % hydrochloric acid twice, with 2.5 wt % ammonia water twice and with ion exchanged water twice, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP1 (3.364 g). The polymer compound CP1 had a polystyrene-equivalent number-average molecular weight (Mn) and a polystyrene-equivalent weight-average molecular weight (Mw) of Mn=$3.5\times10^4$ and Mw=$1.0\times10^5$, respectively. The polymer compound CP1 had a TH of 2.65 eV.

The polymer compound CP1 is estimated to be a polymer compound having the following repeating units and mole fractions and in which a repeating unit of (PA) and a repeating unit selected from (PB) are alternately polymerized, based on the charging ratios of raw material monomers.

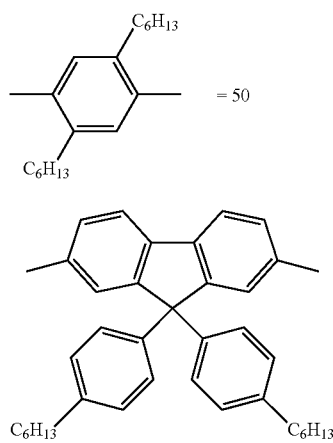

Comparative Example 2

(Synthesis of Polymer Compound CP2)

A gas in a reaction vessel was changed to a nitrogen gas atmosphere, then, a mixture of a compound CC1 (2.2425 g), a compound CC3 (2.3202 g), a compound CC12 (0.5719 g) and toluene (70 ml) was heated at about 80° C., then, bis[tris(2-methoxyphenyl)phosphine]palladium dichloride (3.97 mg) and a 20 wt % tetraethyl ammonium hydroxide aqueous solution (15.9 g) were added, and the mixture was stirred for about 6 hours under reflux of an argon gas. Thereafter, phenylboronic acid (0.1109 g), bis[tris(2-methoxyphenyl)phosphine]palladium dichloride (4.00 mg) and a 20 wt % tetraethyl ammonium hydroxide aqueous solution (15.9 g) were added, and the mixture was further stirred for about 16.5 hours under reflux of an argon gas. Thereafter, a solution prepared by dissolving sodium N,N-diethyldithiocarbamate trihydrate (1.27 g) in ion exchanged water (25 ml) was added, and the mixture was stirred for about 2 hours while heating at 85° C. The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP2 (2.729 g). The polymer compound CP2 had a polystyrene-equivalent number-average molecular weight (Mn) and a polystyrene-equivalent weight-average molecular weight (Mw) of Mn=$8.2 \times 10^4$ and Mw=$2.1 \times 10^5$, respectively. The polymer compound CP2 had a TH of 2.65 eV.

The polymer compound CP2 is estimated to be a polymer compound having the following repeating units and mole fractions and in which a repeating unit of (PA) and a repeating unit selected from (PB) are alternately polymerized, based on the charging ratios of raw material monomers.

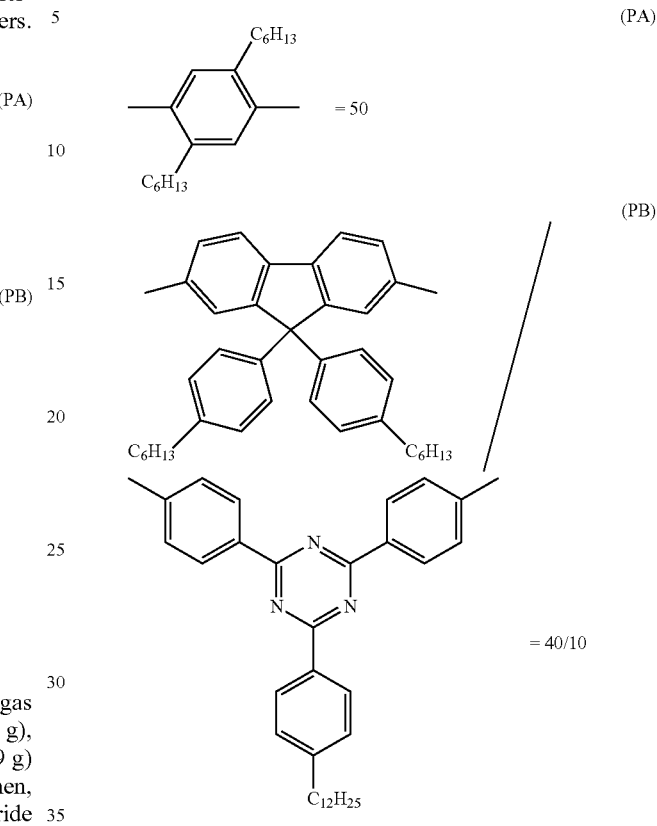

Comparative Example 3

(Synthesis of Polymer Compound CP3)

A gas in a reaction vessel was changed to a nitrogen gas atmosphere, then, a mixture of a compound CC1 (2.7941 g), a compound CC2 (1.8131 g), a compound CC12 (0.7126 g) and toluene (57 ml) was heated at about 80° C., then, palladium acetate (1.31 mg), tris(2-methoxyphenyl)phosphine (7.82 mg) and a 20 wt % tetraethyl ammonium hydroxide aqueous solution (19.8 g) were added, and the mixture was stirred for about 6.5 hours under reflux of an argon gas. Thereafter, 2-isopropylphenylboronic acid (0.1379 g), palladium acetate (1.31 mg), tris(2-methoxyphenyl)phosphine (7.91 mg) and a 20 wt % tetraethyl ammonium hydroxide aqueous solution (19.8 g) were added, and the mixture was further stirred for about 15 hours under reflux. Thereafter, a solution prepared by dissolving sodium N,N-diethyldithiocarbamate trihydrate (1.59 g) in ion exchanged water (32 ml) was added, and the mixture was stirred for about 2 hours while heating at 85° C. The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP3 (2.753 g). The polymer compound CP3 had a polystyrene-equivalent number-average molecular weight (Mn) and a polystyrene-equivalent weight-average molecular weight (Mw) of $Mn=6.6\times10^4$ and $Mw=2.7\times10^5$, respectively. The polymer compound CP3 had a TH of 2.81 eV.

The polymer compound CP3 is estimated to be a polymer compound having the following repeating units and mole fractions and in which a repeating unit of (PA) and a repeating unit selected from (PB) are alternately polymerized, based on the charging ratios of raw material monomers.

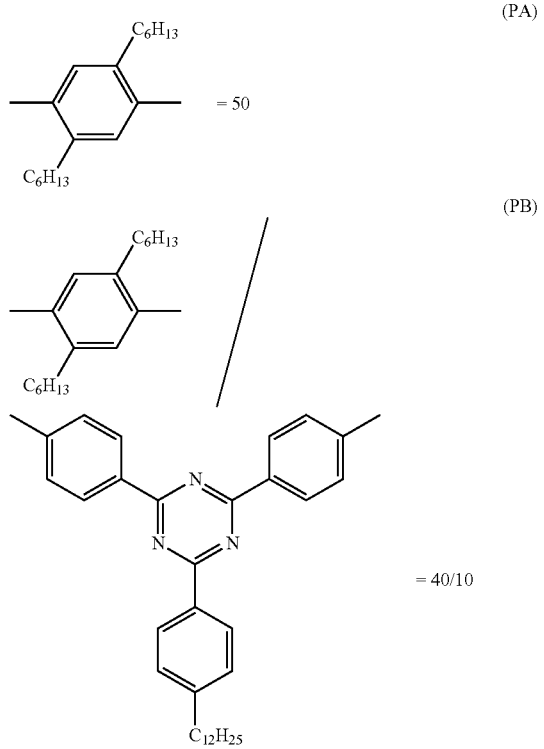

Comparative Example 4

(Synthesis of Polymer Compound CP4)

A gas in a reaction vessel was changed to a nitrogen gas atmosphere, then, a mixture of a compound CC1 (2.7651 g), a compound CC2 (1.7943 g), a compound MM5 (0.7363 g) and toluene (58 ml) was heated at about 80° C., then, palladium acetate (1.31 mg), tris(2-methoxyphenyl)phosphine (7.75 mg) and a 20 wt % tetraethyl ammonium hydroxide aqueous solution (19.6 g) were added, and the mixture was stirred for about 8.5 hours under reflux of an argon gas. Thereafter, 2-isopropylphenylboronic acid (0.1366 g), palladium acetate (1.28 mg), tris(2-methoxyphenyl)phosphine (7.79 mg) and a 20 wt % tetraethyl ammonium hydroxide aqueous solution (19.6 g) were added, and the mixture was further stirred for about 15.5 hours under reflux. Thereafter, a solution prepared by dissolving sodium N,N-diethyldithiocarbamate trihydrate (1.56 g) in ion exchanged water (31 ml) was added, and the mixture was stirred for about 2 hours while heating at 85° C. The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP4 (2.732 g). The polymer compound CP4 had a polystyrene-equivalent number-average molecular weight (Mn) and a polystyrene-equivalent weight-average molecular weight (Mw) of $Mn=6.6\times10^4$ and $Mw=2.9\times10^5$, respectively. The polymer compound CP4 had a TH of 2.95 eV.

The polymer compound CP4 is estimated to be a polymer compound having the following repeating units and mole fractions and in which a repeating unit of (PA) and a repeating unit selected from (PB) are alternately polymerized, based on the charging ratios of raw material monomers.

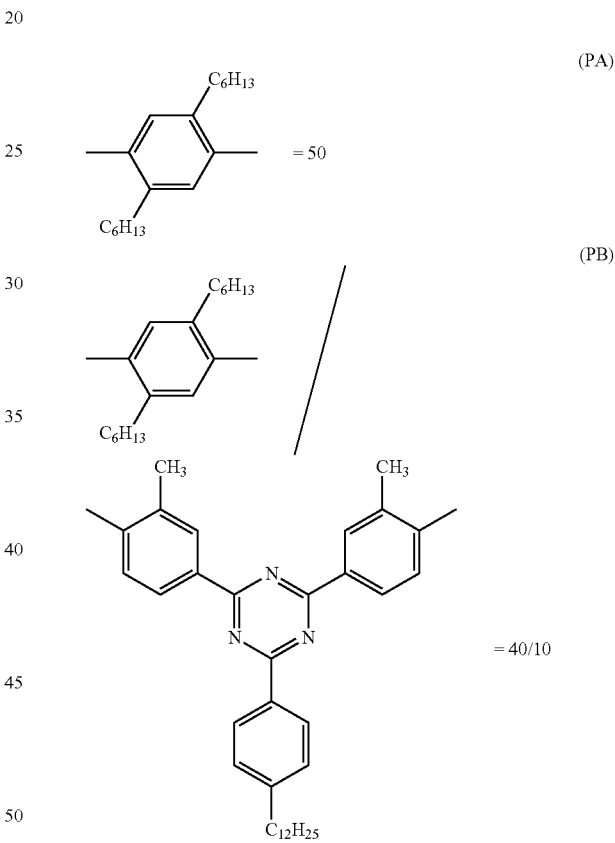

Comparative Example 5

(Synthesis of Polymer Compound CP5)

A gas in a reaction vessel was changed to a nitrogen gas atmosphere, then, a mixture of a compound CC1 (2.0646 g), a compound CC2 (0.6699 g), a compound CC12 (1.5796 g) and toluene (53 ml) was heated at about 80° C., then, palladium acetate (0.95 mg), tris(2-methoxyphenyl)phosphine (5.78 mg) and a 20 wt % tetraethyl ammonium hydroxide aqueous solution (14.7 g) were added, and the mixture was stirred for about 10 hours under reflux of an argon gas. Thereafter, 2-isopropylphenylboronic acid (0.1356 g), palladium acetate (0.86 mg), tris(2-methoxyphenyl)phosphine (5.91 mg) and a 20 wt % tetraethyl ammonium hydroxide aqueous solution (14.6 g) were added, and the mixture was further stirred for about 14.5 hours under reflux of an argon gas. Thereafter, a solution prepared by dissolving sodium N,N-diethyldithiocarbamate trihydrate (1.17 g) in ion exchanged water (24 ml) was added, and the mixture was stirred for about 2 hours while heating at 85° C. The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP5 (2.398 g).

The polymer compound CP5 had a polystyrene-equivalent number-average molecular weight (Mn) and a polystyrene-equivalent weight-average molecular weight (Mw) of Mn=$7.1\times10^4$ and Mw=$2.1\times10^5$, respectively. The polymer compound CP5 had a TH of 2.73 eV.

The polymer compound CP5 is estimated to be a polymer compound having the following repeating units and mole fractions and in which a repeating unit of (PA) and a repeating unit selected from (PB) are alternately polymerized, based on the charging ratios of raw material monomers.

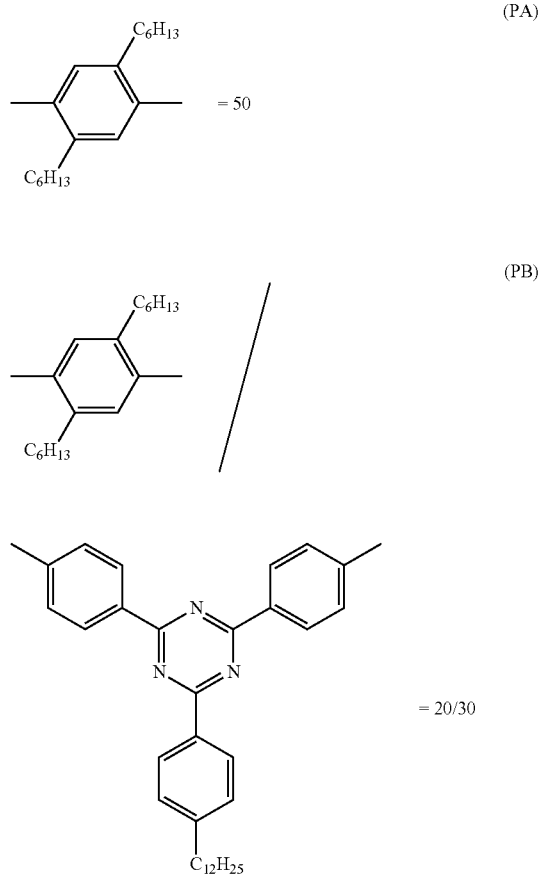

Comparative Example 6

(Synthesis of Polymer Compound CP6)

A gas in a reaction vessel was changed to a nitrogen gas atmosphere, then, a mixture of a compound CC1 (1.7783 g), a compound CC2 (0.5770 g), a compound MM5 (1.4206 g) and toluene (57 ml) was heated at about 80° C., then, palladium acetate (0.85 mg), tris(2-methoxyphenyl)phosphine (5.07 mg) and a 20 wt % tetraethyl ammonium hydroxide aqueous solution (12.6 g) were added, and the mixture was stirred for about 9 hours under reflux of an argon gas. Thereafter, 2-isopropylphenylboronic acid (0.0829 g), palladium acetate (0.78 mg), tris(2-methoxyphenyl)phosphine (5.13 mg) and a 20 wt % tetraethyl ammonium hydroxide aqueous solution (12.6 g) were added, and the mixture was further stirred for about 15 hours under reflux of an argon gas. Thereafter, a solution prepared by dissolving sodium N,N-diethyldithiocarbamate trihydrate (1.00 g) in ion exchanged water (20 ml) was added, and the mixture was stirred for about 3 hours while heating at 85° C. The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP6 (2.064 g). The polymer compound CP6 had a polystyrene-equivalent number-average molecular weight (Mn) and a polystyrene-equivalent weight-average molecular weight (Mw) of Mn=$5.1\times10^4$ and Mw=$1.3\times10^5$, respectively. The polymer compound CP6 had a TH of 2.89 eV.

The polymer compound CP6 is estimated to be a polymer compound having the following repeating units and mole fractions and in which a repeating unit of (PA) and a repeating unit selected from (PB) are alternately polymerized, based on the charging ratios of raw material monomers.

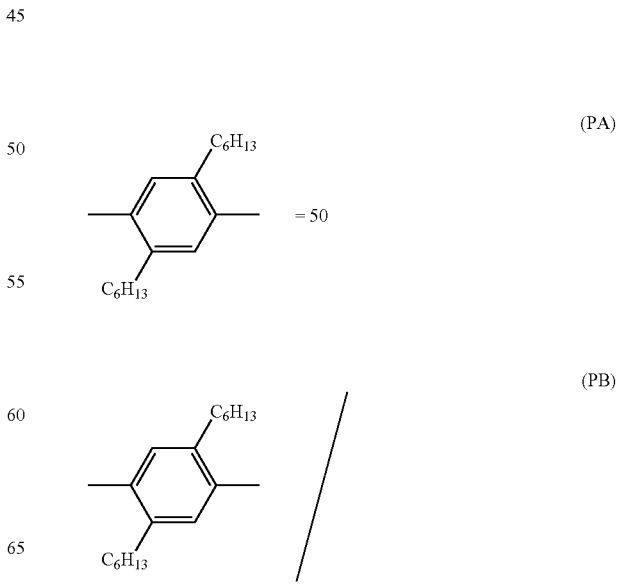

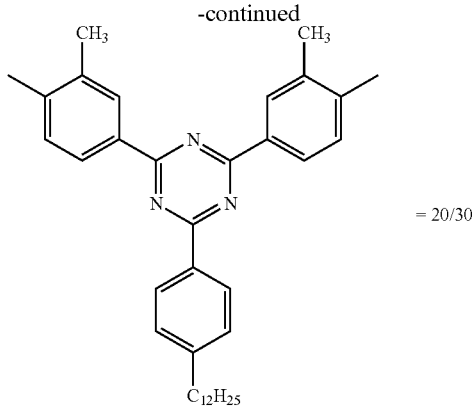

= 20/30

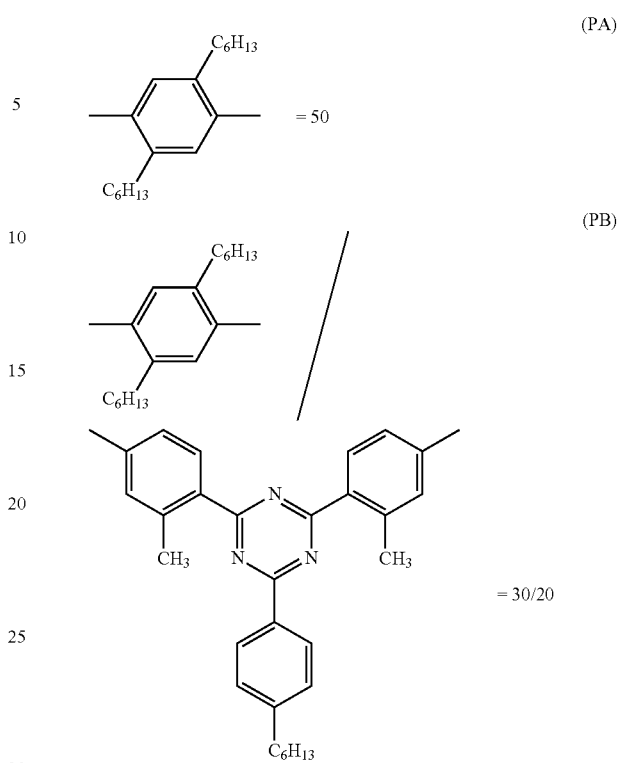

Comparative Example 7

(Synthesis of Polymer Compound CP7)

A gas in a reaction vessel was changed to a nitrogen gas atmosphere, then, a mixture of a compound CC1 (3.2725 g), a compound CC2 (1.5926 g), a compound MM4 (1.5218 g) and toluene (71 ml) was heated at about 80° C., then, palladium acetate (1.47 mg), tris(2-methoxyphenyl)phosphine (9.18 mg) and a 20 wt % tetraethyl ammonium hydroxide aqueous solution (23.2 g) were added, and the mixture was stirred for about 5.5 hours under reflux of an argon gas. Thereafter, 2-isopropylphenylboronic acid (0.2149 g), palladium acetate (1.38 mg), tris(2-methoxyphenyl)phosphine (9.26 mg) and a 20 wt % tetraethyl ammonium hydroxide aqueous solution (23.2 g) were added, and the mixture was further stirred for about 17.5 hours under reflux of an argon gas. Thereafter, a solution prepared by dissolving sodium N,N-diethyldithiocarbamate trihydrate (1.87 g) in ion exchanged water (37 ml) was added, and the mixture was stirred for about 2 hours while heating at 85° C. The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP7 (3.006 g). The polymer compound CP7 had a polystyrene-equivalent number-average molecular weight (Mn) and a polystyrene-equivalent weight-average molecular weight (Mw) of $Mn=1.2\times10^5$ and $Mw=4.3\times10^5$, respectively. The polymer compound CP7 had a TH of 2.81 eV.

The polymer compound CP7 is estimated to be a polymer compound having the following repeating units and mole fractions and in which a repeating unit of (PA) and a repeating unit selected from (PB) are alternately polymerized, based on the charging ratios of raw material monomers.

Comparative Example 8

(Synthesis of Polymer Compound CP8)

A gas in a reaction vessel was changed to a nitrogen gas atmosphere, then, a mixture of a compound CC1 (2.1817 g), a compound CC2 (0.7078 g), a compound MM4 (1.5218 g) and toluene (52 ml) was heated at about 80° C., then, palladium acetate (1.05 mg), tris(2-methoxyphenyl)phosphine (6.11 mg) and a 20 wt % tetraethyl ammonium hydroxide aqueous solution (15.5 g) were added, and the mixture was stirred for about 7 hours under reflux of an argon gas. Thereafter, 2-isopropylphenylboronic acid (0.2878 g), palladium acetate (1.02 mg), tris(2-methoxyphenyl)phosphine (6.18 mg) and a 20 wt % tetraethyl ammonium hydroxide aqueous solution (15.5 g) were added, and the mixture was further stirred for about 15 hours under reflux of an argon gas. Thereafter, a solution prepared by dissolving sodium N,N-diethyldithiocarbamate trihydrate (1.23 g) in ion exchanged water (25 ml) was added, and the mixture was stirred for about 2 hours while heating at 85° C. The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP8 (2.331 g). The polymer compound CP8 had a polystyrene-equivalent number-average molecular weight (Mn) and a polystyrene-equivalent weight-average molecular weight (Mw) of Mn=$5.1\times10^4$ and Mw=$1.4\times 10^5$, respectively. The polymer compound CP8 had a TH of 2.78 eV.

The polymer compound CP8 is estimated to be a polymer compound having the following repeating units and mole fractions and in which a repeating unit of (PA) and a repeating unit selected from (PB) are alternately polymerized, based on the charging ratios of raw material monomers.

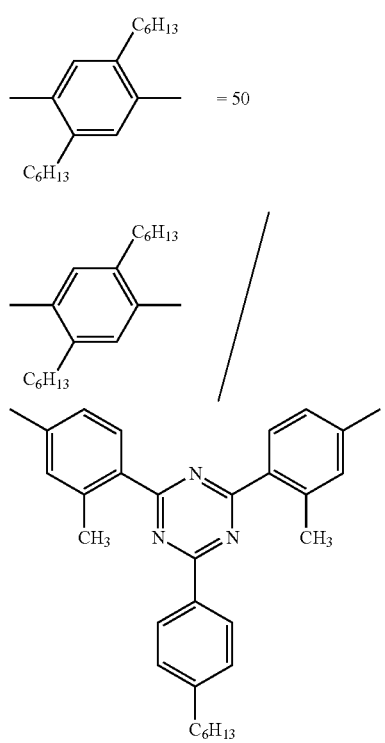

Comparative Example 9

(Synthesis of Polymer Compound CP9)

A gas in a reaction vessel was changed to a nitrogen gas atmosphere, then, a mixture of a compound CC6 (3.3249 g), a compound CC14 (3.4842 g), a compound CC11 (0.2897 g) and toluene (100 ml) was heated at about 80° C., then, palladium acetate (1.5 mg), tris(2-methoxyphenyl)phosphine (9.5 mg) and a 20 wt % tetraethyl ammonium hydroxide aqueous solution (15.2 g) were added, and the mixture was stirred for about 22 hours under reflux of an argon gas. Thereafter, phenylboronic acid pinacol ester (0.9268 g), palladium acetate (1.4 mg) and tris(2-methoxyphenyl)phosphine (9.4 mg) were added, and the mixture was further stirred for about 4 hours under reflux of an argon gas. Thereafter, a solution prepared by dissolving sodium N,N-diethyldithiocarbamate trihydrate (2.74 g) in ion exchanged water (27 ml) was added, and the mixture was stirred for 2 hours while heating at 85° C. The resultant organic layer was washed with ion exchanged water twice, with 3 wt % acetic acid twice and with ion exchanged water twice, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP9 (4.254 g). The polymer compound CP9 had a polystyrene-equivalent number-average molecular weight (Mn) and a polystyrene-equivalent weight-average molecular weight (Mw) of Mn=$4.1\times10^4$ and Mw=$1.6\times 10^5$, respectively.

The polymer compound CP9 is estimated to be a polymer compound having the following repeating units and mole fractions and in which a repeating unit of (PA) and a repeating unit selected from (PB) are alternately polymerized, based on the charging ratios of raw material monomers.

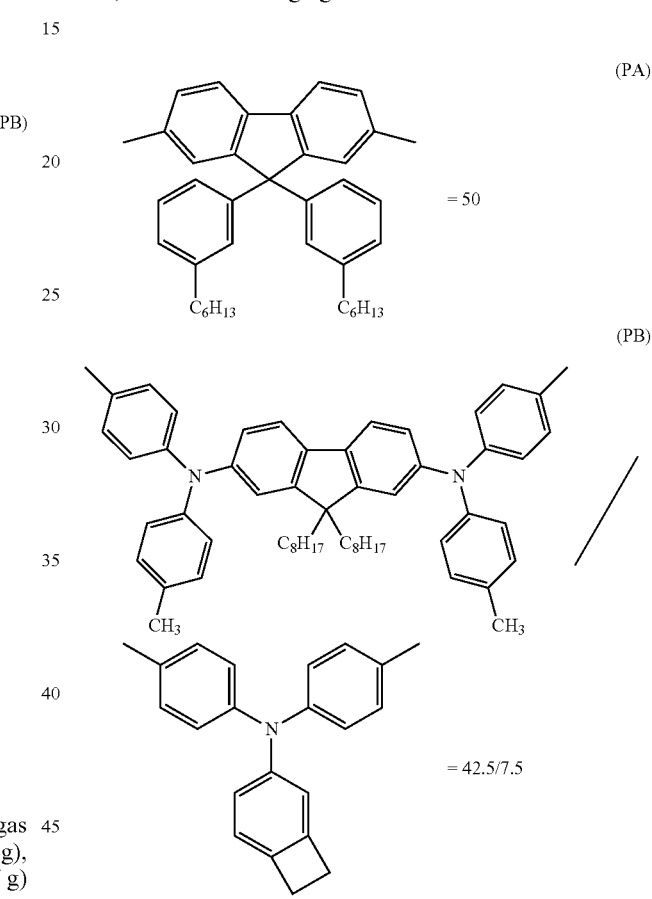

Comparative Example 10

(Synthesis of Polymer Compound CP10)

A gas in a reaction vessel was changed to a nitrogen gas atmosphere, then, a mixture of a compound CC1 (1.1213 g), a compound CC14 (1.2297 g), a compound CC7 (0.2377 g), a compound CC16 (0.2071 g) and toluene (39 ml) was heated at about 80° C., then, bis[tris(2-methoxyphenyl)phosphine]palladium dichloride (1.99 mg) and a 20 wt % tetraethyl ammonium hydroxide aqueous solution (10.0 g) were added, and the mixture was stirred for about 5 hours under reflux of an argon gas. Thereafter, phenylboronic acid (0.0554 g), bis[tris(2-methoxyphenyl)phosphine]palladium dichloride (1.99 mg) and a 20 wt % tetraethyl ammonium hydroxide aqueous solution (10.0 g) were added, and the mixture was further stirred for about 18 hours under reflux of an argon gas. Thereafter, a solution prepared by dissolving sodium N,N-diethyldithiocarbamate trihydrate (0.63 g) in ion exchanged water (12 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP10 (1.663 g). The polymer compound CP10 had a polystyrene-equivalent number-average molecular weight (Mn) and a polystyrene-equivalent weight-average molecular weight (Mw) of Mn=$4.8\times10^4$ and Mw=$6.0\times10^5$, respectively.

The polymer compound CP10 is estimated to be a polymer compound having the following repeating units and mole fractions and in which a repeating unit of (PA) and a repeating unit selected from (PB) are alternately polymerized, based on the charging ratios of raw material monomers.

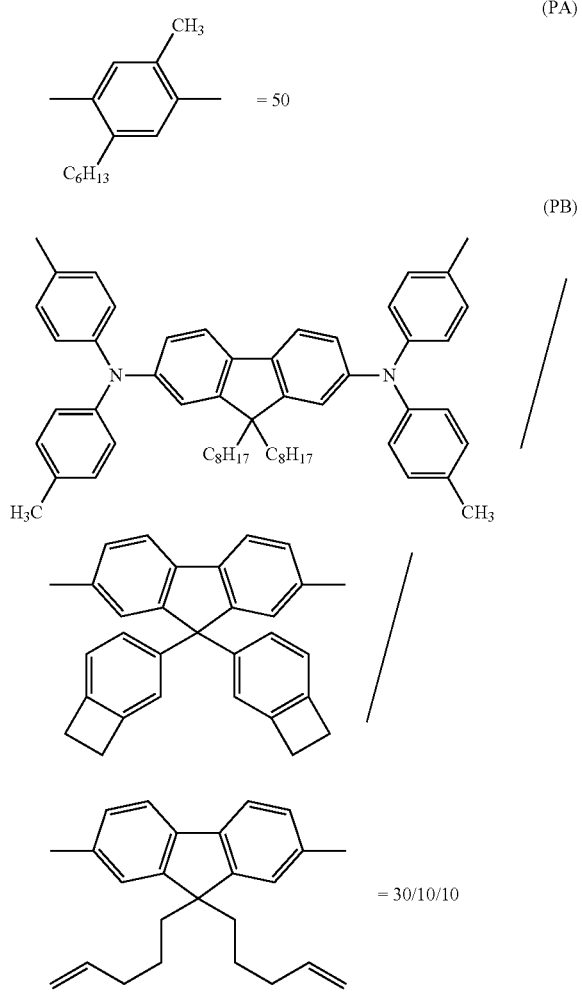

Synthesis Example 1

(Synthesis of Polymer Compound P9)

A gas in a reaction vessel was changed to a nitrogen gas atmosphere, then, a mixture of a compound CC5 (21.218 g), a compound CC6 (5.487 g), a compound CC11 (16.377 g), a compound CC11 (2.575 g), methyltrioctyl ammonium chloride (trade name: Aliquat (registered trademark) 336, manufactured by Aldrich) (5.17 g) and toluene (400 ml) was heated at about 80° C., then, bistriphenylphosphinepalladium dichloride (56.2 mg) and a 17.5 wt % sodium carbonate aqueous solution (109 g) were added, and the mixture was stirred for about 6 hours under reflux of an argon gas. Thereafter, phenylboronic acid (0.49 g) was added, and the mixture was further stirred for about 2 hours under reflux of an argon gas. Thereafter, a solution prepared by dissolving sodium N,N-diethyldithiocarbamate trihydrate (24.3 g) in ion exchanged water (240 ml) was added, and the mixture was stirred for 2 hours while heating at 85° C. The resultant organic layer was washed with ion exchanged water twice, with 3 wt % acetic acid twice and with ion exchanged water twice, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P9 (26.23 g). The polymer compound P9 had a polystyrene-equivalent number-average molecular weight (Mn) and a polystyrene-equivalent weight-average molecular weight (Mw) of Mn=$7.8\times10^4$ and Mw=$2.6\times10^5$, respectively.

The polymer compound P9 is estimated to be a polymer compound having the following repeating units and mole fractions and in which a repeating unit of (PA) and a repeating unit selected from (PB) are alternately polymerized, based on the charging ratios of raw material monomers.

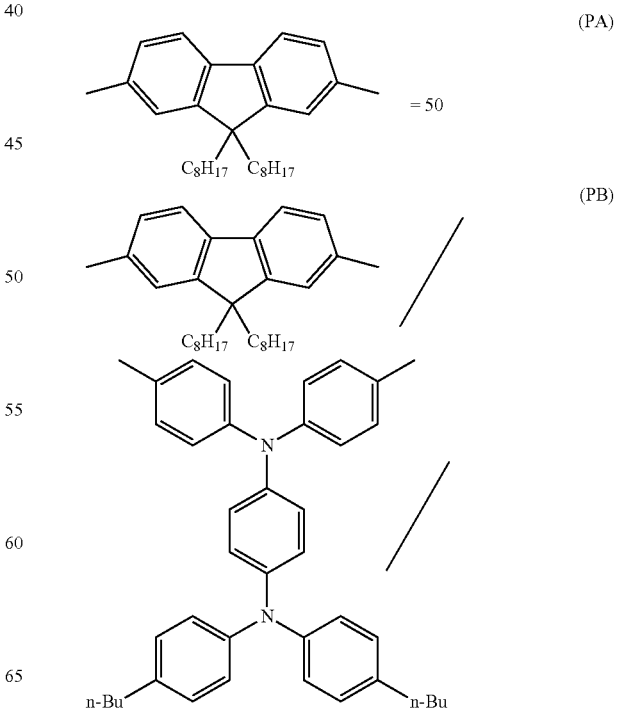

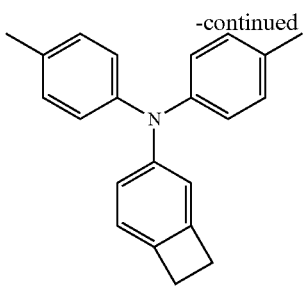

= 12.5/30/7.5

Synthesis Example 2

(Synthesis of Polymer Compound P10)

A gas in a reaction vessel was changed to a nitrogen gas atmosphere, then, a mixture of a compound CC1 (0.8222 g), a compound CC3 (0.8507 g), a compound CC12 (0.2097 g) and toluene (37 ml) was heated at about 80° C., then, palladium acetate (0.41 mg), tris(2-methoxyphenyl)phosphine (2.30 mg) and a 20 wt % tetraethyl ammonium hydroxide aqueous solution (5.8 g) were added, and the mixture was stirred for about 4 hours under reflux of an argon gas. Thereafter, phenylboronic acid (40.6 mg) was added, and the mixture was further stirred for about 2 hours under reflux of an argon gas. Thereafter, a solution prepared by dissolving sodium N,N-diethyldithiocarbamate trihydrate (0.46 g) in ion exchanged water (9 ml) was added, and the mixture was stirred for 2 hours while heating at 85° C. The resultant organic layer was washed with 3.6 wt % hydrochloric acid twice, with a 2.5 wt % ammonia aqueous solution twice and with ion exchanged water five times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P10 (1.110 g). The polymer compound P10 had a polystyrene-equivalent number-average molecular weight (Mn) and a polystyrene-equivalent weight-average molecular weight (Mw) of Mn=$8.7\times10^4$ and Mw=$2.3\times10^5$, respectively.

The polymer compound P10 is estimated to be a polymer compound having the following repeating units and mole fractions and in which a repeating unit of (PA) and a repeating unit selected from (PB) are alternately polymerized, based on the charging ratios of raw material monomers.

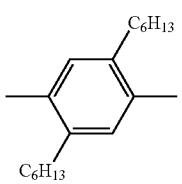

(PA)

= 50

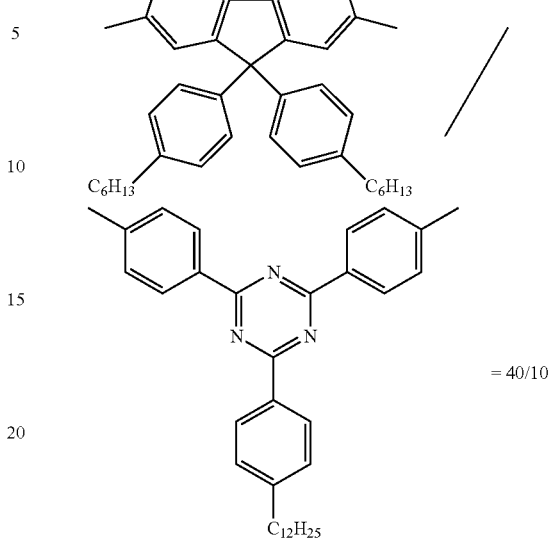

(PB)

= 40/10

Synthesis Example 3

(Synthesis of Polymer Compound P17)

A gas in a reaction vessel was changed to a nitrogen gas atmosphere, then, a mixture of a compound CM6 (9.0 g, 16.4 mmol), a compound CC15 (1.3 g, 1.8 mmol), a compound CC4 (13.4 g, 18.0 mmol), tetraethyl ammonium hydroxide (43.0 g, 58.3 mmol), palladium acetate (8 mg, 0.04 mmol), tri(2-methoxyphenyl)phosphine (0.05 g, 0.1 mmol) and toluene (200 ml) was stirred for about 8 hours with heating at about 90° C. Thereafter, phenylboronic acid (0.22 g, 1.8 mmol) was added, and the mixture was stirred for about 14 hours at about 90° C. Thereafter, the mixture was left to cool, the aqueous layer was removed, a sodium diethyldithiocarbamate aqueous solution was added and the mixture was stirred, then, the aqueous layer was removed, and the resultant organic layer was washed with water and 3% acetic acid water, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound P17 (12.5 g). The polymer compound P17 had a polystyrene-equivalent number-average molecular weight (Mn) and a polystyrene-equivalent weight-average molecular weight (Mw) of Mn=$1.1\times10^5$ and Mw=$3.1\times10^5$, respectively.

The polymer compound P17 is estimated to be a polymer compound having the following repeating units and mole fractions and in which a repeating unit of (PA) and a repeating unit selected from (PB) are alternately polymerized, based on the charging ratios of raw material monomers.

(PA)

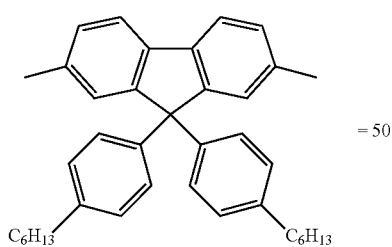

= 50

(PB)

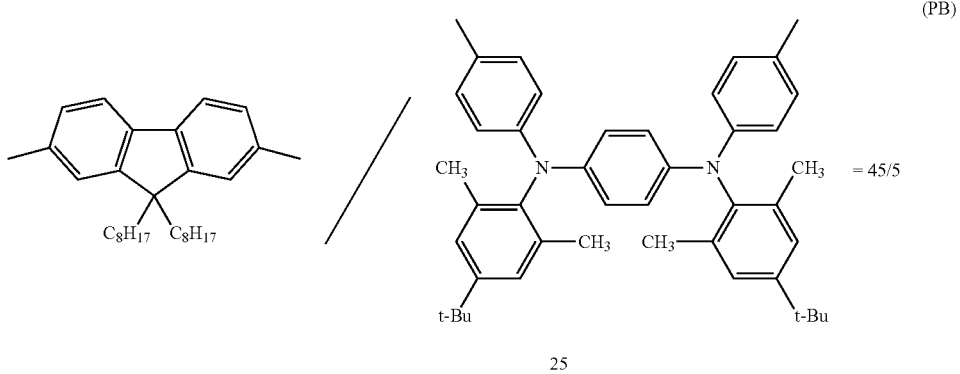

= 45/5

[Preparation of Light Emitting Material]

Synthesis Example 4

(Synthesis of Phosphorescent Compound EM1)

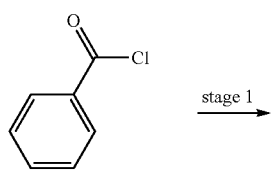

stage 1

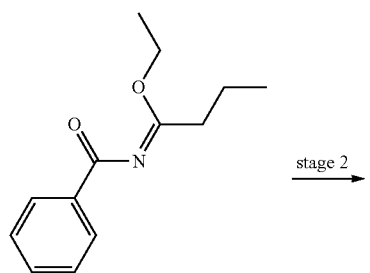

(E1a)

stage 2

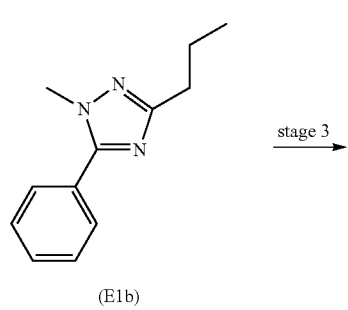

(E1b)

stage 3

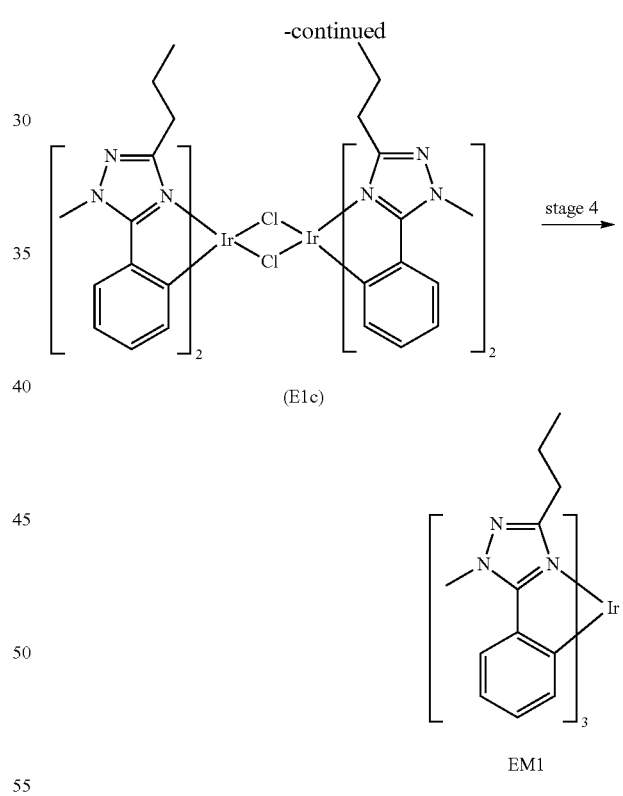

(E1c)

stage 4

EM1

<Stage 1>

In a reaction vessel, 3 ml (26 mmol) of benzoyl chloride and 3.9 g (26 mmol) of ethyl butylimidate hydrochloride were weighed, and dissolved in 300 ml of chloroform, then, a gas in the reaction vessel was changed to a nitrogen gas atmosphere. Thereafter, 25 ml of a chloroform solution of 7.2 ml (52 mmol) of triethylamine was dropped, and the mixture was stirred at room temperature under a nitrogen gas atmosphere. After 15 hours, the solvent chloroform was concentrated and the residue was suspended in 200 ml of water, and this was extracted with dichloromethane. The resultant solution was concentrated under reduced pressure, to obtain 5.3 g (24 mmol) of a compound (E1a) as a pale yellow liquid.

<Stage 2>

In a reaction vessel, 5.3 g (24 mmol) of a compound (E1a) was dissolved in 200 ml of chloroform, then, a gas in the reaction vessel was changed to a nitrogen gas atmosphere. Thereafter, 25 ml of a chloroform solution containing 1.2 ml (26 mmol) of methylhydrazine and 0.5 ml of water was dropped at room temperature under a nitrogen gas atmosphere. After dropping, the solution was stirred for 15 hours at room temperature under a nitrogen gas atmosphere, and 100 ml of water was added to stop the reaction. The resultant reaction solution was transferred to a separating funnel, washed with water, then, the resultant oil layer was recovered and concentrated, to obtain a coarse product. The resultant coarse product was allowed to pass through a silica gel column, and purified by a mixed solvent of dichloromethane and ethyl acetate. The eluent was concentrated, to obtain 2.9 g of a compound (E1b) as a colorless liquid (yield: 60%). The results of $^1$H-NMR analysis are shown below.

$^1$H-NMR (400 MHz/CDCl$_3$): δ (ppm)=7.75 (m, 3H), 7.66 (m, 2H), 3.93 (s, 3H), 2.73 (t, 2H), 1.82 (hex, 2H), 1.02 (t, 3H).

<Stage 3>

In a reaction vessel, 350 mg (1.0 mmol) of iridium chloride and 440 mg (2.2 mmol) of a compound (E1b) were weighed, and 10 ml of 2-ethoxyethanol and 5 ml of water were added, then, a gas in the reaction vessel was changed to a nitrogen gas atmosphere, and the mixture was refluxed with heating for 15 hours. After left to cool, the resultant reaction solvent was concentrated, and water and dichloromethane were added to the resultant residue and the oil layer was washed. The resultant oil layer was recovered, concentrated and dried, then, 660 mg of a compound (E1c) was obtained as a yellow oily substance.

<Stage 4>

In a reaction vessel, 625 mg (0.5 mmol) of a compound (E1c) and 1.0 g (5.0 mmol) of a compound (E1b) were weighed, and 260 mg of silver trifluoromethanesulfonate was added, then, a gas in the reaction vessel was purged with an argon gas. Thereafter, the mixture was reacted with heating at 165° C. for 15 hours, then, left to cool, and 15 ml of dichloromethane was poured. The resultant suspension was filtrated under suction, then, allowed to pass through a silica gel column, and separated and purified with a mixed solvent of dichloromethane and ethyl acetate. As a yellow powder, 630 mg of a phosphorescent compound EM1 [fac-tris(1-methyl-3-propyl-5-phenyl-1H-[1,2,4]-triazolato-N,C2') iridium (III)] was obtained (yield: 80%). The results of $^1$H-NMR analysis are shown below. The phosphorescent compound EM1 had a TM of 2.84 eV.

$^1$H-NMR (400 MHz/CDCl$_3$): δ (ppm)=7.50 (d, 3H), 6.88 (t, 3H), 6.80 (t, 3H), 6.63 (d, 3H), 4.11 (s, 9H), 2.18 (hep, 3H), 1.87 (hep, 3H), 1.38-1.30 (m, 3H), 1.18-1.10 (m, 3H), 0.68 (t, 9H).

Synthesis Example 5

(Synthesis of Phosphorescent Compound EM2)

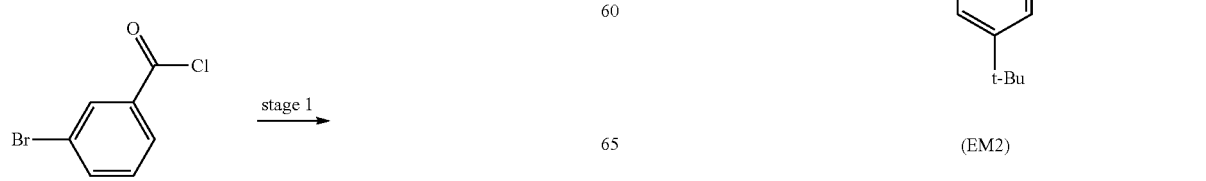

<Stage1>

In a reaction vessel, 6.92 g (31.5=01) of 3-bromobenzoyl chloride and 4.95 g (32.6 mmol) of ethyl butylimidate hydrochloride were weighed, and 150 ml of chloroform was added, then, a gas in the reaction vessel was changed to a nitrogen gas atmosphere. Thereafter, 20 ml of a chloroform solution containing 8.0 ml (60 mmol) of triethylamine was dropped, and the mixture was stirred for 15 hours at room temperature under a nitrogen gas atmosphere. The resultant solution was concentrated, then, suspended in dichloromethane, and introduced into a separating funnel and washed. The resultant oil layer was concentrated and dried, to obtain 9.47 g of a compound (E2a) as a colorless liquid. The results of $^1$H-NMR analysis are shown below.

$^1$H-NMR (400 MHz/CDCl$_3$): δ (ppm)=8.14 (t, 1H), 7.93 (dd, 1H), 7.65-7.63 (m, 1H), 7.31 (t, 1H), 4.29 (Q, 2H), 2.36 (t, 2H), 1.60 (td, 2H), 1.37 (t, 3H), 0.88 (t, 3H).

<Stage2>

In a reaction vessel, 9.0 g (30 mmol) of a compound (E2a) was dissolved in 100 ml of chloroform, then, a gas in the reaction vessel was changed to a nitrogen gas atmosphere. Thereafter, 15 ml of a chloroform solution containing 1.52 g (33 mmol) of methylhydrazine and 0.6 ml of water was dropped, and the mixture was stirred for 7 hours at room temperature under a nitrogen gas atmosphere. Into the resultant reaction solution, 100 ml of water was poured, and the solution was introduced into a separating funnel and washed. The resultant oil layer was recovered and concentrated, and allowed to pass through a silica gel column. The oil layer was separated and purified using a mixed solvent of dichloromethane and ethyl acetate, to obtain 5.8 g (21 mmol) of a compound (E2b) as a pale yellow liquid (yield: 69%). The results of $^1$H-NMR analysis are shown below.

$^1$H-NMR (400 MHz/CDCl$_3$): δ (ppm)=7.85 (d, 1H), 7.60 (m, 2H), 7.37 (dd, 1H), 3.93 (s, 3H), 2.72 (t, 2H), 1.81 (m, 2H), 1.01 (t, 3H).

<Stage3>

In a reaction vessel, 1.3 g (4.6 mmol) of a compound (E2b), 2200 mg (4.7 mmol) of 3,5-di(4-tert-butylphenyl)phenylboronic acid pinacol ester and 1250 mg (11.6 mmol) of sodium carbonate were weighed, and 5 ml of ethanol, 10 ml of water and 10 ml of toluene were added, then, a gas in the reaction vessel was changed to a nitrogen gas atmosphere. Thereafter, 260 mg (0.23 mmol) of tetrakistriphenylphosphinopalladium(0) was added, and the mixture was placed again under a nitrogen gas atmosphere. The resultant reaction mixture was heated at 80° C. for 15 hours. After left to cool, water and toluene were poured and the mixture was washed. The resultant oil layer was recovered, then, concentrated, to obtain a coarse product. The resultant coarse product was allowed to pass through a silica gel column, and separated and purified with a mixed solvent of dichloromethane and ethyl acetate. As a white powder, 2.18 g (4.0 mmol) of a compound (E2c) was obtained with a yield of 88%. The results of $^1$H-NMR analysis are shown below.

$^1$H-NMR (400 MHz/(CD$_3$)$_2$CO): δ (ppm)=8.19 (t, 1H), 7.98 (dt, 1H), 7.93 (d, 2H), 7.91 (t, 1H), 7.80 (t, 1H), 7.77 (dt, 4H), 7.66 (t, 1H), 7.54 (dt, 4H), 4.01 (s, 3H), 2.63 (t, 2H), 1.76 (td, 2H), 1.36 (s, 18H), 0.98 (t, 3H).

<Stage4>

In a reaction vessel, 226 mg (0.64 mmol) of iridium chloride and 760 mg (1.4 mmol) of a compound (E2c) were weighed, and 2 ml of water and 6 ml of 2-butoxyethanol were added, then, a gas in the reaction vessel was changed to a nitrogen gas atmosphere, and the mixture was refluxed with heating for 17 hours. After left to cool, water and dichloromethane were poured, and the resultant oil layer was washed. The resultant oil layer was concentrated and dried, to obtain 840 mg of a brownish-yellow amber-colored solid.

In a reaction vessel, 840 mg of the resultant brownish-yellow amber-colored solid and 1300 mg (2.4 mmol) of a compound (E2c) were weighed, a gas in the reaction vessel was changed to an argon gas atmosphere, then, 165 mg (0.64 mmol) of silver trifluorosulfonate was added. Thereafter, 1.25 ml of diethylene glycol dimethyl ester was added, and the mixture was refluxed with heating for 15 hours under an argon gas atmosphere. After left to cool, dichloromethane was poured, and the resultant suspension was filtrated under suction. The resultant filtrate was introduced into a separating funnel and washed, the resultant oil layer was recovered, then, concentrated, to obtain a coarse product. The resultant coarse product was allowed to pass through a silica gel column, and separated and purified with a mixed solvent of dichloromethane and ethyl acetate. The resultant yellow solid was recrystallized using a mixed solvent of dichloromethane and methanol, then, recrystallized using a mixed solvent of dichloromethane and hexane. As a yellow powder, 850 mg (0.48 mmol) of a phosphorescent compound EM2 [fac-tris(1-methyl-3-propyl-5-(5-(3,5-di(4-tert-butylphenyl)phenyl)phenyl)-1H-[1,2,4]-triazolato-N,C2')iridium(III)] was obtained with a yield of 73%. The results of $^1$H-NMR analysis are shown below. The phosphorescent compound EM2 had a TM of 2.77 eV.

$^1$H-NMR (400 MHz/CDCl$_3$): δ (ppm)=7.82 (d, 3H), 7.75 (d, 6H), 7.72 (d, 3H), 7.62 (d, 12H), 7.48 (d, 12H), 7.20 (dd, 3H), 6.87 (d, 3H), 4.27 (s, 9H), 2.26 (ddd, 3H), 1.96 (ddd, 3H), 1.37 (s, 54H), 1.05 (m, 6H), 0.73 (t, 9H).

Synthesis Example 6

(Synthesis of Phosphorescent Compound EM3)

A phosphorescent compound EM3 was synthesized according to a synthesis method described in WO 2002/066552. The phosphorescent compound EM3 had a TM of 2.52 eV.

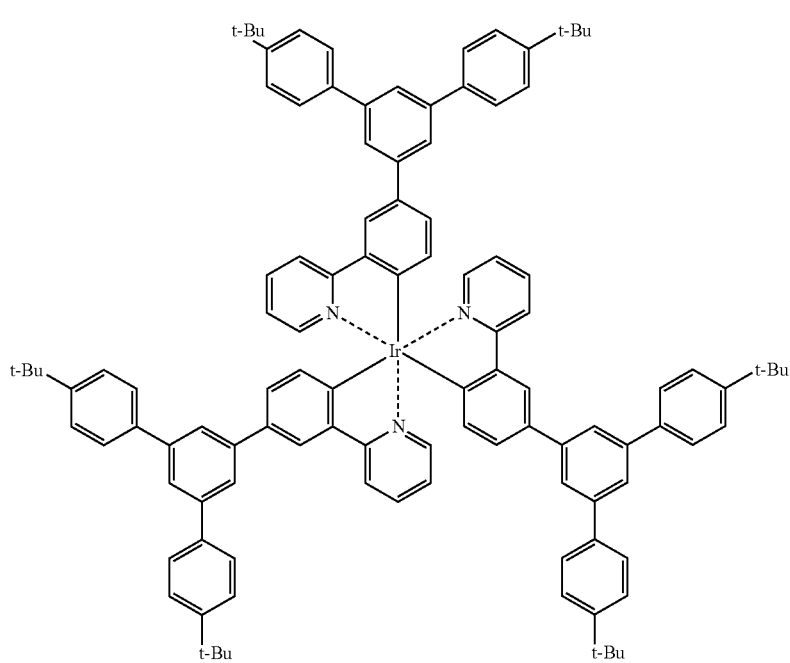

EM3

[Fabrication of Light Emitting Device]

A composition and a liquid composition containing the polymer compound and the phosphorescent compound obtained above were prepared, and various light emitting devices were fabricated using them.

Example D1

(Fabrication and Evaluation of Light Emitting Device D1)

On a glass substrate carrying thereon an ITO film with a thickness of 45 nm formed by a sputtering method, a polythiophene-sulfonic acid type hole injecting agent AQ-1200 (Manufactured by Plextronics. Inc.) was spin-coated to form a film with a thickness of 35 nm, which was dried on a hot plate at 170° C. for 15 minutes. Next, polyvinylcarbazole (manufactured by Aldrich) was dissolved in chlorobenzene at a concentration of 0.6 wt %. The resultant chlorobenzene solution was used and spin-coated at a rotation rate of 2000 rpm to form a film of polyvinylcarbazole with a thickness of 20 nm on the above-described film, then, dried at 180° C. for 60 minutes under a nitrogen gas atmosphere wherein the oxygen concentration and the moisture concentration were 10 ppm or less (by weight). Next, the polymer compound P1 and the phosphorescent compound EM1 were dissolved in xylene each at a concentration of 1.6 wt %, and these were mixed at a weight ratio of polymer compound P1:phosphorescent compound EM1=70:30 to obtain a composition D1. The resultant composition 1 was spin-coated at a rotation rate of 1170 rpm to form a film with a thickness of about 75 nm on the above-described polyvinylcarbazole film, then, dried at 130° C. for 10 minutes under a nitrogen gas atmosphere wherein the oxygen concentration and the moisture concentration were 10 ppm or less (by weight), to obtain a light emitting layer. Next, the pressure was reduced to $1.0 \times 10^{-4}$ Pa or less, then, sodium fluoride was vapor-deposited with a thickness of about 3 nm on the film of the composition 1 as a cathode, then, aluminum was vapor-deposited with a thickness of about 80 nm on the sodium fluoride layer. After vapor deposition, sealing was performed using a glass substrate, to fabricate a light emitting device D1. When voltage was applied to the resultant light emitting device D1, EL light emission having emission spectrum peaks at 455 nm and 490 nm was obtained from this device, and blue light emission of CIE chromaticity coordinate (0.180, 0.331) was observed. At a luminance of 100 cd/m², the driving voltage was 4.5 V and the light emission efficiency was 12.50 lm/W. The results are shown in Table 2.

Example D2

(Fabrication and Evaluation of Light Emitting Device D2)

A light emitting device D2 was fabricated in the same manner as in Example D1, excepting that a solution of a polymer compound P2 dissolved at a concentration of 1.6 wt % in a xylene solvent and a solution of a phosphorescent compound EM1 dissolved at a concentration of 1.6 wt % in a xylene solvent were mixed at a weight ratio of polymer compound P2:phosphorescent compound EM1=70:30 to prepare a composition D2 and the rotation rate of spin coat using the composition was changed from 1170 rpm to 1250 rpm, in Example D1. When voltage was applied to the resultant light emitting device D2, EL light emission having emission spectrum peaks at 455 nm and 485 nm was obtained from this device, and blue light emission of CIE chromaticity coordinate (0.180, 0.331) was observed. At a luminance of 100 cd/m², the driving voltage was 5.56 V and the light emission efficiency was 12.05 lm/W. The results are shown in Table 2.

Example D3

(Fabrication and Evaluation of Light Emitting Device D3)

A light emitting device D3 was fabricated in the same manner as in Example D2, excepting that a solution of a polymer compound P2 dissolved at a concentration of 1.6 wt % in a xylene solvent and a solution of a phosphorescent compound EM2 dissolved at a concentration of 1.6 wt % in a xylene solvent were mixed at a weight ratio of polymer compound P2:phosphorescent compound EM2=70:30 to prepare a composition D3 and the rotation rate of spin coat using the composition was changed from 1250 rpm to 1610 rpm, in Example D2. When voltage was applied to the resultant light emitting device D3, EL light emission having an emission spectrum peak at 480 nm was obtained from this device, and blue light emission of CIE chromaticity coordinate (0.155, 0.331) was observed. At a luminance of 100 cd/m$^2$, the driving voltage was 7.35 V and the light emission efficiency was 10.74 lm/W. The results are shown in Table 3.

Example D4

(Fabrication and Evaluation of Light Emitting Device D4)
A light emitting device D4 was fabricated in the same manner as in Example D1, excepting that a solution of a polymer compound P3 dissolved at a concentration of 1.6 wt % in a xylene solvent and a solution of a phosphorescent compound EM1 dissolved at a concentration of 1.6 wt % in a xylene solvent were mixed at a weight ratio of polymer compound P3:phosphorescent compound EM1=70:30 to prepare a composition D4 and the rotation rate of spin coat using the composition was changed from 1170 rpm to 1220 rpm, in Example D1. When voltage was applied to the resultant light emitting device D4, EL light emission having emission spectrum peaks at 455 nm and 485 nm was obtained from this device, and blue light emission of CIE chromaticity coordinate (0.162, 0.274) was observed. At a luminance of 100 cd/m$^2$, the driving voltage was 5.79 V and the light emission efficiency was 13.34 lm/W. The results are shown in Table 2.

Example D5

(Fabrication and Evaluation of Light Emitting Device D5)
A light emitting device D5 was fabricated in the same manner as in Example D1, excepting that a solution of a polymer compound P3 dissolved at a concentration of 1.6 wt % in a xylene solvent and a solution of a phosphorescent compound EM2 dissolved at a concentration of 1.6 wt % in a xylene solvent were mixed at a weight ratio of polymer compound P3:phosphorescent compound EM2=70:30 to prepare a composition D5 and the rotation rate of spin coat using the composition was changed from 1170 rpm to 1850 rpm, in Example D1. When voltage was applied to the resultant light emitting device D5, EL light emission having an emission spectrum peak at 480 nm was obtained from this device, and blue light emission of CIE chromaticity coordinate (0.153, 0.329) was observed. At a luminance of 100 cd/m$^2$, the driving voltage was 6.81 V and the light emission efficiency was 11.51 lm/W. The results are shown in Table 3.

Example D6

(Fabrication and Evaluation of Light Emitting Device D6)
A light emitting device D6 was fabricated in the same manner as in Example D1, excepting that a solution of a polymer compound P4 dissolved at a concentration of 1.6 wt % in a xylene solvent and a solution of a phosphorescent compound EM1 dissolved at a concentration of 1.6 wt % in a xylene solvent were mixed at a weight ratio of polymer compound P4:phosphorescent compound EM1=70:30 to prepare a composition D6 and the rotation rate of spin coat using the composition was changed from 1170 rpm to 1890 rpm, in Example D1. When voltage was applied to the resultant light emitting device D6, EL light emission having emission spectrum peaks at 455 nm and 480 nm was obtained from this device, and blue light emission of CIE chromaticity coordinate (0.154, 0.225) was observed. At a luminance of 100 cd/m$^2$, the driving voltage was 8.41 V and the light emission efficiency was 3.87 lm/W. The results are shown in Table 2.

Example D7

(Fabrication and Evaluation of Light Emitting Device D7)
A light emitting device D7 was fabricated in the same manner as in Example D1, excepting that a solution of a polymer compound P4 dissolved at a concentration of 1.6 wt % in a xylene solvent and a solution of a phosphorescent compound EM2 dissolved at a concentration of 1.6 wt % in a xylene solvent were mixed at a weight ratio of polymer compound P4:phosphorescent compound EM2=70:30 to prepare a composition D7 and the rotation rate of spin coat using the composition was changed from 1170 rpm to 2130 rpm, in Example D1. When voltage was applied to the resultant light emitting device D7, EL light emission having an emission spectrum peak at 480 nm was obtained from this device, and blue light emission of CIE chromaticity coordinate (0.156, 0.324) was observed. At a luminance of 100 cd/m$^2$, the driving voltage was 10.52 V and the light emission efficiency was 4.67 lm/W. The results are shown in Table 3.

Comparative Example CD1

(Fabrication and Evaluation of Light Emitting Device CD1)
A light emitting device CD1 was fabricated in the same manner as in Example D1, excepting that a solution of a polymer compound CP1 dissolved at a concentration of 1.6 wt % in a xylene solvent and a solution of a phosphorescent compound EM1 dissolved at a concentration of 1.6 wt % in a xylene solvent were mixed at a weight ratio of polymer compound CP1:phosphorescent compound EM1=70:30 to prepare a composition CD1 and the rotation rate of spin coat was changed from 1170 rpm to 1410 rpm, in Example D1. When voltage was applied to the resultant light emitting device CD1, EL light emission having emission spectrum peaks at 460 nm and 485 nm was obtained from this device, and blue light emission of CIE chromaticity coordinate (0.178, 0.296) was observed. At a luminance of 100 cd/m$^2$, the driving voltage was 7.2 V and the light emission efficiency was 1.23 lm/W. The results are shown in Table 2.

Comparative Example CD2

(Fabrication and Evaluation of Light Emitting Device CD2)
A light emitting device CD2 was fabricated in the same manner as in Example D1, excepting that a solution of a polymer compound CP1 dissolved at a concentration of 1.6 wt % in a xylene solvent and a solution of a phosphorescent compound EM2 dissolved at a concentration of 1.6 wt % in a xylene solvent were mixed at a weight ratio of polymer compound CP1:phosphorescent compound EM2=70:30 to prepare a composition CD2 and the rotation rate of spin coat was changed from 1170 rpm to 1690 rpm, in Example D1. When voltage was applied to the resultant light emitting device CD2, EL light emission having an emission spectrum peak at 485 nm was obtained from this device, and blue light emission of CIE chromaticity coordinate (0.170, 0.375) was observed. At a luminance of 100 cd/m$^2$, the driving voltage was 8.38 V and the light emission efficiency was 2.91 lm/W. The results are shown in Table 3.

Comparative Example CD3

(Fabrication and Evaluation of Light Emitting Device CD3)

A light emitting device CD3 was fabricated in the same manner as in Example D1, excepting that a solution of a polymer compound CP2 dissolved at a concentration of 1.6 wt % in a xylene solvent and a solution of a phosphorescent compound EM1 dissolved at a concentration of 1.6 wt % in a xylene solvent were mixed at a weight ratio of polymer compound CP2:phosphorescent compound EM1=70:30 to prepare a composition CD3 and the rotation rate of spin coat was changed from 1170 rpm to 1870 rpm, in Example D1. When voltage was applied to the resultant light emitting device CD3, EL light emission having emission spectrum peaks at 460 nm and 485 nm was obtained from this device, and blue light emission of CIE chromaticity coordinate (0.158, 0.245) was observed. At a luminance of 100 cd/m$^2$, the driving voltage was 12.0 V and the light emission efficiency was 2.38 lm/W. The results are shown in Table 2.

Comparative Example CD4

(Fabrication and Evaluation of Light Emitting Device CD4)

A light emitting device CD4 was fabricated in the same manner as in Example D1, excepting that a solution of a polymer compound CP3 dissolved at a concentration of 1.6 wt % in a xylene solvent and a solution of a phosphorescent compound EM1 dissolved at a concentration of 1.6 wt % in a xylene solvent were mixed at a weight ratio of polymer compound CP3:phosphorescent compound EM1=70:30 to prepare a composition CD4 and the rotation rate of spin coat was changed from 1170 rpm to 650 rpm, in Example D1. When voltage was applied to the resultant light emitting device CD4, EL light emission having emission spectrum peaks at 460 nm and 485 nm was obtained from this device, and blue light emission of CIE chromaticity coordinate (0.173, 0.311) was observed. At a luminance of 100 cd/m$^2$, the driving voltage was 9.49 V and the light emission efficiency was 5.45 lm/W. The results are shown in Table 2.

Comparative Example CD5

(Fabrication and Evaluation of Light Emitting Device CD5)

A light emitting device CD5 was fabricated in the same manner as in Example D1, excepting that a solution of a polymer compound CP4 dissolved at a concentration of 2.0 wt % in a xylene solvent and a solution of a phosphorescent compound EM1 dissolved at a concentration of 2.0 wt % in a xylene solvent were mixed at a weight ratio of polymer compound CP4:phosphorescent compound EM1=70:30 to prepare a composition CD5 and the rotation rate of spin coat was changed from 1170 rpm to 1920 rpm, in Example D1. When voltage was applied to the resultant light emitting device CD5, EL light emission having emission spectrum peaks at 460 nm and 485 nm was obtained from this device, and blue light emission of CIE chromaticity coordinate (0.156, 0.241) was observed. At a luminance of 100 cd/m$^2$, the driving voltage was 8.31 V and the light emission efficiency was 6.96 lm/W. The results are shown in Table 2.

Comparative Example CD6

(Fabrication and Evaluation of Light Emitting Device CD6)

A light emitting device CD6 was fabricated in the same manner as in Example D1, excepting that a solution of a polymer compound CP5 dissolved at a concentration of 1.6 wt % in a xylene solvent and a solution of a phosphorescent compound EM2 dissolved at a concentration of 1.6 wt % in a xylene solvent were mixed at a weight ratio of polymer compound CP5:phosphorescent compound EM2=70:30 to prepare a composition CD6 and the rotation rate of spin coat was changed from 1170 rpm to 1100 rpm, in Example D1. When voltage was applied to the resultant light emitting device CD6, EL light emission having an emission spectrum peak at 480 nm was obtained from this device, and blue light emission of CIE chromaticity coordinate (0.158, 0.344) was observed. At a luminance of 100 cd/m$^2$, the driving voltage was 7.00 V and the light emission efficiency was 3.57 lm/W. The results are shown in Table 3.

Comparative Example CD7

(Fabrication and Evaluation of Light Emitting Device CD7)

A light emitting device CD7 was fabricated in the same manner as in Example D1, excepting that a solution of a polymer compound CP6 dissolved at a concentration of 1.6 wt % in a xylene solvent and a solution of a phosphorescent compound EM1 dissolved at a concentration of 1.6 wt % in a xylene solvent were mixed at a weight ratio of polymer compound CP6:phosphorescent compound EM1=70:30 to prepare a composition CD7 and the rotation rate of spin coat was changed from 1170 rpm to 1080 rpm, in Example D1. When voltage was applied to the resultant light emitting device CD7, EL light emission having emission spectrum peaks at 465 nm and 485 nm was obtained from this device, and blue light emission of CIE chromaticity coordinate (0.165, 0.285) was observed. At a luminance of 100 cd/m$^2$, the driving voltage was 9.15 V and the light emission efficiency was 5.54 lm/W. The results are shown in Table 2.

Comparative Example CD8

(Fabrication and Evaluation of Light Emitting Device CD8)

A light emitting device CD8 was fabricated in the same manner as in Example D1, excepting that a solution of a polymer compound CP6 dissolved at a concentration of 1.6 wt % in a xylene solvent and a solution of a phosphorescent compound EM2 dissolved at a concentration of 1.6 wt % in a xylene solvent were mixed at a weight ratio of polymer compound CP6:phosphorescent compound EM2=70:30 to prepare a composition CD8 and the rotation rate of spin coat was changed from 1170 rpm to 1600 rpm, in Example D1. When voltage was applied to the resultant light emitting device CD8, EL light emission having an emission spectrum peak at 480 nm was obtained from this device, and blue light emission of CIE chromaticity coordinate (0.156, 0.332) was observed. At a luminance of 100 cd/m$^2$, the driving voltage was 7.25 V and the light emission efficiency was 6.75 lm/W. The results are shown in Table 3.

Example D8

(Fabrication and Evaluation of Light Emitting Device D8)

On a glass substrate carrying thereon an ITO film with a thickness of 45 nm formed by a sputtering method, a polythiophene-sulfonic acid type hole injecting agent AQ-1200 (Manufactured by Plextronics. Inc.) was spin-coated to form a film with a thickness of 65 nm, which was dried on a hot plate at 170° C. for 15 minutes. Next, the polymer compound P9 was dissolved in xylene at a concentration of 0.7 wt %. The resultant xylene solution was used and spin-coated at a rotation rate of 2000 rpm to form a film of the polymer compound P9 with a thickness of 20 nm on the above-described film, then, dried at 180° C. for 60 minutes under a nitrogen gas atmosphere wherein the oxygen concentration and the moisture concentration were 10 ppm or less (by weight). Next, the polymer compound P2 and the phosphorescent compound EM3 were dissolved in xylene each at a concentration of 1.6 wt %, and these were mixed at a weight ratio of polymer compound P2:phosphorescent compound EM3=70:30 to obtain a composition D8. The resultant composition D8 was spin-coated at a rotation rate of 1610 rpm to form a film with a thickness of about 80 nm on the above-described film of the polymer compound P9, then, dried at 130° C. for 10 minutes under a nitrogen gas atmosphere wherein the oxygen concentration and the moisture concentration were 10 ppm or less (by weight), to obtain a light emitting layer. The pressure was reduced to $1.0 \times 10^{-4}$ Pa or less, then, sodium fluoride was vapor-deposited with a thickness of about 3 nm on the film of the composition D8 as a cathode, then, aluminum was vapor-deposited with a thickness of about 80 nm on the sodium fluoride layer. After vapor deposition, sealing was performed using a glass substrate, to fabricate a light emitting device D8. When voltage was applied to the resultant light emitting device D8, EL light emission having an emission spectrum peak at 520 nm was obtained from this device, and green light emission of CIE chromaticity coordinate (0.293, 0.641) was observed. At a luminance of 1000 cd/m$^2$, the driving voltage was 6.67 V and the light emission efficiency was 18.16 lm/W. The results are shown in Table 4.

Example D9

(Fabrication and Evaluation of Light Emitting Device D9)

A light emitting device D9 was fabricated in the same manner as in Example D8, excepting that a solution of a polymer compound P4 dissolved at a concentration of 1.6 wt % in a xylene solvent and a solution of a phosphorescent compound EM3 dissolved at a concentration of 1.6 wt % in a xylene solvent were mixed at a weight ratio of polymer compound P4:phosphorescent compound EM3=70:30 to prepare a composition D9 and the rotation rate of spin coat was changed from 1610 rpm to 2570 rpm, in Example D8. When voltage was applied to the resultant light emitting device D9, EL light emission having an emission spectrum peak at 520 nm was obtained from this device, and green light emission of CIE chromaticity coordinate (0.294, 0.640) was observed. At a luminance of 1000 cd/m$^2$, the driving voltage was 7.96 V and the light emission efficiency was 14.75 lm/W. The results are shown in Table 4.

Example D10

(Fabrication and Evaluation of Light Emitting Device D10)

A light emitting device D10 was fabricated in the same manner as in Example D8, excepting that a solution of a polymer compound P5 dissolved at a concentration of 1.6 wt % in a xylene solvent and a solution of a phosphorescent compound EM3 dissolved at a concentration of 1.6 wt % in a xylene solvent were mixed at a weight ratio of polymer compound P5:phosphorescent compound EM3=70:30 to prepare a composition D10 and the rotation rate of spin coat was changed from 1610 rpm to 2170 rpm, in Example D8. When voltage was applied to the resultant light emitting device D10, EL light emission having an emission spectrum peak at 520 nm was obtained from this device, and green light emission of CIE chromaticity coordinate (0.298, 0.639) was observed. At a luminance of 1000 cd/m$^2$, the driving voltage was 6.04 V and the light emission efficiency was 18.50 lm/W. The results are shown in Table 4.

Example D11

(Fabrication and Evaluation of Light Emitting Device D11)

A light emitting device D11 was fabricated in the same manner as in Example D10, excepting that a solution of a polymer compound P6 dissolved at a concentration of 1.4 wt % in a xylene solvent and a solution of a phosphorescent compound EM3 dissolved at a concentration of 1.4 wt % in a xylene solvent were mixed at a weight ratio of polymer compound P6:phosphorescent compound EM3=70:30 to prepare a composition D11 and the rotation rate of spin coat was changed from 1610 rpm to 2970 rpm, in Example D8. When voltage was applied to the resultant light emitting device D11, EL light emission having an emission spectrum peak at 520 nm was obtained from this device, and green light emission of CIE chromaticity coordinate (0.301, 0.638) was observed. At a luminance of 1000 cd/m$^2$, the driving voltage was 5.82 V and the light emission efficiency was 18.47 lm/W. The results are shown in Table 4.

Comparative Example CD9

(Fabrication and Evaluation of Light Emitting Device CD9)

A light emitting device CD9 was fabricated in the same manner as in Example D8, excepting that a solution of a polymer compound CP7 dissolved at a concentration of 1.6 wt % in a xylene solvent and a solution of a phosphorescent compound EM3 dissolved at a concentration of 1.6 wt % in a xylene solvent were mixed at a weight ratio of polymer compound CP7:phosphorescent compound EM3=70:30 to prepare a composition CD9 and the rotation rate of spin coat was changed from 1610 rpm to 1950 rpm, in Example D8. When voltage was applied to the resultant light emitting device CD9, EL light emission having an emission spectrum peak at 520 nm was obtained from this device, and green light emission of CIE chromaticity coordinate (0.297, 0.638) was observed. At a luminance of 1000 cd/m$^2$, the driving voltage was 7.11 V and the light emission efficiency was 8.06 lm/W. The results are shown in Table 4.

Comparative Example CD10

(Fabrication and Evaluation of Light Emitting Device CD10)

A light emitting device CD10 was fabricated in the same manner as in Example D8, excepting that a solution of a polymer compound CP1 dissolved at a concentration of 2.0 wt % in a xylene solvent and a solution of a phosphorescent compound EM3 dissolved at a concentration of 2.0 wt % in a xylene solvent were mixed at a weight ratio of polymer compound CP1:phosphorescent compound EM3=70:30 to prepare a composition CD10 and the rotation rate of spin coat was changed from 1610 rpm to 1720 rpm, in Example D8. When voltage was applied to the resultant light emitting device CD10, EL light emission having an emission spectrum peak at 520 nm was obtained from this device, and green light emission of CIE chromaticity coordinate (0.296, 0.637) was observed. At a luminance of 1000 cd/m$^2$, the driving voltage was 6.73 V and the light emission efficiency was 12.36 lm/W. The results are shown in Table 4.

Comparative Example CD11

(Fabrication and Evaluation of Light Emitting Device CD11)

A light emitting device CD11 was fabricated in the same manner as in Example D8, excepting that a solution of a polymer compound CP4 dissolved at a concentration of 2.0 wt % in a xylene solvent and a solution of a phosphorescent compound EM3 dissolved at a concentration of 2.0 wt % in a xylene solvent were mixed at a weight ratio of polymer compound CP4:phosphorescent compound EM3=70:30 to prepare a composition CD11 and the rotation rate of spin coat was changed from 1610 rpm to 2400 rpm, in Example D8. When voltage was applied to the resultant light emitting device CD11, EL light emission having an emission spectrum peak at 520 nm was obtained from this device, and green light emission of CIE chromaticity coordinate (0.308, 0.634) was observed. At a luminance of 1000 cd/m$^2$, the driving voltage was 9.53 V and the light emission efficiency was 8.47 lm/W. The results are shown in Table 4.

Comparative Example CD12

(Fabrication and Evaluation of Light Emitting Device CD12)

A light emitting device CD12 was fabricated in the same manner as in Example D8, excepting that a solution of a polymer compound CP3 dissolved at a concentration of 1.6 wt % in a xylene solvent and a solution of a phosphorescent compound EM3 dissolved at a concentration of 1.6 wt % in a xylene solvent were mixed at a weight ratio of polymer compound CP3:phosphorescent compound EM3=70:30 to prepare a composition CD12 and the rotation rate of spin coat was changed from 1610 rpm to 1570 rpm, in Example D8. When voltage was applied to the resultant light emitting device CD12, EL light emission having an emission spectrum peak at 520 nm was obtained from this device, and green light emission of CIE chromaticity coordinate (0.309, 0.633) was observed. At a luminance of 1000 cd/m$^2$, the driving voltage was 7.44 V and the light emission efficiency was 8.85 lm/W. The results are shown in Table 4.

Comparative Example CD13

(Fabrication and Evaluation of Light Emitting Device CD13)

A light emitting device CD13 was fabricated in the same manner as in Example D8, excepting that a solution of a polymer compound CP8 dissolved at a concentration of 2.0 wt % in a xylene solvent and a solution of a phosphorescent compound EM3 dissolved at a concentration of 2.0 wt % in a xylene solvent were mixed at a weight ratio of polymer compound CP8:phosphorescent compound EM3=70:30 to prepare a composition CD13 and the rotation rate of spin coat was changed from 1610 rpm to 1640 rpm, in Example D8. When voltage was applied to the resultant light emitting device CD13, EL light emission having an emission spectrum peak at 520 nm was obtained from this device, and green light emission of CIE chromaticity coordinate (0.296, 0.639) was observed. At a luminance of 1000 cd/m$^2$, the driving voltage was 6.44 V and the light emission efficiency was 8.78 lm/W. The results are shown in Table 4.

Comparative Example CD14

(Fabrication and Evaluation of Light Emitting Device CD14)

A light emitting device CD14 was fabricated in the same manner as in Example D8, excepting that a solution of a polymer compound CP6 dissolved at a concentration of 2.0 wt % in a xylene solvent and a solution of a phosphorescent compound EM3 dissolved at a concentration of 2.0 wt % in a xylene solvent were mixed at a weight ratio of polymer compound CP8:phosphorescent compound EM3=70:30 to prepare a composition CD14 and the rotation rate of spin coat was changed from 1610 rpm to 1780 rpm, in Example D8. When voltage was applied to the resultant light emitting device CD14, EL light emission having an emission spectrum peak at 520 nm was obtained from this device, and green light emission of CIE chromaticity coordinate (0.299, 0.635) was observed. At a luminance of 1000 cd/m$^2$, the driving voltage was 8.51 V and the light emission efficiency was 4.58 lm/W. The results are shown in Table 4.

Example D12

(Fabrication and evaluation of light emitting device D12)

On a glass substrate carrying thereon an ITO film with a thickness of 45 nm formed by a sputtering method, a polythiophene-sulfonic acid type hole injecting agent AQ-1200 (Manufactured by Plextronics. Inc.) was spin-coated to form a film with a thickness of 50 nm, which was dried on a hot plate at 170° C. for 15 minutes. Next, the polymer compound P7 was dissolved in xylene at a concentration of 0.7 wt %. The resultant xylene solution was used and spin-coated at a rotation rate of 2680 rpm to form a film of the polymer compound P7 with a thickness of 20 nm on the above-described film, then, dried at 180° C. for 60 minutes under a nitrogen gas atmosphere wherein the oxygen concentration and the moisture concentration were 10 ppm or less (by weight). Next, the polymer compound P10 and the phosphorescent compound EM3 were dissolved in xylene each at a concentration of 2.0 wt %, and these were mixed at a weight ratio of polymer compound P2:phosphorescent compound EM3=70:30 to obtain a composition D12. The resultant composition D12 was spin-coated at a rotation rate of 2350 rpm to form a film with a thickness of about 80 nm on the above-described film of polymer compound P7, then, dried at 130° C. for 10 minutes under a nitrogen gas atmosphere wherein the oxygen concentration and the moisture concentration were 10 ppm or less (by weight), to obtain a light emitting layer. The pressure was reduced to $1.0 \times 10^{-4}$ Pa or less, then, sodium fluoride was vapor-deposited with a thickness of about 3 nm on the film of the composition D12 as a cathode, then, aluminum was vapor-deposited with a thickness of about 80 nm on the sodium fluoride layer. After vapor deposition, sealing was performed using a glass substrate, to fabricate a light emitting device D12. When voltage was applied to the resultant light emitting device D12, EL light emission having an emission spectrum peak at 520 nm was obtained from this device, and green light emission of CIE chromaticity coordinate (0.304, 0.637) was observed. At a luminance of 1000 cd/m$^2$, the driving voltage was 5.57 V and the light emission efficiency was 39.11 lm/W. The results are shown in Table 5.

Example D13

(Fabrication and Evaluation of Light Emitting Device D13)

A light emitting device D13 was fabricated in the same manner as in Example D13, excepting that the polymer compound P8 was used instead of the polymer compound P7 and film formation was performed at a rotation rate of 2200 rpm, in Example D12. When voltage was applied to the resultant light emitting device D13, EL light emission having an emission spectrum peak at 520 nm was obtained from this device, and green light emission of CIE chromaticity coordinate (0.303, 0.637) was observed. At a luminance of 1000 cd/m$^2$, the driving voltage was 6.13 V and the light emission efficiency was 34.56 lm/W. The results are shown in Table 5.

Comparative Example CD15

(Fabrication and Evaluation of Light Emitting Device CD15)

A light emitting device D15 was fabricated in the same manner as in Example D12, excepting that the polymer compound P9 was used instead of the polymer compound P7 and film formation was performed at a rotation rate of 2000 rpm, in Example D12. When voltage was applied to the resultant light emitting device D15, EL light emission having an emission spectrum peak at 520 nm was obtained from this device, and green light emission of CIE chromaticity coordinate (0.313, 0.634) was observed. At a luminance of 1000 cd/m$^2$, the driving voltage was 6.23 V and the light emission efficiency was 23.67 lm/W. The results are shown in Table 5.

Example D14

(Fabrication and Evaluation of Light Emitting Device D14)

A light emitting device D14 was fabricated in the same manner as in Example D1, excepting that a solution of a polymer compound P1 dissolved at a concentration of 1.6 wt % in a xylene solvent, a solution of a polymer compound P4 dissolved at a concentration of 1.6 wt % in a xylene solvent and a solution of a phosphorescent compound EM1 dissolved at a concentration of 1.6 wt % in a xylene solvent were mixed at a weight ratio of polymer compound P1:polymer compound P4:phosphorescent compound EM1=35:35:30 to prepare a composition D14 and the rotation rate of spin coat using the composition was changed from 1170 rpm to 1600 rpm, in Example D1. The composition D14 contains two kinds of polymer compounds and the average mole fraction of repeating units derived from the compound CC12 is 10 mol %. When voltage was applied to the resultant light emitting device D14, EL light emission having emission spectrum peaks at 460 nm and 485 nm was obtained from this device, and blue light emission of CIE chromaticity coordinate (0.179, 0.318) was observed. At a luminance of 100 cd/m$^2$, the driving voltage was 5.36 V and the light emission efficiency was 11.91 lm/W. The results are shown in Table 2.

Example D15

(Fabrication and Evaluation of Light Emitting Device D15)

A light emitting device D15 was fabricated in the same manner as in Example D1, excepting that a solution of a polymer compound P3 dissolved at a concentration of 1.4 wt % in a xylene solvent, a solution of a polymer compound P4 dissolved at a concentration of 1.4 wt % in a xylene solvent and a solution of a phosphorescent compound EM1 dissolved at a concentration of 1.4 wt % in a xylene solvent were mixed at a weight ratio of polymer compound P3:polymer compound P4:phosphorescent compound EM1=35:35:30 to prepare a composition D15 and the rotation rate of spin coat using the composition was changed from 1170 rpm to 2140 rpm, in Example D1. The composition D15 contains two kinds of polymer compounds and the average mole fraction of repeating units derived from the compound MM5 is 10 mol %. When voltage was applied to the resultant light emitting device D15, EL light emission having emission spectrum peaks at 455 nm and 485 nm was obtained from this device, and blue light emission of CIE chromaticity coordinate (0.166, 0.275) was observed. At a luminance of 100 cd/m$^2$, the driving voltage was 6.17 V and the light emission efficiency was 11.66 lm/W. The results are shown in Table 2.

Example D16

(Fabrication and Evaluation of Light Emitting Device D16)

A light emitting device D16 was fabricated in the same manner as in Example D1, excepting that a solution of a polymer compound P2 dissolved at a concentration of 1.6 wt % in a xylene solvent, a solution of a polymer compound P4 dissolved at a concentration of 1.6 wt % in a xylene solvent and a solution of a phosphorescent compound EM1 dissolved at a concentration of 1.6 wt % in a xylene solvent were mixed at a weight ratio of polymer compound P2:polymer compound P4:phosphorescent compound EM1=52.5:17.5:30 to prepare a composition D16 and the rotation rate of spin coat using the composition was changed from 1170 rpm to 1420 rpm, in Example D1. The composition D16 contains two kinds of polymer compounds and the average mole fraction of repeating units derived from the compound MM4 is 10 mol %. When voltage was applied to the resultant light emitting device D16, EL light emission having emission spectrum peaks at 455 nm and 485 nm was obtained from this device, and blue light emission of CIE chromaticity coordinate (0.169, 0.279) was observed. At a luminance of 100 cd/m$^2$, the driving voltage was 6.14 V and the light emission efficiency was 10.25 lm/W. The results are shown in Table 2.

Example D17

(Fabrication and Evaluation of Light Emitting Device D17)

A light emitting device D17 was fabricated in the same manner as in Example D1, excepting that a solution of a polymer compound P11 dissolved at a concentration of 1.6 wt % in a xylene solvent, a solution of a polymer compound P4 dissolved at a concentration of 1.6 wt % in a xylene solvent and a solution of a phosphorescent compound EM1 dissolved at a concentration of 1.6 wt % in a xylene solvent were mixed at a weight ratio of polymer compound P11:polymer compound P4:phosphorescent compound EM1=29.4:40.6:30 to prepare a composition D17 and the rotation rate of spin coat using the composition was changed from 1170 rpm to 2100 rpm, in Example D1. The composition D17 contains two kinds of polymer compounds and the average mole fraction of repeating units derived from the compound MM6 is 10 mol %. When voltage was applied to the resultant light emitting device D17, EL light emission having emission spectrum peaks at 455 nm and 485 nm was obtained from this device, and blue light emission of CIE chromaticity coordinate (0.164, 0.263) was observed. At a luminance of 100 cd/m$^2$, the driving voltage was 5.54 V and the light emission efficiency was 14.36 lm/W. The results are shown in Table 2.

Example D18

(Fabrication and Evaluation of Light Emitting Device D18)

A light emitting device D18 was fabricated in the same manner as in Example D1, excepting that a solution of a polymer compound P11 dissolved at a concentration of 1.6 wt % in a xylene solvent, a solution of a polymer compound P4 dissolved at a concentration of 1.6 wt % in a xylene solvent and a solution of a phosphorescent compound EM1 dissolved at a concentration of 1.6 wt % in a xylene solvent were mixed at a weight ratio of polymer compound P11:polymer compound P4:phosphorescent compound EM1=43.75:26.25:30 to prepare a composition D18 and the rotation rate of spin coat using the composition was changed from 1170 rpm to 2100 rpm, in Example D1. The composition D18 contains two kinds of polymer compounds and the average mole fraction of repeating units derived from the compound MM6 is 15 mol %. When voltage was applied to the resultant light emitting device D18, EL light emission having emission spectrum peaks at 460 nm and 480 nm was obtained from this device, and blue light emission of CIE chromaticity coordinate (0.165, 0.263) was observed. At a luminance of 100 cd/m$^2$, the driving voltage was 5.21 V and the light emission efficiency was 15.65 lm/W. The results are shown in Table 2.

Example D19

(Fabrication and Evaluation of Light Emitting Device D19)
A light emitting device D19 was fabricated in the same manner as in Example D1, excepting that a solution of a polymer compound P11 dissolved at a concentration of 1.6 wt % in a xylene solvent, a solution of a polymer compound P4 dissolved at a concentration of 1.6 wt % in a xylene solvent and a solution of a phosphorescent compound EM1 dissolved at a concentration of 1.6 wt % in a xylene solvent were mixed at a weight ratio of polymer compound P11:polymer compound P4:phosphorescent compound EM1=58.1:11.9:30 to prepare a composition D19 and the rotation rate of spin coat using the composition was changed from 1170 rpm to 1820 rpm, in Example D1. The composition D19 contains two kinds of polymer compounds and the average mole fraction of repeating units derived from the compound MM6 is 20 mol %. When voltage was applied to the resultant light emitting device D19, EL light emission having emission spectrum peaks at 460 nm and 485 nm was obtained from this device, and blue light emission of CIE chromaticity coordinate (0.169, 0.278) was observed. At a luminance of 100 cd/m$^2$, the driving voltage was 5.01 V and the light emission efficiency was 17.18 lm/W. The results are shown in Table 2.

Example D20

(Fabrication and Evaluation of Light Emitting Device D20)
A light emitting device D20 was fabricated in the same manner as in Example D1, excepting that a solution of a polymer compound P12 dissolved at a concentration of 1.6 wt % in a xylene solvent and a solution of a phosphorescent compound EM2 dissolved at a concentration of 1.6 wt % in a xylene solvent were mixed at a weight ratio of polymer compound P12:phosphorescent compound EM2=70:30 to prepare a composition D20 and the rotation rate of spin coat using the composition was changed from 1170 rpm to 2910 rpm, in Example D1. When voltage was applied to the resultant light emitting device D20, EL light emission having an emission spectrum peak at 480 nm was obtained from this device, and blue light emission of CIE chromaticity coordinate (0.154, 0.333) was observed. At a luminance of 100 cd/m$^2$, the driving voltage was 7.14 V and the light emission efficiency was 8.36 lm/W. The results are shown in Table 3.

Example D21

(Fabrication and Evaluation of Light Emitting Device D21)
A light emitting device D21 was fabricated in the same manner as in Example D1, excepting that a solution of a polymer compound P3 dissolved at a concentration of 1.3 wt % in a xylene solvent, a solution of a polymer compound P4 dissolved at a concentration of 1.3 wt % in a xylene solvent and a solution of a phosphorescent compound EM2 dissolved at a concentration of 1.3 wt % in a xylene solvent were mixed at a weight ratio of polymer compound P3:polymer compound P4:phosphorescent compound EM2=52.5:17.5:30 to prepare a composition D21 and the rotation rate of spin coat using the composition was changed from 1170 rpm to 3000 rpm, in Example D1. The composition D21 contains two kinds of polymer compounds and the average mole fraction of repeating units derived from the compound MM5 is 15 mol %. When voltage was applied to the resultant light emitting device D21, EL light emission having an emission spectrum peak at 480 nm was obtained from this device, and blue light emission of CIE chromaticity coordinate (0.153, 0.323) was observed. At a luminance of 100 cd/m$^2$, the driving voltage was 7.40 V and the light emission efficiency was 10.53 lm/W. The results are shown in Table 3.

Example D22

(Fabrication and Evaluation of Light Emitting Device D22)
A light emitting device D21 was fabricated in the same manner as in Example D1, excepting that a solution of a polymer compound P11 dissolved at a concentration of 1.6 wt % in a xylene solvent, a solution of a polymer compound P4 dissolved at a concentration of 1.6 wt % in a xylene solvent and a solution of a phosphorescent compound EM2 dissolved at a concentration of 1.6 wt % in a xylene solvent were mixed at a weight ratio of polymer compound PH:polymer compound P4:phosphorescent compound EM2=29.4:40.6:30 to prepare a composition D22 and the rotation rate of spin coat using the composition was changed from 1170 rpm to 3500 rpm, in Example D1. The composition D22 contains two kinds of polymer compounds and the average mole fraction of repeating units derived from the compound MM6 is 10 mol %. When voltage was applied to the resultant light emitting device D22, EL light emission having an emission spectrum peak at 480 nm was obtained from this device, and blue light emission of CIE chromaticity coordinate (0.151, 0.310) was observed. At a luminance of 100 cd/m$^2$, the driving voltage was 7.02 V and the light emission efficiency was 11.40 lm/W. The results are shown in Table 3.

Example D23

(Fabrication and Evaluation of Light Emitting Device D23)
A light emitting device D23 was fabricated in the same manner as in Example D1, excepting that a solution of a polymer compound P11 dissolved at a concentration of 1.6 wt % in a xylene solvent, a solution of a polymer compound P4 dissolved at a concentration of 1.6 wt % in a xylene solvent and a solution of a phosphorescent compound EM2 dissolved at a concentration of 1.6 wt % in a xylene solvent were mixed at a weight ratio of polymer compound P11:polymer compound P4:phosphorescent compound EM2=43.75:26.25:30 to prepare a composition D23 and the rotation rate of spin coat using the composition was changed from 1170 rpm to 2580 rpm, in Example D1. The composition D23 contains two kinds of polymer compounds and the average mole fraction of repeating units derived from the compound MM6 is 15 mol %. When voltage was applied to the resultant light emitting device D23, EL light emission having an emission spectrum peak at 480 nm was obtained from this device, and blue light emission of CIE chromaticity coordinate (0.154, 0.326) was observed. At a luminance of 100 cd/m$^2$, the driving voltage was 6.83 V and the light emission efficiency was 10.88 lm/W. The results are shown in Table 3.

Example D24

(Fabrication and Evaluation of Light Emitting Device D24)

A light emitting device D24 was fabricated in the same manner as in Example D1, excepting that a solution of a polymer compound P11 dissolved at a concentration of 1.6 wt % in a xylene solvent, a solution of a polymer compound P4 dissolved at a concentration of 1.6 wt % in a xylene solvent and a solution of a phosphorescent compound EM2 dissolved at a concentration of 1.6 wt % in a xylene solvent were mixed at a weight ratio of polymer compound P11: polymer compound P4:phosphorescent compound EM2=58.1:11.9:30 to prepare a composition D24 and the rotation rate of spin coat using the composition was changed from 1170 rpm to 2450 rpm, in Example D1. The composition D24 contains two kinds of polymer compounds and the average mole fraction of repeating units derived from the compound MM6 is 20 mol %. When voltage was applied to the resultant light emitting device D24, EL light emission having an emission spectrum peak at 480 nm was obtained from this device, and blue light emission of CIE chromaticity coordinate (0.152, 0.321) was observed. At a luminance of 100 cd/m$^2$, the driving voltage was 6.62 V and the light emission efficiency was 10.89 lm/W. The results are shown in Table 3.

Comparative Example CD16

(Fabrication and Evaluation of Light Emitting Device CD16)

A light emitting device CD16 was fabricated in the same manner as in Example D1, excepting that a solution of a polymer compound CP5 dissolved at a concentration of 1.6 wt % in a xylene solvent, a solution of a polymer compound CP3 dissolved at a concentration of 1.6 wt % in a xylene solvent and a solution of a phosphorescent compound EM2 dissolved at a concentration of 1.6 wt % in a xylene solvent were mixed at a weight ratio of polymer compound CP5: polymer compound CP3:phosphorescent compound EM2=17.5:52.5:30 to prepare a composition CD16 and the rotation rate of spin coat using the composition was changed from 1170 rpm to 1190 rpm, in Example D1. The composition CD16 contains two kinds of polymer compounds and the average mole fraction of repeating units derived from the compound CC12 is 15 mol %. When voltage was applied to the resultant light emitting device CD16, EL light emission having an emission spectrum peak at 480 nm was obtained from this device, and blue light emission of CIE chromaticity coordinate (0.155, 0.334) was observed. At a luminance of 100 cd/m$^2$, the driving voltage was 7.84 V and the light emission efficiency was 6.46 lm/W. The results are shown in Table 3.

Comparative Example CD17

(Fabrication and Evaluation of Light Emitting Device CD17)

A light emitting device CD17 was fabricated in the same manner as in Example D1, excepting that a solution of a polymer compound CP4 dissolved at a concentration of 1.6 wt % in a xylene solvent, a solution of a polymer compound CP6 dissolved at a concentration of 1.6 wt % in a xylene solvent and a solution of a phosphorescent compound EM2 dissolved at a concentration of 1.6 wt % in a xylene solvent were mixed at a weight ratio of polymer compound CP4: polymer compound CP6:phosphorescent compound EM2=52.5:17.5:30 to prepare a composition CD17 and the rotation rate of spin coat using the composition was changed from 1170 rpm to 1000 rpm, in Example D1. The composition CD17 contains two kinds of polymer compounds and the average mole fraction of repeating units derived from the compound MM5 is 15 mol %. When voltage was applied to the resultant light emitting device CD17, EL light emission having an emission spectrum peak at 480 nm was obtained from this device, and blue light emission of CIE chromaticity coordinate (0.159, 0.351) was observed. At a luminance of 100 cd/m$^2$, the driving voltage was 8.89 V and the light emission efficiency was 7.30 lm/W. The results are shown in Table 3.

Example D25

(Fabrication and Evaluation of Light Emitting Device D25)

A light emitting device D25 was fabricated in the same manner as in Example D8, excepting that a solution of a polymer compound P1 dissolved at a concentration of 1.6 wt % in a xylene solvent, a solution of a polymer compound P4 dissolved at a concentration of 1.6 wt % in a xylene solvent and a solution of a phosphorescent compound EM3 dissolved at a concentration of 1.6 wt % in a xylene solvent were mixed at a weight ratio of polymer compound P1:polymer compound P4:phosphorescent compound EM3=35:35:30 to prepare a composition D25 and the rotation rate of spin coat using the composition was changed from 1610 rpm to 2100 rpm, in Example D8. The composition D25 contains two kinds of polymer compounds and the average mole fraction of repeating units derived from the compound CC12 is 10 mol %. When voltage was applied to the resultant light emitting device D25, EL light emission having an emission spectrum peak at 520 nm was obtained from this device, and green light emission of CIE chromaticity coordinate (0.291, 0.643) was observed. At a luminance of 1000 cd/m$^2$, the driving voltage was 6.94 V and the light emission efficiency was 19.13 lm/W. The results are shown in Table 4.

Example D26

(Fabrication and Evaluation of Light Emitting Device D26)

A light emitting device D26 was fabricated in the same manner as in Example D8, excepting that a solution of a polymer compound P12 dissolved at a concentration of 1.6 wt % in a xylene solvent and a solution of a phosphorescent compound EM3 dissolved at a concentration of 1.6 wt % in a xylene solvent were mixed at a weight ratio of polymer compound P12:phosphorescent compound EM3=70:30 to prepare a composition D26 and the rotation rate of spin coat was changed from 1610 rpm to 3500 rpm, in Example D8. When voltage was applied to the resultant light emitting device D26, EL light emission having an emission spectrum peak at 520 nm was obtained from this device, and green light emission of CIE chromaticity coordinate (0.292, 0.642) was observed. At a luminance of 1000 cd/m², the driving voltage was 6.40 V and the light emission efficiency was 15.52 lm/W. The results are shown in Table 4.

Example D27

(Fabrication and Evaluation of Light Emitting Device D27)

A light emitting device D27 was fabricated in the same manner as in Example D8, excepting that a solution of a polymer compound P3 dissolved at a concentration of 1.2 wt % in a xylene solvent, a solution of a polymer compound P4 dissolved at a concentration of 1.2 wt % in a xylene solvent and a solution of a phosphorescent compound EM3 dissolved at a concentration of 1.2 wt % in a xylene solvent were mixed at a weight ratio of polymer compound P3:polymer compound P4:phosphorescent compound EM3=35:35:30 to prepare a composition D27 and the rotation rate of spin coat was changed from 1610 rpm to 1750 rpm, in Example D8. The composition D27 contains two kinds of polymer compounds and the average mole fraction of repeating units derived from the compound MM5 is 10 mol %. When voltage was applied to the resultant light emitting device D27, EL light emission having an emission spectrum peak at 520 nm was obtained from this device, and green light emission of CIE chromaticity coordinate (0.289, 0.644) was observed. At a luminance of 1000 cd/m², the driving voltage was 7.45 V and the light emission efficiency was 17.46 lm/W. The results are shown in Table 4.

Example D28

(Fabrication and Evaluation of Light Emitting Device D28)

A light emitting device D28 was fabricated in the same manner as in Example D8, excepting that a solution of a polymer compound P3 dissolved at a concentration of 1.2 wt % in a xylene solvent, a solution of a polymer compound P4 dissolved at a concentration of 1.2 wt % in a xylene solvent and a solution of a phosphorescent compound EM3 dissolved at a concentration of 1.2 wt % in a xylene solvent were mixed at a weight ratio of polymer compound P3:polymer compound P4:phosphorescent compound EM3=52.5:17.5:30 to prepare a composition D28 and the rotation rate of spin coat was changed from 1610 rpm to 2230 rpm, in Example D8. The composition D28 contains two kinds of polymer compounds and the average mole fraction of repeating units derived from the compound MM5 is 15 mol %. When voltage was applied to the resultant light emitting device D28, EL light emission having an emission spectrum peak at 520 nm was obtained from this device, and green light emission of CIE chromaticity coordinate (0.291, 0.642) was observed. At a luminance of 1000 cd/m², the driving voltage was 6.86 V and the light emission efficiency was 15.50 lm/W. The results are shown in Table 4.

Example D29

(Fabrication and Evaluation of Light Emitting Device D29)

A light emitting device D29 was fabricated in the same manner as in Example D8, excepting that a solution of a polymer compound P2 dissolved at a concentration of 1.6 wt % in a xylene solvent, a solution of a polymer compound P4 dissolved at a concentration of 1.6 wt % in a xylene solvent and a solution of a phosphorescent compound EM3 dissolved at a concentration of 1.6 wt % in a xylene solvent were mixed at a weight ratio of polymer compound P2:polymer compound P4:phosphorescent compound EM3=52.5:17.5:30 to prepare a composition D29 and the rotation rate of spin coat was changed from 1610 rpm to 2280 rpm, in Example D8. The composition D29 contains two kinds of polymer compounds and the average mole fraction of repeating units derived from the compound MM4 is 10 mol %. When voltage was applied to the resultant light emitting device D29, EL light emission having an emission spectrum peak at 520 nm was obtained from this device, and green light emission of CIE chromaticity coordinate (0.290, 0.643) was observed. At a luminance of 1000 cd/m², the driving voltage was 7.11 V and the light emission efficiency was 17.25 lm/W. The results are shown in Table 4.

Example D30

(Fabrication and Evaluation of Light Emitting Device D30)

A light emitting device D30 was fabricated in the same manner as in Example D8, excepting that a solution of a polymer compound P11 dissolved at a concentration of 1.6 wt % in a xylene solvent, a solution of a polymer compound P4 dissolved at a concentration of 1.6 wt % in a xylene solvent and a solution of a phosphorescent compound EM3 dissolved at a concentration of 1.6 wt % in a xylene solvent were mixed at a weight ratio of polymer compound P11:polymer compound P4:phosphorescent compound EM3=58:12:30 to prepare a composition D30 and the rotation rate of spin coat was changed from 1610 rpm to 2210 rpm, in Example D8. The composition D30 contains two kinds of polymer compounds and the average mole fraction of repeating units derived from the compound MM6 is 20 mol %. When voltage was applied to the resultant light emitting device D30, EL light emission having an emission spectrum peak at 520 nm was obtained from this device, and green light emission of CIE chromaticity coordinate (0.293, 0.641) was observed. At a luminance of 1000 cd/m², the driving voltage was 6.41 V and the light emission efficiency was 14.09 lm/W. The results are shown in Table 4.

Comparative Example CD18

(Fabrication and Evaluation of Light Emitting Device CD18)

A light emitting device CD18 was fabricated in the same manner as in Example D8, excepting that a solution of a polymer compound CP5 dissolved at a concentration of 1.6 wt % in a xylene solvent, a solution of a polymer compound CP3 dissolved at a concentration of 1.6 wt % in a xylene solvent and a solution of a phosphorescent compound EM3 dissolved at a concentration of 1.6 wt % in a xylene solvent were mixed at a weight ratio of polymer compound CP5:polymer compound CP3:phosphorescent compound EM3=17.5:52.5:30 to prepare a composition CD18 and the rotation rate of spin coat using the composition was changed from 1610 rpm to 1800 rpm, in Example D8. The composition CD18 contains two kinds of polymer compounds and the average mole fraction of repeating units derived from the compound CC12 is 15 mol %. When voltage was applied to the resultant light emitting device CD18, EL light emission having an emission spectrum peak at 520 nm was obtained from this device, and green light emission of CIE chromaticity coordinate (0.305, 0.635) was observed. At a luminance of 1000 cd/m², the driving voltage was 7.23 V and the light emission efficiency was 7.47 lm/W. The results are shown in Table 4.

Comparative Example CD19

(Fabrication and Evaluation of Light Emitting Device CD19)

A light emitting device CD19 was fabricated in the same manner as in Example D8, excepting that a solution of a polymer compound CP4 dissolved at a concentration of 1.6 wt % in a xylene solvent, a solution of a polymer compound CP6 dissolved at a concentration of 1.6 wt % in a xylene solvent and a solution of a phosphorescent compound EM3 dissolved at a concentration of 1.6 wt % in a xylene solvent were mixed at a weight ratio of polymer compound CP4:polymer compound CP6:phosphorescent compound EM3=52.5:17.5:30 to prepare a composition CD19 and the rotation rate of spin coat using the composition was changed from 1610 rpm to 1300 rpm, in Example D8. The composition CD19 contains two kinds of polymer compounds and the average mole fraction of repeating units derived from the compound MM5 is 15 mol %. When voltage was applied to the resultant light emitting device CD19, EL light emission having an emission spectrum peak at 520 nm was obtained from this device, and green light emission of CIE chromaticity coordinate (0.306, 0.635) was observed. At a luminance of 1000 cd/m$^2$, the driving voltage was 8.80 V and the light emission efficiency was 8.09 lm/W. The results are shown in Table 4.

Example D31

(Fabrication and Evaluation of Light Emitting Device D31)

A light emitting device D31 was fabricated in the same manner as in Example D1, excepting that a solution of a polymer compound P13 dissolved at a concentration of 1.6 wt % in a xylene solvent and a solution of a phosphorescent compound EM1 dissolved at a concentration of 1.6 wt % in a xylene solvent were mixed at a weight ratio of polymer compound P13:phosphorescent compound EM1=70:30 to prepare a composition D31 and the rotation rate of spin coat was changed from 1170 rpm to 3720 rpm, in Example D1. When voltage was applied to the resultant light emitting device D31, EL light emission having emission spectrum peaks at 460 nm and 480 nm was obtained from this device, and blue light emission of CIE chromaticity coordinate (0.167, 0.283) was observed. At a luminance of 100 cd/m$^2$, the driving voltage was 5.18 V and the light emission efficiency was 14.17 lm/W. The results are shown in Table 2.

Example D32

(Fabrication and Evaluation of Light Emitting Device D32)

A light emitting device D32 was fabricated in the same manner as in Example D1, excepting that a solution of a polymer compound P14 dissolved at a concentration of 1.4 wt % in a xylene solvent and a solution of a phosphorescent compound EM1 dissolved at a concentration of 1.4 wt % in a xylene solvent were mixed at a weight ratio of polymer compound P14:phosphorescent compound EM1=70:30 to prepare a composition D32 and the rotation rate of spin coat was changed from 1170 rpm to 2990 rpm, in Example D1. When voltage was applied to the resultant light emitting device D32, EL light emission having emission spectrum peaks at 460 nm and 480 nm was obtained from this device, and blue light emission of CIE chromaticity coordinate (0.179, 0.300) was observed. At a luminance of 100 cd/m$^2$, the driving voltage was 5.21 V and the light emission efficiency was 8.69 lm/W. The results are shown in Table 2.

Example D33

(Fabrication and Evaluation of Light Emitting Device D33)

A light emitting device D33 was fabricated in the same manner as in Example D1, excepting that a solution of a polymer compound P15 dissolved at a concentration of 1.6 wt % in a xylene solvent and a solution of a phosphorescent compound EM1 dissolved at a concentration of 1.6 wt % in a xylene solvent were mixed at a weight ratio of polymer compound P15:phosphorescent compound EM1=70:30 to prepare a composition D33 and the rotation rate of spin coat was changed from 1170 rpm to 1340 rpm, in Example D1. When voltage was applied to the resultant light emitting device D33, EL light emission having emission spectrum peaks at 460 nm and 480 nm was obtained from this device, and blue light emission of CIE chromaticity coordinate (0.187, 0.333) was observed. At a luminance of 100 cd/m$^2$, the driving voltage was 5.77 V and the light emission efficiency was 7.10 lm/W. The results are shown in Table 2.

Example D34

(Fabrication and Evaluation of Light Emitting Device D34)

A light emitting device D34 was fabricated in the same manner as in Example D1, excepting that a solution of a polymer compound P13 dissolved at a concentration of 1.6 wt % in a xylene solvent and a solution of a phosphorescent compound EM2 dissolved at a concentration of 1.6 wt % in a xylene solvent were mixed at a weight ratio of polymer compound P13:phosphorescent compound EM2=70:30 to prepare a composition D34 and the rotation rate of spin coat was changed from 1170 rpm to 1980 rpm, in Example D1. When voltage was applied to the resultant light emitting device D34, EL light emission having an emission spectrum peak at 480 nm was obtained from this device, and blue light emission of CIE chromaticity coordinate (0.158, 0.338) was observed. At a luminance of 100 cd/m$^2$, the driving voltage was 6.68 V and the light emission efficiency was 11.92 lm/W. The results are shown in Table 3.

Example D35

(Fabrication and Evaluation of Light Emitting Device D35)

A light emitting device D35 was fabricated in the same manner as in Example D1, excepting that a solution of a polymer compound P14 dissolved at a concentration of 1.2 wt % in a xylene solvent and a solution of a phosphorescent compound EM2 dissolved at a concentration of 1.2 wt % in a xylene solvent were mixed at a weight ratio of polymer compound P14:phosphorescent compound EM2=70:30 to prepare a composition D35 and the rotation rate of spin coat was changed from 1170 rpm to 3500 rpm, in Example D1. When voltage was applied to the resultant light emitting device D35, EL light emission having an emission spectrum peak at 480 nm was obtained from this device, and blue light emission of CIE chromaticity coordinate (0.157, 0.351) was observed. At a luminance of 100 cd/m$^2$, the driving voltage was 6.92 V and the light emission efficiency was 7.50 lm/W. The results are shown in Table 3.

Example D36

(Fabrication and Evaluation of Light Emitting Device D36)

A light emitting device D36 was fabricated in the same manner as in Example D1, excepting that a solution of a polymer compound P15 dissolved at a concentration of 1.6 wt % in a xylene solvent and a solution of a phosphorescent compound EM2 dissolved at a concentration of 1.6 wt % in a xylene solvent were mixed at a weight ratio of polymer compound P15:phosphorescent compound EM2=70:30 to prepare a composition D36 and the rotation rate of spin coat was changed from 1170 rpm to 1810 rpm, in Example D1. When voltage was applied to the resultant light emitting device D36, EL light emission having an emission spectrum peak at 480 nm was obtained from this device, and blue light emission of CIE chromaticity coordinate (0.158, 0.338) was observed. At a luminance of 100 cd/m$^2$, the driving voltage was 6.96 V and the light emission efficiency was 7.28 lm/W. The results are shown in Table 3.

Example D37

(Fabrication and Evaluation of Light Emitting Device D37)

A light emitting device D37 was fabricated in the same manner as in Example D12, excepting that the polymer compound P16 was used instead of the polymer compound P7 and film formation thereof was performed at a rotation rate of 1590 nm, and a composition D37 prepared by dissolving the polymer compound P17 at a concentration of 1.3 wt % in a xylene solvent was used instead of the composition D12, and spin-coated at a rotation rate of 2750 rpm to form a film with a thickness of about 60 nm on the above-described film of the polymer compound P16, in Example D12. When voltage was applied to the resultant light emitting device D37, EL light emission having an emission spectrum peak at 455 nm was obtained from this device, and blue light emission of CIE chromaticity coordinate (0.149, 0.151) was observed. At a luminance of 100 cd/m$^2$, the driving voltage was 3.49 V and the light emission efficiency was 7.29 lm/W. The results are shown in Table 5.

The dependency properties of light emission efficiency on the mole fraction of a repeating unit derived from the compound CC12, a repeating unit derived from the compound MM5, a repeating unit derived from the compound MM4 and a repeating unit derived from the compound MM6 contained in the polymer compound (or the average mole fraction of a repeating unit derived from the compound CC12, a repeating unit derived from the compound MM5, a repeating unit derived from the compound MM4 and a repeating unit derived from the compound MM6 contained in the several polymer compounds contained in the composition), when the phosphorescent compound EM1 was used, when the phosphorescent compound EM2 was used and when the phosphorescent compound EM3 was used, in the above-described examples and comparative examples, are summarized in Tables 6 to 8, respectively.

TABLE 2

| | Polymer compound | Current efficiency [cd/A] @100 cd/m$^2$ | Light emission efficiency [lm/W] @100 cd/m$^2$ |
|---|---|---|---|
| Example D1 | P1 | 18.03 | 12.50 |
| Comparative Example CD3 | CP2 | 9.08 | 2.38 |
| Comparative Example CD4 | CP3 | 16.46 | 5.45 |
| Example D2 | P2 | 21.33 | 12.05 |
| Example D4 | P3 | 24.60 | 13.34 |

TABLE 2-continued

| | Polymer compound | Current efficiency [cd/A] @100 cd/m$^2$ | Light emission efficiency [lm/W] @100 cd/m$^2$ |
|---|---|---|---|
| Comparative Example CD5 | CP4 | 18.39 | 6.96 |
| Comparative Example CD7 | CP6 | 16.12 | 5.54 |
| Example D6 | P4 | 10.37 | 3.87 |
| Comparative Example CD1 | CP1 | 2.82 | 1.23 |
| Example D14 | P1 + P4 (50:50) | 20.31 | 11.91 |
| Example D15 | P3 + P4 (50:50) | 22.88 | 11.66 |
| Example D16 | P2 + P4 (75:25) | 20.02 | 10.25 |
| Example D17 | P11 + P4 (42:58) | 25.32 | 14.36 |
| Example D18 | P11 + P4 (62.5:37.5) | 25.94 | 15.65 |
| Example D19 | P11 + P4 (83:17) | 27.39 | 17.18 |
| Example D31 | P13 | 23.35 | 14.17 |
| Example D32 | P14 | 14.41 | 8.69 |
| Example D33 | P15 | 13.03 | 7.10 |

(Polyvinylcarbazole was used as the hole transporting layer and EM1 was used as the phosphorescent compound.)

TABLE 3

| | Polymer compound | Current Efficiency [cd/A] @100 cd/m$^2$ | Light emission efficiency [lm/W] @100 cd/m$^2$ |
|---|---|---|---|
| Comparative Example CD6 | CP5 | 7.95 | 3.57 |
| Example D3 | P2 | 25.11 | 10.74 |
| Example D5 | P3 | 24.94 | 11.51 |
| Comparative Example CD8 | CP6 | 15.58 | 6.75 |
| Example D7 | P4 | 15.62 | 4.67 |
| Comparative Example CD2 | CP1 | 7.76 | 2.91 |
| Example D20 | P12 | 19.01 | 8.36 |
| Example D21 | P3 + P4 (75:25) | 24.80 | 10.53 |
| Comparative Example D16 | CP5 + CP3 (25:75) | 16.13 | 6.46 |
| Comparative Example D17 | CP4 + CP6 (75:25) | 20.63 | 7.30 |
| Example D22 | P11 + P4 (42:58) | 25.47 | 11.40 |
| Example D23 | P11 + P4 (62.5:37.5) | 23.65 | 10.88 |
| Example D24 | P11 + P4 (83:17) | 22.95 | 10.89 |
| Example D34 | P13 | 25.35 | 11.92 |
| Example D35 | P14 | 16.51 | 7.50 |
| Example D36 | P15 | 16.13 | 7.28 |

(Polyvinylcarbazole was used as the hole transporting layer and EM2 was used as the phosphorescent compound.)

TABLE 4

| | Polymer compound | Current efficiency [cd/A] @1000 cd/m² | Light emission efficiency [lm/W] @1000 cd/m² |
|---|---|---|---|
| Example D8 | P2 | 38.52 | 18.16 |
| Comparative Example CD9 | CP7 | 18.23 | 8.06 |
| Comparative Example CD13 | CP8 | 17.99 | 8.78 |
| Example D9 | P4 | 37.38 | 14.75 |
| Comparative Example CD10 | CP1 | 26.46 | 12.36 |
| Example D10 | P5 | 35.54 | 18.50 |
| Comparative Example CD11 | CP4 | 25.70 | 8.47 |
| Comparative Example CD14 | CP6 | 12.40 | 4.58 |
| Example D11 | P6 | 34.22 | 18.47 |
| Comparative Example CD12 | CP3 | 20.95 | 8.85 |
| Example D25 | P1 + P4 (50:50) | 42.23 | 19.13 |
| Example D26 | P12 | 31.62 | 15.52 |
| Example D27 | P3 + P4 (50:50) | 41.41 | 17.46 |
| Example D28 | P3 + P4 (75:25) | 33.85 | 15.50 |
| Example D29 | P2 + P4 (75:25) | 39.02 | 17.25 |

TABLE 4-continued

| | Polymer compound | Current efficiency [cd/A] @1000 cd/m² | Light emission efficiency [lm/W] @1000 cd/m² |
|---|---|---|---|
| Comparative Example CD18 | CP5 + CP3 (25:75) | 17.19 | 7.47 |
| Comparative Example CD19 | CP4 + CP6 (75:25) | 22.67 | 8.09 |
| Example D30 | P11 + P4 (83:17) | 28.72 | 14.09 |

(The polymer compound P9 was used as the hole transporting layer and EM3 was used as the phosphorescent compound.)

TABLE 5

| | Hole transporting layer | Light emitting layer | Current Efficiency [cd/A] @1000 cd/m² | Light emission efficiency [lm/W] @1000 cd/m² |
|---|---|---|---|---|
| Example D12 | P7 | C26 | 69.30 | 39.11 |
| Example D13 | P8 | C26 | 67.40 | 34.56 |
| Comparative Example CD15 | P9 | C26 | 36.87 | 17.54 |
| Example D37 | P16 | P17 | 8.10 | 7.29 |

TABLE 6

| EM1 | Formula (2) or (3) | 0 | 10 | 15 | 20 | 30 |
|---|---|---|---|---|---|---|
| Example | CC12 | 3.87 lm/W | 11.91 lm/W | | 12.50 lm/W | |
| | MM5 | | 11.66 lm/W | | 13.34 lm/W | |
| | MM4 | | 10.25 lm/W | 12.05 lm/W | | |
| Comparative Example | CC12 | 1.23 lm/W | 5.45 lm/W | | | |
| | MM5 | | 6.96 lm/W | | | 5.54 lm/W |
| | MM4 | | | | | |
| Example | MM6 | | 14.36 lm/W | 15.65 lm/W | 17.18 lm/W | |

(MM6 is a group represented by the formula (1).)

TABLE 7

| EM2 | Formula (2) or (3) | 0 | 10 | 15 | 20 | 30 |
|---|---|---|---|---|---|---|
| Example | CC12 | 4.67 lm/W | | 8.36 lm/W | | |
| | MM5 | | 10.53 lm/W | | 11.51 lm/W | |
| | MM4 | | 10.74 lm/W | | | |
| Comparative Example | CC12 | 2.91 lm/W | | 6.46 lm/W | | 3.57 lm/W |
| | MM5 | | | 7.30 lm/W | | 6.75 lm/W |
| | MM4 | | | | | |
| Example | MM6 | | 11.40 lm/W | 10.88 lm/W | 10.89 lm/W | |

(MM6 is a group represented by the formula (1).)

TABLE 8

| EM3 | Formula (2) or (3) | 0 | 10 | 15 | 20 | 30 |
|---|---|---|---|---|---|---|
| Example | CC12 | 14.75 lm/W | 19.13 lm/W | 15.52 lm/W | | |
| | MM5 | | 17.46 lm/W | 15.50 lm/W | | |
| | MM4 | | 17.25 lm/W | 18.16 lm/W | | |

TABLE 8-continued

| EM3 | Formula (2) or (3) | 0 | 10 | 15 | 20 | 30 |
|---|---|---|---|---|---|---|
| Comparative Example | CC12 | 12.36 lm/W | 8.85 lm/W | 7.47 lm/W | | |
| | MM5 | | 8.47 lm/W | 8.09 lm/W | | 4.58 lm/W |
| | MM4 | | | | 8.06 lm/W | 8.78 lm/W |
| Example | MM6 | | | | 14.09 lm/W | |

(MM6 is a group represented by the formula (1).)

INDUSTRIAL APPLICABILITY

The polymer compound of the present invention is useful for production of a light emitting device excellent in current efficiency and light emission efficiency, and particularly useful as a host material of a phosphorescent compound showing an emission color in the blue range.

The invention claimed is:

1. A polymer compound comprising as a repeating unit a group represented by formula (1B):

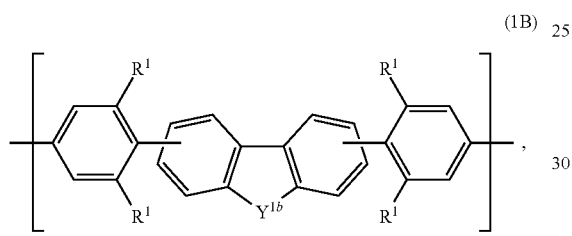

(1B)

in the formula (1B), $Y^{1b}$ represents —O—, —S—, —N(Ra)-, —C(Ra)$_2$- or —[C(Ra)$_2$]$_2$-, Ra represents an optionally substituted alkyl group, an optionally substituted aryl group, an optionally substituted monovalent aromatic heterocyclic group or an optionally substituted aralkyl group, and when there is a plurality of Ra groups, each Ra group can be the same or different and can be linked to form a ring structure together with a carbon atom to which they are attached, and $R^1$ represents an optionally substituted alkyl group, an optionally substituted aryl group, an optionally substituted monovalent aromatic heterocyclic group or an optionally substituted aralkyl group, and when there is a plurality of $R^1$ groups, each $R^1$ group can be the same or different.

2. The polymer compound according to claim 1, further comprising as a repeating unit at least one group selected from the group consisting of a group represented by formula (2) and a group represented by formula (3):

(2)

in the formula (2), $Ar^2$ represents an optionally substituted arylene group, an optionally substituted divalent aromatic heterocyclic group, or an optionally substituted divalent group obtained by mutually linking 2 to 10 groups selected from the group consisting of an optionally substituted arylene group and an optionally substituted divalent aromatic heterocyclic group, provided that in the group represented by the formula (2), at least one of the carbon atoms adjacent to a carbon atom forming a bond to the other repeating unit has an alkyl group, an aryl group, a monovalent aromatic heterocyclic group or an aralkyl group as a substituent,

(3)

in the formula (3), $Ar^3$ represents an optionally substituted arylene group, an optionally substituted divalent aromatic heterocyclic group, an optionally substituted divalent aromatic amine residue, or an optionally substituted divalent group obtained by mutually linking 2 to 10 groups selected from the group consisting of an optionally substituted arylene group and an optionally substituted divalent aromatic heterocyclic group, provided that the group represented by the formula (3) is different from the group represented by formula (1B) and the group represented by formula (2).

3. The polymer compound according to claim 2, wherein the group represented by formula (2) is a group represented by formula (2C):

(2C)

in the formula (2C), $Ar^{2c}$ represents an optionally substituted arylene group or an optionally substituted divalent aromatic heterocyclic group, provided that in the group represented by formula (2C), at least one of the carbon atoms adjacent to a carbon atom forming a bond to the other repeating unit has an alkyl group, an aryl group, a monovalent aromatic heterocyclic group or an aralkyl group as a substituent.

4. The polymer compound according to claim 3, wherein the group represented by formula (2C) is a group represented by formula (2D):

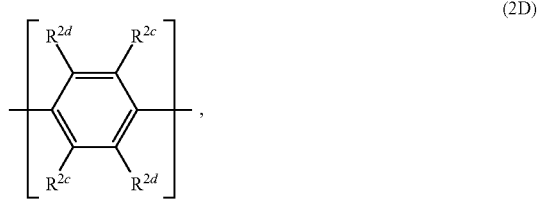

(2D)

in the formula (2D), $R^{2c}$ represents an optionally substituted alkyl group, an optionally substituted aryl group, an optionally substituted monovalent aromatic heterocyclic group or an optionally substituted aralkyl group, wherein a plurality of $R^{2c}$ groups can be the same or different, and $R^{2d}$ represents a hydrogen atom, an optionally substituted alkyl group, an optionally substituted aryl group, an optionally substituted monovalent aromatic heterocyclic group or an optionally substituted aralkyl group, and a plurality of $R^{2d}$ atom or groups can be the same or different.

5. The polymer compound according to claim 2, wherein the group represented by formula (3) is a group represented by formula (3B):

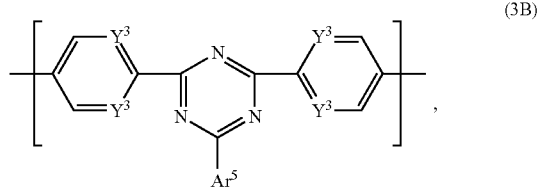

in the formula (3B), $Y^3$ represents a carbon atom or a nitrogen atom, wherein the carbon atom is optionally substituted with an alkyl group, an aryl group, a monovalent aromatic heterocyclic group or an aralkyl group, and a plurality of $Y^3$ atoms or groups can be the same or different, and $Ar^5$ represents an optionally substituted aryl group or an optionally substituted monovalent aromatic heterocyclic group.

6. The polymer compound according to claim 5, wherein the group represented by formula (3B) is a group represented by formula (3C):

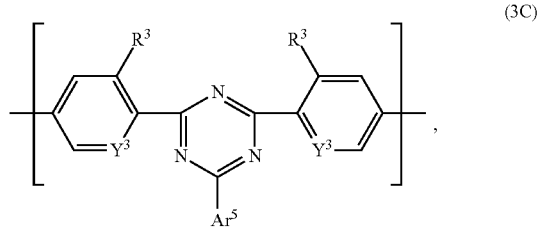

in the formula (3C), $Y^3$ represents a carbon atom or a nitrogen atom, wherein the carbon atom is optionally substituted with an alkyl group, an aryl group, a monovalent aromatic heterocyclic group or an aralkyl group, and a plurality of $Y^3$ atoms or groups can be the same or different, $Ar^5$ represents an optionally substituted aryl group or an optionally substituted monovalent aromatic heterocyclic group, and $R^3$ represents an alkyl group, an aryl group, a monovalent aromatic heterocyclic group or aralkyl group, and a plurality of $R^3$ groups can be the same or different.

7. The polymer compound according to claim 2, wherein the group represented by formula (2) is a group represented by formula (2B):

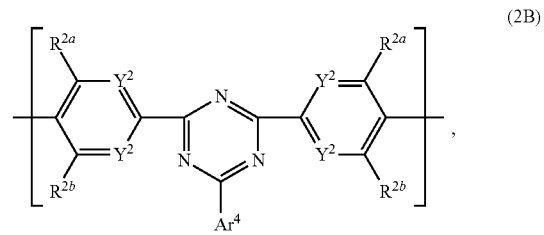

in the formula (2B), $Y^2$ represents a carbon atom or a nitrogen atom, wherein the carbon atom is optionally substituted with an alkyl group, an aryl group, a monovalent aromatic heterocyclic group or an aralkyl group, a plurality of $Y^2$ can be the same or different, $R^{2a}$ represents an optionally substituted alkyl group, an optionally substituted aryl group, an optionally substituted monovalent aromatic heterocyclic group or an optionally substituted aralkyl group, wherein a plurality of $R^{2a}$ groups can be the same or different, $R^{2b}$ represents a hydrogen atom, an optionally substituted alkyl group, an optionally substituted aryl group, an optionally substituted monovalent aromatic heterocyclic group or an optionally substituted aralkyl group, wherein a plurality of $R^{2b}$ groups can be the same or different, and $Ar^4$ represents an optionally substituted aryl group or an optionally substituted monovalent aromatic heterocyclic group.

8. The polymer compound according to claim 2, wherein the content of the groups represented by formula (3) is 50 mol % or less with respect to the total content of repeating units contained in the polymer compound and the groups represented by formula (3) are not substantially adjacent.

9. The polymer compound according to claim 2, wherein the content of the group represented by formula (2) is 50 mol % or more with respect to the total content of repeating units contained in the polymer compound and the groups represented by formula (1B), and the group represented by formula (1B) and the group represented by formula (3) are not substantially adjacent.

10. A composition comprising the polymer compound according to claim 1 and at least one material selected from the group consisting of a hole transporting material, an electron transporting material and a light emitting material.

11. The composition according to claim 10, wherein the light emitting material is a phosphorescent compound.

12. A liquid composition comprising the polymer compound according to claim 1 and a solvent.

13. An organic film comprising the polymer compound according to claim 1.

14. A light emitting device comprising an anode, a cathode and an organic layer disposed between the anode and the cathode, wherein the organic layer contains the polymer compound according to claim 1.

15. A compound represented by formula (M1):

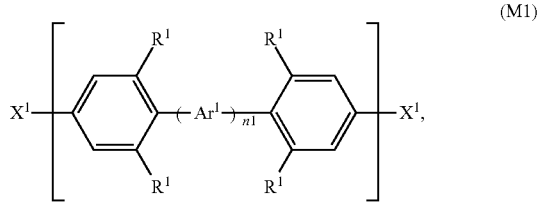

in the formula (M1), n1 represents 1, $Ar^1$ represents an optionally substituted 9,10-dihydrophenanthrene-2,7-diyl group, an optionally substituted fluorene-3,6-diyl group, an optionally substituted fluorene-2,7-diyl group, an optionally substituted carbazole-3,6-diyl group, an optionally substituted carbazole-2,7-diyl group, an optionally substituted dibenzofuran-4,7-diyl group, an optionally substituted dibenzofuran-3,8-diyl group, an optionally substituted dibenzothiophene-4,7-diyl group or an optionally substituted dibenzothiophene-3,8-diyl group, $R^1$ represents an optionally substituted alkyl group, an optionally substituted aryl group, an optionally substituted monovalent aromatic heterocyclic group or an optionally substituted aralkyl group, wherein a plurality of $R^1$ groups can be the same or different, $X^1$ represents a group selected from the following substituent group (a) or a group selected from the following substituent group (b), and a plurality of $X^1$ groups can be the same or different:

Substituent group (a) is selected from the group consisting of:

a chlorine atom, a bromine atom, an iodine atom and a group represented by $-O-S(=O)_2R^{20}$, wherein $R^{20}$ represents an alkyl group, or an aryl group optionally substituted with an alkyl group, an alkoxy group, a nitro group, a fluorine atom or a cyano group;

Substituent group (b) is selected from the group consisting of:

a group represented by $-B(OR^{21})_2$, wherein $R^{21}$ represents a hydrogen atom or an alkyl group, a plurality of $R^{21}$ can be the same or different and can be linked to form a ring together with an oxygen atom to which they are attached; a group represented by $-BF_4Q^1$, wherein $Q^1$ represents a monovalent cation of lithium, sodium, potassium, rubidium or cesium; a group represented by $-Sn(R^{22})_3$, wherein $R^{22}$ represents a hydrogen atom or an alkyl group, a plurality of $R^{22}$ atoms or groups can be the same or different and can be linked to form a ring together with a tin atom to which they are linked; a group represented by $-MgY^1$, wherein $Y^1$ represents a chlorine atom, a bromine atom or an iodine atom; and a group represented by $-ZnY^2$, wherein $Y^2$ represents a chlorine atom, a bromine atom or an iodine atom.

* * * * *